US012576114B2

(12) United States Patent
Rafii et al.

(10) Patent No.: US 12,576,114 B2
(45) Date of Patent: Mar. 17, 2026

(54) METHODS OF FUNCTIONAL VASCULARIZATION OF PANCREATIC ISLETS AND BETA-CELL ORGANOIDS

(71) Applicant: CORNELL UNIVERSITY, Ithaca, NY (US)

(72) Inventors: Shahin Rafii, New York, NY (US); Brisa Palikuqi, San Francisco, CA (US); Ge Li, Syosset, NY (US); Sina Rabbany, Great Neck, NY (US)

(73) Assignee: Cornell University, Ithaca, NY (US)

( * ) Notice: Subject to any disclaimer, the term of this patent is extended or adjusted under 35 U.S.C. 154(b) by 913 days.

(21) Appl. No.: 17/623,493

(22) PCT Filed: Jul. 2, 2020

(86) PCT No.: PCT/US2020/040637
§ 371 (c)(1),
(2) Date: Dec. 28, 2021

(87) PCT Pub. No.: WO2021/003352
PCT Pub. Date: Jan. 7, 2021

(65) Prior Publication Data
US 2022/0354901 A1 Nov. 10, 2022

Related U.S. Application Data

(60) Provisional application No. 62/870,288, filed on Jul. 3, 2019.

(51) Int. Cl.
| | |
|---|---|
| *A61K 35/39* | (2015.01) |
| *C12M 3/00* | (2006.01) |
| *C12M 3/06* | (2006.01) |
| *C12N 5/071* | (2010.01) |

(52) U.S. Cl.
CPC ............. *A61K 35/39* (2013.01); *C12M 21/08* (2013.01); *C12M 23/16* (2013.01); *C12N 5/0677* (2013.01); *C12N 5/0679* (2013.01); *C12N 5/0691* (2013.01); *C12N 5/0697* (2013.01); *C12N 2510/00* (2013.01); *C12N 2513/00* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 6,156,306 A * | 12/2000 | Brownlee et al. ... | C12N 5/0676 |
| 6,899,822 B2 | 5/2005 | McKedy | |
| 2015/0361398 A1 | 12/2015 | Sandler et al. | |
| 2019/0100728 A1 | 4/2019 | Sato et al. | |

FOREIGN PATENT DOCUMENTS

| | | | | | |
|---|---|---|---|---|---|
| CN | 109847102 A | 6/2019 | | | |
| EP | 3026110 A1 | 6/2016 | | | |
| WO | 2008111064 A1 | 9/2008 | | | |
| WO | 2015012158 A | 1/2015 | | | |
| WO | 2016141137 A1 | 9/2016 | | | |
| WO | WO-2017205511 A1 * | 11/2017 | ............. | A61K 35/39 |
| WO | 2018132720 A | 7/2018 | | | |
| WO | 2018144725 A1 | 8/2018 | | | |
| WO | WO-2018144860 A1 * | 8/2018 | ............. | A61K 35/12 |

OTHER PUBLICATIONS

Hayashi, M., et al., "Endothelialization and altered hematopoiesis by persistent Etv2 expression in mice," Exp Hematol 40(9): 738-750. doi: 10.1016/j.exphem.2012.05.012. (Year: 2012).*
Takebe, T., et al., "Vascularized and Complex Organ Buds from Diverse Tissues via Mesenchymal Cell-Driven Condensation," Cell Stem Cell 16(5): 556-565. doi: 10.1016/j.stem.2015.03.004. (Year: 2015).*
Im et al. "Chondrogenesis of adipose tissue stem cells in porous PLGA scaffold impregnated with plasmid DNA containing SOX trio genes" Biomaterials (Year: 2011).*
Stevanovic et al. "SOX transcription factors as important regulators of neuronal and glial differentiation during nervous system development and adult neurogenesis" Front Mol Neurosci (Year: 2021).*
First Office Action dated May 31, 2024 received in Chinese Application No. 202080061996.0, 23 pages.
Notice of Reason(s) for Rejection dated Jun. 25, 2024 received in Japanese Application No. 2022-500071, 13 pages.
Palikuqi, B., et al., "Adaptable haemodynamic endothelial cells for organogenesis and tumorigenesis", Nature, Received: Dec. 6, 2017, Accepted: Jun. 8, 2020, Published online: Sep. 9, 2020, Sep. 17, 2020, pp. 426-432, vol. 585.
Paul, A., et al., "Mus musculus SRY (sex determining region Y)-box 15 (Sox15), mRNA", GenBank DataBase, Accession No. NM_009235.2, Sep. 22, 2018, 3 pages.
Ribeiro, D., et al., "3D-Models of Insulin-Producing β-Cells: from Primary Islet Cells to Stem Cell-Derived Islets", Stem Cell Reviews and Reports (2018), Published online Nov. 27, 2017, pp. 177-188, 14.

(Continued)

*Primary Examiner* — Robert M Kelly
*Assistant Examiner* — John David Moore
(74) *Attorney, Agent, or Firm* — Scully, Scott, Murphy & Presser, P.C.

(57) ABSTRACT

The instant disclosure is directed to a method for vascularizing a pancreatic islet comprising culturing the pancreatic islet or β-cells with an endothelial cell comprising an exogenous nucleic acid encoding an ETV2 transcription factor under conditions wherein the endothelial cell expresses the ETV2 transcription factor. The instant disclosure is further directed to a method for making a vascularized β-cell organoid comprising culturing the pancreatic islet or β-cells with an endothelial cell comprising an exogenous nucleic acid encoding an ETV2 transcription factor under conditions wherein the endothelial cell expresses the ETV2 transcription factor. Disclosed also are vascularized islets and vascularized β-cell organoids produced by the methods of the instant disclosure, as well as methods for using the same.

22 Claims, 59 Drawing Sheets
(59 of 59 Drawing Sheet(s) Filed in Color)
Specification includes a Sequence Listing.

(56) References Cited

OTHER PUBLICATIONS

Extended European Search Report received on Jul. 5, 2023 in EP Application No. 20835027.2, 7 pages.

Zudaire, E., et al., "A Computational Tool for Quantitative Analysis of Vascular Networks", PLos ONE, Nov. 2011, pp. 1-12, vol. 6, Issue 11, e27385.

Li, G., et al., "Multifunctional in vivo imaging of pancreatic islets during diabetes development", Journal of Cell Science (2016), Received Apr. 11, 2016, Accepted May 27, 2016, pp. 2865-2875, vol. 129.

Li, S., et al., "Plasma Mesothelin as a Novel Diagnostic and Prognostic Biomarker in Colorectal Cancer", Journal of Cancer 2017, Received Oct. 20, 2016, Accepted Feb. 27, 2017, Published May 12, 2017, pp. 1355-1361, vol. 8.

Liao, Y., et al., "featureCounts: an efficient general purpose program for assigning sequence reads to genomic feature", Bioinformatics 2014, Received on Jul. 11, 2013; revised on Nov. 6, 2013; accepted on Nov. 7, 2013, pp. 923-930, vol. 30, No. 7.

Liu, F., et al., "Induction of hematopoietic and endothelial cell program orchestrated by ETS transcription factor ER71/ETV2", EMBO Reports, Received Dec. 2, 2014, Revised Feb. 24, 2015, Accepted Feb. 26, 2015, Published online Mar. 23, 2015, pp. 654-669, vol. 16, No. 5.

Liu, Y., et al., "Epigenetic profiles signify cell fate plasticity in unipotent spermatogonial stem and progenitor cells", Nature Communications, Received Jan. 18, 2016, Accepted Mar. 9, 2016, Published Apr. 27, 2016, pp. 1-13, 7:11275.

Love, M.I., et al., "Moderated estimation of fold change and dispersion for RNA-seq data with DESeq2", Genome Biology (2014), Received May 27, 2014 Accepted Nov. 19, 2014, Published online Dec. 5, 2014, pp. 1-21, 15:550.

Lyden, D., et al., "Id1 and Id3 are required for neurogenesis, angiogenesis and vascularization of tumour xenografts", Nature, Oct. 14, 1999, pp. 670-677, vol. 401.

Machnicka, M.A., et al., "MODOMICS: a database of RNA modification pathways—2013 update", Nucleic Acids. Research (2013), received Sep. 15, 2012, Accepted Oct. 1, 2012, Published online Oct. 30, 2012, pp. D262-D267, vol. 41.

Miller, K.M., et al., "Current State of Type 1 Diabetes Treatment in the U.S.: Updated Data From the T1D Exchange Clinic Registry", Diabetes Care, Jun. 2015, pp. 971-978, vol. 38.

Mitry, R.R., et al., "Human Cell Culture Protocols", Third Edition, Humana Press Publishing, 2012, 433 pages.

Morita, R., et al., "ETS transcription factor ETV2 directly converts human fibroblasts into functional endothelial cells", PNAS, Jan. 6, 2015, pp. 160-165, vol. 12, No. 1.

Moss, J., et al., "Comprehensive human cell-type methylation atlas reveals origins of circulating cell-free DNA in health and disease", Nature Communications, 2018, pp. 1-12, 9:5068.

Murphy, S.V., et al., "3D bioprinting of tissues and organs", Nature Biotechnology, Received Dec. 5, 2013, accepted Jun. 12, 2014, published online Aug. 5, 2014 pp. 773-785, vol. 32, No. 8.

Nguyen, D.-H., et al., "Biomimetic model to reconstitute angiogenic sprouting morphogenesis in vitro", PNAS, Apr. 23, 2013, pp. 6712-6717, vol. 110, No. 17.

Nikolova, G., et al., "The Vascular Basement Membrane: Short Article a Niche for Insulin Gene Expression and beta Cell Proliferation", Developmental Cell, Received Sep. 12, 2005, Revised Dec. 17, 2005, Accepted Jan. 23, 2006, Published online Mar. 6, 2006 pp. 397-405, 10.

Nolan, D.J., et al., "Molecular Signatures of Tissue-Specific Microvascular Endothelial Cell Heterogeneity in Organ Maintenance and Regeneration", Developmental Cell, Jul. 29, 2013, pp. 204-219, 26.

O'Rourke, K.P., et al., "Immunofluorescent Staining of Mouse Intestinal Stem Cells", Bio Protoc, Feb. 20, 2016, 9 pages, 6(4).

O'Rourke, K.P., et al., "Isolation, Culture, and Maintenance of Mouse Intestinal Stem Cells", Bio Protoc., Feb. 20, 2016, 15 pages, 6(4).

Park, C., et al., "Injury-Mediated Vascular Regeneration Requires Endothelial ER71/ETV2", Arteriosclerosis, Thrombosis, and Vascular Biology, Received on Aug. 15, 2015, final version accepted on Nov. 7, 2015, pp. 86-96.

Pauli, C., et al., "Personalized In Vitro and In Vivo Cancer Models to Guide Precision Medicine", Cancer Discovery, May 2017, pp. 462-477.

Pellegata, A.F., et al., "Whole Organ Tissue Vascularization: Engineering the Tree to Develop the Fruits", Front. Bioeng. Biotechnol., May 14, 2018, Sec. Tissue Engineering and Regenerative Medicine.

Phan, D.T.T., et al., "A vascularized and perfused organ-on-a-chip platform for large-scale drug screening applications", Lab Chip. Author manuscript; available in PMC Feb. 1, 2020, Published in final edited form as: Lab Chip: Jan. 3, 20171, pp. 511-520, 17(3).

Rafii, S., et al., "Angiocrine functions of organ-specific endothelial cells", Nature. Author manuscript; available in PMC May 24, 2016, Published in final edited form as: Nature. Jan. 21, 2016, pp. 316-325, 529(7586).

Ramasamy, SK., "Regulation of tissue morphogenesis by endothelial cell-derived signals", Trends Cell Biol. Author manuscript; available in PMC Jul. 13, 2016, Published in final edited form as: Trends Cell Biol. Mar. 2015, pp. 148-157, 25(3).

Richards, O.C., et al., "The Role of Blood Vessels, Endothelial Cells, and Vascular Pericytes in Insulin Secretion and Peripheral Insulin Action", Endocrine Reviews, Jun. 2010, pp. 343-363, 31(3).

Ritchie, M.E., "limma powers differential expression analyses for RNA-sequencing and microarray studies", Published online Jan. 20, 2015 Nucleic Acids Research, 2015, pp. 1-13, vol. 43, No. 7.

Rutter, G.A., et al., "Pancreatic β-cell identity, glucose sensing and the control of insulin secretion", Biochem. J. (2015), Received Nov. 7, 2014/Dec. 1, 2014, accepted Dec. 5, 2014, Published on the Internet Feb. 20, 2015, pp. 203-218, 466.

Samuel, R., et al., "Vascular diseases await translation of blood vessels engineered from stem cells", Sci Transl Med. Author manuscript; available in PMC Oct. 14, 2016, Published in final edited form as: Sci Transl Med. Oct. 14, 2015; 7(309), 22 pages.

Schachterle, W., et al., "Sox17 drives functional engraftment of endothelium converted from non-vascular cells", Nature Communications, Received Apr. 7, 2016, Accepted Nov. 16, 2016, Published Jan. 16, 2017, 12 pages, 8:13963.

Stan, R.V., et al., "The Diaphragms of Fenestrated Endothelia:Gatekeepers of Vascular Permeability and Blood Composition", Developmental Cell, Dec. 11, 2012, pp. 1203-1218, 23.

Strilic, B., et al., "The Molecular Basis of Vascular Lumen Formation in the Developing Mouse Aorta", Developmental Cell, Oct. 20, 2009, pp. 505-515, 17.

Sugimoto, S., et al., "Establishment of 3D Intestinal Organoid Cultures from Intestinal Stem Cells", Zuzana Koledova (ed.), 3D Cell Culture: Methods and Protocols, Methods in Molecular Biology, vol. 1612, Chapter 7, pp. 97-105.

Sumanas, S., et al., "ETS Transcription Factor ETV2/ER71/Etsrp in Hematopoietic and Vascular Development", Current Topics in Developmental Biology, vol. 118, Chapter 4, pp. 77-111.

Sumanas, S., et al., "Identification of novel vascular endothelial-specific genes by the microarray analysis of the zebrafish cloche mutants", Submitted Dec. 6, 2004, accepted Mar. 22, 2005, Prepublished online as Blood First Edition Paper, Mar. 31, 2005, Blood, Jul. 15, 2005, pp. 534-541, vol. 106, No. 2.

Thorvaldsdottir, H., et al., "Integrative GenomicsViewer (IGV):high-performance genomics data visualization and exploration", Submitted Feb. 3, 2012, Received (in revised form) Mar. 14, 2012, Advance Access published on Apr. 19, 2012, Briefings in Bioinformatics, pp. 178-192, vol. 14, No. 2.

Tsai, et al., "A Method for Cryogenic Preservation of Human Biopsy Specimens and Subsequent Organoid Culture", Cellular and Molecular Gastroenterology and Hepatology, Received Jun. 28, 2017, Accepted Apr. 23, 2018, 12 pages, vol. 6, No. 2.

Van de Wetering, M., et al., "Prospective Derivation of a Living Organoid Biobank of Colorectal Cancer Patients", Cell, May 7, 2015, pp. 933-945, 161.

Wang, X., et al., "Engineering anastomosis between living capillary networks and endothelial cell-lined microfluidic channels", Lab (56)

References Cited

OTHER PUBLICATIONS

Chip. Author manuscript; available in PMC May 17, 2016, Published in final edited form as: Lab Chip. Jan. 21, 2016; 16(2): pp. 282-290.

Wareing, S., et al., "ETV2 Expression Marks Blood and Endothelium Precursors, Including Hemogenic Endothelium, at the Onset of Blood Development", Developmental Dynamics, Accepted Jun. 12, 2012, pp. 1454-1464, 241.

Weis, S.M., et al., "Tumor angiogenesis: molecular pathways and therapeutic targets", Nature Medicine, Nov. 2011, pp. 1359-1370, vol. 17, No. 11.

Xu, K., et al., "Blood Vessel Tubulogenesis Requires Rasip1 Regulation of GTPase Signaling", Developmental Cell, Apr. 19, 2011, pp. 526-539, 20.

Xu, R., et al., "Rasip1 is required for endothelial cell motility, angiogenesis and vessel formation", Developmental Biology (2009), Received for publication Dec. 23, 2008, Revised Feb. 20, 2009, Accepted Feb. 24, 2009, Available online Mar. 6, 2009, pp. 269-279, 329.

Yao, Y., et al., "SOX Transcription Factors in Endothelial Differentiation and Endothelial-Mesenchymal Transitions", Frontiers in Cardiovascular Medicine, Mar. 2019, pp. 1-8, vol. 6, Article 30.

Yin, X., et al., "Engineering Stem Cell Organoids", Cell Stem Cell, Jan. 7, 2016, pp. 25-38, 18.

Yu, J., et al., "Anti-GD2/4-1BB chimeric antigen receptor T cell therapy for the treatment of Chinese melanoma patients", Journal of Hematology & Oncology (2018), Received Jul. 14, 2017 Accepted Dec. 26, 2017, Published online Jan. 3, 2018, pp. 1-15, 11:1.

Zang, C., "A clustering approach for identification of enriched domains from histone modification ChIP-Seq data", Bioinformatics, Received on Mar. 3, 2009, revised on May 7, 2009, accepted on May 27, 2009, Advance Access publication Jun. 8, 2009, pp. 1952-1958, vol. 25, No. 15.

Zhang, Y., et al., "Model-based Analysis of ChIP-Seq (MACS)", Genome Biology 2008, Published Sep. 17, 2008, 9 pages, vol. 9, Issue 9, Article R137.

Zhang, B., et al., "Biodegradable scaold with built-in vasculature for organ-on-a-chip engineering and direct surgical anastomosis", Nature Materials, Jun. 2016, pp. 669-680, vol. 15.

Zhang, Y.S., et al., "Bioprinting the Cancer Microenvironment", ACS Biomater Sci Eng. PMC Feb. 27, 2017, 24 pages.

Zhou, Q., et al., "Pancreas regeneration", Nature, PMC Nov. 16, 2018, 22 pages.

Atkinson, M.A., et al., "Type 1 diabetes", Lancet, Jan. 4, 2014, pp. 69-82, 383(9911).

Augustin, H. G., et al., "Organotypic vasculature: From descriptive heterogeneity to functional pathophysiology", Science, Aug. 25, 2017, 12 pages, 357.

Barry, D. M., et al., "Rasip1-Mediated Rho GTPase Signaling Regulates Blood Vessel Tubulogenesis via Nonmuscle Myosin II", Circulation Research, Original received May 15, 2016; revision received Jul. 29, 2016; accepted Aug. 2, 2016, pp. 810-826, 119.

Baudin, B. et al., "A protocol for isolation and culture of human umbilical vein endothelial cells", Nature Protocols, Published online Mar. 15, 2007, pp. 481-485, vol. 2, No. 3.

Blundell, C. et al., "A microphysiological model of the human placental barrier", Lab Chip, Aug. 2, 2016, pp. 3065-3073, 16(16).

Bonner-Weir, S. et al., "New perspectives on the microvasculature of the islets of Langerhans in the rat", Diabetes, Oct. 1982, pp. 883-889, vol. 31.

Butler, A. et al., "Integrating single-cell transcriptomic data across different conditions, technologies, and species", Nat Biotechnol, Jun. 2018, 33 pages, 36(5).

Campisi, M. et al., "3D self-organized microvascular model of the human blood-brain barrier with endothelial cells, bericytes and astrocytes", Biomaterials, Received Feb. 13, 2018, Received in revised form Jul. 6, 2018, Accepted Jul. 10, 2018, Available online Jul. 12, 2018, pp. 117-129, 180.

Cao, Z., et al., "Molecular Checkpoint Decisions Made by Subverted Vascular Niche Transform Indolent Tumor Cells Into Chemoresistant Cancer Stem Cells", Cancer Cell 31, Jan. 9, 2017, pp. 110-126.

Cao, Z. et al., "Angiocrine factors deployed by tumor vascular niche induce B cell lymphoma invasiveness and chemoresistance", Cancer Cell 25, Mar. 17, 2014, pp. 350-365.

Carmeliet, P., et al., "Principles and mechanisms of vessel normalization for cancer and other angiogenic diseases", Nature Reviews Drug Discovery, Jun. 2011, pp. 417-427, vol. 10.

Carmeliet, P., et al., "Molecular mechanisms and clinical applications of angiogenesis", Nature, May 19, 2011, 28 pages, 473(7347).

Chen, M. B. et al., "On-chip human microvasculature assay for visualization and quantification of tumor cell extravasation dynamics", Nature Protocols 2017, Published online Mar. 30, 2017, pp. 865-880, vol. 12, No. 5.

Chen, C.-C., et al., "Endothelial chimerism and vascular sequestration protect pancreatic islet grafts from antibody-mediated rejection", The Journal of Clinical Investigation, Jan. 2018, Submitted Feb. 23, 2017, Accepted Oct. 12, 2017, pp. 219-232, vol. 128, No. 1.

Choi, K. D., et al. Hematopoietic and endothelial differentiation of human induced pluripotent stem cells, Stem Cells, Mar. 2009, 14 pages, 27(3).

Citro, A., et al., "Biofabrication of a vascularized islet organ for type 1 diabetes", Biomaterials 2019, Received Sep. 26, 2018; Received in revised form Nov. 27, 2018; Accepted Jan. 18, 2019, Available online Jan. 24, 2019, pp. 40-51, 199.

Cohrs, C.M., et al., "Vessel Network Architecture of Adult Human Islets Promotes Distinct Cell-Cell Interactions In Situ and is Altered After Transplantation", Endocrinology, May 2017, Received Mar. 20, 2016, Accepted Jan. 24, 2017, First Published Online Jan. 27, 2017, pp. 1373-1385, 158(5).

Ding, B.S., et al., "Inductive angiocrine signals from sinusoidal endothelium are required for liver regeneration", Nature, Nov. 2010, pp. 310-317, vol. 468.

Ding, B.S., et al., "Endothelial-Derived Angiocrine Signals Induce and Sustain Regenerative Lung Alveolarization", Cell 2011, Oct. 28, 2011, Received May 10, 2011, Revised Aug. 15, 2011, Accepted Oct. 5, 2011, Published Oct. 27, 2011, pp. 539-553, 147(3).

Ding, B.S., et al., "Divergent angiocrine signals from vascular niche balance liver regeneration and fibrosis", Nature, Jan. 2, 2014, Received Apr. 23, 2013, accepted Sep. 16, 2013, Published online Nov. 20, 2013, pp. 97-103, vol. 505.

Dobin, A., et al., "STAR: ultrafast universal RNA-seq aligner", Bioinformatics, Received on May 29, 2012; revised on Oct. 17, 2012; accepted on Oct. 19, 2012, Advance Access publication Oct. 25, 2012, pp. 15-21, vol. 29, No. 1.

Elcheva, I., et al., "Direct Induction of Hemogenic Endothelium and Blood by Overexpression of Transcription Factors In Human Pluripotent Stem Cells", Journal of Visualized Experiments JoVE, Dec. 2015, pp. 1-8, 106, e52910.

Elliott, M. J., et al., "Stem-cell-based, tissue engineered tracheal replacement in a child: a 2-year follow-up study", ancet, Published Online Jul. 26, 2012, pp. 1-7.

Garry, D. J., "Etv2 is a Master Regulator of Hematoendothelial Lineages", Transactions of the American Clinical and Climatological Association, 2016, pp. 212-223, vol. 127.

Ginsberg, M., et al., "Efficient Direct Reprogramming of Mature Amniotic Cells into Endothelial Cells by ETS Factors and TGFb Suppression", Cell, Oct. 26, 2012, pp. 559-575, 151(3).

Ginsberg, M., et al., "Direct conversion of human amniotic cells into endothelial cells without transitioning through a pluripotent state", Nat Protoc. 2015, Dec. 2015, pp. 1975-1985, 10(12).

Goel, S., et al., "Normalization of the vasculature for treatment of cancer and other diseases", Physiol Rev., Jul. 2011, pp. 1071-1121, 91(3).

Grapensparr, L., et al., "Bioengineering with Endothelial Progenitor Cells Improves the Vascular Engraftment of Transplanted Human Islets", Cell transplantation, 2018, Submitted Nov. 15, 2017, Revised Jan. 18, 2018, Accepted Jan. 22, 2018, pp. 948-956, 27(6).

(56) References Cited

OTHER PUBLICATIONS

Han, J. K., et al., "Direct conversion of adult skin fibroblasts to endothelial cells by defined factors", Circulation, Sep. 30, 2014, pp. 1168-1178, 130.

Hebrok, M., et al., "Generating beta Cells from Stem Cells—The Story So Far", Cold Spring Harbor Perspectives in Medicine, 2012, pp. 1-12, 2:a007674.

Heinz, S., et al., "Simple Combinations of Lineage-Determining Transcription Factors Prime cis-Regulatory Elements Required for Macrophage and B Cell Identities", Molecular Cell, May 28, 2010, pp. 576-589, 38.

Helgason, C.D., et al., "Basic Cell Culture Protocols", Third Edition, Methods in Molecular Biology, vol. 290, Human Press Publishing, 2005, pp. 1-364.

Huang, D.W., et al., "Systematic and integrative analysis of large gene lists using DAVID bioinformatics resources", Nature Protocols 2009, Published online Dec. 18, 2008, pp. 44-57, vol. 4, No. 1.

Huh, D., et al., "Reconstituting organ-level lung functions on a chip", Science, Jun. 25, 2010, pp. 1662-1668, vol. 328.

Huh, D., "From 3D cell culture to organs-on-chips", Trends Cell Biol., Dec. 2011, pp. 745-754, 21(12).

Kabir, A.U., et al., "Requisite endothelial reactivation and effective siRNA nanoparticle targeting of Etv2/Er71 in tumor angiogenesis", JCI Insight, Submitted Sep. 6, 2017, Accepted Mar. 20, 2018, Published Apr. 19, 2018, pp. 1-19, 3(8):e97349.

Kao, D.-I., et al., "Endothelial Cells Control Pancreatic Cell Fate at Defined Stages through EGFL7 Signaling", Stem Cell Reports, Feb. 10, 2015, pp. 181-189, vol. 4.

Kataoka, H., et al., "Etv2/ER71 induces vascular mesoderm from Flk1+PDGFRalpha+ primitive mesoderm", Blood, Dec. 22, 2011, pp. 6975-6986, vol. 118, No. 26.

Khademhosseini, A., et al., "A decade of progress in tissue engineering", Nature Protocols 2016, Received May 3, accepted June 8, published online Sep. 1, 2016, pp. 1775-1781, vol. 11, No. 10.

Kim, S., et al., "Engineering of functional, perfusable 3D microvascular networks on a chip", Lab Chip 2013, Received Nov. 29, 2012, Accepted Jan. 16, 2013, pp. 1489-1500, 13.

Kobayashi, H., et al., "Angiocrine factors from Akt-activated endothelial cells balance self-renewal and differentiation of haematopoietic stem cells", Nat Cell Biol, Nov. 2010, pp. 1046-1056, 12(11).

Kobayashi, K., Ding, G., Nishikawa, S. & Kataoka, H. Role of Etv2-positive cells in the remodeling morphogenesis during vascular development. Genes Cells 18, 704-721, doi:10.1111/gtc.12070 (2013).

Koyano-Nakagawa, N., et al., "Etv2 as an essential regulator of mesodermal lineage development", Cardiovascular Research (2017), Received Mar. 9, 2017; revised May 19, 2017; editorial decision Jun. 2, 2017; accepted Jul. 24, 2017; online publish-ahead-of-print Jul. 26, 2017, pp. 1294-1306, 113.

Ammert, E., Cleaver, O. & Melton, D. Induction of pancreatic differentiation by signals from blood vessels Science, Oct. 19, 2001, pp. 564-567, vol. 294.

Lammert, E., et al., "Role of endothelial cells in early pancreas and liver development", Mechanisms and Development (2003), pp. 59-64, 120.

Lancaster, M. A., et al., "Organogenesis in a dish: modeling development and disease using organoid technologies", Science, Jul. 18, 2014, 11 pages, vol. 345, Issue 6194.

Lee, D., et al., "ER71 acts downstream of BMP, Notch, and Wnt signaling in blood and vessel progenitor specification", Cell Stem Cell, May 2008, pp. 497-507, 2.

Lee, S., et al. "Direct Reprogramming of Human Dermal Fibroblasts Into Endothelial Cells Using ER71/ETV2", Circulation Research, Mar. 3, 2017, Original received Aug. 25, 2016; revision received Dec. 15, 2016; accepted Dec. 21, 2016, pp. 848-861.

Li, B., et al., "The role of chromatin during transcription", Cell, Feb. 23, 2007, pp. 707-719, 128.

Li, H., et al., "Fast and accurate short read alignment with Burrows-Wheeler transform", Bioinformatics, Received on Feb. 20, 2009, revised on May 6, 2009, accepted on May 12, 2009, Advance Access publication May 18, 2009, pp. 1754-1760, vol. 25, No. 14.

* cited by examiner

C
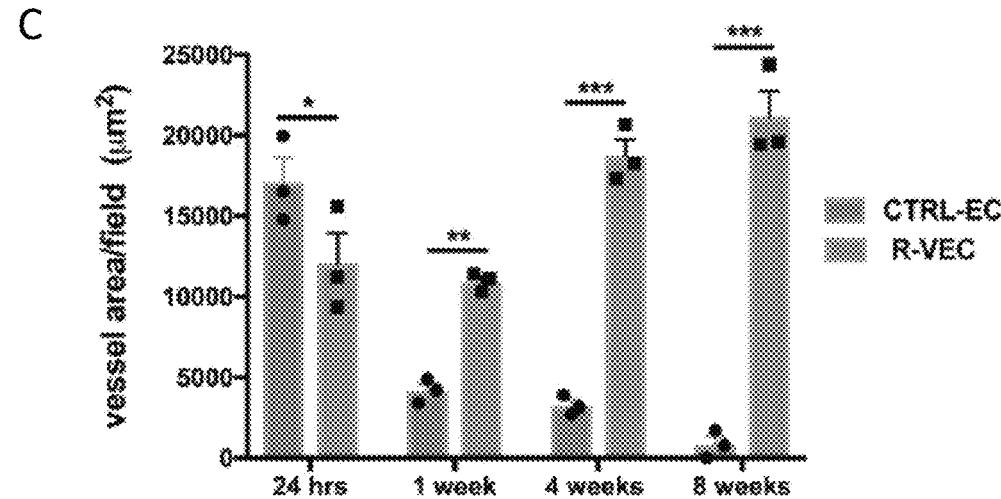
D
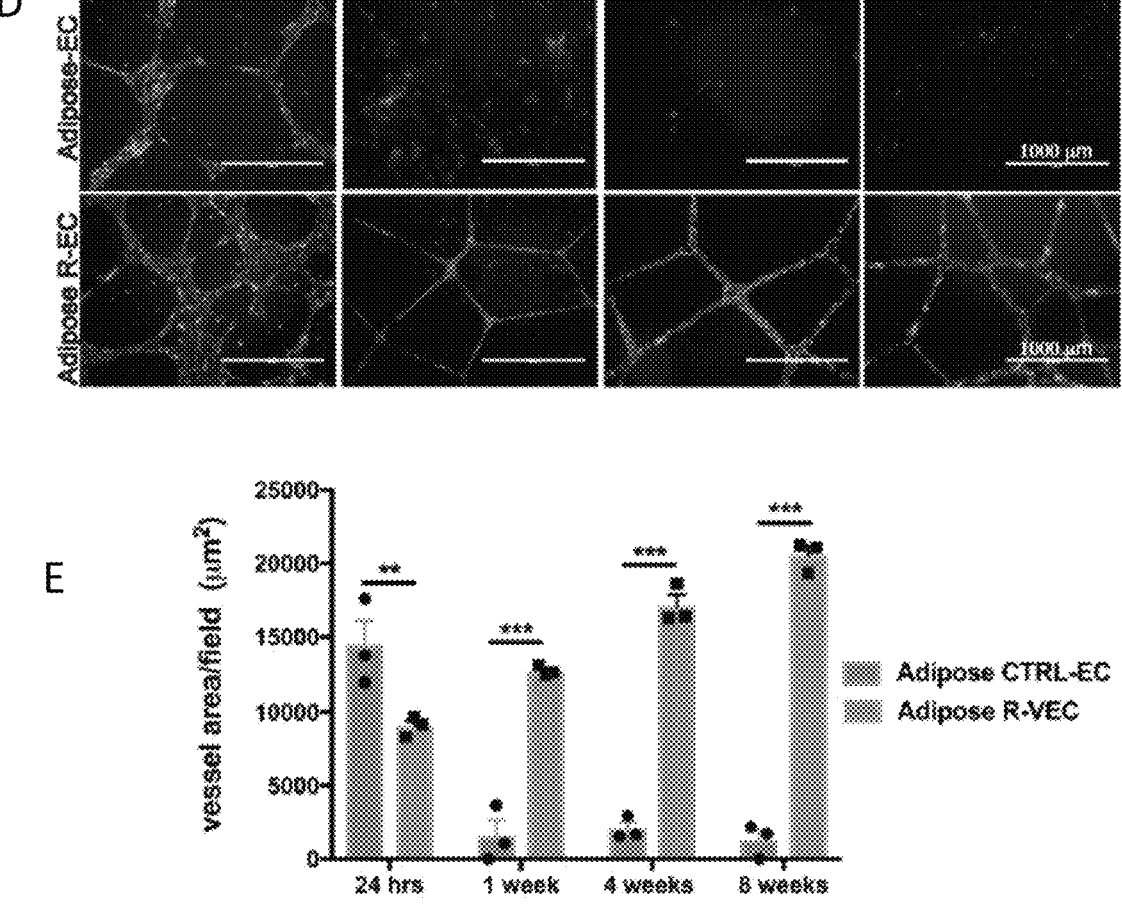
FIG. 1C-1E

F

G     Laminin/Podocalyxin/DAPI

H

I

J

K
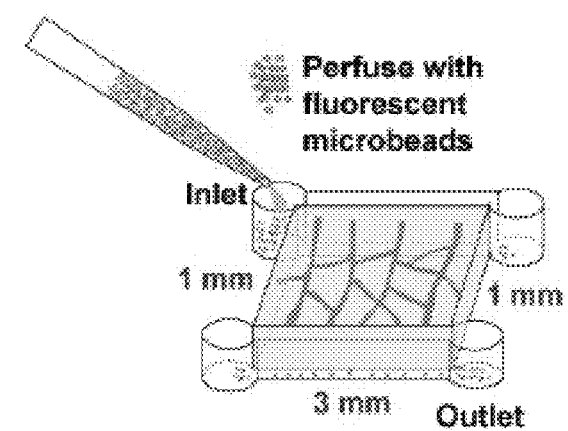
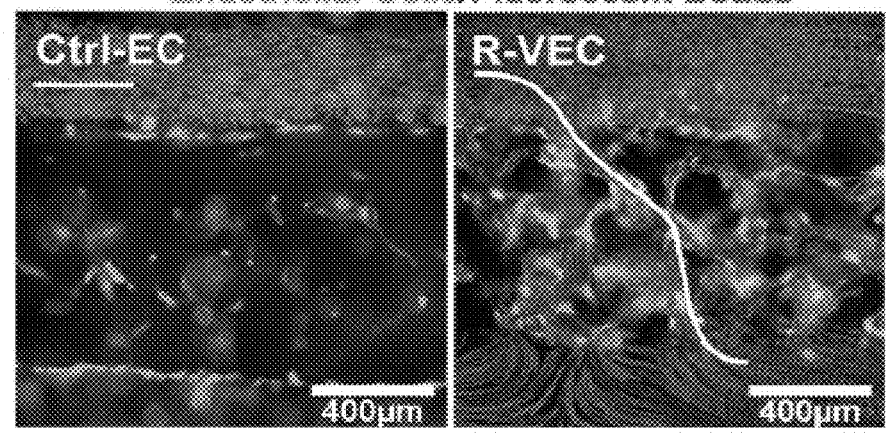
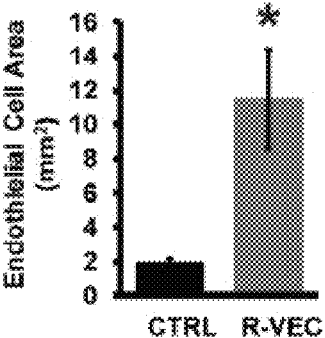
FIG. 1K-1L

L

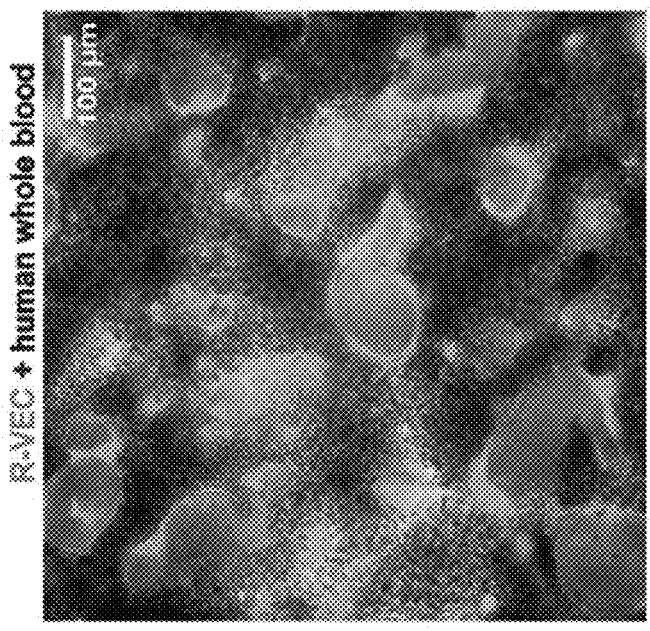
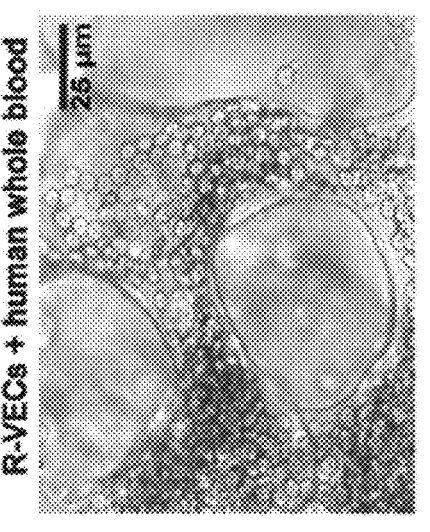
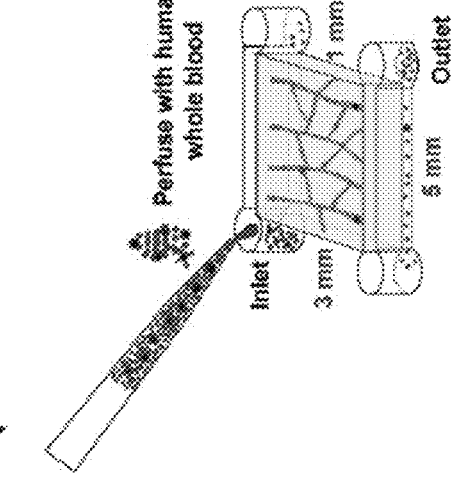
FIG. 1M

A

Laminin/Entactin/CollagenIV
+ single cell suspension
CTRL or R-VECs (Stage 1- Induction)

B

D

E

G

H

A

D
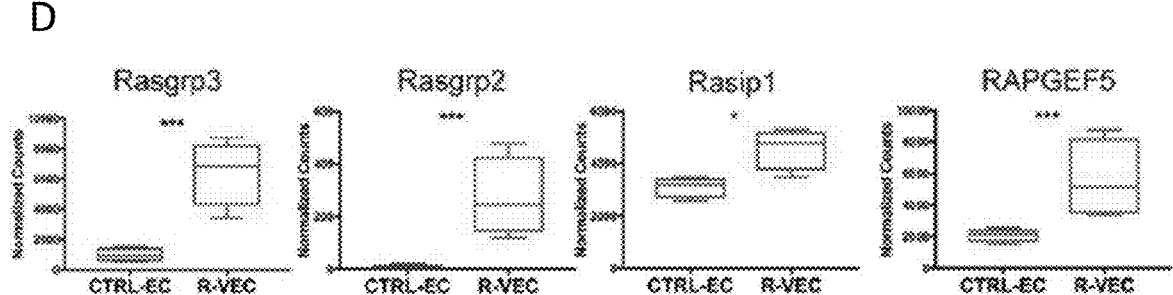
E
F
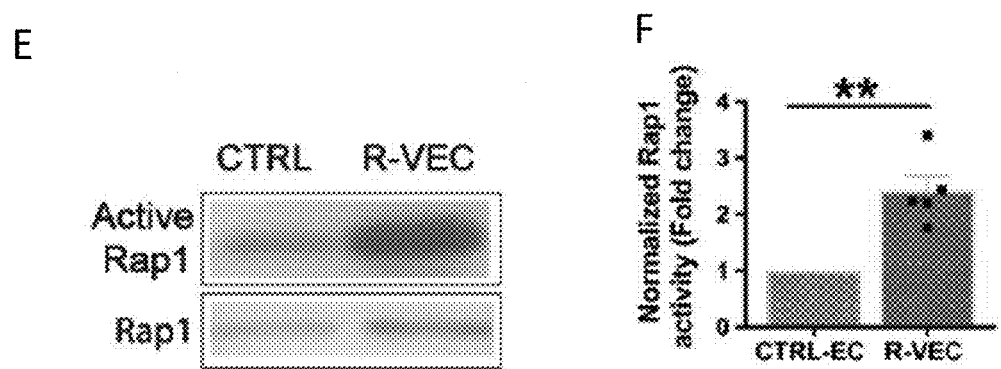
G
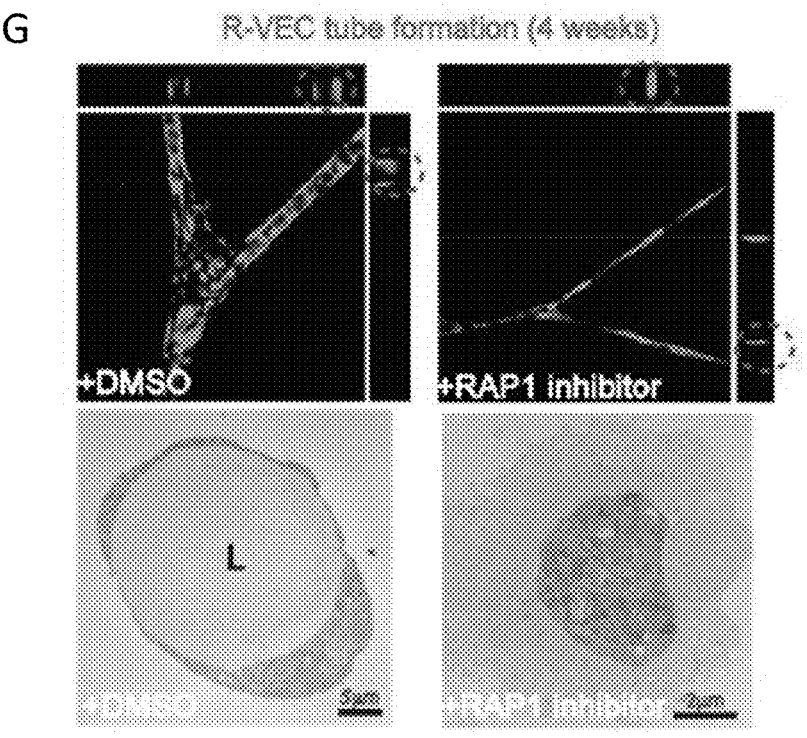
R-VEC tube formation (4 weeks)
FIG. 3D-3G

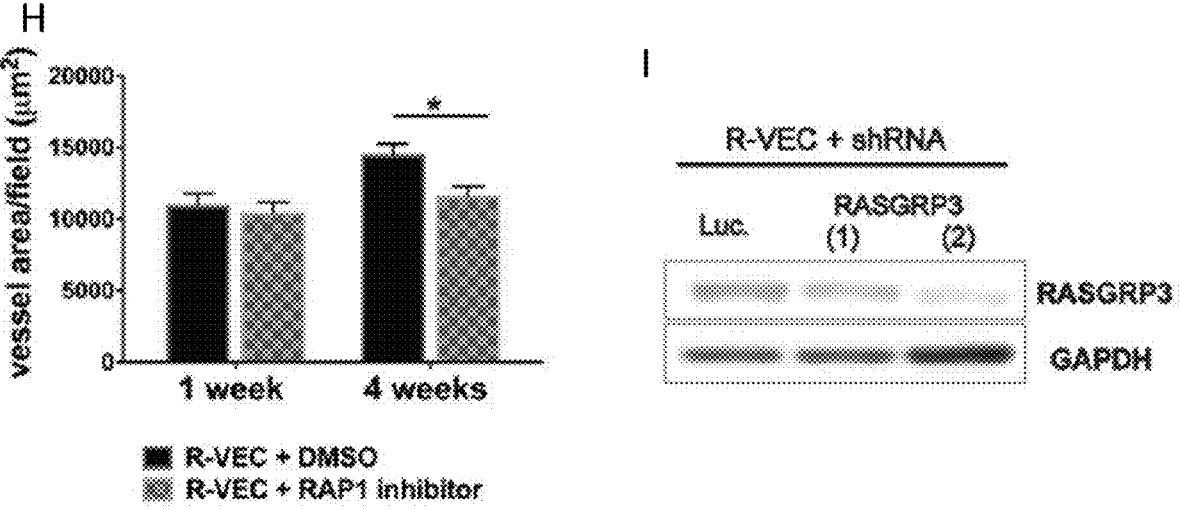
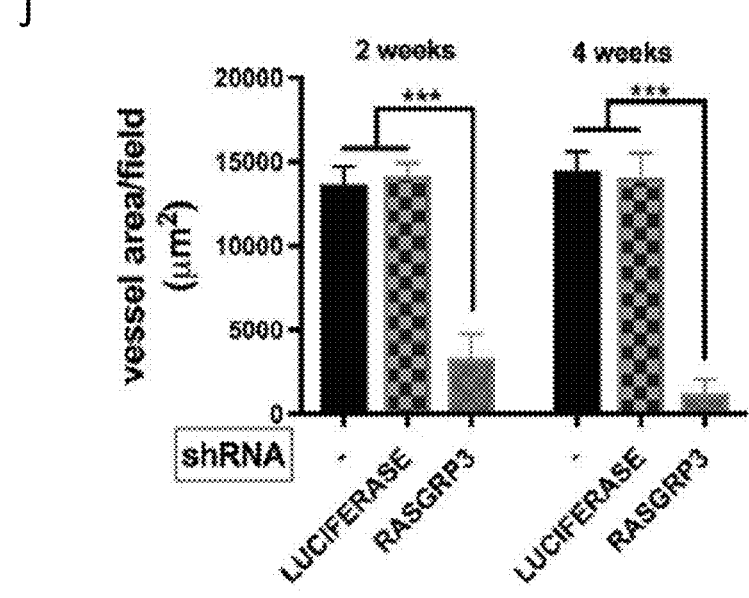
FIG. 3H-3J

K

A

B

C

D

K
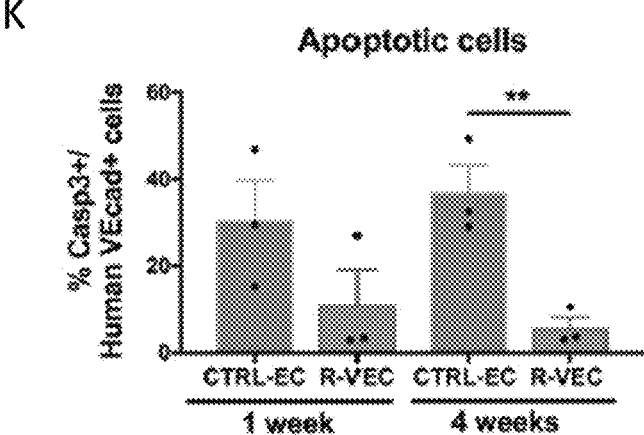
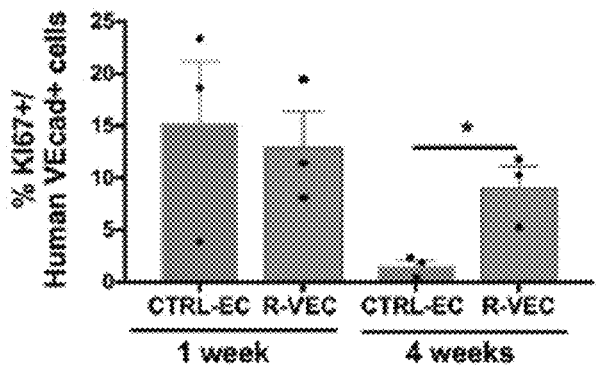
FIG. 4K

A
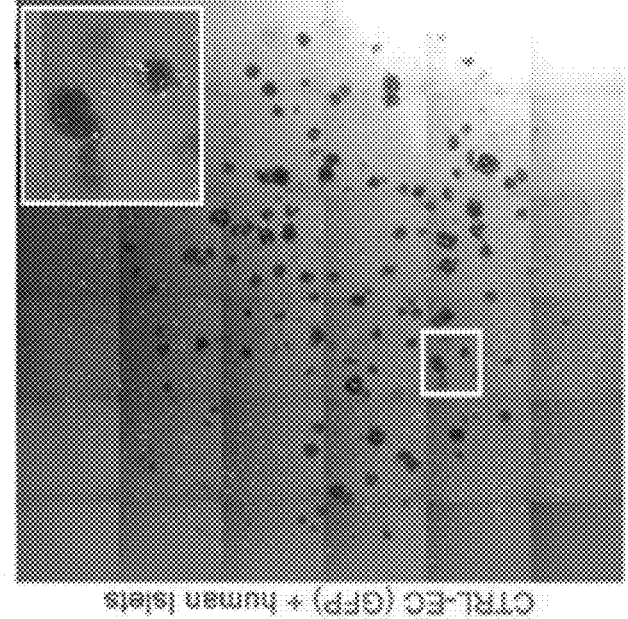
CTRL-EC (GFP) + human Islets
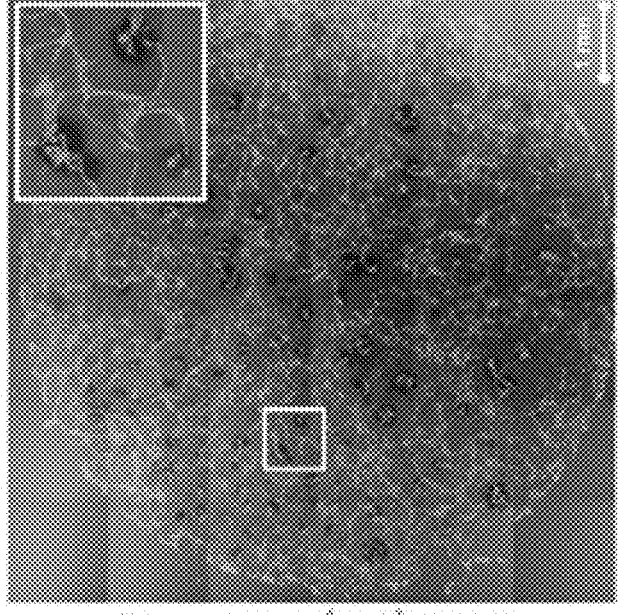
R-VEC (GFP) + human Islets
FIG. 5A

F

I
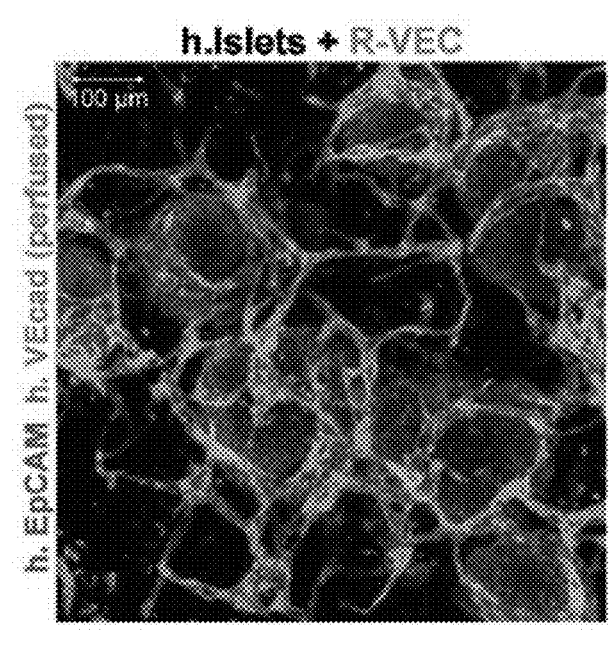
J
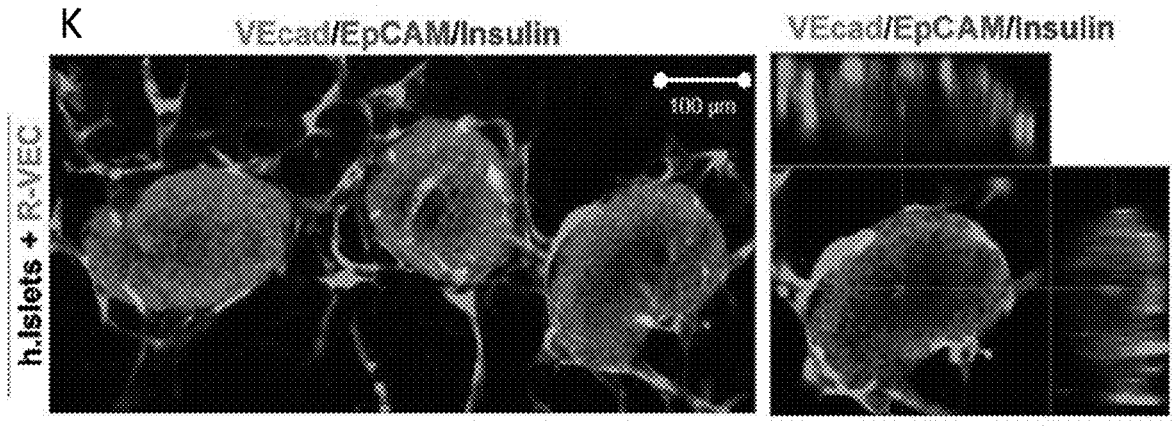
FIG. 5I-5K

L

M

C

D

E

F

G

Colon + CTRL-EC
Colon + R-VEC

H

J

A
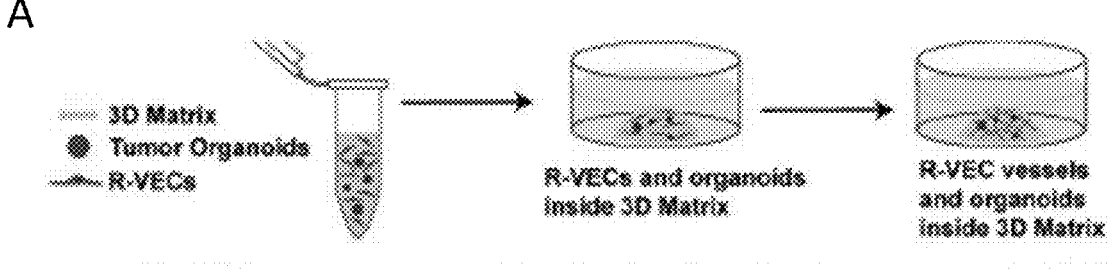
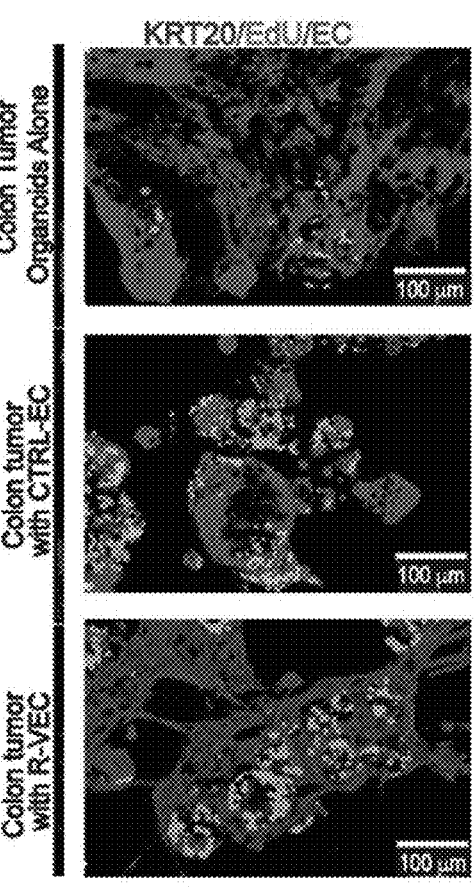
FIG. 7A

H

I

B
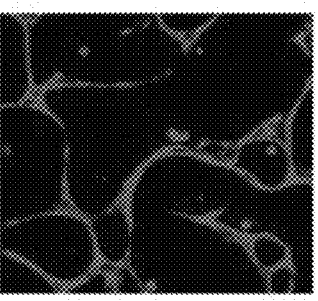 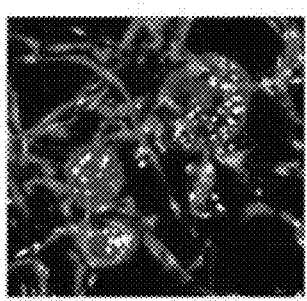
R-VEC alone
R-VEC+ Normal Colon
(EC fraction)
Merged EC fraction
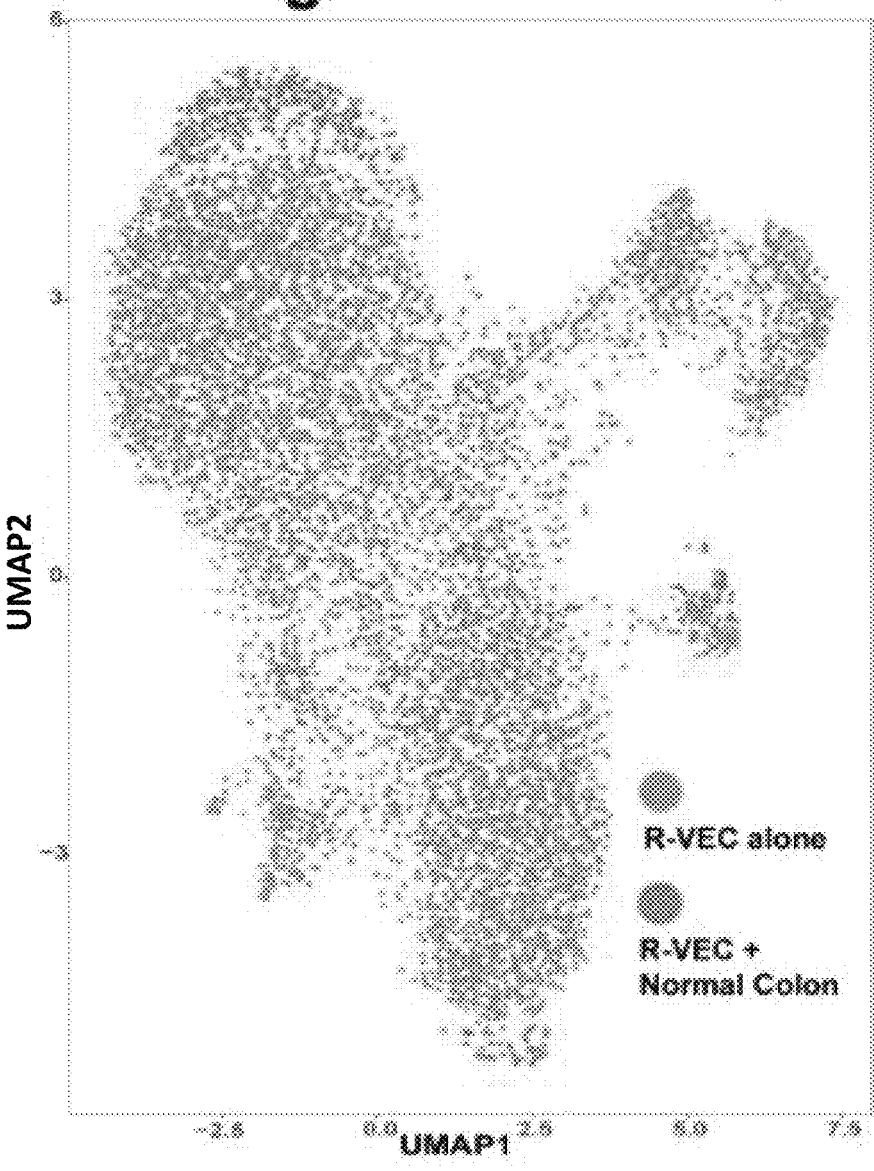
FIG. 8B

D

F
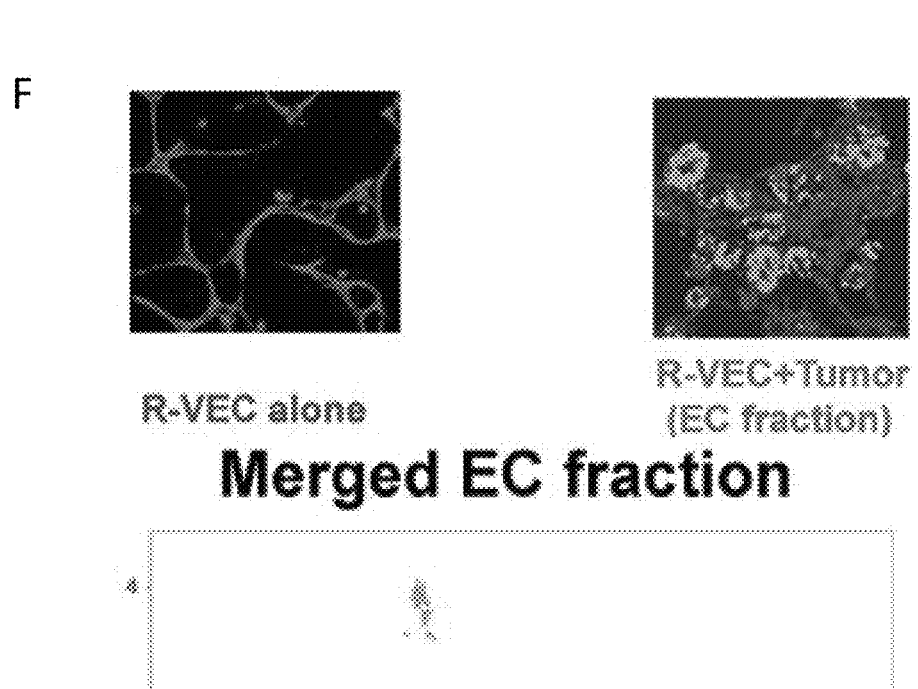
Merged EC fraction
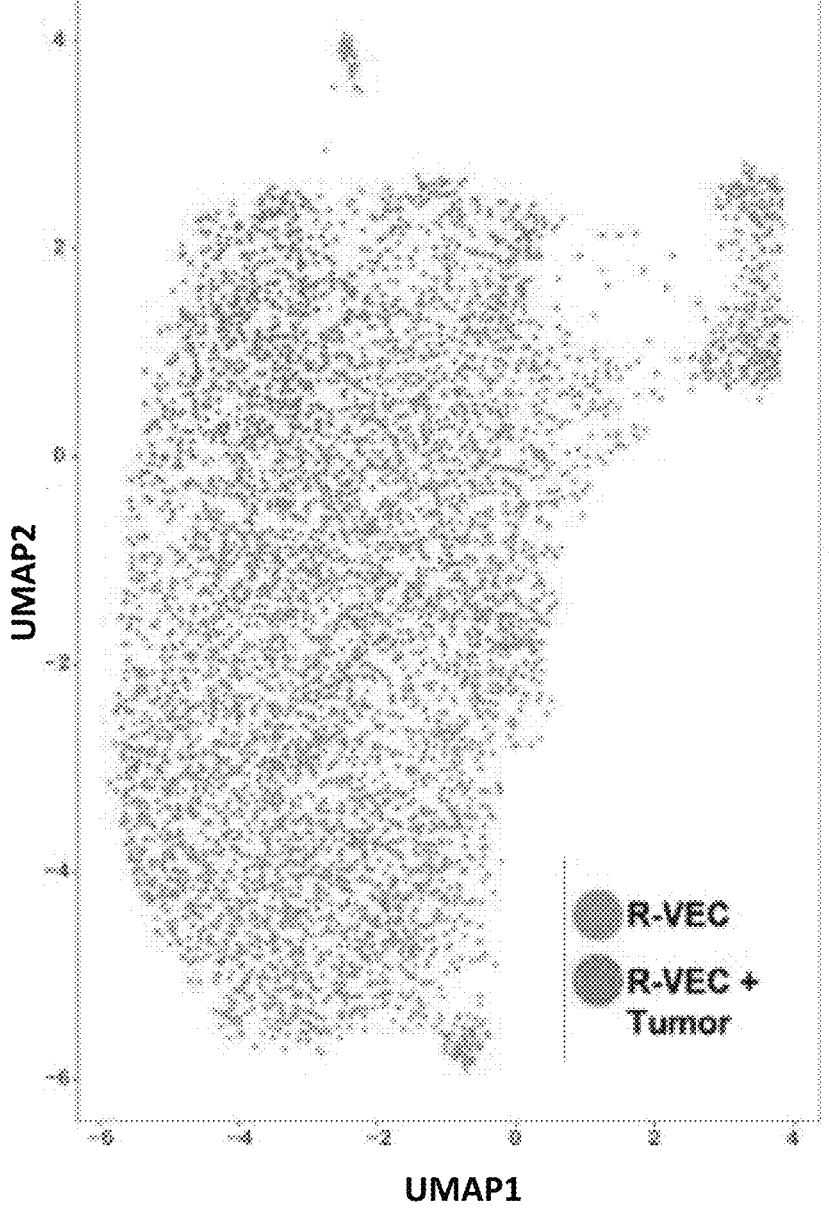
FIG. 8F

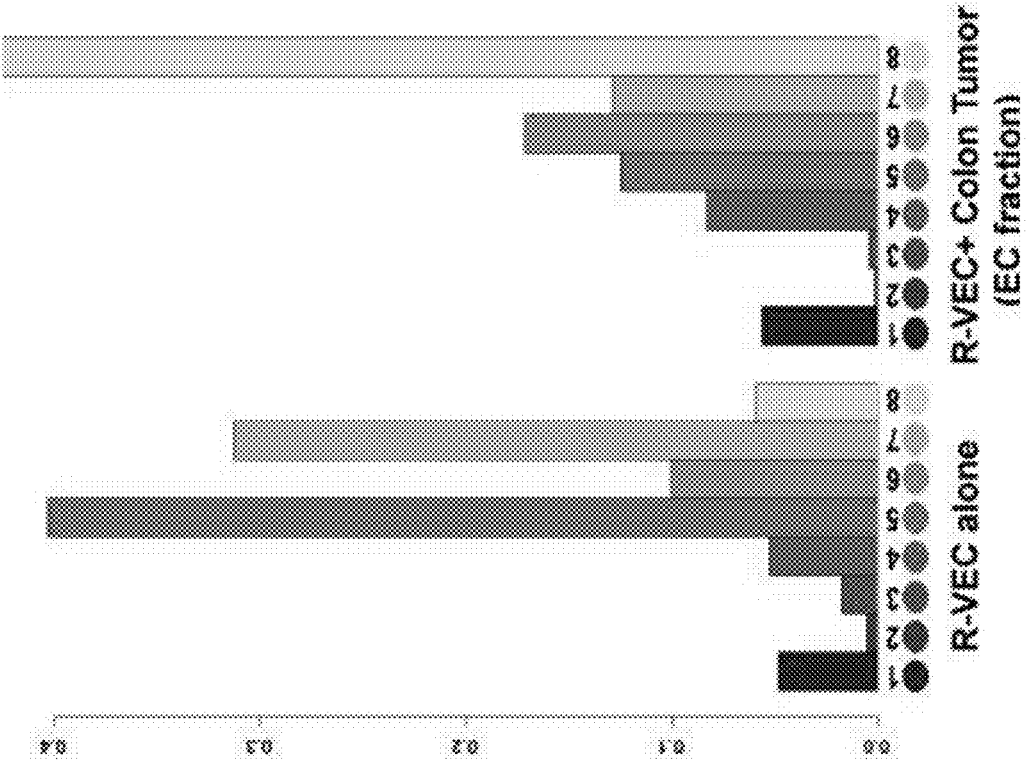
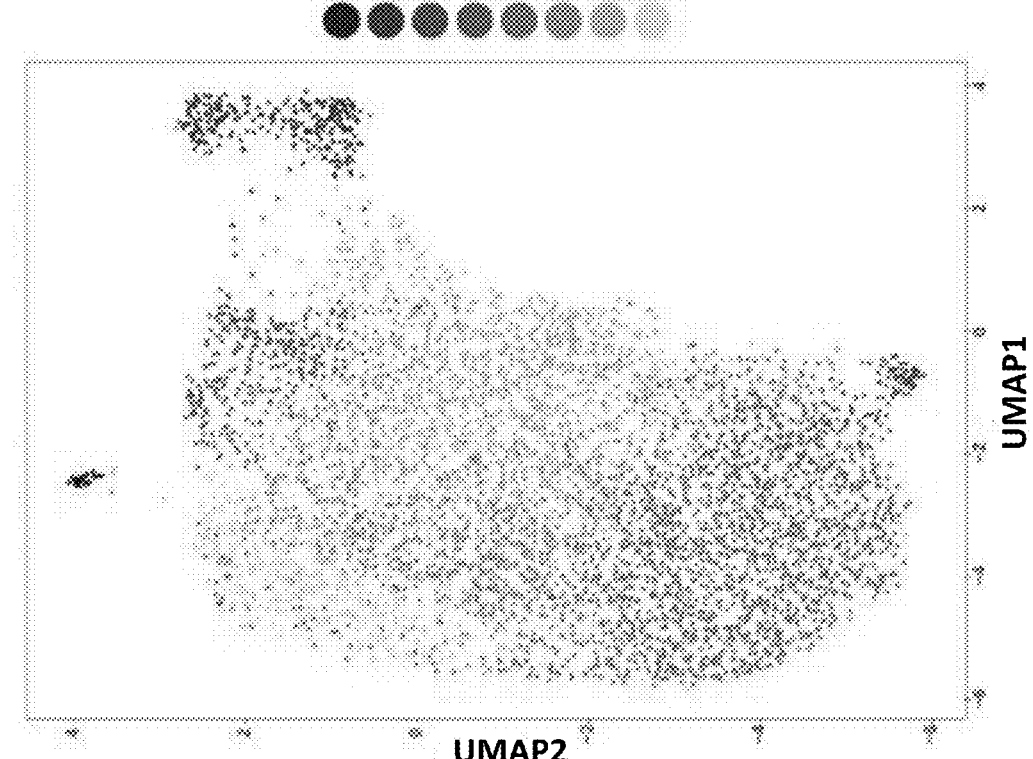
FIG. 8G

A

B

C

METHODS OF FUNCTIONAL VASCULARIZATION OF PANCREATIC ISLETS AND BETA-CELL ORGANOIDS

CROSS REFERENCE TO RELATED APPLICATION

This application claims the benefit of priority from U.S. Provisional Application No. 62/870,288, filed Jul. 3, 2019, the entire contents of which are incorporated herein by reference.

INCORPORATION BY REFERENCE OF SEQUENCE LISTING

The Sequence Listing in the ASCII text file, named as 37494_8830_03 U.S. Sequence_Listing.txt of 16 KB, created on Dec. 28, 2021, and submitted to the United States Patent and Trademark Office via EFS-Web, is incorporated herein by reference.

BACKGROUND

The incidence of diabetes is increasing at the alarming rate of 2 to 5% every year. As of 2017, 9.3% of the U.S. population is afflicted with diabetes, with major morbidity and mortality associated with microvascular diabetic complications, including skin ulcers, retinopathy, nephropathy, cardio- and cerebro-vascular diseases. Type 1 diabetes is one of the two major types of diabetes, and often develop in childhood with 70,000 new cases annually. Without a cure, type 1 diabetes is life-long burden to the patients and their families. Although islet transplantation is promising in achieving normoglycemia, its application is hampered by the difficulty in harvesting functional intact vascularized non-necrotic islets. Furthermore, over a 3-year period of those patients that are engrafted with allogeneic islet cells and achieve full glycemic control, on average 50% fail to sustain normoglycemia. This islet graft failure is not only due to immune rejection, but also it is believed that islets malfunction because of as yet unrecognized poor quality, possibly due to the loss of the intra-islet capillaries.

The mainstay treatment for type I diabetes in which the insulin producing β-cells are injured, is allogeneic islet transplant. However, the current approaches to isolate sufficient islets for transplanting into a single individual, requires procuring islets from two or more donors. These islets often do not engraft failing to provide long-lasting normoglycemia. This bottleneck is due to the long lag-time and harsh culture conditions necessary for isolating islets, which often lead to necrosis and loss of the intra-islet vascular endothelial cells (ECs). Indeed, islet-specific ECs that form a unique niche are not only essential for rapid revascularization of the islets, but also for the proper functioning and immune homeostasis of the β-cells. Notably, Islet-specific ECs by supplying key angiocrine paracrine factors, such as Eglf7 and Notch-ligands among others; choreograph the survival and function of β-cells. Direct cellular interaction between β-cells and islet-specific ECs is essential for immune surveillance and physiological insulin secretion. Because of technical challenges in preparing islets, there is regression of the capillaries within the donor-derived islets resulting in loss of β-cells. In addition, after portal vein Islet transplantation into patients, the majority of islets fail to rapidly anastomose to the host vasculature and die from hypoxic cell death.

Current approaches for islet cell transplantation are inefficient because donor-derived islets fail to sustain viability and functionality before transplantation into the patients, and undergo islet cell necrosis. In addition, upon portal vein transplantation into the liver those surviving islets fail to anastomose to their remaining intra-islet capillaries leading to graft failure. Thus, approaches to sustain the viability of donor-derived islets before and after transplantation are essential for durable islet engraftment.

Notably, the existing protocols for procuring donor-derived islets for transplantation lack technical sophistication to keep the islets intact for more effective engraftment. Typically a patient receives at least 10,000 islet "equivalents" per kilogram of body weight, extracted from at least two donors. The islets are infused though portal vein and lodge in the liver's microcirculation engrafting within the portal vasculature. On average, after harvesting islets from deceased donors, it may take additional 3 to 4 days for characterization and delivery of islets for portal vein infusion into the patients. Because of this prolonged time lapse, few of the native intra-islet endothelial cells survived at the time of transplantation. Thus, restoration of signals from the vascular niche cells, within the islets will rescue the proper engraftment, differentiation and insulin production by the donor-derived islet. Therefore, vascular arborization of the harvested fragile donor islets with the recipient ECs that can rebuild islet's vascular network, will increase survival, functionality and engraftability of these islets and potentially also minimize immune rejection.

Indeed, pancreas is richly arborized by specialized islet-specific ECs that are required for proper islet function. Importantly, blood vessels are not just passive conduits for delivery of oxygen and nutrients, but are active participants in organ function. Tissue-specific ECs within each organ, including intra-islet capillaries, compose of unique professional ECs that are delegated with the herculean task of supporting organ homeostasis. Notably, the inventors have pioneered the transformative concept that tissue-specific ECs produce paracrine mediators and trophogens, known as "Angiocrine Factors" that induce tissue regeneration and normal function. For example, deposition of laminin by the intra-islet ECs contributes to the proper glucose-mediated insulin secretion. Notably, the inventors have shown that intra-islet ECs by supplying the angiocrine factor Egfl7 by modulating Notch signaling, promotes maturation of β-cells.

Embryonic organogenesis and adult tissue regeneration are dependent on vascularization with durable and instructive blood vessels. Proper functioning of the endothelial cells (ECs) within capillaries is not only critical for sustaining tissue-specific homeostasis, but also for supplying paracrine factors to guide proper pattering and morphogenesis of the developing and adult regenerative organs. In contrast, the dysfunction of the vascular niche contributes to fibrosis and the progression and therapeutic resistance of tumors. However, the mechanism by which adult ECs acquire adaptive tissue-specific paracrine heterogeneity or undergo aberrant maladaptation within tumor microenvironment is not known and requires the development of malleable ECs to uncover the remarkable plasticity of the ECs. In addition, in vitro generation of hemodynamically stable and malleable vascular networks is also important to functionalize decellularized scaffolds, tissue-specific organ-on-chip and tumor organoid cultures, as well as ex vivo tissues, such as highly vascularized pancreatic islets.

Attempts to induce the formation of new blood vessels to instruct the repair of injured adult organs have confronted with hurdles. Injection of angiogenic factors, (including FGF-2 and VEGF-A isoforms), into damaged organs, have not been effective in establishing durable capillaries. Approaches to microfabricate stable human blood vessels in vitro require the implementation of challenging and costly technical interventions, including pre-fabrication of scaffolds that limit the cellular freedom of ECs to interact and adapt to non-vascular cells. In addition, the use of clinically incompatible synthetic extracellular matrix components, such as Matrigel, limit the remodeling and patterning of putative capillary networks in normal and tumorigenic organoid cultures.

While technologies to generate decellularized scaffolds organ-on-chip models and three dimensional bioprinting, have vastly improved disease modeling and drug screening, the incorporation of physiologically relevant adaptive vascular cells into these regenerative modules has lagged behind. Specifically, in these approaches, direct endothelial cellular interaction with tissue-specific epithelial and tumor cells is restricted due to physical constraints introduced by synthetic biomaterials. Furthermore, ECs plated within the space-restricted scaffolds of a total volume of approximately 2 microliters and restrictive biomaterial interfaces do not have the liberty to interact with parenchymal cells and undergo remodeling and adapt to the normal epithelial or tumor cells. In other cases, such as type 1 diabetes which involves active interaction between hematopoietic cells and R cells across the endothelial cells, perfusable vasculature with hematopoietic and immune cells will be essential to facilitate in vitro disease modeling. Therefore, new approaches to generate tissue-specific instructive malleable ECs that can arborize decellularized scaffolds, organoids or tumoroids, tissue explants, such as pancreatic islets, will improve translation to the clinical setting for promoting organ regeneration, drug screening, and tumor targeting, as well as uncovering the molecular determinants of paracrine vascular heterogeneity.

ETV2 is expressed in ECs during the nascent phases of vasculogenesis and is immediately turned off mid-gestation when the vascular networks are established within each organ. ETV2 is not expressed in the adult ECs except during angiogenic or tumor growth, when it is induced in a subset of the perinatal or stressed adult ECs. The inventors' group and others, have shown that transient re-introduction of ETV2 in the non-vascular cells is sufficient to establish a stable EC fate. In addition, as ETV2 null mice do not develop blood or a vascular system, it is plausible ETV2 functions as the key factor determining vascular cell specification, morphogenesis and plasticity.

SUMMARY OF THE DISCLOSURE

The methods of the present disclosure allow for generation of a specialized intra-islet-specific vascular niche that is essential for the functional in vitro sustenance of β-cells within the donor-derived purified islets (or β-cell organoids) and long-term engraftment of these islets (or organoids) in the recipient after transplantation to cure diabetes thereby preventing the long-term microvascular complications associated with diabetes. Revascularization of the purified donor-derived pancreatic islets (or β-cell organoids) with reprogrammed autologous (i.e., harvested from the patient) or genetically-matched allogeneic (i.e., harvested from a genetically-matched individual) endothelial cells (ECs) increases the integrity and functionality of the donor-derived islets, and augments the engraftment and immune integrity of the transplanted islets/organoids.

An aspect of the disclosure is directed to a method for vascularizing a pancreatic islet comprising coculturing a pancreatic islet comprising 3 cells with an endothelial cell which comprises an exogenous nucleic acid encoding an ETV2 transcription factor, wherein the ETV2 transcription factor is expressed in the endothelial cell, thereby generating a vascularized pancreatic islet.

In some embodiments, the endothelial cell further comprises an exogenous nucleic acid encoding a Sox17 transcription factor, and wherein the Sox17 is expressed in the endothelial cell.

In some embodiments, the coculturing is performed for at least 3-4 weeks.

In some embodiments, the pancreatic islet and the endothelial cell are cocultured for an additional period of time, wherein the further coculturing occurs under conditions wherein the endothelial cell does not express the ETV2 transcription factor.

In some embodiments, the further coculturing is performed for at least one week.

In some embodiments, the endothelial cell comprises a human umbilical vein endothelial cell (HUVEC), an adipose-derived endothelial cell, or an organ-specific endothelial cell.

In some embodiments, the organ-specific endothelial cell is selected from the group consisting of a heart-specific endothelial cell, a muscle-specific endothelial cell, a kidney-specific endothelial cell, a testis-specific endothelial cell, an ovary-specific endothelial cell, a lymphoid-specific endothelial cell, a liver-specific endothelial cell, a pancreas-specific endothelial cell, a brain-specific endothelial cell, a lung-specific endothelial cell, a bone marrow-specific endothelial cell, a spleen-specific endothelial cell, a large intestine-specific endothelial cell, and a small intestine-specific endothelial cell.

In some embodiments, the coculturing comprises culturing in media comprising basic FGF (FGF-2) and heparin.

In some embodiments, the coculturing is performed in a bioreactor or a microfluidic device.

In some embodiments, the coculturing is performed on an extracellular matrix comprising a laminin and entactin mixture of between about 10 and about 12 mg/ml final combined concentration and collagen IV of between about 0.2 and about 0.5 mg/ml.

In some embodiments, the vascularization comprises the formation of an artery, a vein, a capillary, an arteriole, a venule, lymphatic vessels, or a combination thereof.

Another aspect of the disclosure is directed to a vascularized pancreatic islet obtained according to the methods of the instant disclosure.

Another aspect of the disclosure is directed to a method comprising administering the vascularized pancreatic islet obtained according to the methods of the instant disclosure to a subject in need. In some embodiments, the pancreatic islet is autologous to the subject. In some embodiments, the pancreatic islet is allogeneic to the subject; in some embodiments, an allogeneic pancreatic islet is genetically matched to the subject. In some embodiments, the islet is administered to the subject by surgical or catheter implantation or infused through an intravascular route. In some embodiments, the islet is administered to the subject subcutaneously or through intravascular infusion.

Another aspect of the disclosure is directed to a method for making a vascularized β-cell organoid, comprising coculturing β-cells with an endothelial cell comprising an exogenous nucleic acid encoding an ETV2 transcription factor under conditions wherein the adult endothelial cell expresses the ETV2 transcription factor.

In some embodiments, the endothelial cell further comprises an exogenous nucleic acid encoding a Sox17 transcription factor.

In some embodiments, the coculturing comprises culturing in media comprising basic FGF (FGF-2) and heparin.

In some embodiments, the coculturing is performed for at least 3-4 weeks.

In some embodiments, the method further comprises coculturing β-cells and the endothelial cell for an additional period of time, wherein the further coculturing is performed under conditions wherein the endothelial cell does not express the ETV2 transcription factor. In some embodiments, the further coculturing is performed for at least one week.

In some embodiments, endothelial cell comprises a human umbilical vein endothelial cell (HUVEC), an adipose-derived endothelial cell or an organ-specific endothelial cell. In some embodiments, the organ-specific endothelial cell is selected from the group consisting of a heart-specific endothelial cell, a muscle-specific endothelial cell, a kidney-specific endothelial cell, a testis-specific endothelial cell, an ovary-specific endothelial cell, a lymphoid-specific endothelial cell, a liver-specific endothelial cell, a pancreas-specific endothelial cell, a brain-specific endothelial cell, a lung-specific endothelial cell, a bone marrow-specific endothelial cell, a spleen-specific endothelial cell, a large intestine-specific endothelial cell, and a small intestine-specific endothelial cell.

In some embodiments, the coculturing is carried out on an extracellular matrix comprising a laminin and entactin mixture of between about 10 and about 12 mg/ml final combined concentration and collagen IV of between about 0.2 and about 0.5 mg/ml.

In some embodiments, the coculturing is performed in a bioreactor or a microfluidic device.

In some embodiments, the vascularization comprises the formation of an artery, a vein, a capillary, an arteriole, a venule or lymphatic vessels or a combination thereof.

Another aspect of the disclosure is directed to a vascularized β-cell organoid obtained according to the methods of this disclosure.

Another aspect of the disclosure is directed to a method, comprising administering the vascularized β-cell organoid obtained according to the methods of this disclosure to a subject in need. In some embodiments, the vascularized β-cell organoid is administered to the subject by surgical or catheter implantation or infused through an intravascular route. In some embodiments, the vascularized β-cell organoid islet is administered to the subject subcutaneously.

In some embodiments, the β-cells used in the instant methods comprise cells selected from the group consisting of (1) β-cells derived from Embryonic Pluripotent Stem Cells (ESC), (2) β-cells derived from induced Pluripotent Cells (iPS), (3) β-cells derived from direct transcriptional conversion of fibroblasts, and (4) β-cells isolated from the adult subjects.

In some embodiments, the β-cells are autologous to the subject. In some embodiments, the β-cells are allogeneic to the subject; in some embodiments, allogeneic β-cells are genetically matched to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1M. R-VECs self-assemble into three dimensional, durable, lumenized and hemodynamically stable perfusable vessels in vitro. (A) Overview of experimental set up for vessels on Matrigel and in microfluidic devices. (B) Representative images of a time course of tube formation from 24 hours to 8 weeks for CTRL-EC and R-VEC. 100,000 GFP labeled control-EC (CTRL-EC) or ETV2 Reset-Vascular Endothelial Cells (R-VECs) were plated on Matrigel in Stem Span+Knock out serum+cytokines and monitored over time. (C) Quantification of vessel area for CTRL-EC and R-VEC at various time points through 8 weeks of culture on Matrigel. Two-way ANOVA with Sidak's post-test (n=3 independent HUVEC lines, 24 hrs p=0.0234, 1 week p<0.0024, 4 weeks p<0.0001, 8 weeks p<0.0001). (D) Representative images of a time course of tube formation from 24 hours to 8 weeks for Adipose CTRL-EC and Adipose R-VEC on Matrigel. (E) Quantification of vessel area for Adipose CTRL-EC and Adipose R-VEC through 8 weeks of culture on Matrigel. Two-way ANOVA with Sidak's post-test (n=3 independent adipose lines, 24 hrs p=0.0015, 1 week, 4 weeks, 8 weeks p<0.0001). (F) Representative image of R-VEC vessels at week 16. Z-stack image was acquired with a tile-scan mode to show the presence of a stable and organized vessel plexus over a whole culture within a well of 24 well plate. (G) Immunostaining of R-VEC-tubes displayed proper polarity with podocalyxin inside the lumen (apical side, in red) and laminin outside the vessel (basal side, in green). (H) Quantification of R-VEC vessel formation on Matrigel and defined laminin, entactin, collagenIV (L.E.C.) matrix over 8 weeks. R-VEC formed robust and stable vessels similarly in both Matrigel and L.E.C. Two-way ANOVA with Sidak's post-test (n=3 independent experiments, 24 hrs p=0.9504, 1 week p=0.8226, 4 weeks p=0.7778, 8 weeks p=0.9659). i) A lumen is present in R-VEC vessels at stage 3 formed in both Matrigel and L.E.C. as shown by electron microscopy. (J) A schematic depicting the experimental set up in a microfluidic device. CTRL-EC and R-VEC (in green) were seeded in a fibrin gel in a microfluidic device. Devices ranged in size from 3×1×1 milimeter$^3$ (volume 3 microliters) to 5×3×1 millimeter$^3$ (volume 15 microliters). (K) Red fluorescent beads (4 μm) were injected into the microfluidic devices (3×1×1 milimeter$^3$) through a syringe pump to assess perfusion of the vessels. Multiple images of a time-lapse movie depicting streams of fluorescent beads overlaid with R-VEC vessels (right) demonstrating that R-VEC formed lumenized and perfusable vessels, while CTRL-EC (in green) failed to form vessels in the device (left image). Quantification of vessel area for CTRL-EC and R-VEC at day 6 in the microfluidic devices. Two-tailed Student's t-test (n=3 independent experiments, p=0.0214). (L) Fifteen microliter large sized microfluidic chamber (5×3×1 millimeter$^3$) arborized with R-VECs. 60,000 R-VECs in 15 microliter of fibrin were implanted in each device. Fluorescently-labeled antibody against human VEcad was perfused through the inlet subsequently staining all the vessels before fixation. Maximum intensity images of the whole device and an orthogonal subset are shown. (M) Intact heparinized human whole peripheral blood was infused though the inlet of the chamber. Intact heparinized human peripheral blood cells, composed of full complement of RBCs, WBCs, platelets and unperturbed plasma readily perfuse through multi-layered continuous network of R-VEC capillaries without collapsing or obstruction flow. For each perfusion experiment, 100 μl of the peripheral blood were injected and perfused without any indication of hemodynamic compromise. The perfused blood could be washed with media. The R-VEC vascular plexus within the device could tolerate multiple rounds of peripheral blood injection and washing steps without vascular collapse. Data are represented as mean+/−S.E.M. ns=not significant; *<0.05, <0.01, and *<0.001 indicate statistical significance.

FIGS. 3A-3K. Transcriptome analysis of R-VECs reveals activation of Rap1 pathway and a plastic transcriptional signature. (A) R-VECs or CRTL-HUVECs (n=4 independent EC lines) in 2D monolayers (stage 1 induction) were analyzed by RNA sequencing. GO Term analysis was performed on differentially expressed genes. The orange line represents the number of differentially expressed (DE) genes within each GO category; gray bar graph represents p-value for enrichment. GO categories are ordered based on number of DE genes. (B) Heatmaps of selected genes within top enriched GO categories. Genes shown were detected as differentially expressed with DESeq2 (log$_2$FC ≥±1.5 and adjusted p<0.05). Values are log$_2$ normalized counts per million, centered and scaled by row. ETV2 binding from ChIP-seq at the promoter of each differentially expressed gene is shown in the yellow-green heatmap. (C) ETV2 ChIP sequencing was performed on R-VECs during stage 1 induction phase (2D) using an anti-flag antibody. Mouse IgG was used as a control for ETV2 ChIP. Histone modification ChIP for H3K4me3, H3K27ac and H3K27me3 was performed on both CTRL-EC and on R-VEC at the induction stage 1 (2D). Enriched regions were analyzed by ChIP sequencing. Black bar, ETV2 enriched regions. Green bar, region with increased K4me3 modification. Blue bar, region with increased K27ac modification. Promoter regions bound by ETV2 are highlighted in cream. (D) Boxplots for RNA expression of genes in the Rap1 pathway in R-VECs versus CTRL-EC during stage 1 induction phase. Line represents mean value. Differentially expressed genes were detected using DESeq2 (adj. p<0.05), (n=4 independent HUVEC lines). (E) Western blot analysis of a pulldown assay for active Rap1-GTP compared to total Rap1 input in R-VECs (stage 1 induction) versus CTRL-EC. (F) Quantification of the expression level of active Rap1 over total Rap1 demonstrated higher Rap1 activity in R-VECs (stage 1 induction) than in CTRL-EC. Two tailed paired ratio t test (n=5 independent experiments, p=0.0013). (G) Z-stack confocal images and electron microscopy images of R-VEC vessels with Rap1 inhibitor or DMSO at 4 weeks. Red circles point at orthogonal cross-sections. (H) Quantification of R-VEC vessel formation at 1 and 4 weeks with Rap1 inhibitor or DMSO demonstrated that inhibition of Rap1 pathway significantly decreased formation of vessel networks. Two-way ANOVA with Sidak's post-test (n=3 biological replicates, 1 week p=0.8279, 4 weeks p=0.0131). (I) Knockdown of RASGRP3 by two different shRNAs in R-VECs. R-VEC transduced with shRNA against Luciferase were used as control. (J) Quantification of vessel formation at 2 and 4 weeks with RASGRP3 knockdown R-VECs, Luciferase shRNA R-VECs, or naïve R-VECs. Two-way ANOVA followed by Sidak's post-test (n=3 independent Knockdown R-VEC lines, 2 weeks: R-VECs vs Luciferase shRNA p=0.9847, 4 weeks: R-VECs vs Luciferase shRNA p=0.9692; 2 weeks and 4 weeks: R-VECs vs RASGRP3 knockdown and Luciferase shRNA vs RASGRP3 knockdown p<0.0001). (K) Heatmap of differentially expressed genes at each stage of vessel formation: Induction, Remodeling, Stabilization. Differentially expressed genes were detected with DESeq2 using a paired model ratio test to detect differences between the Induction and Stabilization stages (adjusted p<0.05). Values are log 2 normalized counts per million, centered and scaled by row, (n=3 independent R-VEC lines). Data are represented as mean+/−S.E.M. ns=not significant; *<0.05, <0.01, and *<0.001 indicate statistical significance.

FIGS. 4A-4K. R-VECs and iR-VECs engraft and proliferate in the vasculature of a decellularized intestine and engraft within host vasculature upon heterotopical implantation of the re-endothelialized intestine. (A) A schematic described the experimental procedure of heterotopical implantation in decellularized intestine. (B) Harvested rat intestines were cannulated through lumen, mesenteric artery and mesenteric vein (scale bar 1 cm). (C) Decellularized intestine macroscopically preserves the native vasculature, scale bar 5 mm. (D) Seeded R-VECs can spread evenly and reach distal capillaries, scale bar 5 mm. (E) R-VECs and doxycycline-inducible-ETV2 R-VECs (iR-VECs) repopulated the vasculature lining blood vessels in the whole vasculature including distal capillaries (scale bar 500 µm). For inducible ETV2, doxycycline was removed three days after seeding the de-cellularized intestines. CTRL-ECs are unable to achieve the same repopulation and endothelization. (F) Quantification of area covered by R-VECs and iR-VECs compared to control ECs showed an increased re-endothelialization by R-VECs (n=3 independent intestines per group, Two tailed Student's t-test, Endothelial coverage: CTRL-EC vs. R-VEC p=0.0065, CTRL-EC vs. iR-VEC p=0.0052, R-VEC vs. iR-VEC p=0.0512, Average vessel length: CTRL-EC vs. R-VEC p=0.0301, CTRL-EC vs. iR-VEC p=0.0022, R-VEC vs. iR-VEC p=0.0538, Total vessel length: CTRL-EC vs. R-VEC p=0.0026, CTRL-EC vs. iR-VEC p=0.0366, R-VEC vs. iR-VEC p=0.5301; Junctions density: CTRL-EC vs. R-VEC p=0.0094, CTRL-EC vs. iR-VEC p=0.0296, R-VEC vs. iR-VEC p=0.3267). (G) After 7 days of culture in the bioreactor, perfusion with fluorescent LDL showed patent vessels of R-VECs (scale bar 50 µm). (H-I) Heterotopic implantation of re-endothelialized intestines shows engraftment after 1 and 4 weeks of the cells and anastomosis to the host vasculature as indicated by intravital intravenous injection of anti-human VEcadherin antibody (scale bars 50 µm). Representative H&E staining showed anatomical normal perfused vessels. (J) Quantification of area covered by R-VEC compared to CTRL-EC in implanted re-endothelialized intestines at 1 week and 4 weeks (n=3-5 animals per group, Two tailed Student's t-test, Area covered by human VEcad⁺ cells 1 week p=0.0317, 4 weeks, p=0.0028, Vessel length of human VEcad⁺ cells: 1 week p=0.0378, 4 week p=0.0062, Total number of junctions: 1 week p=0.0342, 4 weeks p=0.004). (K) Quantification of EC proliferation and apoptosis in implanted re-endothelialized intestines at 1 and 4 weeks (n=3 animals per group, Two tailed Student's t-test, Apoptosis: 1 week p=0.1832, 4 weeks p=0.0096, Proliferation: 1 week p=0.7528, 4 weeks p=0.0213). Data are represented as mean+/−S.E.M. ns=not significant; *<0.05, <0.01, and *<0.001 indicate statistical significance.

FIGS. 6A-6J. ETV2 ECs arborize organoids derived from normal colon tissue. (A) Normal colon organoids alone or together with 250,000 CTRL-ECs or R-VECs were seeded in 50 microliter Matrigel domes. Maximum intensity confocal projections of the whole 50 microliter Matrigel dome for patient-derived human normal colon organoids alone, or co-cultured with CTRL-EC or R-VEC in Matrigel. Images were taken at day 8 (Representative images of n>15 experiments). (B) Zoomed in maximum intensity and (C) orthogonal projection images of R-VECs with human normal colon organoids at day 8. (D) EdU⁺ cells per organoid at day 8. The cells were given a 16-hour EdU pulse and post-stained with EpCAM to identify the organoids. Kruskal-Wallis Test followed by Dunn's post-test (n=3 independent experiments, No EC=105 organoids, CTRL-EC=258 organoids, R-VEC=467 organoids No EC vs. CTRL-EC p<0.0001, No EC vs. R-VEC p<0.0001, CTRL-EC vs. R-VEC p=0.0062). (E) Quantification of colon area (as stained by KRT20)/field at day 8. Kruskal Wallis Test followed by Dunn's post-test (n=9 wells over 3 independent experiments, No EC vs CTRL-EC p>0.9999, CTRL-EC vs. R-VEC p=0.0293, R-VEC vs. CTRL-EC p=0.0029). (F) Quantification of the number of colon organoids/field at day 8. One way ANOVA, with Tukey's post-test (n=9 wells over 3 independent experiments, No EC vs CTRL-EC p=0.7729, CTRL-EC vs. R-VEC p=0.1191, R-VEC vs. CTRL-EC p=0.0289. (G) Quantification of vessel area/field in CTRL-EC vs. R-VEC in co-cultures with patient-derived normal colon at day 8. Two tailed t-test with Welch's correction (n=9 wells over 3 independent experiments p<0.0001). (H) Kinetics of area of ECs (R-VEC or CTRL-EC) interacting with patient-derived normal colon organoids in L.E.C. was quantified over a 72 hour time lapse using multi-zonal confocal microscopy. R-VEC significantly interacted with patient-derived normal colon as compared to CTRL-EC. Mann-Whitney U-test (n=14 organoids for CTRL-EC and n=19 organoids for R-VEC). (I) Schematic of human normal >40 colon organoids seeded together with 60,000 R-VECs in 15 microliter of fibrin gel in microfluidic devices. After 4 days the self-assembled R-VEC vessels was perfused with VEcad from the inlet to stain the vascular network. Human colon organoids were identified by post-staining for EpCAM. Maximum intensity projection of region indicated in left image. (J) Fluorescent beads (4 μm) were pushed through the inlet and images captured as they perfused through the vessel network in the microfluidic device. Data are represented as mean+/−S.E.M. *<0.05, <0.01, and *<0.001 indicate statistical significance.

FIGS. 7A-7I. R-VECs arborize and support growth of patient-derived tumor colon organoids. (A) Colon tumor organoids (~100) alone or together with 250,000 CTRL-ECs or R-VECs were seeded in 50 microliter Matrigel domes. Representative confocal images of human colon tumor organoids alone, or co-cultured with CTRL-EC or R-VECs in Matrigel. The organoids were post-stained for KRT20 and EdU at day 8 of co-culture after a 4.5 hour EdU pulse. (B) Representative immunofluorescent images of tumor colon organoids co-cultured with R-VEC and post-stained for EpCAM and VEcad. The maximum intensity and (C) orthogonal projections are shown. (D) Quantification of levels of EdU in colon tumor organoids alone, or co-cultured with CTRL-EC or R-VEC at day 8, One-way ANOVA, followed by Tukey's post-test. (n=5 wells for No-EC, n=6 wells for CTRL-EC, n=6 wells for R-VECs, over 3 independent experiments, No EC vs. CTRL-EC p<0.0001, CTRL-EC vs. R-VEC p=0.0010, No EC vs. R-VECs p<0.0001). (E) Kinetics of surface area of ECs (R-VEC or CTRL-EC) interacting with human tumor colon organoids in Matrigel (left panel) or L.E.C. (right panel) was quantified over a 78 hour time lapse using multi-zonal confocal microscopy. Mann-Whitney U-test. For co-culture experiment in Matrigel (left panel), a total of 36 organoids for CTRL-EC and 43 organoids for R-VEC conditions was used to quantify the co-opting EC area. For co-culture experiment in L.E.C (right panel), a total of 20 organoids for CTRL-EC and 26 organoids for R-VEC conditions were used to quantify the co-opting EC area. (F) Quantification of vessel area in CTRL-EC or R-VEC co-cultures at day 8 with CTRL-EC or with R-VEC. Two-tailed Student's t-test with Welch's correction (n=6 wells over 3 independent experiments, p=0.0003). (G) Single cell suspension of CTRL-EC or R-VEC (mCherry) (stage 1 induction) were implanted subcutaneously with patient-derived human colon tumor organoids (GFP) in Matrigel. The mice were sacrificed after 5 months. Representative image of a tumor-section with R-VEC (thickness=100 m). (H) Sections (thickness=50 m) of tumors with CTRL-EC or R-VEC post-stained with mouse endomucin and DAPI. (I) Quantification of human vessel area was calculated by percentage of mCherry fluorescent area/section area. Two-tailed t-test with Welch's corR-VECtion (n=3 tumors/group, p=0.0191). Data are represented as mean+/−S.E.M. *<0.05, <0.01, and *<0.001 indicate statistical significance.

FIG. 8A-8I. Single cell RNA-seq analysis of cross-talk of R-VEC with normal and tumor colon organoids in 3D co-culture. (A) Schema for single cell RNA-seq experiments. R-VECs (250,000—stage 1 induction) were seeded alone or together with ~100 normal or tumor colon organoids in 50 microliter L.E.C. matrix domes. 12 domes were prepared for each condition. At day 7 the co-cultures were dissociated and submitted for single cell RNA-seq (10× Chromium platform). (B) Single cell suspension R-VECs (stage 1 induction) were cultured either alone or co-mingled with normal colon or tumor colon organoids and submitted for 10× Chromium analysis at day 7 of co-culture. Endothelial cells were identified from co-cultures with organoids as positive for either VEcad (CDH5), PECAM1 (CD31) or VEGFR2 (KDR) and negative for the epithelial cell markers. UMAP plots for endothelial cell fractions of R-VECs alone and R-VECs co-cultured with normal colon organoids. (C) Endothelial cells combined from R-VECs alone and R-VECs co-cultured with normal colon organoids group in 9 unique clusters. Cluster 5 is uniquely enriched in R-VECs co-cultured with normal colon organoids vs. R-VECs alone. (D) Heatmap and (E) Dotplot of differentially expressed genes from cluster 5. (F) Single cell suspension R-VECs (stage 1 induction) were cultured either alone or co-mingled with colon tumor organoids and submitted for 10× Chromium analysis at day 7 of co-culture. Endothelial cells from co-cultures with organoids were identified as positive for either VEcad (CDH5), PECAM1 (CD31) or VEGFR2 (KDR) and negative for the epithelial cells markers. UMAP plots for endothelial cells fraction of R-VECs alone and R-VECs co-cultured with colon tumor organoids. (G) Endothelial cells combined from R-VECs alone and R-VECs co-cultured with normal colon organoids group in 8 unique clusters. Cluster 8 is uniquely enriched in R-VECs co-cultured with colon-tumor organoids vs. R-VECs alone. (H) Heatmap and (I) Dotplot of differentially expressed genes from cluster 8, which is enriched among R-VECs in culture with colon tumor organoids vs. R-VECs alone. Differential expression was performed using Wilcoxon rank sum test FDR p<0.05.

DETAILED DESCRIPTION

Figure 1A:
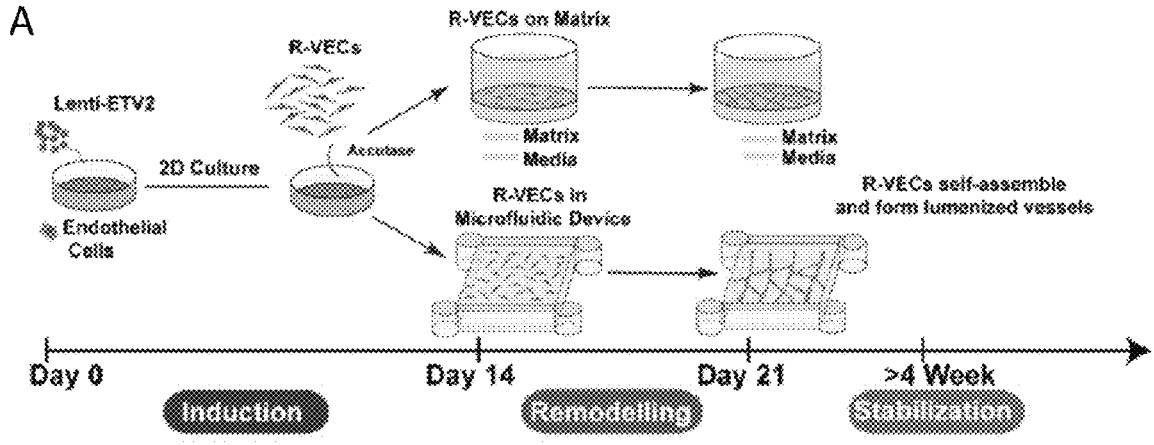

An aspect of this disclosure provides a method of vascularizing pancreatic islets by culturing isolated/purified pancreatic islets with reprogrammed (reset) endothelial cells (R-VECs). Without limiting to any particular theory, the inventors discovered that co-culturing pancreatic islets with R-VECs enables vascular arborization of the pancreatic islets in vitro, and, upon transplantation, safeguards and augments islet functionality and accelerates anastomosis to the host vessels in vivo.

Another aspect of this disclosure provides a method of vascularizing β-cell organoids by culturing β-cell organoids with reprogrammed adult human endothelial cells (R-VECs). This aspect of the disclosure is based on the capacity of ETV2$^+$ transduced adult endothelial cells (R-VECs) to augment rapid arborization β-cell organoids and facilitation of anastomosis (forming connection between two blood vessels) to the recipient's circulation once transplanted into the patient.

In one aspect, the disclosure provides a product obtained from the present methods, e.g., vascularized pancreatic islets or β-cell organoids.

In a further aspect, a resulting product from the present methods, e.g., vascularized pancreatic islets or β-cell organoids, is administered to a subject in need, such as a subject suffering from diabetes.

The term "about," as used throughout this disclosure, refers to ±10% of any given value.

Subject in Need

A "subject in need", referred to herein, is a person suffering from diabetes or at risk of developing diabetes. In some embodiments, the subject suffers from Type 1 diabetes. In some embodiments, the subject is at risk of developing Type 1 diabetes. In some embodiments, the subject suffers from Type 2 diabetes. In some embodiments, the subject suffers from advanced Type 2 diabetes, for example, Type 2 diabetes characterized by at least 50% decrease in pancreatic islet mass or pancreatic islet function.

Reprogrammed, Reset Vascular Endothelial Cells (R-VECs)

The R-VECs (reprogrammed, reset endothelial cells) of the present disclosure are derived from endothelial cells (ECs), which are "reprogrammed" or "reset" through the incorporation and expression of an exogenous ETV2 encoding nucleic acid in the endothelial cells.

In some embodiments, the ECs are adult human endothelial cells that could be isolated from any tissue-specific organs. In some embodiments, the ECs comprise generic endothelial cells, which can be derived from any tissue that ECs can be isolated from. In some embodiments, the ECs are of the same donor origin as the islet or β cell organoid. In some embodiments, the ECs are of a donor origin different from the islet or β cell organoid; in some such embodiments, the donor of the ECs and the donor of the islet or β cell organoid are genetically matched. In some embodiments, the ECs are autologous ECs isolated from tissue subject in need of the treatment disclosed herein. In a specific embodiment, the autologous ECs are isolated from a subject's own adipose tissue. In some embodiments, the ECs are allogeneic ECs derived from a genetically-matched donor. In some embodiments, the ECs are derived from circulating or tissue-specific EC progenitor or stem cells.

In some embodiments, the endothelial cell is a differentiated (mature) endothelial cell. The term "differentiated" or "differentiated endothelial cell" as used herein refers to a developmental process whereby an endothelial cell becomes specialized for a particular function, for example, where cells acquire one or more morphological characteristics and/or functions different from that of the initial cell type. The term "differentiation" includes both lineage commitment and development of a cell into a mature, fully differentiated adult endothelial cell. Differentiation may be assessed, for example, by monitoring the presence or absence of lineage markers, using immunohistochemistry or other procedures known to one skilled in the art.

Endothelial cells can be obtained by methods known in the art. For example, endothelial cells can be isolated from tissue using a collagenase-based digestion approach as described in Ginsberg, M. et al. *Cell;* 151, 559-575, (2012) and U.S. Pat. No. 6,899,822 to Ferrara et al. Endothelial lineage can be verified by staining with, for example, an anti-CD31 antibody, VE-cadherin or anti-von Willebrand factor antibody. Isolation of ECs can be achieved using antibodies specific for EC surface markers, such as VE-cadherin, CD31 or VEGFR2, attached to magnetic beads or fluorophores for use in Magnetic or Fluorescence Activated Cell Sorting (MACS or FACS). In some embodiments, the ECs are derived from direct transcriptional conversion of non-vascular cells, such as fibroblasts into endothelial cell fate. In some embodiments, non-vascular cells are directly converted into endothelial cells by introducing transcription factors Fli1 and Erg into the non-vascular cells.

In the alternative, endothelial cells may be obtained from commercial sources. Endothelial cells can be cultured and maintained (expanded) under conditions that maintain their differentiated lineage and the ability to replicate. Such conditions have been well documented in the art. For example, isolated endothelial cells can be cultured in coated tissue culture dishes in complete media including endothelial cell growth supplement. The endothelial cells can then be split and passaged until used.

In some embodiments, the differentiated endothelial cell is a human mature blood vessel associated endothelial cell. In certain embodiments, the differentiated human endothelial cell is a human umbilical vein derived endothelial cell (HUVEC), a human adipose derived endothelial cell, or a tissue/organ specific human fetal or adult-derived endothelial cell. In some embodiments of the present methods the differentiated endothelial cells are organ-specific endothelial cells including, but not limited to, endothelial cells of the heart, kidney, testis, ovary, retina, liver, pancreas, brain, lungs, spleen, large or small intestine, ovary or testis, or other endocrine organs. In other embodiments, the differentiated endothelial cells are tissue-specific endothelial cells from muscle, lymph tissue, olfactory tissue, osteogenic tissue, oral (dental) tissue, or glandular tissue (e.g., endocrine, thymic).

A differentiated endothelial cell can be cultured to initiate the formation of stable three-dimensional blood vessels. Cells can be cultured in any culture medium capable of sustaining growth of endothelial cells such as, but not limited to, DMEM (high or low glucose), advanced DMEM, DMEM/MCDB 201, Eagle's basal medium, Ham's F10 medium (F10), Ham's F-12 medium (F12), Hayflick's Medium, Iscove's modified Dulbecco's medium, Mesenchymal Stem Cell Growth Medium (MSCGM), DMEM/F12, RPMI 1640, and CELL-GRO-FREE (Corning cellgro, Corning, NY). The culture medium can be supplemented with one or more components including, for example fetal bovine serum, preferably about 2-15% (v/v); equine serum; human serum; fetal calf serum; beta-mercaptoethanol, preferably about 0.001% (v/v); one or more growth factors, for example, platelet-derived growth factor (PDGF), epidermal growth factor (EGF), fibroblast growth factor (FGF), vascular endothelial growth factor-A (VEGF-A), insulin-like growth factor-1 (IGF-1), leukocyte inhibitory factor (LIF) and erythropoietin; amino acids, including L-valine; and one or more antibiotic and/or antimycotic agents to control microbial contamination, such as, for example, penicillin G, streptomycin sulfate, amphotericin B, gentamicin, and nystatin, either alone or in combination.

The endothelial cell can be cultured to expand the cell numbers, prior to reprogramming. Sufficient numbers of endothelial cells may be isolated from an initial sample; however, even if an acceptable number of differentiated endothelial cells are present in the initial sample, expansion of the cells in culture can provide an even greater supply of endothelial cells for reprogramming. Methods of culturing and expanding cells are known in the art. See, for example, Helgason et al., *Basic Cell Culture Protocols,* 4th Edition, Human Press Publishing, 2013; and Mitry et al, *Human Cell Culture Protocols,* 3rd Edition, Human Press Publishing, 2012.

The differentiated endothelial cells are "reprogrammed" or "reset" through the incorporation and expression of an exogenous ETV2 encoding nucleic acid in the differentiated endothelial cells.

An endothelial cell is "reprogrammed" or "reset" (directed to de-differentiate into a more plastic, adaptable, durable and hemodynamically stable state) by expressing an exogenous ETV2 transcription factor protein, which alters the endothelial cell's ability to form tubular (lumenized) vessels and other vascular structures.

The term "ETV2" or "ETV2 transcription factor" are used interchangeably herein to refer to the human ETS-transcription factor variant 2, ETV2 (ER71, ETSRP71) set forth in RefSeq Gene ID 2116, NCBI Reference Sequence No. NC_000019.10, which encodes a DNA binding transcription factor protein having an amino acid sequence set forth in NP 055024. An ETV2 nucleic acid of the present disclosure can include the ETV2 DNA sequence or a portion thereof, as well as an RNA transcript thereof such as that set forth in Accession Nos: NM_001300974.1, NM_014209.3 and NM_001304549.1. Functional derivatives and homologs of ETV2 are further contemplated for use in the disclosed methods. As used herein, a "functional derivative" is a molecule that possesses the capacity to perform the biological function of ETV2. For example, a functional derivative of ETV2 as disclosed herein is a molecule that is able to bind DNA as the ETV2 transcription factor is and reprogram differentiated endothelial cells. Functional derivatives include fragments, variants, parts, portions, equivalents, analogs, mutants, mimetics from natural, synthetic or recombinant sources including fusion proteins. A "homolog" is a protein related to the ETV2 transcription factor by descent from a common ancestral nucleic acid sequence. Homologs contemplated herein include, but are not limited to, ETV2 proteins derived from different species, such as, for example, mouse, rat, and monkey.

In a specific embodiment of the present methods, the exogenous ETV2 encoding nucleic acid present in an endothelial cell is human ETV2 as set forth in SEQ ID NO: 37, which encodes the human ETV2 transcription factor protein set forth in SEQ ID NO: 38. In another embodiment, the exogenous ETV2 encoding nucleic acid present in an endothelial cell is a human ETV2 ribosomal nucleic acid (RNA) transcript, which encodes the human ETV2 transcription factor protein. In other embodiments, the exogenous ETV2 encoding nucleic acid provided to a differentiated endothelial cell is a modified synthetic RNA. Modified synthetic RNA molecules can be produced by methods known by one of ordinary skill in the art, such as those set forth in Machnicka, M A, et al. Nucleic Acids Res., 41 pp. D262-D267, (2013). Exemplary modified synthetic molecules for use in the present invention include chemical modifications to the RNA polynucleotide that modulate the stability (alter nuclease resistance) or cellular uptake (e.g., conjugation of the RNA polynucleotide to a cholesterol, linker, lipid, polymer, peptide or apamer).

The nucleic acid encoding ETV2 transcription factor can be provided to a cell by methods well known to those of ordinary skill in the art. For example, the ETV2 encoding nucleic acid can integrate the ETV2 nucleic acid sequence into the endothelial cell genome, or non-integrative, meaning the ETV2 gene is expressed from an extrachromosomal location. In some embodiments, the ETV2 encoding nucleic acid sequence is provided by a vector into which the nucleic acid sequence is cloned by techniques known in the art. The vector can be introduced by any suitable method, such as by transfection or by viral-mediated transduction.

Vectors for use in expressing the ETV2 transcription factor include, for example, retrovirus, lentivirus, adenovirus, adeno-associated virus, and other vectors that, once introduced into a cell, integrate into a chromosomal location within the genome of the subject and provide stable, long-term expression of ETV2. Other vectors include episomal vectors, as well as engineered lentivirus vector variants that are non-integrative. Here, the ETV2 nucleotide sequence can be cloned into the vector sequence; the vector is grown in differentiated endothelial cells, and used to reprogram the endothelial cells using the methods described herein.

In one embodiment, the ETV2 nucleic acid is included in a lentiviral vector and provided to an endothelial cell by lentivirus-mediated transduction. In a specific embodiment, the nucleic acid encoding ETV2 of SEQ ID NO: 37 is transduced into a differentiated endothelial cell using a lentiviral vector. In one embodiment, the lentiviral vector is lenti pgk-vector. In specific embodiments the exogenous ETV2 encoding nucleic acid of SEQ ID NO: 37 is provided to an endothelial cell by transduction with an inducible expression system such as, for example, the reverse tet-transactivator (rtTA)-doxycycline inducible expression system.

In other embodiments, the ETV2 nucleic acid is an RNA transcript that is delivered to an endothelial cell. In certain specific embodiments, the ETV2 RNA delivered to a cell is a modified synthetic RNA molecule. Methods for introducing RNA molecules to a cell are well known by those of ordinary skill in the art, and such methods can be used here. For example, an ETV2 RNA transcript such as an mRNA transcript can be delivered to an endothelial cell by transfections. In another non-limiting example, an ETV2 RNA transcript is delivered to a cell by electroporation.

The present methods include culturing a differentiated endothelial cell including the exogenous ETV2 encoding nucleic acid under conditions that express the ETV2 transcription factor protein. In certain embodiments, the ETV2 protein is expressed constitutively. In other embodiments, the ETV2 protein is expressed transiently, such as under the control of an inducible promoter. In certain embodiments, the exogenous ETV2 transcription factor is expressed in an endothelial cell for at least 3 weeks, at least 4 weeks, at least 5 weeks, at least six weeks, at least 7 weeks, at least 8 weeks, at least 9 weeks, at least 10 weeks, at least 11 weeks, at least 12 weeks or more to induce the endothelial cell(s) to form lumenized blood vessels. In a specific embodiment, exogenous ETV2 protein is expressed for at least 4 weeks to induce blood vessel formation. In another embodiment, the exogenous ETV2 protein is expressed for at least 3 to 4 weeks to induce lumen formation.

In other embodiments, the present methods include culturing an endothelial cell having an exogenous ETV2 encoding nucleic acid under conditions that express the ETV2 transcription factor protein, followed by a further culturing period under conditions where the endothelial cell(s) do not express exogenous ETV2. Here, the endothelial cell can first be cultured under conditions that express exogenous ETV2 transcription factor for a first period of time, then undergo a second culturing under conditions that do not express exogenous ETV2 such as in the absence of a substance capable of activating an inducible promoter (e.g., doxycycline, tetracycline). In one embodiment, the exogenous ETV2 encoding nucleic acid is a modified synthetic RNA molecule, which results in transient ETV2 transcription factor expression during culture.

In some embodiments, the present methods include culturing an endothelial cell having an exogenous ETV2 encoding nucleic acid under conditions that express the ETV2 transcription factor protein for a period of at least 3 weeks, at least 4 weeks, at least 5 weeks, at least six weeks, at least 7 weeks, at least 8 weeks, at least 9 weeks, at least 10 weeks, at least 11 weeks, at least 12 weeks or more, followed by a second culture under conditions that do not express exogenous ETV2, such as in the absence of doxycycline for a period of days, weeks or months. In a specific embodiment, the endothelial cell is cultured under conditions that express an exogenous ETV2 transcription factor protein for a period of at least 3 to 4 weeks, then the endothelial cell is cultured under conditions that do not express the ETV2 transcription factor for a period of time ranging from 7 days to 6 months, from 7 days to 5 months, from 7 days to 4 months, from 7 days to 3 months, from 7 days to 2 months, or from 7 days to 1 month.

In some embodiments, the R-VECs used in the present methods express an exogenous nucleic acid encoding for an ETV2 transcription factor. In some embodiments, the R-VECs further express an exogenous nucleic acid encoding for a Sox17 transcription factor.

In one embodiment of the present methods, the endothelial cells including an exogenous ETV2 encoding nucleic acid are cultured in serum free media for a period of time. In some embodiments, the present methods include culturing the endothelial cells in serum free media for at least 7 days, at least 10 days, at least 2 weeks, at least 3 weeks, at least 4 weeks, at least 5 weeks, at least 6 weeks, at least 7 weeks, at least 8 weeks or more.

In other embodiments, the present methods include culturing the endothelial cells including an exogenous ETV2 encoding nucleic acid are cultured in serum free media at low oxygen tension. In some embodiments, the endothelial cells are cultured in serum free media at less than atmospheric oxygen tension, i.e., 20%. In specific embodiments, the endothelial cells are cultured in serum free media at an oxygen tension from between 4% and 15%, 5% and 10%, 4% and 8% or 4% and 6%. In one embodiment, the endothelial cells are cultured in serum free media at an oxygen tension of 1% to 5%. In a specific embodiment, the present method includes culturing the endothelial cells including an exogenous ETV2 encoding vector in serum free media at an oxygen tension of 1% to 5% for 7 days.

In some embodiments, the EC culturing for reprogramming is performed in a bioreactor or a microfluidic device. In some embodiments, the microfluidic device is capable of transporting human blood or other specialized media, solutions, chemicals or biopharmaceutical drugs or reagents.
Methods of Vascularizing Pancreatic Islets An aspect of this disclosure is directed to methods of vascularizing a pancreatic islet comprising coculturing the pancreatic islet with an endothelial cell which comprises an exogenous nucleic acid encoding an ETV2 transcription factor and wherein the ETV2 is expressed in the endothelial cell, thereby generating a vascularized pancreatic islet.

In some embodiments, the pancreatic islet is surgically isolated from a person. In some embodiments, the pancreatic islet is isolated from a healthy donor. In some embodiments, the pancreatic islet is isolated from a subject in need. In some embodiments, the pancreatic islet is obtained from a commercial source. In some embodiments, pancreatic islets are isolated from cadavers (e.g., cadavers genetically matched to a recipient).

In some embodiments, the pancreatic islets used in the coculturing are not decellularized, i.e., the pancreatic islets still retain existing tissue structure and differentiated, insulin-producing β cells. In some embodiments, the pancreatic islets comprise at least an extracellular matrix and β cells that produce insulin. In some embodiments, pancreatic islets comprise cells from cell types other than β cells (e.g., alpha cells that produce glucagon, pancreatic polypeptide (PP) cells that produce pancreatic polypeptide, epsilon cells that produce ghrelin, and delta cells that produce somatostatin).

According to the present method, a pancreatic islet is co-cultured with an endothelial cell comprising an exogenous nucleic acid encoding an ETV2 transcription factor, wherein the ETV2 is expressed in the endothelial cell.

In some embodiments, the endothelial cell is a vascular endothelial cell comprising an exogenous nucleic acid encoding an ETV2 transcription factor, wherein the ETV2 is expressed in the endothelial cell—such a vascular endothelial cell is also referred to as a reprogrammed/reset vascular endothelial cell or "R-VEC."

The expression "an endothelial cell" is understood to include a population of endothelial cells. In some embodiments, a population of endothelial cells is a substantially pure population of endothelial cells. In some embodiments, a substantially pure population of endothelial cells refers to a population with at least 95%, at least 96%, at least 97%, at least 98%, at least 99% or a higher percentage of the cells in the population being endothelial cells, e.g., endothelial cells having the same origin (e.g., vascular endothelial cells) and reprogrammed to express an ETV2 transcription factor.

In some embodiments, the cocultured endothelial cell is at a starting concentration of at least 3 million cells/ml, at least 3.5 million cells/ml, at least 4 million cells/ml, at least 4.5 million cells/ml, at least 5 million cells/ml, at least 5.5 million cells/ml, at least 6 million cells/ml, at least 6.5 million cells/ml, or at least 7 million cells/ml. In a specific embodiment, the endothelial cell is at a starting concentration of about 5 million cells/ml.

In some embodiments, the coculturing is carried out in a medium supplemented with molecules, such as basic FGF (FGF-2) and heparin. In some embodiments, the medium comprises between about 5 ng/ml and about 20 ng/ml FGF2. In some embodiments, the medium comprises about 5 ng/ml, about 10 ng/ml, about 15 ng/ml, or about 20 ng/ml FGF2. In a specific embodiment, medium comprises about 10 ng/ml FGF-2. In some embodiments, the medium comprises between about 20 µg/ml and about 200 µg/ml heparin. In some embodiments, the medium comprises about 20 µg/ml, about 30 µg/ml, about 40 µg/ml, about 45 µg/ml, about 50 µg/ml, about 60 µg/ml, about 70 µg/ml, about 80 µg/ml, about 90 µg/ml, about 100 µg/ml, about 110 µg/ml, about 125 µg/ml, about 150 µg/ml, 175 about µg/ml, or about 200 µg/ml heparin. In a specific embodiment, medium comprises about 100 µg/ml heparin.

In some embodiments, the coculturing is carried out in a medium further supplemented with molecules in addition to FGF-2 and/or heparin, such as human serum albumin (between 0.05% and 2%, e.g., about 0.05%, about 0.1%, about 0.5%, about 1%, about 1.5%, or about 2%), human transferring (between 5 μg/ml and 20 μg/ml, e.g., about 5 μg/ml, about 10 μg/ml, about 15 μg/ml, or about 20 μg/ml), ethanolamine (between 20 μM and 100 PM, e.g., about 20 PM, about 30 μM, about 40 μM, about 50 μM, about 60 μM, about 70 μM, about 80 PM, about 90 μM, or about 100 μM), phosphoethanolamine (between 20 μM and 100 μM, e.g., about 20 μM, about 30 μM, about 40 μM, about 50 μM, about 60 μM, about 70 μM, about 80 μM, about 90 μM, or about 100 μM), sodium selenite (between 3 μg/ml and 10 μg/ml, e.g., about 3 μg/ml, about 3.5 μg/ml, about 3.5 μg/ml, about 4 μg/ml, about 4.5 μg/ml, about 5 μg/ml, about 5.5 μg/ml, about 6 μg/ml, about 6.5 μg/ml, about 7 μg/ml, about 7.5 μg/ml, about 8 μg/ml, about 8.5 μg/ml, about 9 μg/ml, about 9.5 μg/ml, or about 10 μg/ml), glucose (between 2 mM and 10 mM, e.g., about 2 mM, about 2.5 mM, about 3 mM, about 3.5 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, or about 10 mM), Triiodothyronine (T3) (between 0.3 ng/mL and 1 ng/mL, e.g., about 0.3 ng/mL, about 0.4 ng/mL, about 0.5 ng/mL, about 0.6 ng/mL, about 0.65 ng/mL, about 0.7 ng/mL, about 0.8 ng/mL, about 0.9 ng/mL, about 1 ng/mL), Prolactin (PRL) (between 10 ng/mL and 30 ng/mL, e.g., about 10 ng/mL, about 15 ng/mL, about 20 ng/mL, about 23 ng/mL, about 25 ng/mL, about 28 ng/mL, about 30 ng/mL), IGF-I (between 1 ng/mL and 10 ng/mL, e.g., about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL) or a combination thereof. In a specific embodiment, the medium comprises 10 ng/ml FGF-2, 100 μg/ml heparin, 0.1% human serum albumin, 10 μg/ml human transferrin, 50 μM Ethanolamine, 50 μM Phosphoethanolamine, 6.7 μg/ml sodium selenite, 5.5 mM glucose, 0.65 ng/mL Triiodothyronine (T3), 23 ng/mL Prolactin (PRL), and 5 ng/mL IGF-I.

In some embodiments, the co-culturing is carried out on a matrix. In fact, the present disclosure identifies essential extracellular matrix components, i.e., laminin, entactin and collagen IV, which when used to culture reprogrammed endothelial cells results in the formation of stable and functional three-dimensional artificial vessels in vitro and in vivo without the use of pericytes, perfusion and cumbersome scaffolds. Therefore, in certain embodiments, the matrix is composed of extracellular matrix components, such as laminin, entactin and/or collagen.

In some embodiments, a matrix for use coculturing can include laminin and entactin at a combined concentration of at least about 5 mg/mL. As laminin and entactin can bind to each other and form a complex, a matrix for use in the present methods can include a complex of laminin and entactin. For example, the matrix can include at least about 5 mg/mL of a complex of laminin and entactin. In an exemplary embodiment, the coculturing is carried out on a matrix including laminin and entactin at a combined concentration of at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL or at least 15 mg/mL. In specific embodiments, the matrix used in the present methods is composed of a combination of laminin, entactin and collagen IV (L.E.C.). For example, the coculturing can be carried out on a matrix containing at least 5 mg/mL of laminin and entactin, and at least 0.2 mg/mL collagen IV to form long-lasting, functional three-dimensional artificial blood vessels. In some embodiments, the L.E.C. matrix combination comprises at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, or at least 1 mg/mL collagen IV. In a specific embodiment, the L.E.C. matrix is composed of between a combined concentration 9 mg/mL and 13 mg/mL of laminin and entactin, and between 0.2 mg/mL and 0.5 mg/mL of collagen IV. In a specific embodiment, the L.E.C. matrix is composed of laminin and entactin at a combined concentration of about 11 mg/mL and about 0.2 mg/mL collagen IV.

In some embodiments, the coculturing of the pancreatic islet and the endothelial cell is performed in a bioreactor or a microfluidic device. In some embodiments, the microfluidic device is capable of transporting human blood or other specialized media, solutions, chemicals or biopharmaceutical drugs or reagents. In some embodiments, the coculturing of the pancreatic islet and the endothelial cell is performed in a 3D gel. There is no requirement for any specific manner by which the islet and the EC cell are combined or mixed. The mixture of islet-EC can self-assemble into a 3D structure, i.e., the vascularized islet.

In some embodiments, the coculturing is carried out for at least 1-4 weeks. In some embodiments, the coculturing is done for at least 3-4 weeks. In some embodiments, the coculturing is done for at least 1 week, at least 2 weeks, at least 3 weeks, at least 24 days, at least 4 weeks, at least 32 days, at least 5 weeks, at least 38 days, at least 6 weeks, at least 45 days, at least 7 weeks, at least 52 days, at least 8 weeks, but not more than 4 months or not more than 3 months. In some embodiments, the coculturing is performed for about 3 weeks, about 24 days, about 4 weeks, about 32 days, about 5 weeks, about 38 days, about 6 weeks, about 45 days, about 7 weeks, about 52 days, or about 8 weeks.

In some embodiments, the pancreatic islet and the endothelial cell are cocultured for an additional period of time under conditions wherein the endothelial cell does not express the ETV2 transcription factor. In some embodiments, the pancreatic islet and the endothelial cell are cocultured for an additional period of time under conditions wherein the expression of the ETV2 transcription factor in the endothelial cell is transient or reduced (turned down). In some embodiments, the additional period of time is at least 5 days, at least 6 days, at least 7 days, at least 8 days, at least 9 days, at least 10 days, at least 11 days, but not more than 18 days, not more than 16 days or not more than 14 days.

In some embodiments, the pancreatic islet and the endothelial cell can be cocultured until sufficient islet vascularization has been achieved. The extent of vascularization can be assessed by various means. In some embodiments, vascularization is measured by the fold increase in the amount of glucose-stimulated insulin secretion. In some embodiments, vascularization is considered to be sufficient when a vascularized islet produces at least 2 folds, at least 3 folds, at least 4 folds, at least 5 folds more insulin in response to glucose as compared to an islet that has not been vascularized (e.g., an islet that was not cocultured with any endothelial cell, or an islet that was cocultured with a wild type endothelial cell that does not express an exogenous nucleic acid encoding the ETV2 transcription factor). In some embodiments, increase in glucose-stimulated insulin secretion in a pancreatic islet is measured by incubating the islet with low glucose (e.g., between about 1 mM and about 4 mM) to determine the basal insulin secretion, and then incubating the islet with high glucose (about 16.7 mM) to determine the stimulated insulin secretion. In some embodiments, the extent of vascularization is determined based on visual assessment, for example, as the vascularization progresses, tubular structures representing blood vessels are observed. In some embodiments, the vascularization is measured by the increase in vessel area. In some embodiments, vascularization is considered to be sufficient when the vessel area in a vascularized islet reaches at least at least 4%, 5%, at least 6%, at least 7%, at least 8%, at least 9% or at least 10% of a total area of the islet under examination.

Vascularized Pancreatic Islet

In some embodiments, the vascularized pancreatic islets of the present disclosure comprise regular islet structure and vasculature formed by the endothelial cells expressing an exogenous nucleic acid encoding the ETV2 transcription factor.

In some embodiments, the vascularization comprises the formation of an artery, a vein, a capillary, an arteriole, a venule, lymphatic vessels, or a combination thereof, within the pancreatic islet. In some embodiments, a vascularized pancreatic islet includes a network, a 2-dimensional or 3-dimensional network, of vascular vessels formed by the endothelial cells ("arborization of the pancreatic islet").

In some embodiments, the vascularized pancreatic islet comprises β-cells and vasculature (blood vessels, e.g., arteries, veins) that allows delivery of nutrients to the pancreatic islet and that allows removal of the insulin produced by the pancreatic islet. In some embodiments, the vascularized pancreatic islet is functional in glucose sensing and insulin production in tissue culture (in vitro) or when administered to a host (in vivo). In some embodiments, the vasculature formed within a vascularized pancreatic islet in vitro is capable of connecting with host vessels in vivo and/or promoting further vascularization of the pancreatic islet in vivo. In some embodiments, the vascularized pancreatic islet can stay functional in glucose sensing and insulin production in vivo for an extended period of time. As used in, the phrase "extended period of time" refers to at least 2 weeks, at least 3 weeks, at least a month, at least 6 weeks, at least 2 months, at least 10 weeks, at least 3 months, at least 4 months, at least 5 months, at least 6 months or at least a year.

Methods of Forming Vascularized β-Cell Organoids

An aspect of this disclosure is directed to methods of making a vascularized β-cell organoid comprising coculturing β-cells with an endothelial cell which comprises an exogenous nucleic acid encoding an ETV2 transcription factor, wherein the ETV2 is expressed in the endothelial cell, thereby generating a vascularized β-cell organoid.

As used herein, the term "β-cell organoid" refers to man-made composition of cells made up entirely, or almost entirely (≥90%) of β-cells. In some embodiments, intact pancreatic islets undergo enzymatic digestion to generate single cell suspension of the various endocrine cells present within the islets, which predominantly compose of β-cells. Replating of single suspension cells results in re-assembly into β-cells organoids that could be used for further studies, including therapeutic vascularization or implantation (Zhou Q, and Melton D A. *Nature;* 557(7705):351-8, (2018)). In some embodiments, the β-cell organoids comprise β-cells derived from stem cells or induced Pluripotent Cell (iPS) cells (Zhou Q, and Melton D A. *Nature;* 557(7705):351-8 (2018); Hebrok M. *Cold Spring Harb Perspect Med;* 2(6): a007674 (2012); both incorporated herein by reference). In some embodiments, the β-cell organoids comprise β cells derived from direct conversion of fibroblasts (Zhou Q, and Melton D A. *Nature;* 557(7705):351-8, (2018)). In some embodiments, the β-cell organoids comprise β cells isolated from adult subjects (Zhou Q, and Melton D A. *Nature;* 557(7705):351-8 (2018)).

In some embodiments, the β-cell organoid is made from 1-cells obtained from the pancreas of a subject (a healthy donor, a subject in need, or cadavers). In some embodiments, β-cells are obtained from cadavers genetically matched to a recipient.

In some embodiments, the endothelial cell is a vascular endothelial cell comprising an exogenous nucleic acid encoding an ETV2 transcription factor wherein the ETV2 is expressed in the endothelial cell; for example, a reprogrammed/reset vascular endothelial cell (R-VEC).

In some embodiments, the cocultured endothelial cell is at a starting concentration of at least 3 million cells/ml, at least 3.5 million cells/ml, at least 4 million cells/ml, at least 4.5 million cells/ml, at least 5 million cells/ml, at least 5.5 million cells/ml, at least 6 million cells/ml, at least 6.5 million cells/ml, or at least 7 million cells/ml. In a specific embodiment, the endothelial cell is at a starting concentration of about 5 million cells/ml.

In some embodiments, the coculturing is carried out in a medium supplemented with molecules, such as basic FGF (FGF-2), and heparin. In some embodiments, the medium comprises between about 5 ng/ml and about 20 ng/ml FGF2. In some embodiments, the medium comprises about 5 ng/ml, about 10 ng/ml, about 15 ng/ml, or about 20 ng/ml FGF2. In a specific embodiment, medium comprises about 10 ng/ml FGF-2. In some embodiments, the medium comprises between about 20 μg/ml and 200 μg/ml about heparin. In some embodiments, the medium comprises about 20 μg/ml, about 30 μg/ml, about 40 μg/ml, about 45 μg/ml, about 50 μg/ml, about 60 μg/ml, about 70 μg/ml, about 80 μg/ml, about 90 μg/ml, about 100 μg/ml, about 110 μg/ml, about 125 μg/ml, about 150 μg/ml, 175 about μg/ml, or about 200 μg/ml heparin. In a specific embodiment, medium comprises about 100 μg/ml heparin.

In some embodiments, the coculturing is carried out in a medium further supplemented with molecules additional to FGF-2 and/or heparin, such as human serum albumin (between 0.05% and 2%, e.g., about 0.05%, about 0.1%, about 0.5%, about 1%, about 1.5%, or about 2%), human transferring (between 5 μg/ml and 20 μg/ml, e.g., about 5 μg/ml, about 10 μg/ml, about 15 μg/ml, or about 20 μg/ml), ethanolamine (between 20 μM and 100 PM, e.g., about 20 PM, about 30 μM, about 40 μM, about 50 μM, about 60 μM, about 70 μM, about 80 PM, about 90 μM, or about 100 μM), phosphoethanolamine (between 20 μM and 100 μM, e.g., about 20 μM, about 30 μM, about 40 μM, about 50 μM, about 60 μM, about 70 μM, about 80 μM, about 90 μM, or about 100 μM), sodium selenite (between 3 μg/ml and 10 μg/ml, e.g., about 3 μg/ml, about 3.5 μg/ml, about 3.5 μg/ml, about 4 μg/ml, about 4.5 μg/ml, about 5 μg/ml, about 5.5 μg/ml, about 6 μg/ml, about 6.5 μg/ml, about 7 μg/ml, about 7.5 μg/ml, about 8 μg/ml, about 8.5 μg/ml, about 9 μg/ml, about 9.5 μg/ml, or about 10 μg/ml), glucose (between 2 mM and 10 mM, e.g., about 2 mM, about 2.5 mM, about 3 mM, about 3.5 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, or about 10 mM), Triiodothyronine (T3) (between 0.3 ng/mL and 1 ng/mL, e.g., about 0.3 ng/mL, about 0.4 ng/mL, about 0.5 ng/mL, about 0.6 ng/mL, about 0.65 ng/mL, about 0.7 ng/mL, about 0.8 ng/mL, about 0.9 ng/mL, about 1 ng/mL), Prolactin (PRL) (between 10 ng/mL and 30 ng/mL, e.g., about 10 ng/mL, about 15 ng/mL, about 20 ng/mL, about 23 ng/mL, about 25 ng/mL, about 28 ng/mL, about 30 ng/mL), IGF-I (between 1 ng/mL and 10 ng/mL, e.g., about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL) or a combination thereof. In a specific embodiment, the medium comprises 10 ng/ml FGF-2, 100 μg/ml heparin, 0.1% human serum albumin, 10 μg/ml human transferrin, 50 μM Ethanolamine, 50 μM Phosphoethanolamine, 6.7 μg/ml sodium selenite, 5.5 mM glucose, 0.65 ng/mL Triiodothyronine (T3), 23 ng/mL Prolactin (PRL), and 5 ng/mL IGF-I.

In some embodiments, the co-culturing is carried out on a matrix. The present disclosure identifies essential extracellular matrix components, i.e., laminin, entactin and collagen IV, which when used to culture reprogrammed endothelial cells results in the formation of stable and functional three-dimensional artificial vessels in vitro and in vivo without the use of pericytes, perfusion and cumbersome scaffolds. Therefore, in certain embodiments, the matrix is composed of extracellular matrix components, such as laminin, entactin and/or collagen.

In some embodiments, a matrix for use coculturing can include laminin and entactin at a combined concentration of at least about 5 mg/mL. As laminin and entactin can bind to each other and form a complex, a matrix for use in the present methods can include a complex of laminin and entactin. For example, the matrix can include at least 5 mg/mL of a complex of laminin and entactin. In an exemplary embodiment, the coculturing is carried out on a matrix including laminin and entactin at a combined concentration of at least 5 mg/mL, at least 6 mg/mL, at least 7 mg/mL, at least 8 mg/mL, at least 9 mg/mL, at least 10 mg/mL, at least 11 mg/mL, at least 12 mg/mL, at least 13 mg/mL, at least 14 mg/mL or at least 15 mg/mL. In specific embodiments, the matrix used in the present methods is composed of a combination of laminin, entactin and collagen IV (L.E.C.). For example, the coculturing can be carried out on a matrix containing at least about 5 mg/mL of laminin and entactin, and at least about 0.2 mg/mL collagen IV to form long-lasting, functional three-dimensional artificial blood vessels. In some embodiments, the L.E.C. matrix combination comprises at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, or at least 1 mg/mL collagen IV. In a specific embodiment, the L.E.C. matrix is composed of between a combined concentration 9 mg/mL and 13 mg/mL of laminin and entactin, and between 0.2 mg/mL and 0.5 mg/mL of collagen IV. In a specific embodiment, the L.E.C. matrix is composed of laminin and entactin at a combined concentration of about 11 mg/mL and about 0.2 mg/mL collagen IV.

In some embodiments, the coculturing of the β-cells and the endothelial cell is performed in a bioreactor or a microfluidic device. In some embodiments, the microfluidic device is capable of transporting human blood or other specialized media, solutions, chemicals or biopharmaceutical drugs or reagents. In some embodiments, the coculturing of the β-cells and the endothelial cell is performed in a 3D gel. There is no requirement for any specific manner by which the β-cells and the EC cell are combined or mixed. The mixture of β-cells-EC can self-assemble into a 3D structure, i.e., the vascularized the β-cell organoid. See, also, Zhou Q, and Melton D A. *Nature;* 557(7705):351-8 (2018); Hebrok M. *Cold Spring Harb Perspect Med;* 2(6):a007674 (2012), incorporated herein by reference.

In some embodiments, the coculturing is done for at least 1 week, at least 10 days, at least 2 weeks, at least 18 days, at least 3 weeks, at least 24 days, at least 4 weeks, at least 32 days, at least 5 weeks, at least 38 days, at least 6 weeks, at least 45 days, at least 7 weeks, at least 52 days, at least 8 weeks, but not more than 4 months or not more than 3 months. In some embodiments, the coculturing is performed for about 3 weeks, about 24 days, about 4 weeks, about 32 days, about 5 weeks, about 38 days, about 6 weeks, about 45 days, about 7 weeks, about 52 days, or about 8 weeks.

In some embodiments, the β-cells and the endothelial cell can be cocultured for an additional period of time under conditions wherein the endothelial cell does not express the ETV2 transcription factor. In some embodiments, the β-cells and the endothelial cell are cocultured for an additional period of time under conditions wherein the expression of the ETV2 transcription factor in the endothelial cell is transient or reduced (turned down). In some embodiments, the additional period of time is at least 5 days, at least 6 days, at least 7 days, at least 8 days, at least 9 days, at least 10 days, at least 11 days, but no more than 18 days, not more than 16 days, or not more than 14 days.

In some embodiments, the β-cells and the endothelial cell are cocultured until a β-cell organoid with sufficient vascularization is achieved. In some embodiments, sufficient vascularization is measured by the fold increase in the amount of glucose-stimulated insulin secretion. In some embodiments, a vascularized β-cell organoid produces at least 2 folds, at least 3 folds, at least 4 folds, at least 5 folds more insulin in response to glucose as compared to a β-cell organoid that have not been vascularized (e.g., a β-cell organoid that was not cocultured with any other endothelial cell or a β-cell organoid cocultured with a wild type endothelial cell that does not express an exogenous nucleic acid encoding the ETV2 transcription factor). In some embodiments, increase in glucose-stimulated insulin secretion of a β-cell organoid is measured by incubating the organoid with low glucose (e.g., between about 1 mM and about 4 mM) to determine the basal insulin secretion, and then incubating the organoid with high glucose (about 16.7 mM) to determine the stimulated insulin secretion.

Vascularized β-Cell Organoid

In some embodiments, the vascularized β-cell organoids of the present disclosure comprise β-cells and vasculature formed by the endothelial cells expressing an exogenous nucleic acid encoding the ETV2 transcription factor. In some embodiments, the vascularization comprises the formation of an artery, a vein, a capillary, an arteriole, a venule, lymphatic vessels, or a combination thereof, within the pancreatic islet. In some embodiments, a vascularized β-cell organoid includes a network, a 2-dimensional or 3-dimensional network, of vascular vessels formed by the endothelial cells ("arborization of the β-cell organoid").

In some embodiments, the vascularized β-cell organoid comprises β-cells and vasculature (blood vessels, e.g., arteries, veins) that allows delivery of nutrients to the pancreatic islet and that allows removal of the insulin produced by the pancreatic islet. In some embodiments, the vascularized β-cell organoid is functional in glucose sensing and insulin production in tissue culture (in vitro) or when administered to a host (in vivo). In some embodiments, the vasculature formed within a vascularized β-cell organoid in vitro is capable of connecting with host vessels in vivo and/or promoting further vascularization of the β-cell organoid in vivo. In some embodiments, the vascularized β-cell organoid can stay functional in glucose sensing and insulin production in vivo for an extended period of time. As used in, the phrase "extended period of time" refers to at least 2 weeks, at least 3 weeks, at least a month, at least 6 weeks, at least 2 months, at least 10 weeks, at least 3 months, at least 4 months, at least 5 months, at least 6 months or at least a year.

Methods for Treating a Subject in Need by Administering Vascularized Pancreatic Islets In another aspect, the disclosure is directed to a method of treating a subject in need comprising administering to the subject in need a vascularized pancreatic islet as described hereinabove. By "treating" it is meant to ameliorate or eliminate the severity of the symptoms (e.g., symptoms of diabetes), or reduce the risk or delay the onset of developing the disease (e.g., diabetes).

In some embodiments, the pancreatic islet is autologous to the recipient subject. In some embodiments, the pancreatic islet is allogeneic to the recipient subject; in some such embodiments, the pancreatic islet is genetically matched to the recipient subject.

In some embodiments, the administration of the vascularized pancreatic islet is achieved by subcutaneous transplantation, direct injection into endocrine organs, liver or other relevant organs. In some embodiments, the administration of the vascularized pancreatic islet is achieved by surgical or catheter implantation. In some embodiments, the administration of the vascularized pancreatic islet is achieved by infusion through an intravascular route.

In some aspects, the administered vascularized pancreatic islet is functional in vivo. As used herein, the term "functional" refers to an islet that can sense changes in blood sugar and release insulin into bloodstream in response to an increase in blood glucose levels to result in normoglycemia (normal blood glucose levels). In some embodiments, the vasculature formed within a vascularized pancreatic islet in vitro connects with host vessels in vivo and/or promoting further vascularization of the islet in vivo. In some embodiments, the administered vascularized pancreatic islet remains engrafted and functional for at least 2 weeks, at least 3 weeks, at least a month, at least 6 weeks, at least 2 months, at least 10 weeks, at least 3 months, at least 4 months, at least 5 months, at least 6 months or at least a year.

Methods for Treating a Subject in Need by Administering Vascularized β-Cell Organoids In another aspect, the disclosure is directed to a method of treating a subject in needs comprising administering to the subject in need a vascularized β-cell organoid as described hereinabove.

In some embodiments, the β-cells used in the present methods to make vascularized β-cell organoids are autologous to the recipient subject. In some embodiments, the β-cells are allogeneic to the recipient subject; in some such embodiments, the β-cells are genetically matched to the recipient subject.

In some embodiments, the administration of the vascularized β-cell organoid is achieved by subcutaneous transplantation, direct injection into endocrine organs, liver or other relevant organs. In some embodiments, the administration of the vascularized β-cell organoid is achieved by surgical or catheter implantation. In some embodiments, the administration of the vascularized β-cell organoid is achieved by infusion through an intravascular route.

In some aspects, the administered vascularized β-cell organoid is functional in vivo. As used herein, the term "functional" refers to β-cell organoid that can sense changes in blood sugar and release insulin into bloodstream in response to an increase in blood glucose levels to result in normoglycemia (normal blood glucose levels). In some embodiments, the vasculature formed within a vascularized pancreatic islet in vitro connects with host vessels in vivo and/or promoting further vascularization of the β-cell organoid in vivo. In some embodiments, the administered vascularized β-cell organoid remains engrafted and functional for at least 2 weeks, at least 3 weeks, at least a month, at least 6 weeks, at least 2 months, at least 10 weeks, at least 3 months, at least 4 months, at least 5 months, at least 6 months or at least a year.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present methods are further supported and illustrated by the following non-limiting examples.

EXAMPLES

Example 1

Previous reports have studied co-culture of ECs with R cells (Kao D I et al., *Stem cell reports;*4(2):181-9, (2015); Rutter G A et al., *Biochem J;*466(2):203-18, (2015); Nikolova G et al., *Dev Cell;*10(3):397-405, (2006); Lammert E et al., *Mech Dev;* 120(1):59-64, (2003)). However, these studies used generic adult ECs, and attempts to vascularize purified whole islets in vitro were not successful, with the majority of the β-cells within the islets dying. This suboptimal outcome is likely due to the use of generic mature adult human ECs, which lack the capacity to establish long-lasting islet-specific EC niche. In addition, adult human non-islet ECs lack the potential to arborize or interact with purified human islet cells, to sustain their survival and functionality. This in vitro deficiency of generic ECs could lead to a more profound impaired function of the islets as these adult ECs do not form durable long-lasting vessels that can anastomose to the pre-existing vessels. To generate a malleable endothelial vascular niche in vitro from the adult ECs is a major challenge in that mature adult ECs, because autologous or genetically matched adipose ECs, lack the capacity to establish long-lasting lumenized capillaries. Moreover, these ECs fail to adapt to various organotypic niches, such as intra-islet that are introduced into. R-VECs could also establish interconnected vascular network within a large volume 15 microliters of microfluidic devices that can transport full compliment of human peripheral blood containing innate and immune cells. This will enable assessment of autoimmunity to islet cells as well.

The inventors have discovered that introducing the transcription factor ETV2 into adult human autologous or genetically matched allogeneic ECs converts these ECs into adaptable durable reprogrammed, or reset ECs (R-VECs) for tissue-specific organogenesis. The inventors have shown in three-dimensional (3D) cultures of reprogrammed or reset vascular ECs (R-VECs) in defined extracellular matrix (composed of Laminin, entactin, Collagen, LEC) can readily vascularize commercially procured human islets. Employing these malleable R-VECs, the inventors also show that interaction of R-VECs improve their insulin secretion by the β-cells in response to glucose elevation.

In short, the inventors have developed a technology to manufacture adult human adaptable, durable and hemodynamically ECs that can vascularize human islets with high efficiency. This was enabled by the transient expression of the embryonic restricted ETS-transcription factor ETV2 along with defined extracellular matrix, molecularly and structurally "reset" adult human tissue-specific mature ECs to adaptable vascular ECs (R-VECs). As Matrigel cannot be used in patients, the inventors identified the minimum components of extracellular matrix, Laminin-Entactin-CollagenIV (LEC) that enable long-lasting tubulogenesis of R-VECs and encapsulation with islets for transplantation.

These malleable and durable as well as adaptable R-VECs are capable of remodeling into long-lasting functional compliant as well as perfusable vascular network that last for more than 8 weeks. Importantly, during 3D co-culture, R-VECs efficiently arborized human islet during 3D co-culture microfluidic devices in about a week, when CTRL-ECs had little interaction with human islets. By examining the islet function as glucose stimulated insulin secretion (GSIS), the inventors found that R-VECs not only physically interact with islet cells but also actively improve islet function, with beneficial effects lasting for at least 2 weeks. In the large volume microfluidic devices, R-VEC vascularized human islet could sense glucose and produce insulin at the outlet. This enables assessing and augmenting the functionality of the procured islets as well as set the stage for implantation in vivo for treatment of diabetes.

Example 2: ETV2 Enables Self-Assembly of ECs into Long-Lasting, Stable Patterned Human Vessels In Vitro Mature post-natal and adult human ECs organize into nascent vascular networks in Matrigel in vitro or in vivo, yet these vessels are not stable, lack a sustainable large pore lumen in vitro, have limited remodeling potential, and regress within a few days. In addition, organ-on-chip or vascular scaffolding approaches often require separation by layer(s) of semipermeable synthetic biomaterials impairing intimate physical cell-cell interaction between EC and non-vascular cells, thereby impeding cell-contact dependent co-adaptive EC remodeling (Huh, D. et al., *Science* 328, 1662-1668, (2010); Blundell, C. et al., *Lab Chip* 16, 3065-3073, (2016)). Moreover, mature naïve ECs fail to self-assemble into extended vascular networks in large perfusion microfluidic chambers, limiting their vascular plexus volume to approximately 2 microliters (Chen, M. B. et al., *Nat Protoc* 12, 865-880, (2017); Campisi, M. et al., *Biomaterials* 180, 117-129, (2018); Phan, D. T. T. et al., *Lab Chip* 17, 511-520, (2017)). The inventors hypothesized that enforced re-expression of ETV2 in mature human ECs will enable these cells to develop durability and patterning plasticity to form 3D vessels, as well as acquire enhanced cellular affinity and adaptability for non-vascular cells in vitro and in vivo.

Indeed, ETV2 expressing human ECs (Reset-VECs, R-VECs) transitioned into 3D vessels through three stages (FIG. 1A). At the first induction stage (days 1-14), ETV2 upregulates vasculogenic and tubulogenic factors. During the $2^{nd}$ remodeling stage (days 14-21) the R-VECs self-assemble into organized geometrically patterned lumenized vessels. At the $3^{rd}$ stabilization stage, R-VECs are no longer motile or proliferative and transition into durable and adaptable vessels. In contrast, naïve human ECs were unable to transition through these stages to form durable vessels, even when different standard medium formulations (e.g., Stem Span, EGM2 or EC media) were used.

Figure 1B:
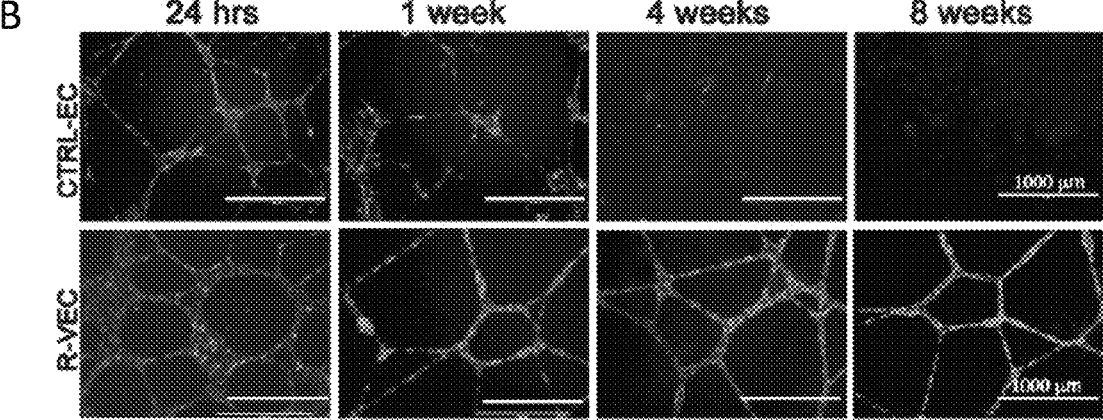
Figure 1F:
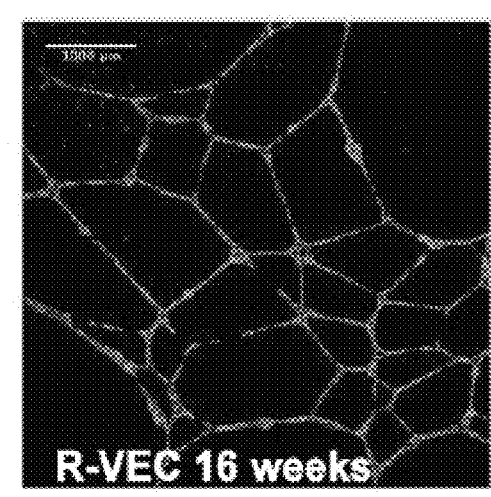
Figure 1G:
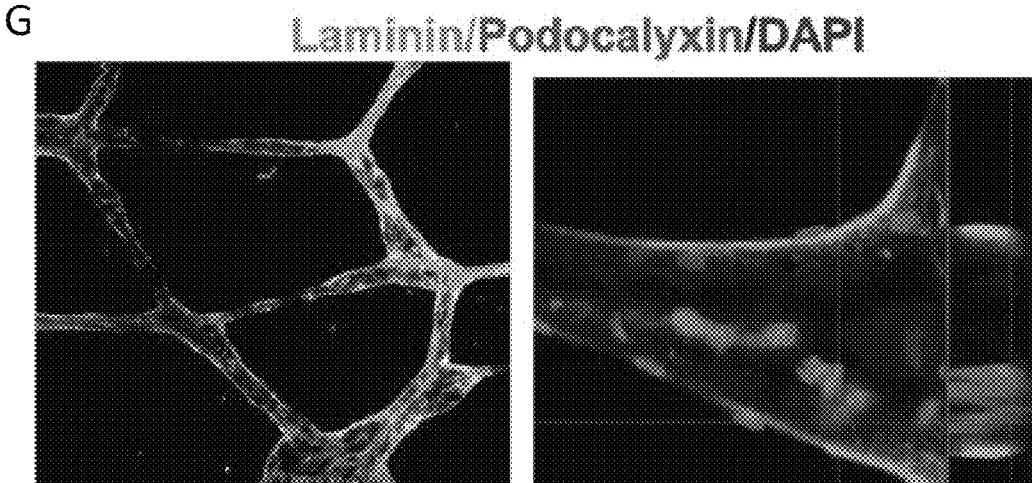

Human umbilical vein EC (HUVECs) expressing ETV2 showed a 50 fold increase in vessel area formation over 8 weeks (FIGS. 1B-1C). This capacity for ETV2 to induce R-VECs was not restricted to HUVECs. All tissue-specific adult human mature EC populations isolated from adipose, cardiac, aortic, and dermal tissues (purified from human subjects ages 4 to 50+) transduced with ETV2, gave rise to R-VECs with consistently durable branched vascular networks (FIGS. 1D-1E). The inventors were able to maintain patterned R-VEC vessels in vitro for over 16 weeks (FIG. 1F). Proper lumen formation is required for functional 3D vessels. Confocal microscopy indicated that R-VECs formed continuous uninterrupted network of vessels. These capillary-like large bore tubes manifested proper polarization with podocalyxin expressed on the apical side and laminin on the basal side (FIG. 1G).

Atomic force microscopy (AFM) is an ideal tool to assess the structural stiffness of the R-VECs. Both stage 1 induction adult adipose ECs and HUVECs transduced with ETV2 were less stiff than the control non-ETV2 transduced cells, a property that is necessary for lumen formation during vasculogenesis. Furthermore, although smooth muscle cells are not essential for R-VEC lumen formation, these perivascular cells can be readily recruited to the R-VEC generated vessels, when introduced during the stabilization stage. Therefore, R-VECs self-organize into vessels that phenocopy the 3D structure of lumenized capillaries.

As EC proliferation can modulate the degree of lumen formation, the inventors also measured cell proliferation over time by EdU labeling. When grown in flat two dimensional (2D) cultures, control and stage 1 induction phase ETV2-transduced ECs proliferated at similar rates. During the stage 2 remodeling phase, control ECs underwent proliferation at a faster rate than R-VECs. At the stage 3 stabilization phase, R-VECs reached homeostasis and EC turnover was much lower than in 2D cultures.

To determine whether the capacity of ETV2 transduced human ECs to spontaneously self-assemble into lumenized tubes is a common attribute of other ETS-family of transcription factors, the inventors transduced human ECs with another ETS transcription factor, ETS1, that plays a major role in capillary development. Moreover, to examine whether ETV2 primarily confers vascular functions by increasing the survival of ECs, the inventors transduced mature human ECs with constitutively active myristoylated-AKT1 (myrAKT1). Neither ETS1 nor myrAKT1 activation drove the generation of durable vessels as ETV2 did. Thus, ETV2 uniquely confers adult human ECs with the capacity to self-assemble into durable patterned large bore vessels without the constraints of artificial scaffolds, pericyte coverage, or enforced shear stress.

The inventors set to resolve whether ETV2 expression levels influenced the efficient generation of lumenized vessels. R-VEC single cell clones at stage 1 induction phase were isolated by FACS and mRNA abundance measured by qRT-PCR. The inventors divided the clones into low-ETV2, mid-ETV2 and high-ETV2 expression patterns based on ETV2 mRNA levels during the stage 1 induction phase. ETV2 RNA levels tightly correlated with ETV2 protein levels. The clones with mid-ETV2 levels gave rise to vessels of significantly higher density and stability. Next, the inventors quantified the ETV2 mRNA and protein levels over time in heterogeneous non-clonal generated R-VECs. ETV2 protein levels peaked during the stage 2 remodeling phase. Subsequently, ETV2 protein levels were downregulated by over 90% during the stage 3 stabilization phase, as compared to the stage 1 induction phase. ETV2 protein levels were restored by six-fold in the presence of a proteasome inhibitor (MG132), indicating post-translational modifications, such as ubiquitination, play a role in downregulating ETV2 protein levels over time. Thus, ETV2 induces R-VEC formation, but only low levels of ETV2 were detected once the vessels were stabilized. This observation raised the notion that transient ETV2 expression might be sufficient to initiate and sustain lumenized R-VECs.

To test this possibility, the inventors used a reverse tet-transactivator (rtTA)-doxycycline (dox) inducible system, where the presence of doxycycline induces ETV2 expression (hereafter referred to as iR-VECs). The inducible system was tested to be efficiently turned off, with both ETV2 mRNA and protein levels successfully downregulated upon doxycycline removal. ETV2 was expressed for two weeks by doxycycline supplementation during the stage 1 induction and iR-VEC cells were then allowed to form networks during vessel formation assay. Next, doxycycline was removed at different time points: day 0 (onset of stage 2 remodeling phase), 1 week after the initiation of stage 2 remodeling phase, or 4 weeks after the initiation of stage 2 remodeling phase. Notably, ETV2 expression was required for only a minimum of 1 week after the start of the stage 2 remodeling stage, to enable the formation of lumenized stage 3 stable vessels, and was dispensable thereafter. Indeed, iR-VECs sustain their vascular stability even after ETV2 is shut down as shown by both vessel quantification and electron microscopy.

Example 3: R-VECs Form Vessels in a Defined Matrix of Laminin, Entactin, CollagenIV (L.E.C)

Figure 1H:
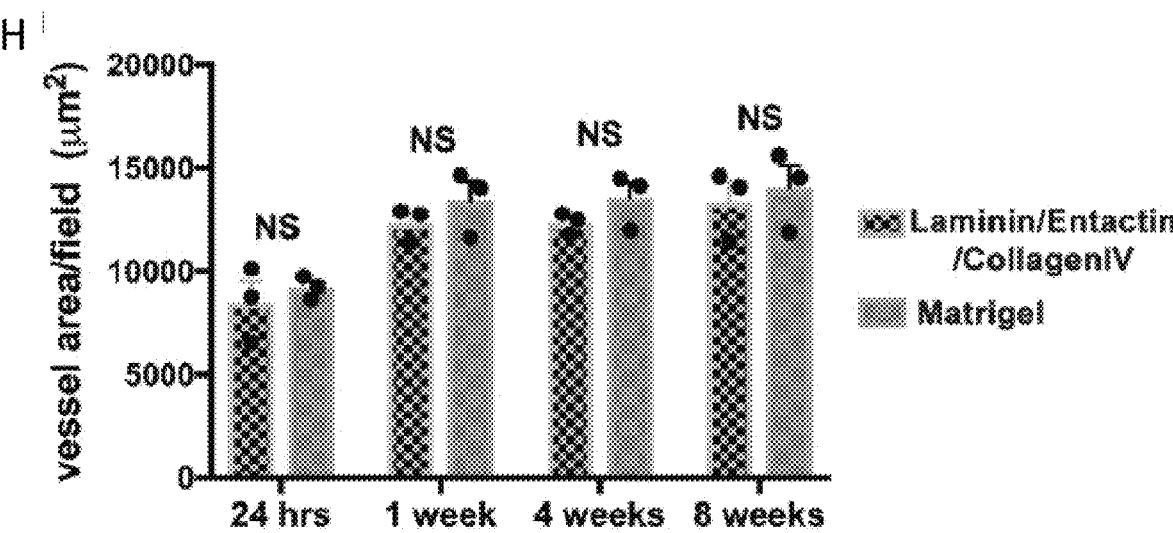
Figure 1I:
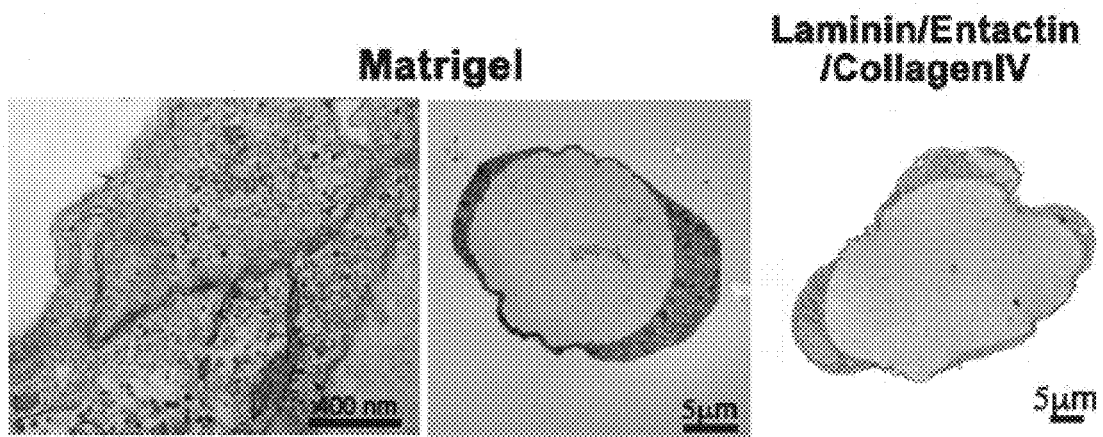

Current approaches for in vitro vascular patterning and organoid formation require the use of a crude preparation of extracellular matrix, such as Matrigel. Matrigel contains numerous digested matrix components rendering it difficult to isolate factors regulating durable vessel formation or their interaction with organoid cellular components. By screening numerous combinations of vascular extracellular matrices, the inventors identified a stoichiometrically defined matrix of Laminin, Entactin, and CollagenIV (L.E.C) that is sufficient for the self-assembly of stable lumenized ETV2-driven vessels similar to those formed when using Matrigel. Notably, control naïve human ECs did not form stable vessel networks on L.E.C. R-VEC vessels generated on both L.E.C and Matrigel showed similar durable vessel area and branching to 8 weeks (FIG. 1H). Electron microscopy revealed that stage 3 R-VECs formed vessels with open patent lumens and tight junctions on both L.E.C. and Matrigel (FIG. 1I). A neutralizing antibody against the integrin ITGβ1 abrogated vessel formation in L.E.C, indicating that interaction of integrins expressed on R-VECs with the L.E.C matrix is important for tube formation. Employing defined matrix components could facilitate identification of the peri-vascular interactions with adhesion molecules and chemokines that regulate tubulogenesis.

Figure 1J:
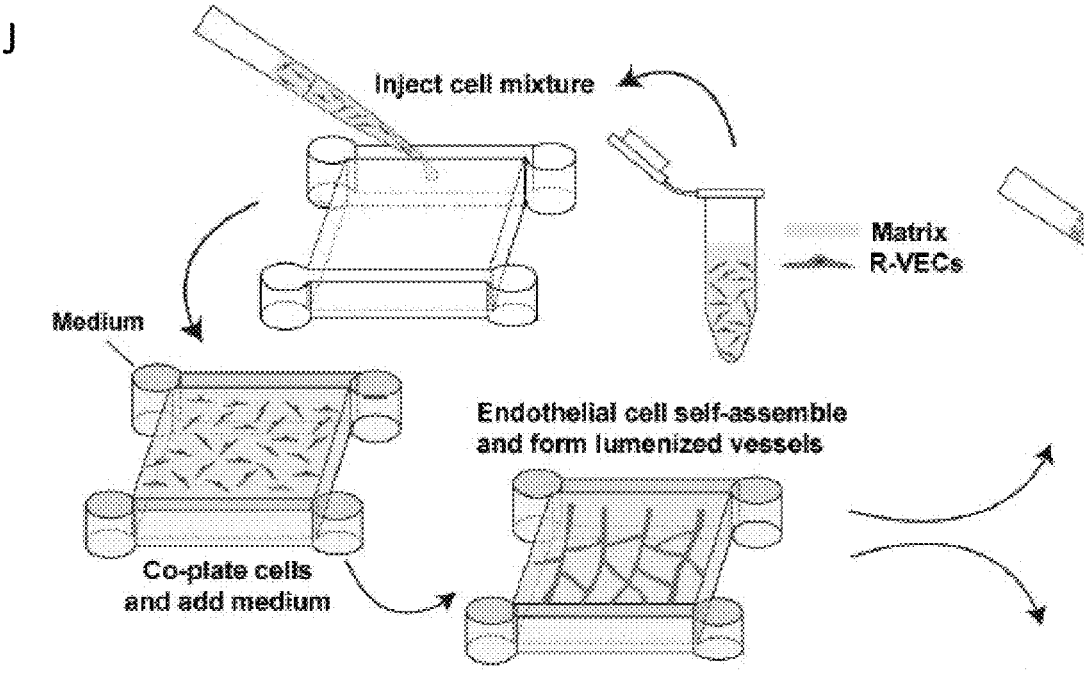
Figures 1K, 1L:
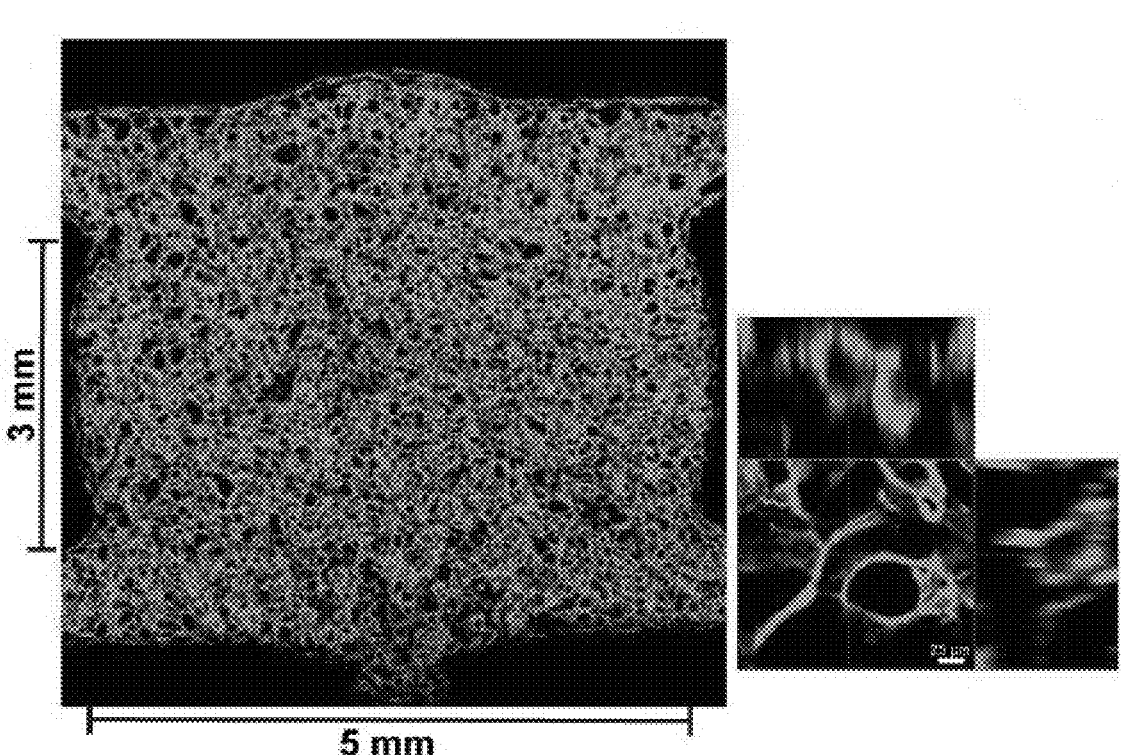

Example 4: R-VECs Self-Organize into Stable Lumenized and Perfusable Vessels in Large Volume Microfluidic Devices that Sustain Hemodynamic Laminar Flow of Whole Human Peripheral Blood Perfusion capacity and the ability of R-VEC vessels to sustain laminar flow were tested by seeding the cells in a 3×1×1 millimeter³ microfluidic device with a volume of 3 microliters (FIG. 1J). Within 3 to 5 days, R-VECs organized and self-assembled into lumenized vessels while control cells failed to generate vessels (FIG. 1K). Once a vessel network was fully established, by day 6, the inventors cycled mCherry-labeled beads (4 μm) through the inlet and the R-VEC vessels enabled the flow of the beads into the outlet channel of the device. The inventors did not observe flow of beads across the channels with control non-ETV2 transduced ECs (FIG. 1K).

In anticipation of accommodating relatively large organoids and tissue explants, such as pancreatic islets or epithelial and tumor organoids, the inventors designed a microfluidic device with a larger perfusion chamber size of 5×3×1 millimeters³ (15 microliters total volume), capable of accommodating >60,000 stage 1 R-VECs within a fibrin gel matrix. After 1 to 3 days of implantation into the device, R-VECs self-assembled into continuous and extensive multi-layered and patterned vascular plexus spanning >3 millimeters connecting the inlet channel to the outlet channel of the device (FIG. 1L).

Notably, the R-VEC vessels self-organized into hemodynamically stable vessels enabling the transit of heparinized whole human peripheral blood, (freshly obtained through phlebotomy), containing the full complement of white and red blood cells as well as platelets and intact plasma (FIG. 1M). During perfusion of whole blood cells, R-VEC capillary network remained patent and manifested minimal leakiness to RBC, platelets and WBC allowing the homogenous flow of blood from inlet to the outlet of the microfluidic chamber. Thus, R-VECs self-assemble into a continuous capillary network capable of sustaining hemodynamically microfluidic perfusion in large volume vascular chamber without the requirement for perivascular support, the limiting confines of artificial scaffolds or supraphysiological use of angiogenic growth factors.

Figure 2A:
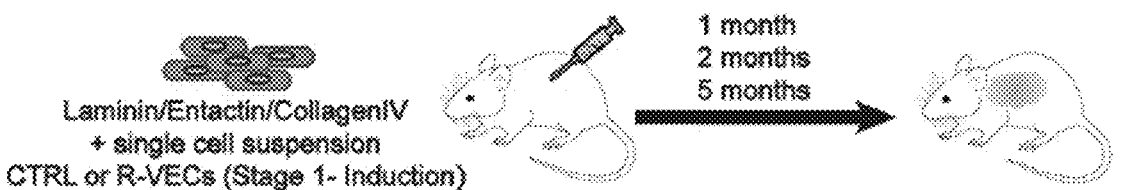
FIGS. 2A-2H. R-VECs organize into robust, long-lasting and anastomosed vessels in vivo. (A) A schematic of in vivo plug experiment where fluorescently labeled CTRL-ECs or stage 1 induction R-VECs were subcutaneously injected as a single cell suspension in Laminin, Entactin, CollagenIV (L.E.C) mixture in SCID beige mice. Formation of perfused vessels was assessed over several time points. (B) Representative images of CTRL-EC and R-VEC plugs at 2 months (n=3 mice). (C) Whole mount confocal images of L.E.C plugs isolated at a 2 month time point and at a 5 month time point of R-VEC plugs compared to CTRL-EC plugs (n=3 mice). Anti-human VEcadherin (VEcad) antibody conjugated to Alexa647 (white) was injected retro-orbitally in the mice eight minutes before sacrifice to evaluate for the perfusion and anastomosis of human vessels to the mouse vasculature. Scale bar=100 μm. (D) Quantification of vessel area measured as the percentage of EC fluorescence intensity in several sections (12-18 sections) at one, two and five months. Two-way ANOVA with Sidak's post-test (n=3 mice/ condition, 1 month p<0.0001, 2 months p=0.0002, 5 months p<0.0001)). (E) Sections of whole L.E.C. Plug for CTRL-EC or R-VEC 2 months post implantation stained for mouse ECs with an anti-mouse endomucin antibody. Human specific VEcad antibody was injected intravitally right before sacrifice, identifying properly organized human R-VECs anastomosing with mouse Endomucin$^+$ vessels. (F) Sections of R-VEC plugs in L.E.C. 2 months post-implantation post-stained with anti-mouse SMA antibody. Human specific VEcad antibody was injected intravitally right prior to sacrifice. (G) In vivo plug assay, where mice were subcutaneously injected with either control ECs (HUVECs transduced only with tTA lentivirus) or stage 1 doxycycline-inducble-ETV2 ECs (iR-VECs: HUVECs transduced with both tTA and inducible ETV2 lentivirus) in L.E.C. One group of mice was on doxycycline (ETV2 continuously on) and another group of mice was on doxycycline food diet for 1 week (ETV2 on) and then switched to regular food (ETV2 off). All mice were sacrificed 2 months post-implantation. Red indicates the mCherry-labeled human ECs, white: Anti-VEcad antibody that was retro-orbitally injected before sacrificing the mice. Scale bar=100 μm. (H) Quantification of vessel area for tTA only plugs, mice on dox for 1 week, and mice continuously on doxycycline diet (ETV2 on). All mice were sacrificed 2 months post-implantation. One way ANOVA, with Tukey's post-test (n=3-4, tTA vs. iR-VEC dox 1 week p=0.0028, tTA vs. iR-VEC dox p=0.0046, iR-VEC dox 1 week vs iR-VEC dox p=0.0028). Data are represented as mean+/−S.E.M. ns=not significant; *<0.05, <0.01, and *<0.001 indicate statistical significance.
Figure 2B:
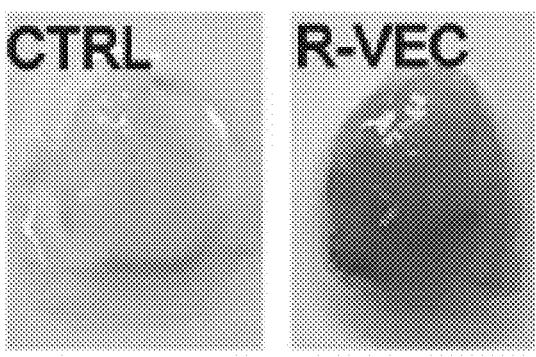
Figure 2C:
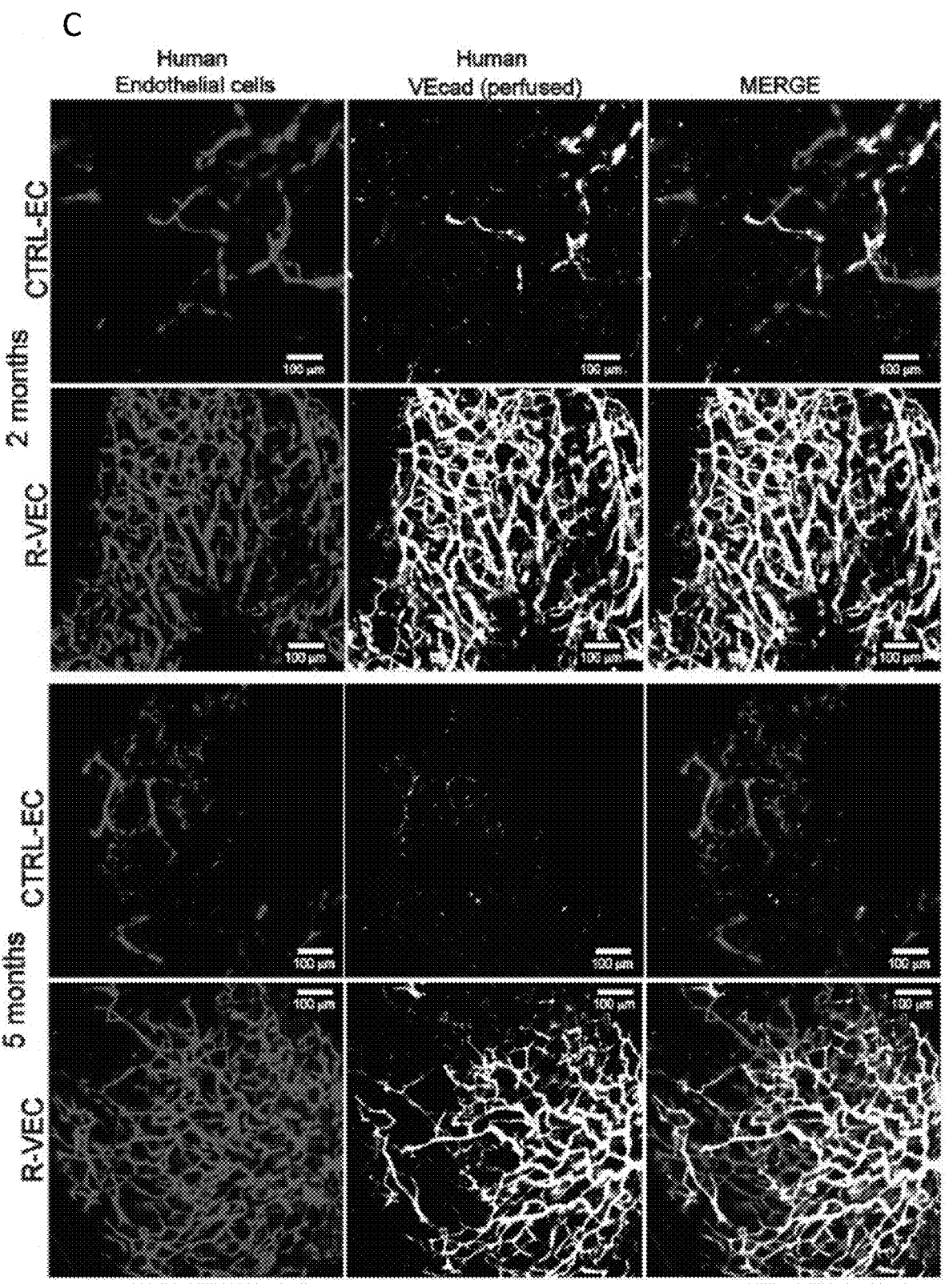
Figure 2D:
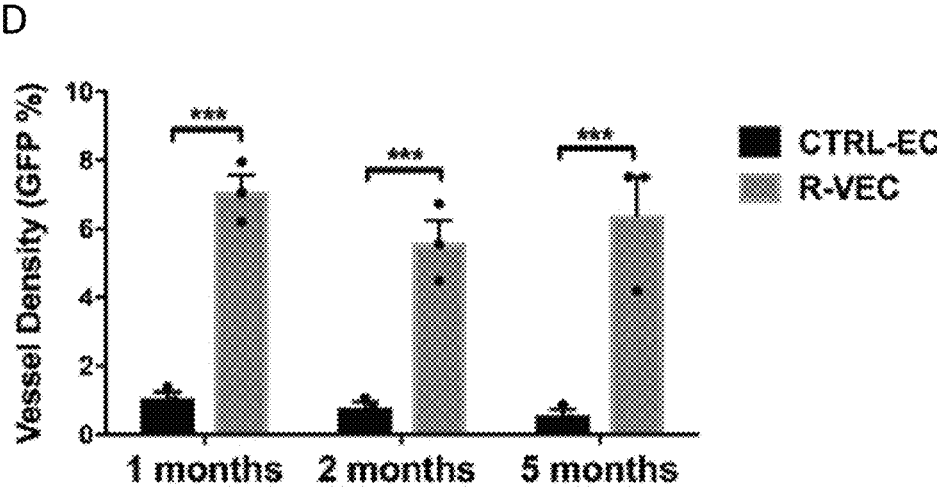

Example 5: R-VEC Vessels Form Stable Long-Lasting Functional Vessels in In Vivo Plug Implants To assess whether R-VECs could sustain functional patterned vessels in vivo, SCID-beige mice were implanted subcutaneously with mCherry or GFP-labeled control human ECs or R-VECs suspended in L.E.C matrix. One to five months post implantation, the degree of vessel persistence of R-VEC or human adipose R-VEC, and anastomosis to the pre-existing murine circulation was assessed by anti-human VEcadherin (VEcad) antibody intravital staining (FIG. 2A-2C). R-VEC loaded plugs were visibly more vascularized than control non-ETV2 cell plugs (FIG. 2B). Both whole mount confocal pictures and post sectioning of the plugs, revealed much higher vessel lumen area, organization and patterning in the R-VEC implanted plugs as compared to control non-ETV2 EC plugs (FIG. 2C-2D). Human vessel area was significantly higher in R-VEC plugs than control EC plugs at all time-points (n=3 mice/group per time point) (FIG. 2D).

Figure 2E:
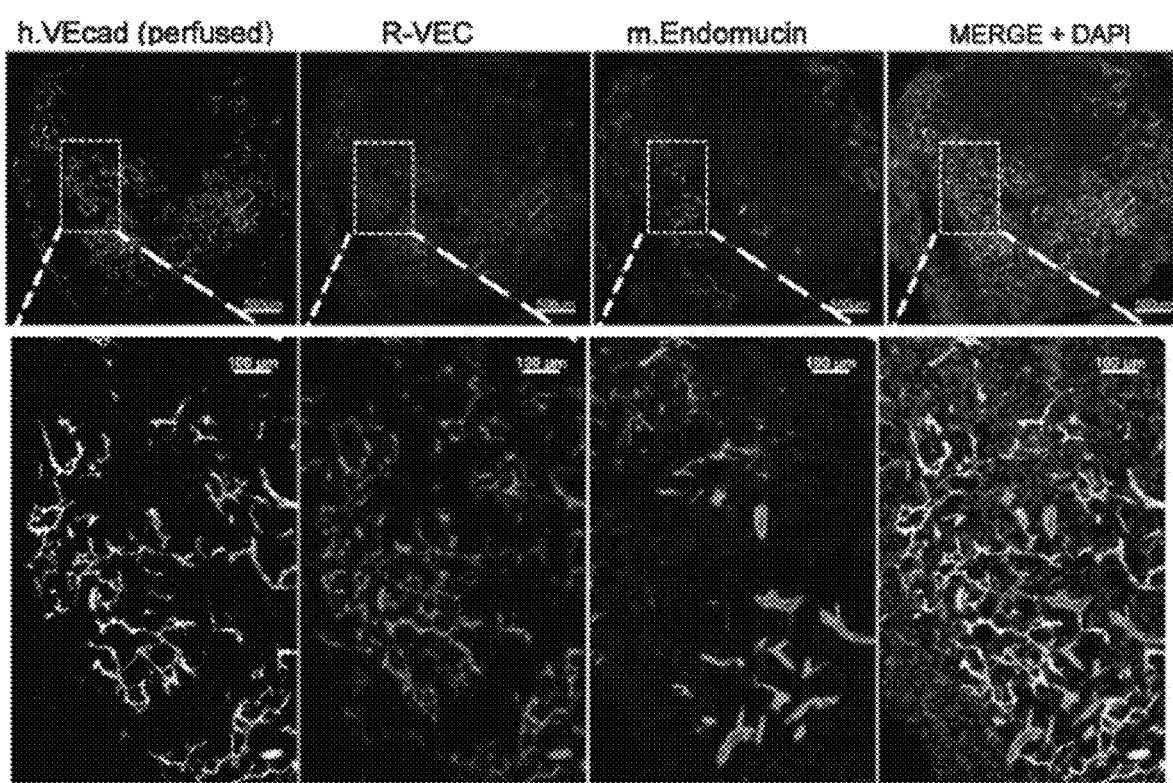
Figure 2F:
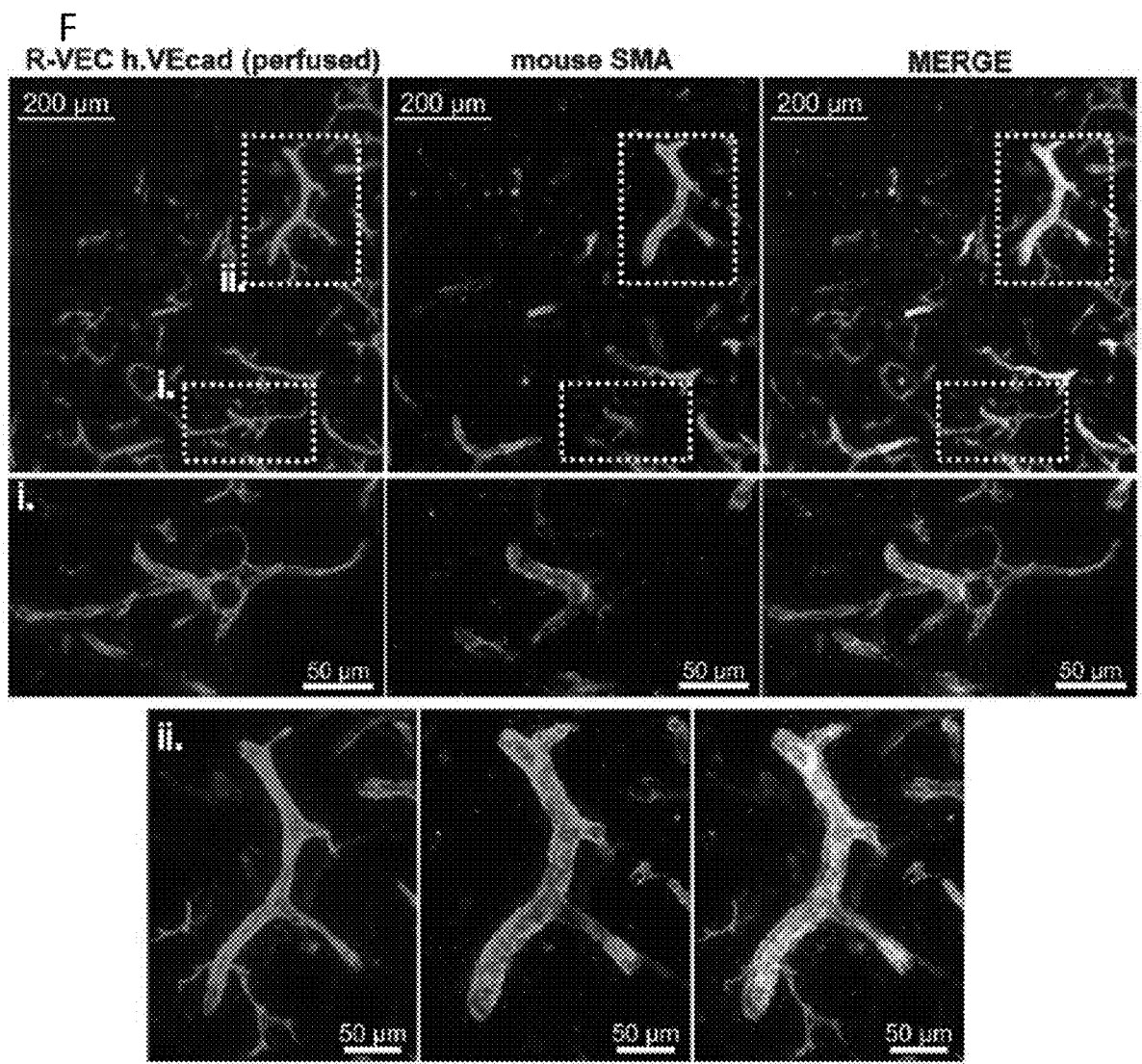
Figure 2G:
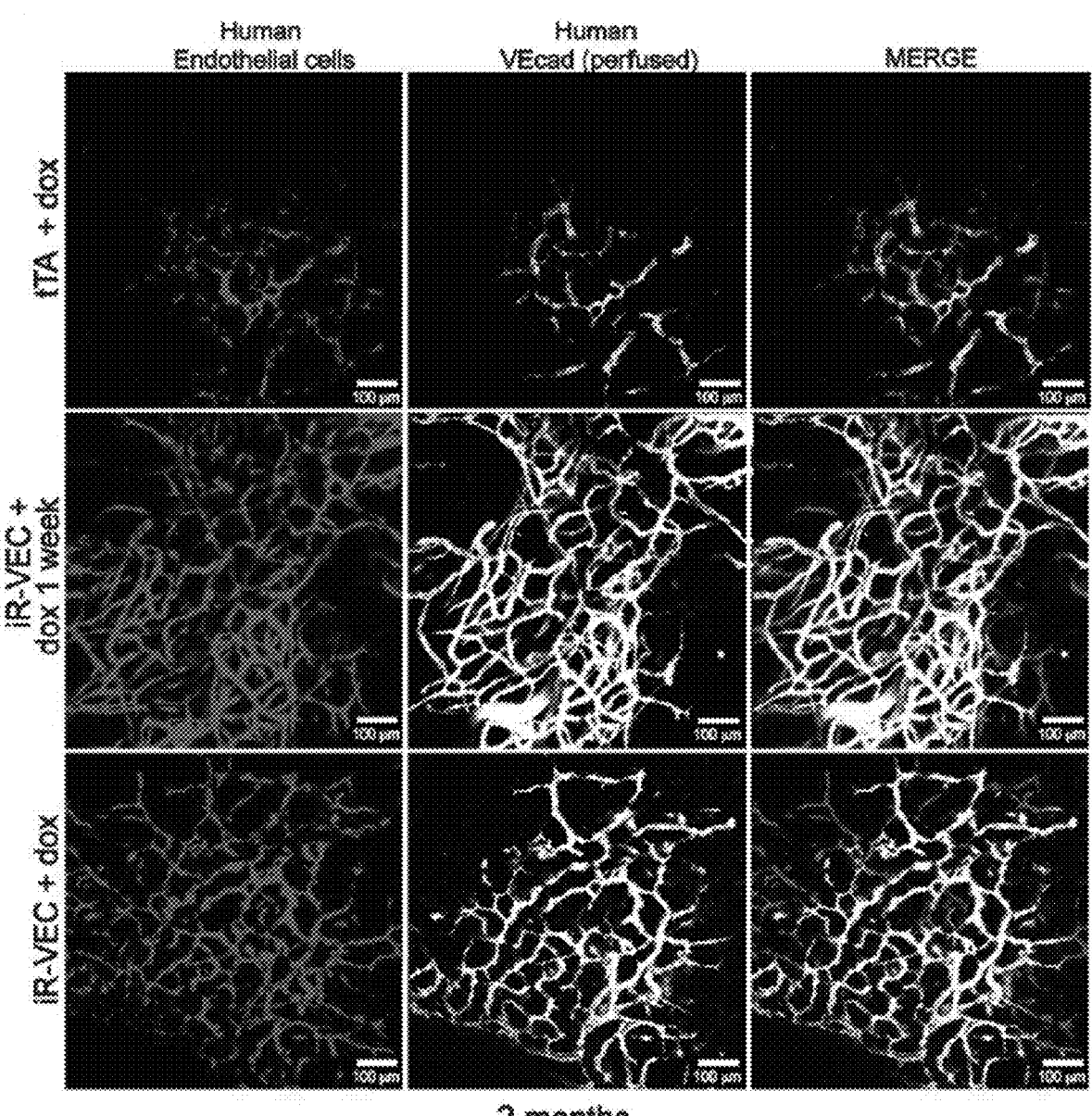
Figure 2H:
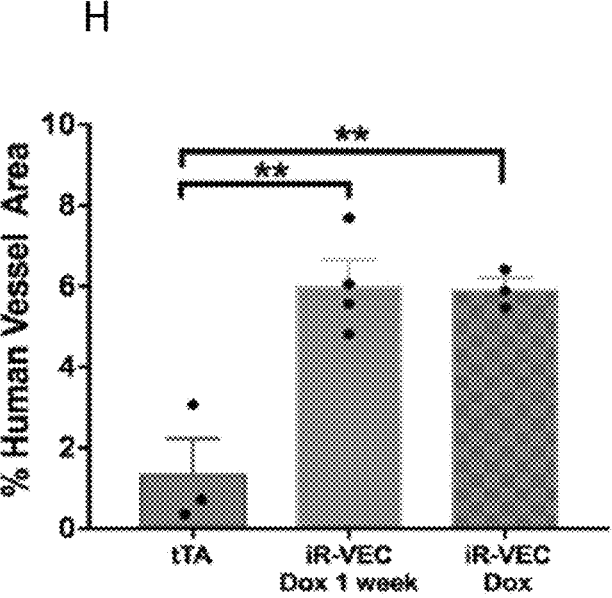

In addition, intravital injection of mice with an antibody directed to human VEcad showed that R-VEC vessels anastomose to the Endomucin⁺ mouse vasculature, establishing mosaic perfused vessels throughout the plug (FIG. 2E). R-VEC vessels were invested by mouse perivascular supporting cells as revealed by post-staining with anti-mouse smooth muscle and pericyte specific antibodies (FIG. 2F). Differential smooth muscle coverage in vivo indicated vessel hierarchy in R-VEC vessels, with larger arterioles covered with a thicker layer of smooth muscle cells and less coverage in smaller capillaries (FIG. 2F). Consistent with in vitro experiments, iR-VECs also assembled into stable vessels in L.E.C, and one week of doxycycline in vivo was sufficient to retain vascular stability (representative images of n=3-4 mice/group) (FIG. 2G-2H). R-VEC and iR-VEC vessels in in vivo plugs were also shown to be non leaky and patent when injected intravenously with dextran (MW 70 kDa). As a control, the inventors also transduced human naïve ECs with K-RAS that form prototypical leaky and disorganized tumor-like vessels. In sharp contrast to R-VECs, K-RAS transduced human ECs formed vessels reminiscent of hemangiomas, manifesting leakiness and a disorganized structure.

To rule out the possibility that ETV2 could instigate the emergence of hemangiomas, metastatic or vascular malformations, the inventors implanted R-VECs in immunocompromised SCID-Beige mice for 10 months and analyzed the plugs and organs of the mice for any evidence of tumors or metastatic lesions. R-VEC plugs retrieved 10 months post implantation did not manifest aberrant growth over time and appeared normal, while also retaining R-VEC perfused localized and well organized vessel structures. No hemangiomas or tumors were observed in R-VEC plugs at 10 months by H&E and Masson stainings, in contrast to K-RAS plugs which formed aberrant and disorganized structures. No tumors, metastatic lesions or abnormalities were present in any of the other examined organs of mice that were implanted with R-VECs for 10 months.

The H&E sections from R-VEC, myrAkt1, K-RAS and ETS1 plugs were impartially assessed for any potential malignant features. R-VEC vessels were assessed to establish normal vascularized and patterned capillary structures. By contrast, myrAkt1 ECs were noted to have formed engorged and disorganized vessels, representing a capillary hemangioma. K-RAS ECs appear to have formed typical hemangiomas, with the features of sarcomatoid tumors. ETS1-transduced ECs were assessed to have linear capillary structures, but that lack a lumen. Therefore, R-VECs form durable structurally normal and anastomosed vessels without vascular anomalies or tumors in the interrogated time period of 10 months.

Figure 3A:
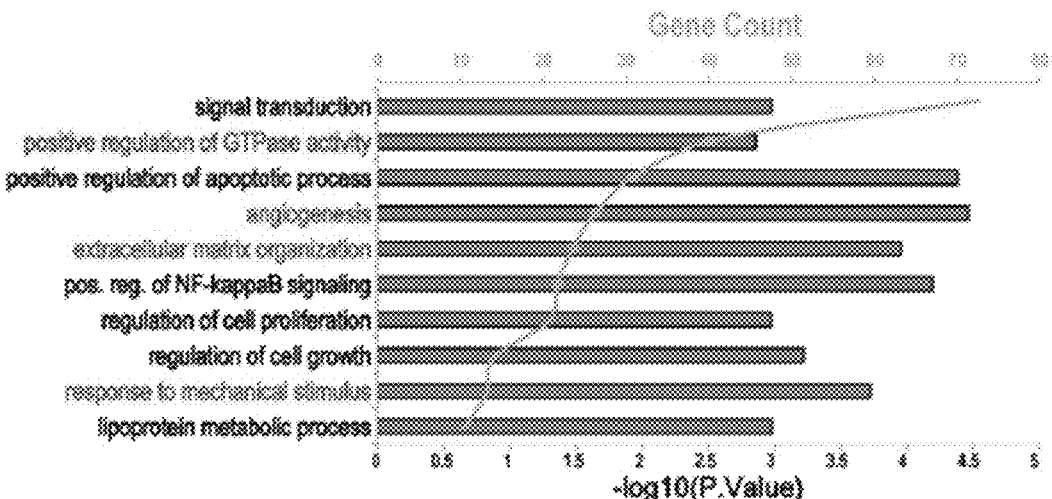
Figure 3B:
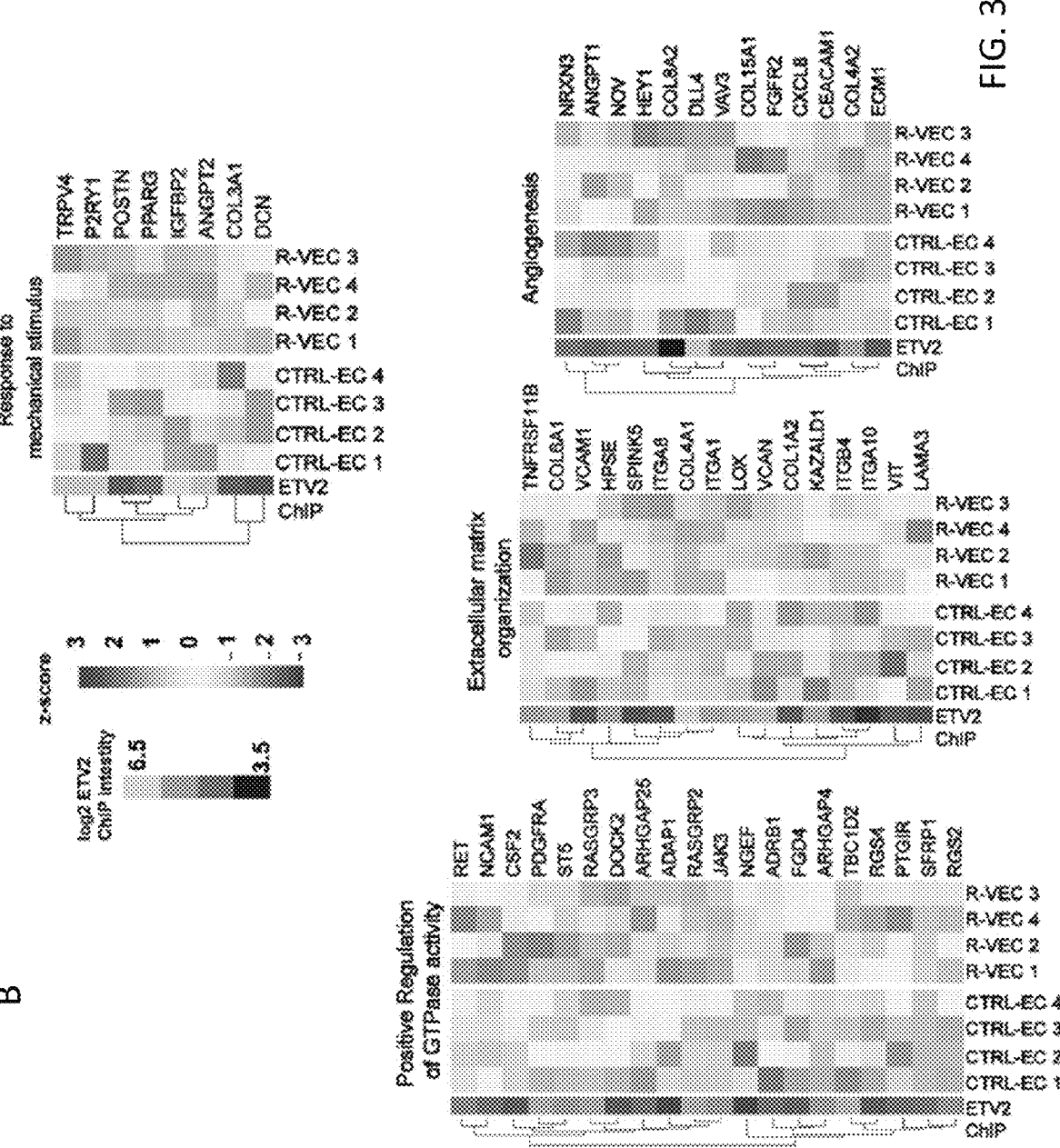

Example 6: ETV2 Mediates Vessel Formation Through Chromatin Remodeling and Transcriptional Regulation Next, to uncover the mechanism by which ETV2 expression induces long-lasting patterned lumenized vessel formation, the inventors performed RNA sequencing (RNA-seq) analysis of human naïve ECs without and with ETV2 transduction at the stage 1 induction phase (n=4) (FIGS. 3A-3B). Gene ontology (GO) analyses revealed upregulation of genes in pathways regulating angiogenesis, positive regulation of GTPase activity, extracellular matrix organization and response to mechanical stimulus (FIGS. 3A-3B). During the stage 1 induction phase, R-VECs maintain their vascular identity by sustaining the expression of EC specific markers, including VEcad, CD31 (PECAM1) and VEGFR2 (KDR). Upon ETV2 induction, a group of 490 genes was differentially expressed among various tissue-specific adult human EC, including cardiac, dermal, aortic and adipose-derived R-VECs.

Figure 3C:
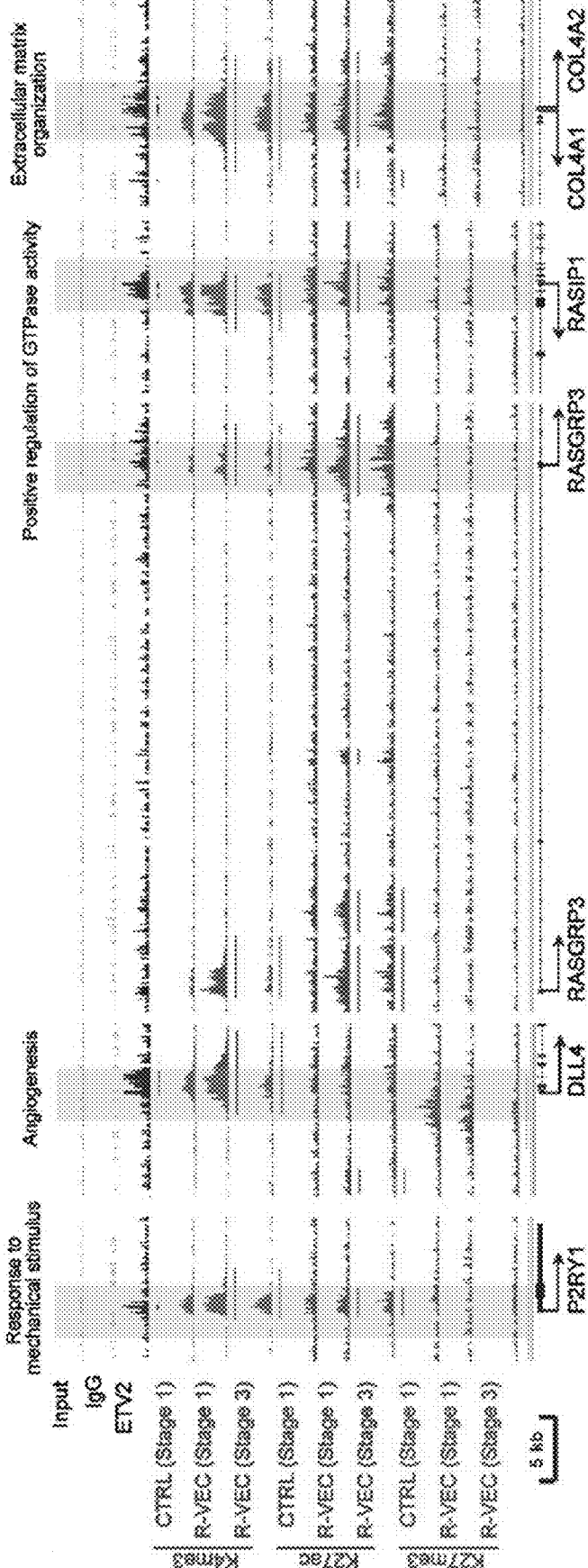

The inventors performed ETV2 chromatin immunoprecipitation (ChIP) sequencing (ChIP-seq) analysis on R-VECs during the stage 1 induction phase. The inventors also performed ChIP-seq analysis of transcription activation-associated trimethylation on histone H3 lysine 4 (K4me3), acetylation on histone H3 lysine 27 (K27ac) and transcription repression-associated trimethylation on histone H3 lysine 27 (K27me3) on both R-VECs and control ECs (CTRL-ECs) (FIGS. 3B-3C). ChIP-seq analysis revealed binding of ETV2 to promoters of several differentially expressed genes in R-VECs, and to the promoters of genes in numerous pro-tubulogenesis pathways that are silenced in mature ECs (FIGS. 3B-3C). Therefore, ETV2 resets the chromatin and transcriptome of mature ECs with direct re-activation of tubulogenesis and angiogenesis genes during the induction phase in R-VECs.

Example 7: Rap1 Activation is Essential for ETV2-Mediated Tube Formation in R-VECs A cluster of genes involved in the activation of the small GTPase Rap1, was robustly upregulated in stage 1 induction R-VECs as shown by GO analysis (FIG. 3A-3B). Upon ETV2 induction, three GEFs (RASGRP2, RASGRP3, RAPGEF5) and RASIP1, were also significantly upregulated (FIG. 3D). ChIP-seq and ChIP-qPCR analyses confirmed direct binding of ETV2 to promoters of RASGRP3 and RASIP1, and subsequent increase in K4me3 and K27ac at these genes (FIG. 3C). Western Blot analysis confirmed that levels of RASGRP3 correlate with levels of ETV2 in R-VECs. R-VECs also express higher levels of the RASGRP3 protein, when compared to control, ETS1 transduced, or myrAKT1-transduced ECs.

Rap1 activation has been shown to be crucial for lumen formation in development for both aorta and vascular plexus formation[47,53,54]. Similar differentially expressed genes in the Rap1 pathway, were found in other adult human tissue-specific ECs upon ETV2 overexpression, as well as in ETV2 positive FACS sorted ECs isolated from ETV2-venus reporter mouse embryos at Embryonic stage of 9.5 (E9.5). A pull down of active Rap1-GTP during the stage 1 induction phase, showed a higher level of active Rap1-GTP in R-VECs compared to naïve ECs (n=5) (FIG. 3E-3F). Vessel formation was significantly reduced and no lumen was present following treatment with Rap1 inhibitor GGTI298 (FIG. 3G-3H). Likewise, knockdown of RASGRP3 by shRNA resulted in significant disruption of R-VEC mediated vessel formation (FIG. 3I-3J). Therefore, ETV2 potentiates vessel and lumen formation in part through upregulation of Rap1 GEFs. d

Figure 3K:
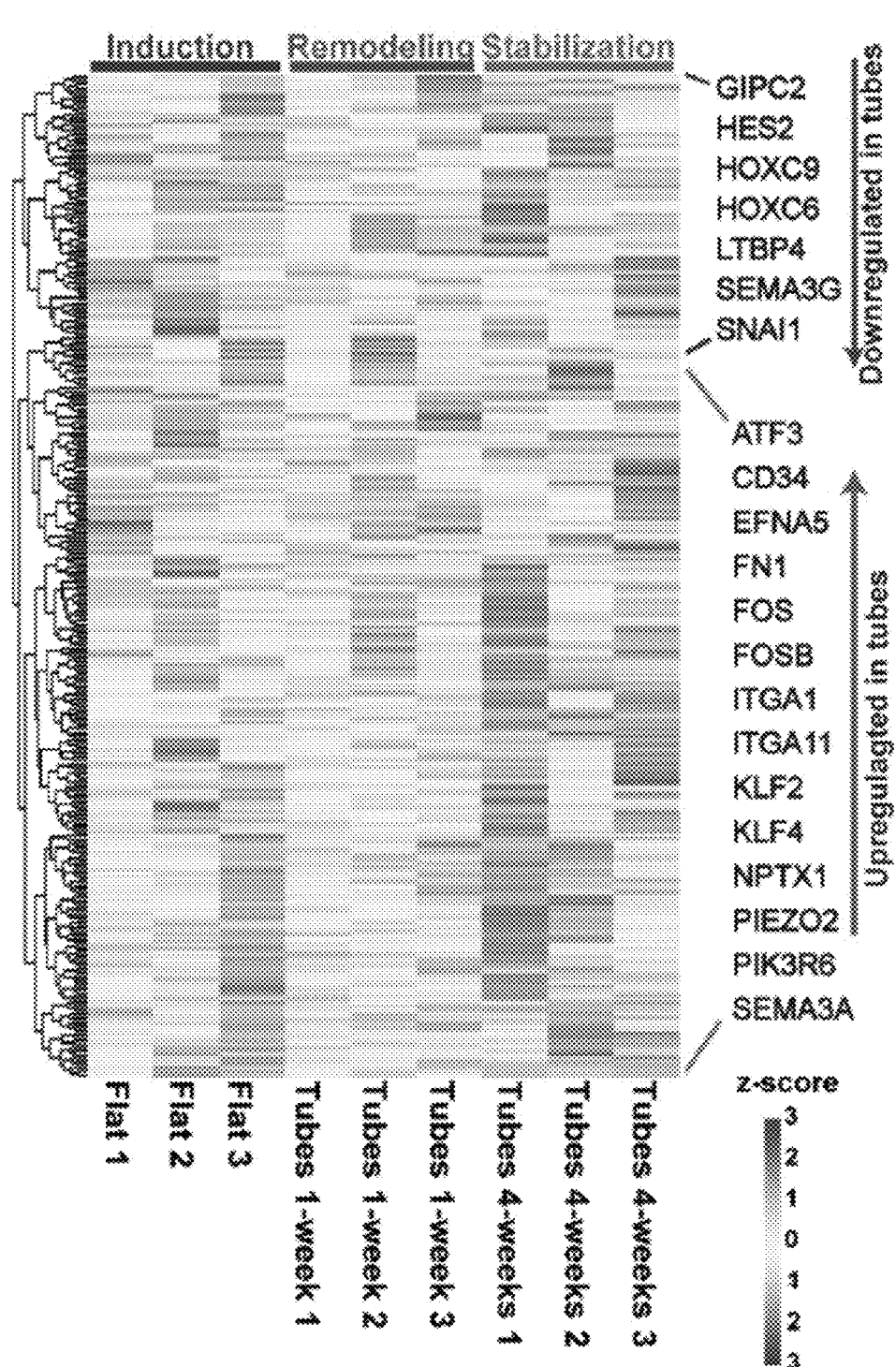

Example 8: R-VECs Undergo a Stage-Specific Transcriptional Expression Pattern In addition to the aforementioned genes turned on during the R-VECs stage 1 induction phase, R-VECs undergo a dynamic transcriptional expression as they transition from 2D cultures to 3D vessels in the induction-remodeling-stabilization stages (FIG. 3K). Notably, as the R-VEC vessels reached their final stable patterning they acquire transcriptional signatures similar to freshly isolated ECs, when compared to in vitro cultured ECs. In the stage 3 stabilization phase, R-VECs upregulate genes involved in mechanosensing (PIEZO2, KLF2, and KLF4) and EC remodeling (ATF3) that are lost upon culture of mature ECs in vitro (FIG. 3K), therefore 3D stable R-VEC vessels at stage 3 behave similarly to physiological vessels in vivo. This was further confirmed by isolating R-VECs from in vivo plugs and comparing their transcriptome to freshly isolated HUVECs and R-VEC stage 3 stable vessels. Notably, stage 3 differentially expressed genes in 3D vessels, such as PIEZO2, KLF2 and KLF4 were found to already be bound and epigenetically primed for expression by ETV2 during stage 1 induction. Thus, ETV2 resets the chromatin purview of mature ECs during the induction phase into a configuration that is pro-tubulogenic and potentially more reminiscent of generic ECs that could be reset in response to extrinsic signals. This is borne out in studies in which R-VECs are challenged to respond to various microenvironmental cues for remodeling and tubulogenesis as described in the following sections.

Example 9: R-VECs Vascularize Decellularized Tissue Scaffolds

Great progress has been made towards decellularizing organs into extracellular matrix scaffolds that can be recellularized and transplanted into patients. During the decellularization procedure, osmotic pressure and detergent can remove the cellular matter in a variety of tissues leaving sheaths of matrix intact that support parenchymal tissue as well as stroma, small capillaries and larger vascular structures. Despite recent advances in this technology, the generation of long-lasting functional vessels, especially the small caliber capillaries, for the vascularization of decellularized scaffolds has been challenging. Specifically, while large caliber vessels in the decellularized scaffolds could be colonized with ECs, it is difficult to arborize the smaller capillary size vessels, which are crucial for cell survival and functional specialization.

Figure 4A:
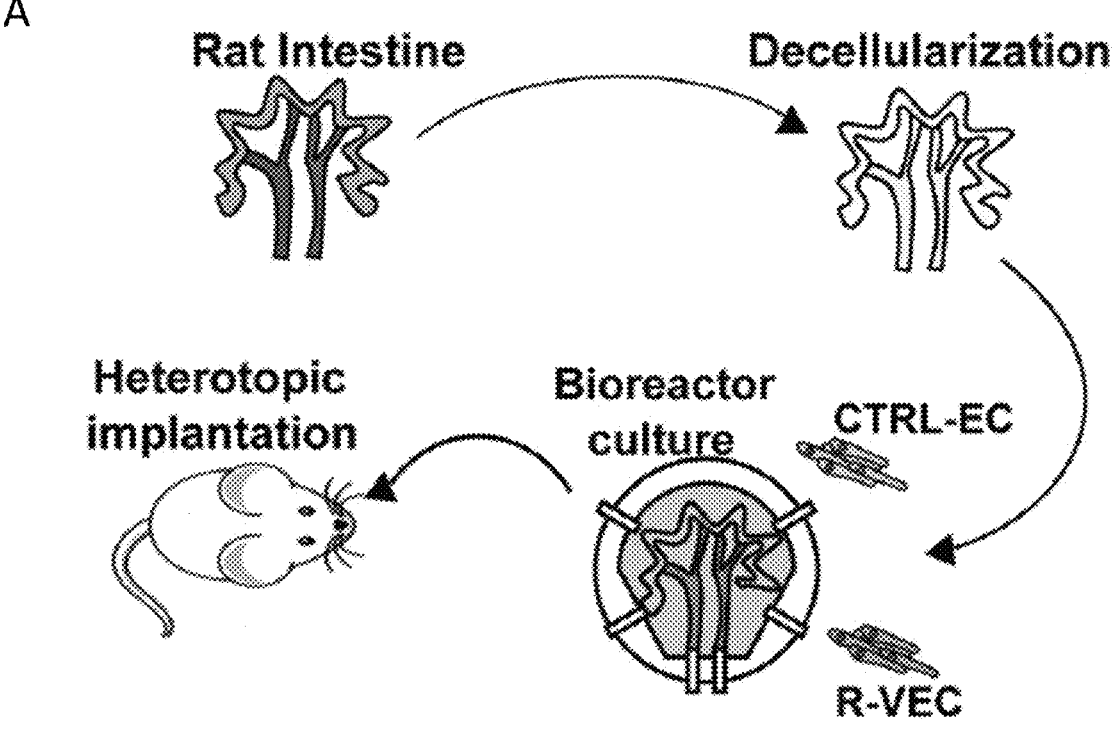
Figure 4B:
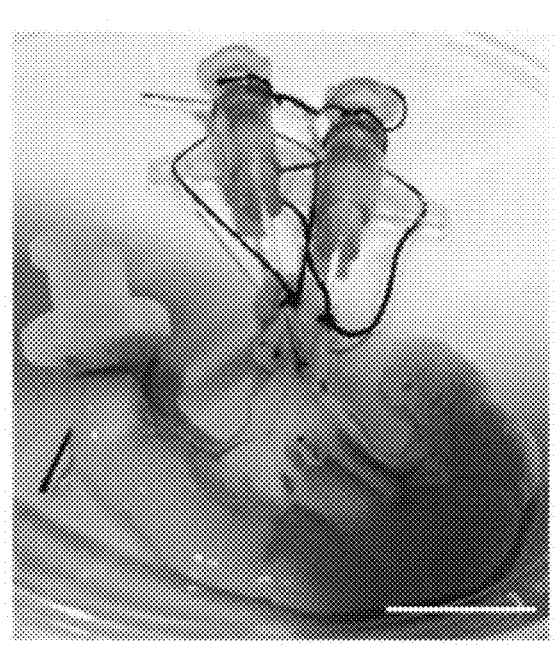
Figure 4C:
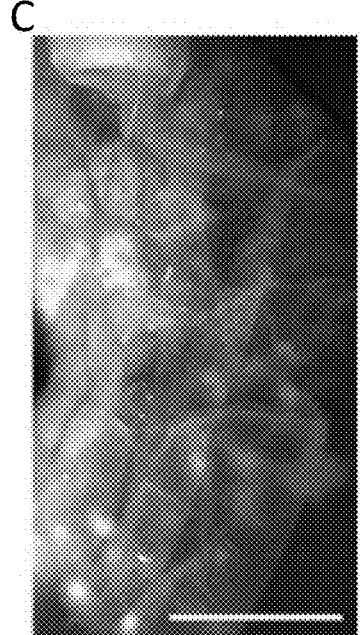
Figure 4D:
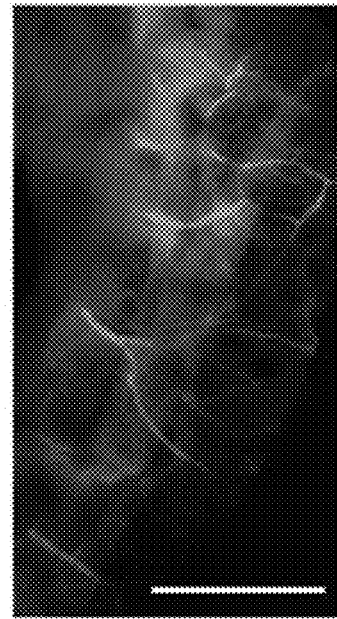
Figure 4E:
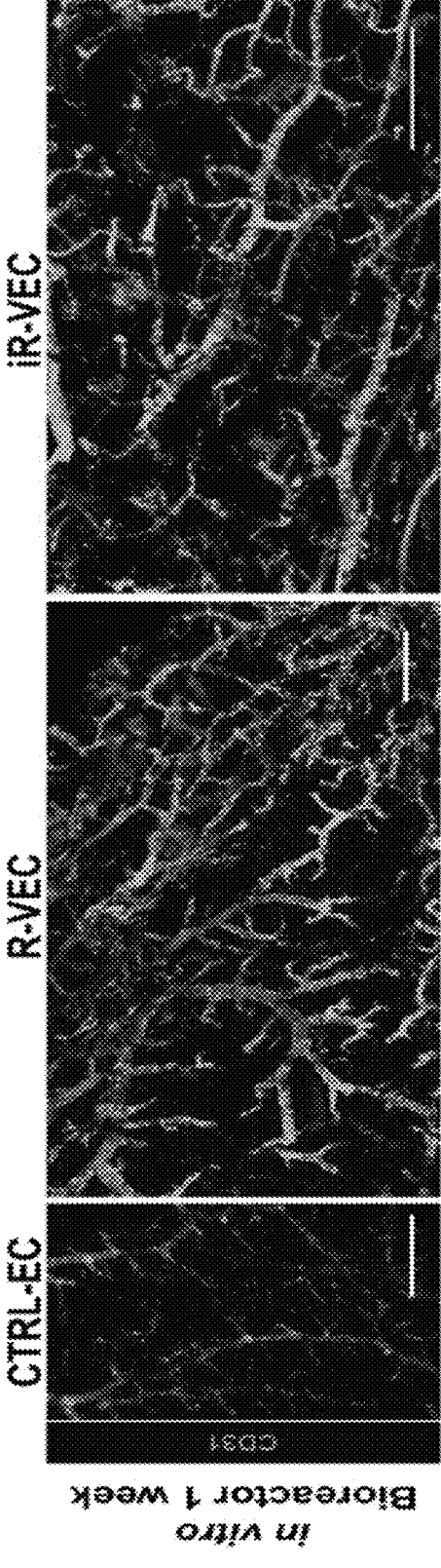
Figure 4F:
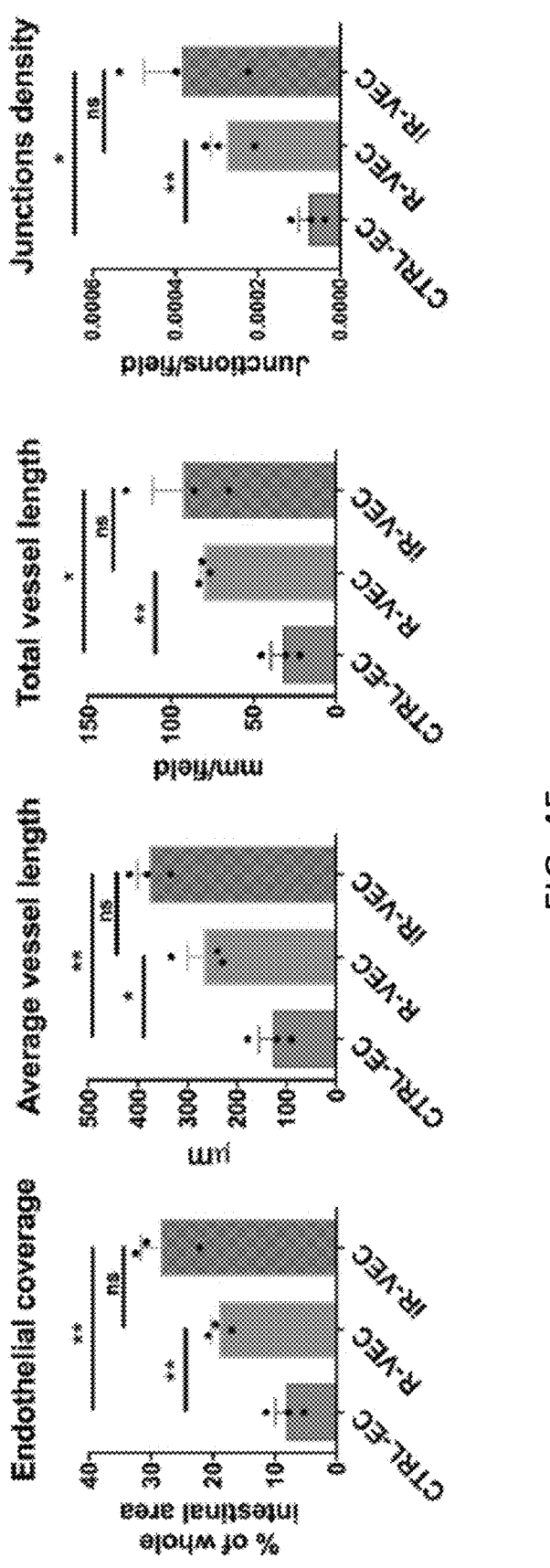

To address this issue, the inventors introduced stage 1 induction generated R-VECs in a decellularized intestinal model where they were able to re-establish the vasculature in a decellularized rat intestine bioreactor ex vivo (FIG. 4A-4G). Notably, R-VECs profusely populated the small capillaries of the decellularized intestine (FIG. 4D). Staining with a CD31 antibody, revealed a much higher vascular coating when using R-VECs or iR-VECs compared to non-ETV2 transduced ECs (CTRL-ECs) (FIG. 4E-4G) (n=3 scaffolds per condition). Notably, as compared to CTRL-ECs that transiently coated larger caliber vessels, R-VECs and iR-VECs colonized the narrow small capillaries evenly throughout the decellularized scaffolds.

Figures 4G, 4H:
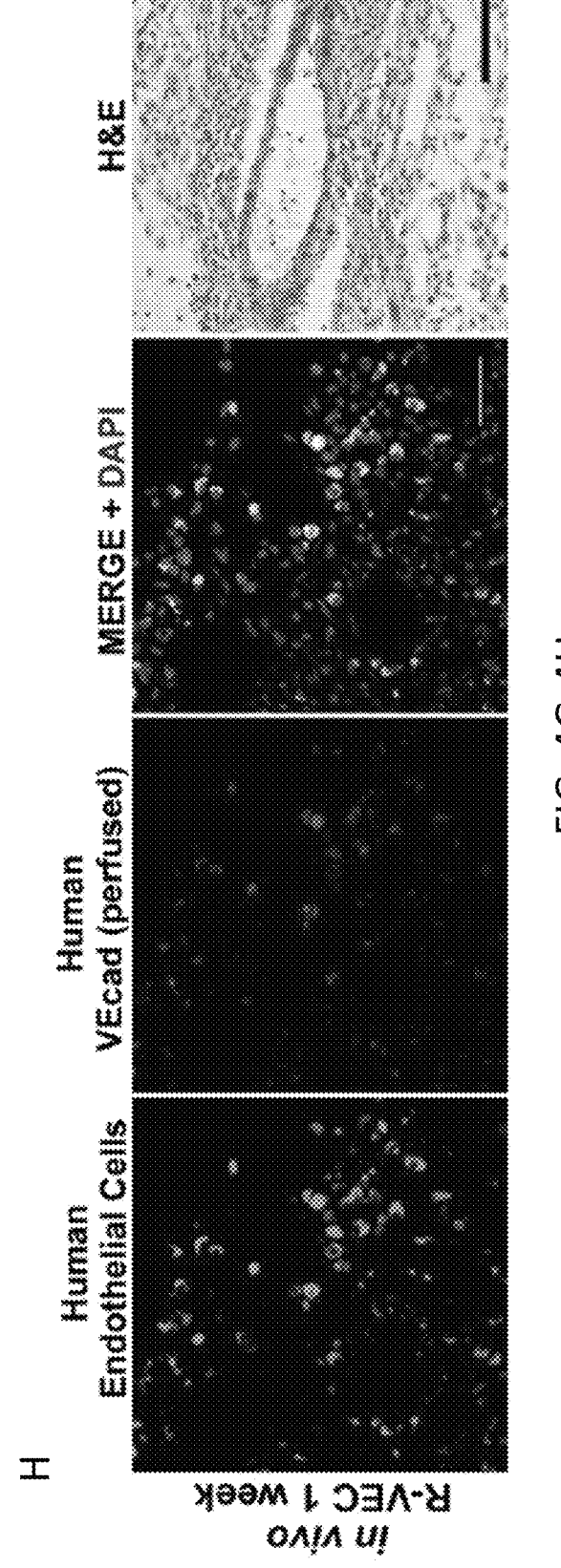
Figures 4I, 4J:
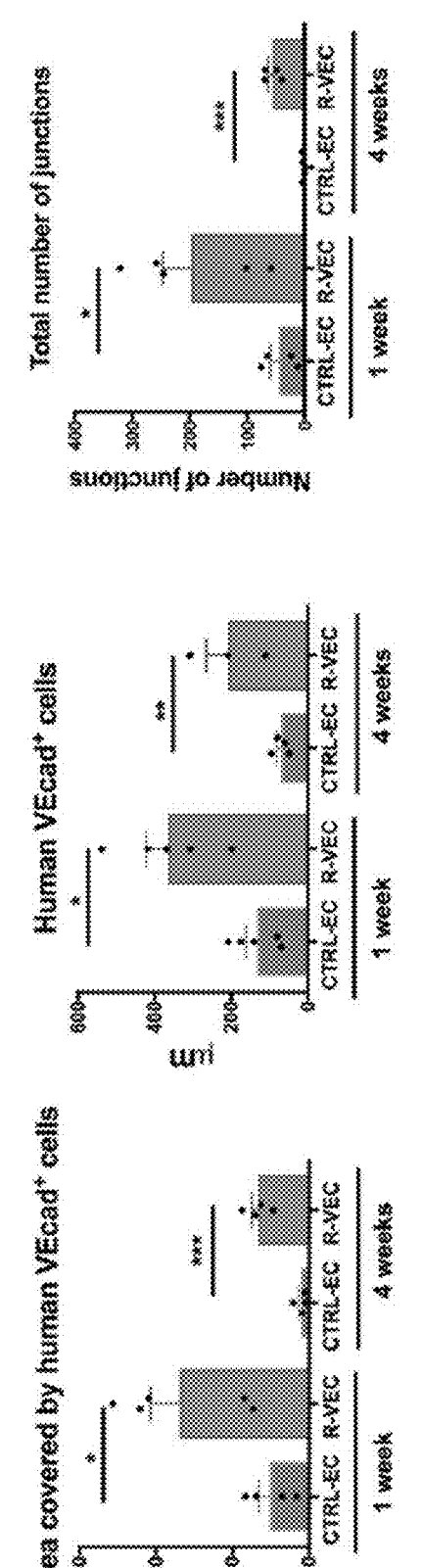

After 1 week ex vivo culture, the re-vascularized intestinal explants were implanted in the momentum of immuno-compromised mice. R-VEC vascularized scaffolds retained their patency and anastomosed to the mouse vasculature as shown by intravital anti-human VEcad staining at both 1 and 4 weeks (FIGS. 4H-4I). Quantification of the frequency of human ECs, revealed that R-VEC vessels persisted at a significantly higher rate in vivo than CTRL-ECs through a 4 week time point, and this persistence was in part due to their integrity and lower rate of apoptosis (FIG. 4J-4K).

Figures 5B, 5C, 5D, 5E:
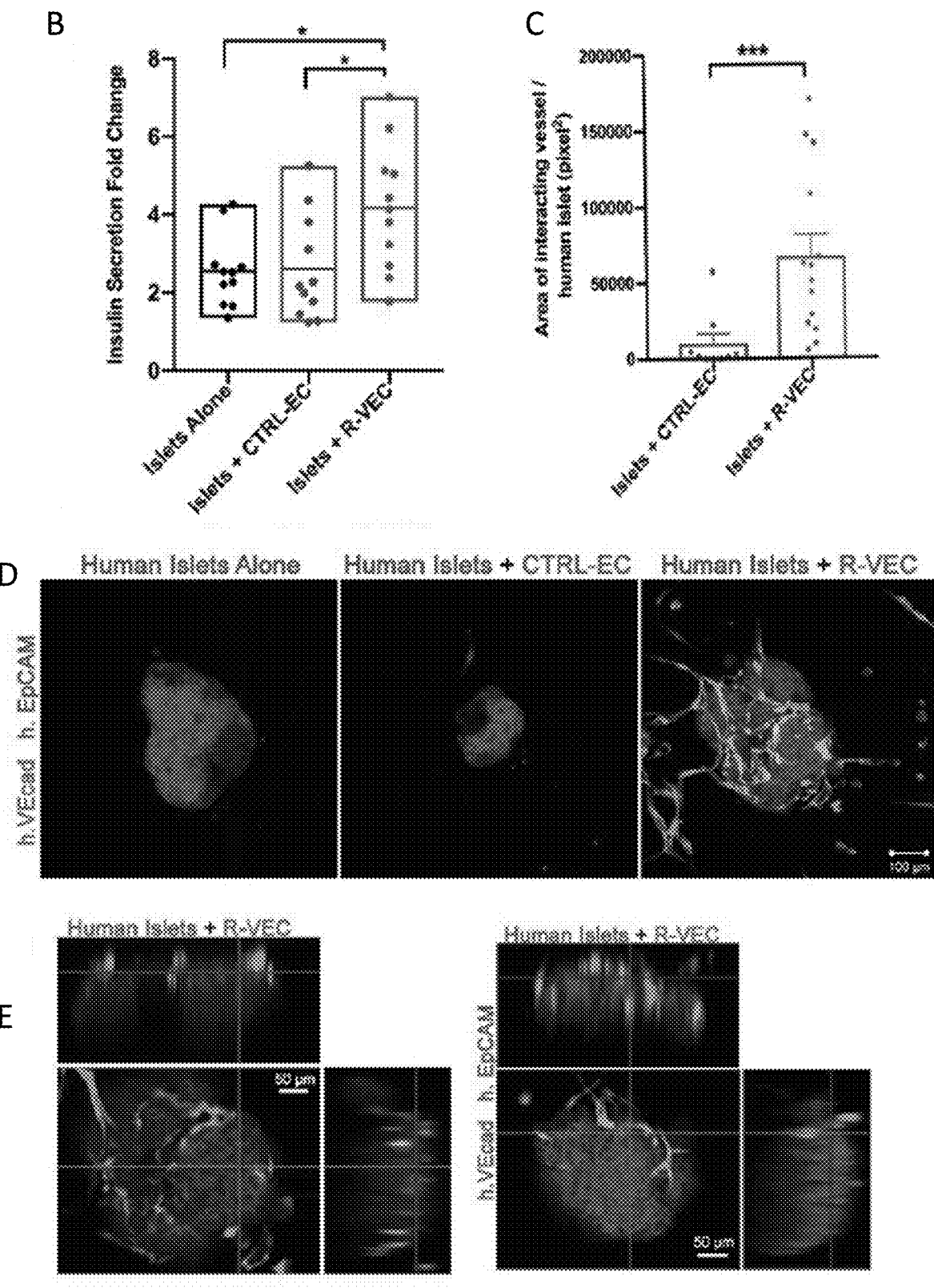
FIGS. 5A-5N. Hemodynamically stable R-VECs vascularized human islet explants in vitro and enhance islet insulin secretion. (A) Representative images of human islet explants in a 50 microliter static Matrigel dome in vitro either alone or co-cultured with CTRL-EC or R-VEC at day 4. 250,000 CTRL-EC or R-VEC were seeded together with 200 human islets in 50 µl Matrigel domes. (B) Insulin secretion fold change in Matrigel domes post glucose stimulation determined as the fold change between secreted insulin at 16.7 mM and 2 mM glucose. For insulin measurements 25 human islet explants were cultured alone or together with 200,000 CTRL-EC or R-VECs in 40 µl Matrigel domes and insulin measured after 2 weeks. One way ANOVA with Tukey's post test (n=11 replicates of 4 different human donors non-diabetic islets, Islet alone vs. Islet+CTRL-EC p=0.9931, Islet alone vs. Islet+R-VEC p=0.0200, Islet+CTRL-EC vs. Islet+R-VEC p=0.0261). (C) Vessel area of endothelial cells directly interacting with islets at week 2, Mann Whitney U-test (n=9: islets+CTRL-EC and n=14: islets+R-VEC from 3 biological replicates, p=0.0003). (D) EpCAM and VEcadherin (VEcad) staining of islets co-cultured in a Matrigel dome at 2 weeks. (E) Orthogonal projections of R-VECs in co-culture with human islets at two weeks. (F) Overview of the large volume 5×3×1 millimeter³ capacity microfluidic device used to seed islets alone, in the presence of CTRL-EC or in the presence of R-VECs. The volume of the microfluidic device was 15 microliters and accommodated 60,000 endothelial cells and ~40 islets in fibrin gel. (G) Fluorescently labeled heparinized whole human blood was perfused through the microfluidic devices in the three conditions (day 4). Only devices where islets were seeded in the presence of R-VEC could be perfused with blood and had formed an interconnected vascular network. (H) Representative maximum intensity projections of whole devices of islet explants post-stained with EpCAM and VEcad (day 4). (I-J) Whole human heparinized blood captured flowing through the vessels surrounding the islets and in vessels going through the islet. The red circle is drawn around the human islet. (K) Islets were co-cultured with R-VECs in a microfluidic device (day 4) and the vessel network perfused with an antibody against human VEcad before fixation. Subsequently the whole vessel network was post-stained with an antibody against EpCAM to visualize the human islets. Representative maximum intensity and orthogonal projections of human islets vascularized by R-VECs in microfluidic device and stained for VEcad, EpCAM and insulin. (L) Diagram depicting glucose stimulation test under physiological conditions in microfluidic devices on day 4. The size of the device was 5 mm×3 mm×1 mm and accommodated 60,000 endothelial cells and ~40 islets in 15 microliter of fibrin gel. (M) Total insulin secretion/device collected at the outlet of each device. Insulin levels were measured at basal low glucose levels (2 mM) and upon high glucose stimulation (16.7 mM) over time. Two-way ANOVA with Tukey's post test. Star symbols (*) represent comparisons between Islets alone groups and Islets+R-VEC; and pound symbols (#) represent comparisons between Islets+CTRL-EC and Islets+R-VEC (Data is from experiments with islets from three different human donors. Circle symbols represent individual devices. Islets alone=4 devices, Islets+CTRL-EC=4 devices, Islets+R-VEC=8 devices, 9 min: Islets alone vs. Islets+CTRL-EC p=0.8204, Islets alone vs. Islets+R-VEC p=0.0004, Islets+CTRL-EC vs. Islets+R-VEC p<0.0001 24 min: Islets alone vs. Islets+CTRL-EC p=0.7109, Islets alone vs. Islets+R-VEC p=0.0033, Islets+CTRL-EC vs. Islets+R-VEC p=0.0002). (N) Insulin fold change at the outlet (insulin levels at 16.7 mM/insulin levels at 2 mM) 9 min post high glucose stimulation. Kruskal-Wallis test with Dunn's post test (Data is from experiments with islets from three different human donors. Circle symbols represent individual devices. Islets alone=4 devices, Islets+CTRL-EC=4 devices, Islets+R-VEC=8 devices, Islets alone vs. Islets+CTRL-EC p>0.9999, Islets alone vs. Islets+R-VEC p=0.0207, Islets+CTRL-EC vs. Islets+R-VEC p=0.0267).

Example 10: Physiological R-VEC Vascularization of Human Pancreatic Islet Explants R-VECs, but not CTRL-ECs, also arborize human pancreatic islet explants procured from cadaveric samples obtained from commercial sources (FIGS. 5A-5E). Intact pancreatic islets (200 islets/experiment), 4 days post procurement, were co-cultured with R-VECs (250,000 cells) or CTRL-ECs (250,000 cells) in large 50 microliter Matrigel static domes. Notably, stage 2 R-VECs rapidly arborized pancreatic islets within 24 hours of co-culture and this arborization extended to at least two weeks (FIG. 5A). The functionality of the human islets was investigated through the glucose stimulated insulin secretion (GSIS) test two weeks after 25 islets were cultured alone, or co-cultured with CTRL-EC or R-VEC (n=3 independent deceased subjects) (FIG. 5B). Insulin response upon high glucose stimulation was significantly higher when islets were co-cultured with R-VECs, than in the other conditions. Interacting vessel area with human islets was also quantified to be higher in R-VEC co-cultures compared to CTRL-EC, with R-VEC vessels sprouting deeply into the human islets (FIGS. 5C-5E).

Figure 5F:
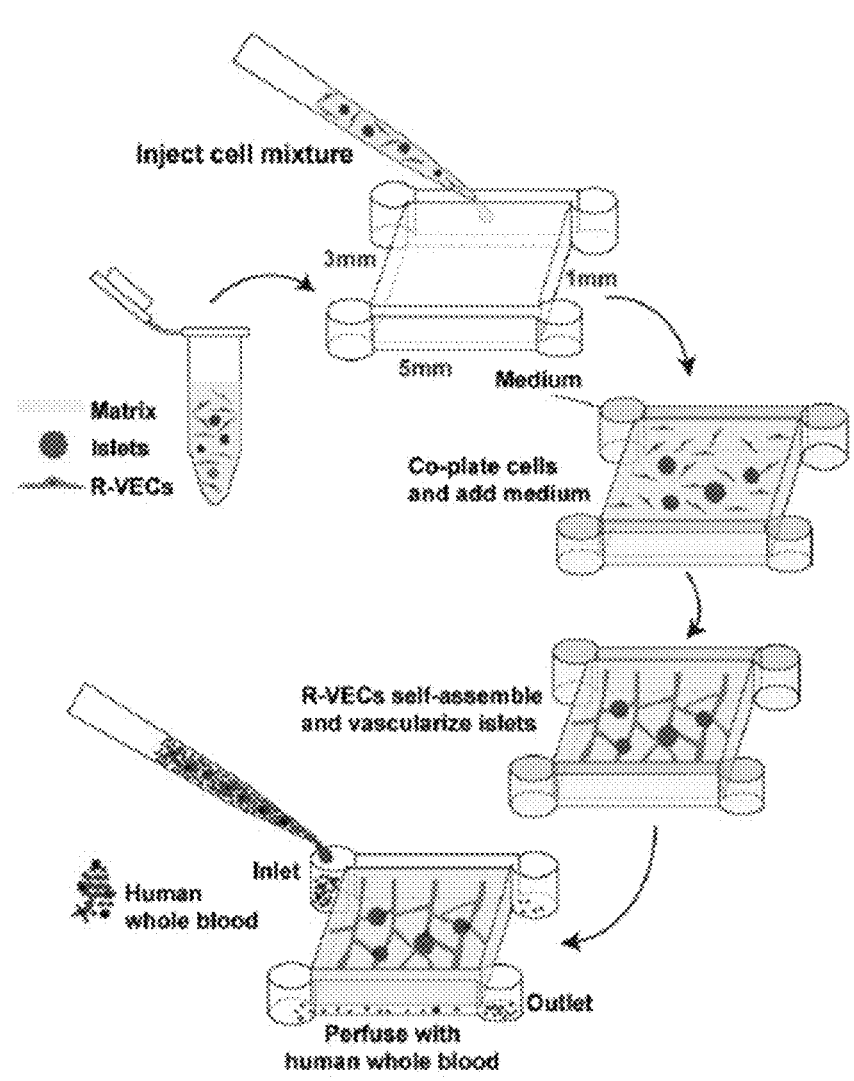

As native pancreatic islets in vivo are abundantly vascularized to perform glucose sensing and insulin secretion activities, the inventors embarked upon assessing whether R-VECs could enable physiological perfusion of the pancreatic islet explants in vitro. Current available devices are often limited by a height of up 150 microns, which would render implantation of islets with average diameter size of 250 micron impractical. Other Organ-on-Chip devices contain artificial membranes separating the endothelial cells from other cell types, which significantly hinder their physical interaction and crosstalk. To this end, the inventors employed the large size chamber of $5 \times 3 \times 1$ millimeter$^3$ (volume 15 microliters) microfluidic device described in FIG. 1J, allowing us to accommodate more than >40 intact human pancreatic islets, intermingled with 60,000 R-VECs. The ability to accommodate and vascularize these relatively bulky islets in large volume microfluidic devices is essential to monitor and quantify their physiological functionality, and was enabled by the R-VECs capability to self-assemble into continuous and lumenized vascular networks (FIG. 5F).

Figures 5G, 5H:
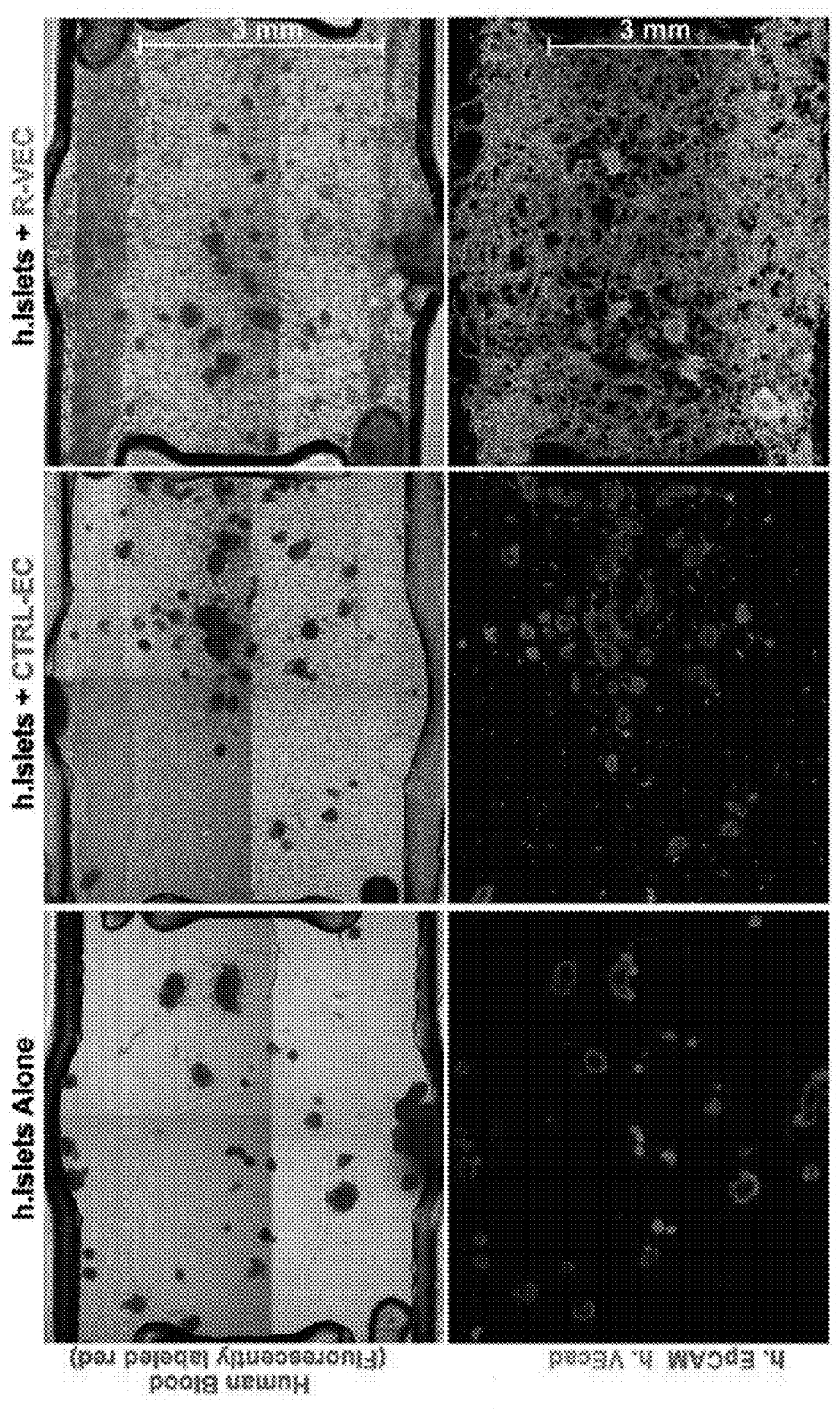

On average, within one to three days of co-implantation of R-VECs with human pancreatic islets, the majority of the islets in the microfluidic device were arborized with R-VECs (FIGS. 5G-5H). To assess the hemodynamic stability of the vessels co-opting the islets, the inventors infused undiluted heparinized complete whole human peripheral blood, (obtained from a fresh phlebotomy), as described in FIG. 1M, through the inlet of the microfluidic device (FIGS. 5F-5G). Throughout the device, hematopoietic cells could be observed crisscrossing R-VEC vessels that arborized or delved deep into human islets. This was in stark contrast to lack of perfusion of fluorescently labeled blood cells in the devices, which were implanted with islets alone (without ECs) or with islets with CTRL-EC (FIGS. 5G-5I). In addition, intravital injection of fluorescent-conjugated antibody to VE-cadherin through the inlet of the microfluidic device demonstrated that almost all of the vessels vascularizing the EpCAM$^+$Insulin$^+$ islets were perfusable and capable of transporting blood and fluids (FIGS. 5J-5K). Thus, R-VEC vessels can not only self-organize into an extensive continuous hemodynamically stable network, but also co-op and vascularize intact islets.

Figure 5L:
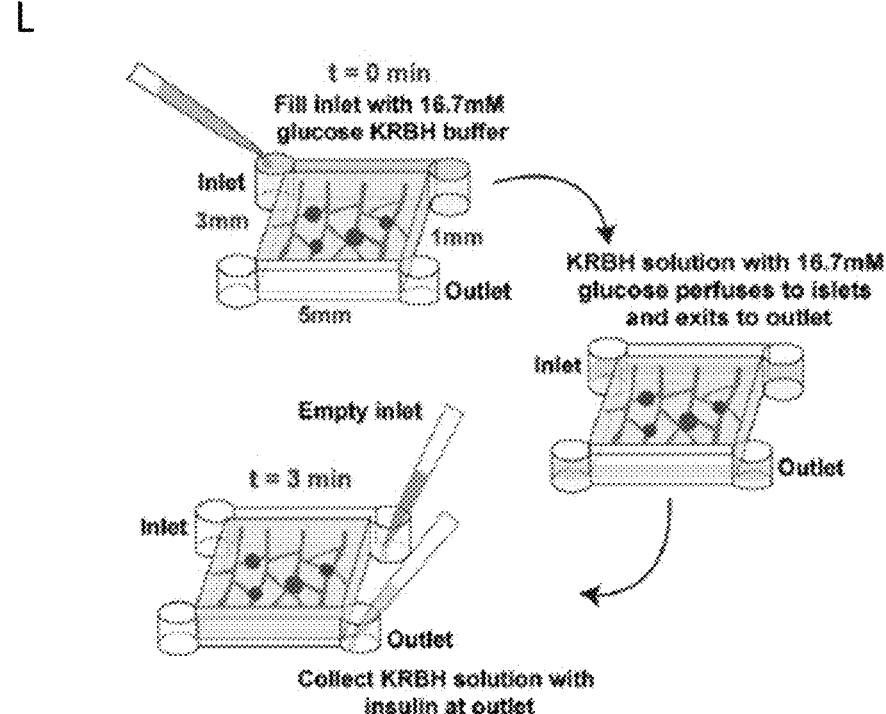
Figure 5M:
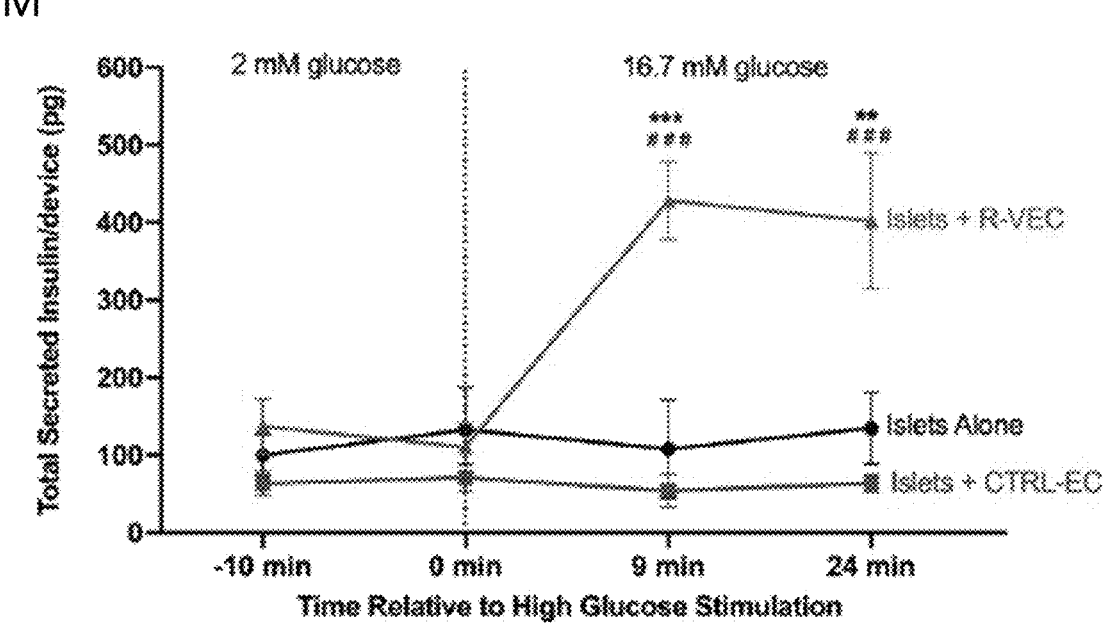
Figure 5N:
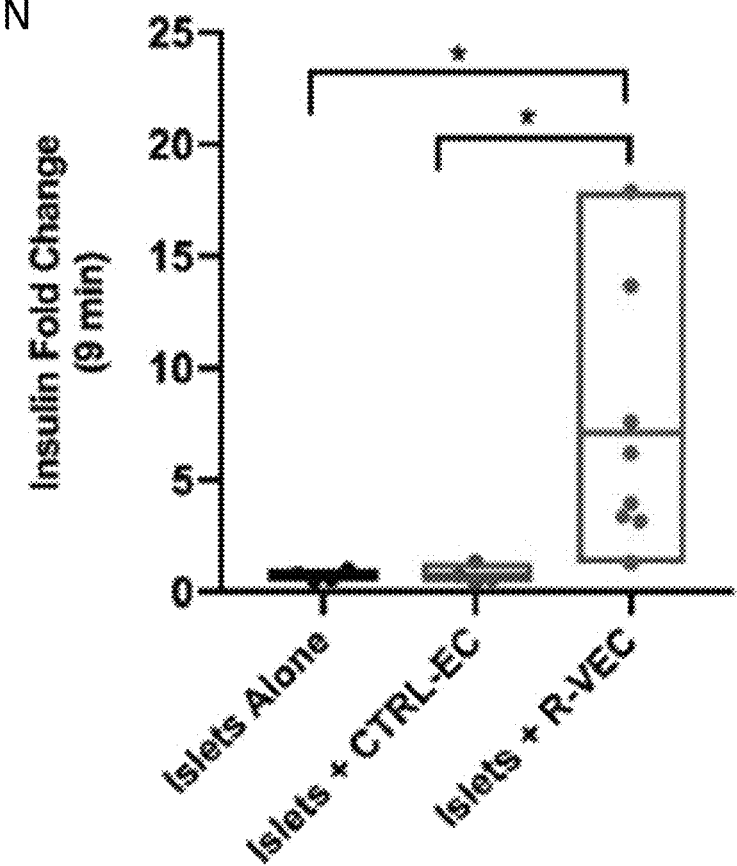

Next, to demonstrate that R-VEC vessels are capable of physiological vascularization of the islets, the inventors performed a glucose stimulation test by infusion of glucose through the inlet of the microfluidic vascular chamber (FIG. 5L). Human islets co-cultured with R-VECs properly detected and responded to high levels of glucose by secreting insulin, as measured at the outlet at 9 and 24 minutes (n=3 independent deceased subjects) (FIG. 5M). On average, the inventors detected a 7-fold increase in the production of insulin upon glucose stimulation (FIG. 5M-5N). Those microfluidic chambers containing human islets alone or islets with CTRL-ECs showed very low insulin production at the outlet, indicating that there is minimal functional vascularization or interstitial convection transfer of fluid (FIGS. 5M-5N). Thus, ETV2 enables ECs to physiologically perfuse islet explants forming cross-interactive vascular plexus sustaining the functionality of the human insulin-producing beta cells.

Example 11: R-VECs Efficiently Arborize Tissue-Specific Organoids

Figure 6A:
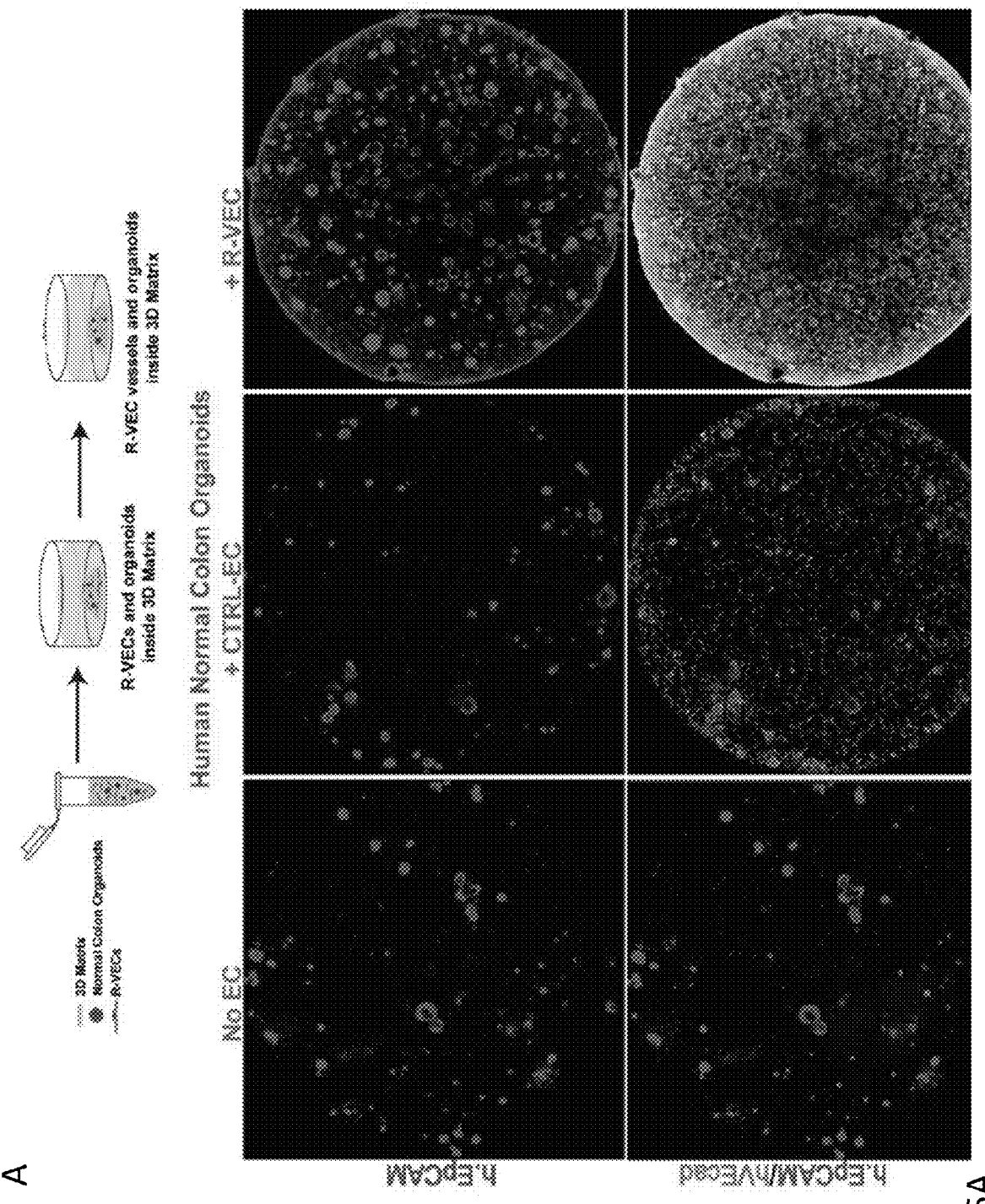
Figure 6B:
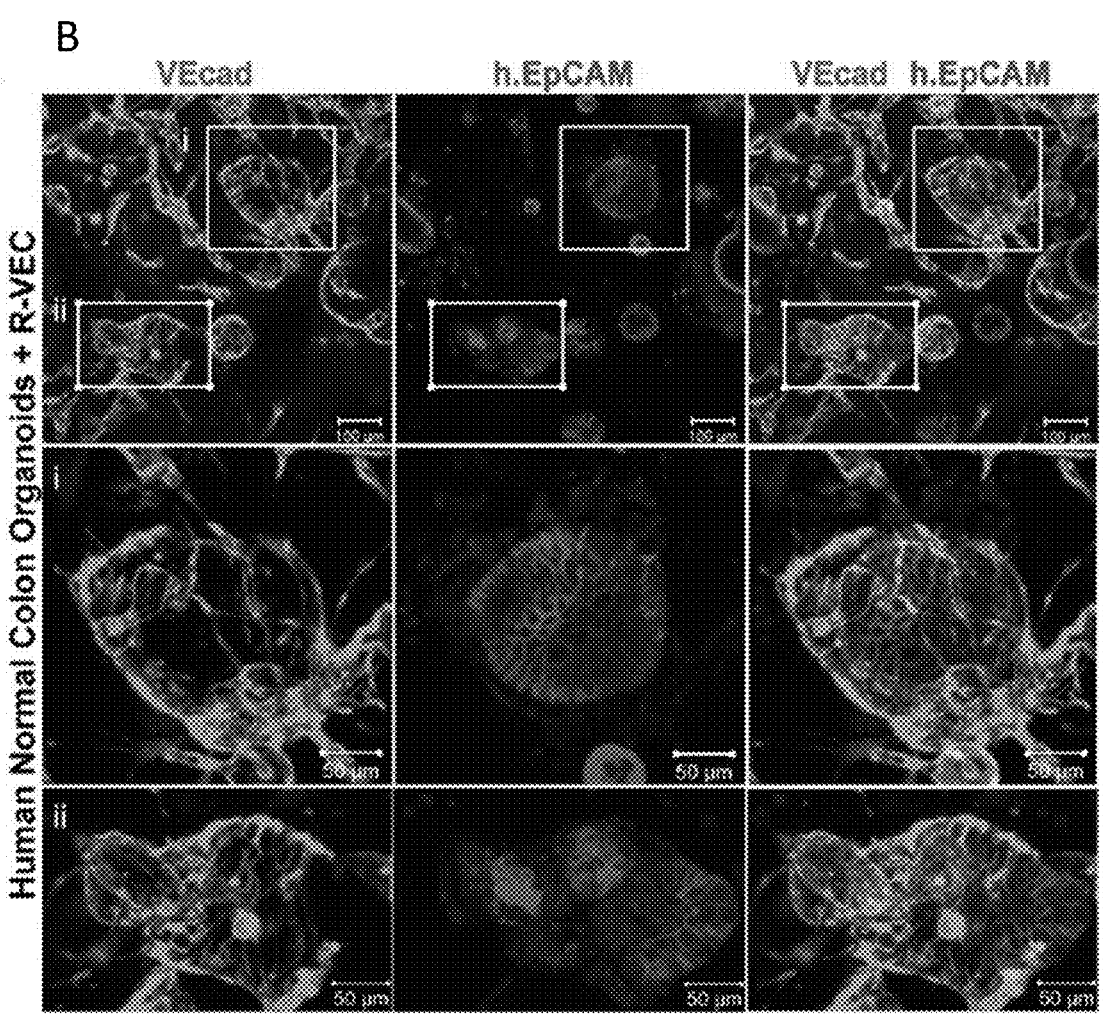
Figure 6C:
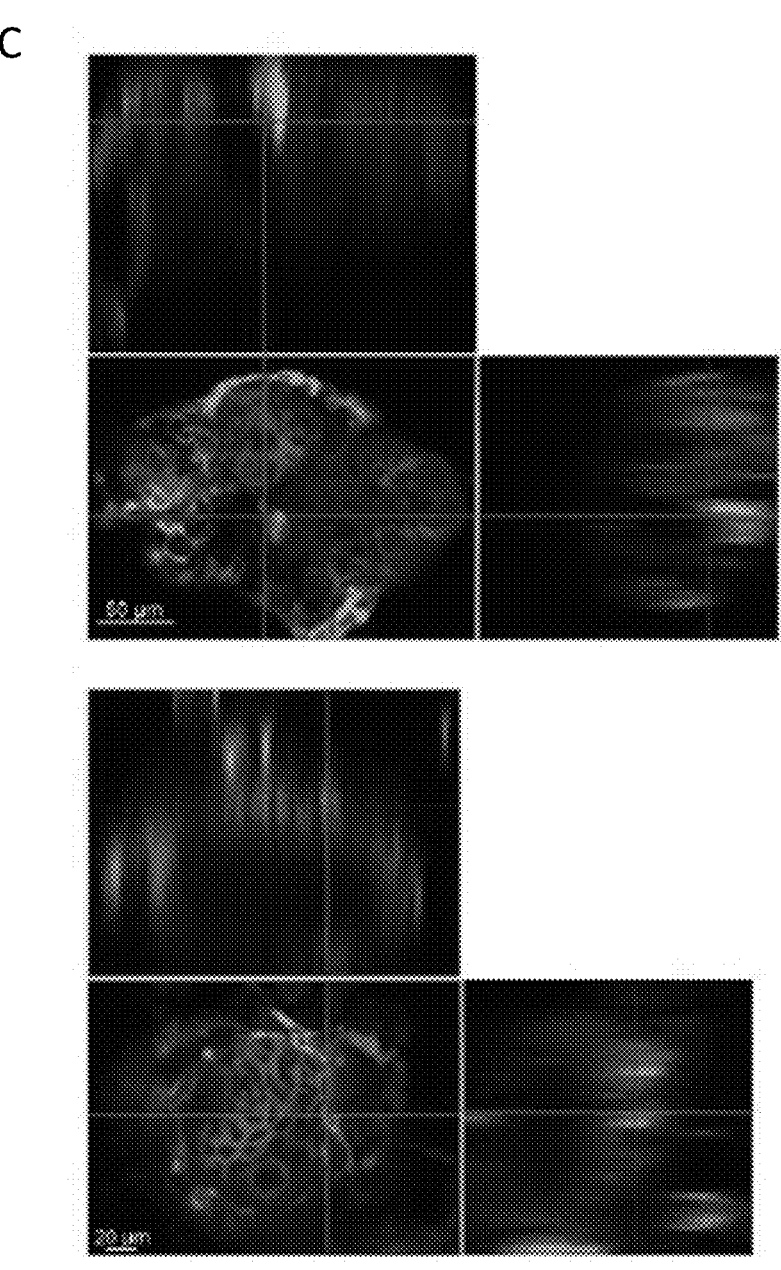
Figure 6D:
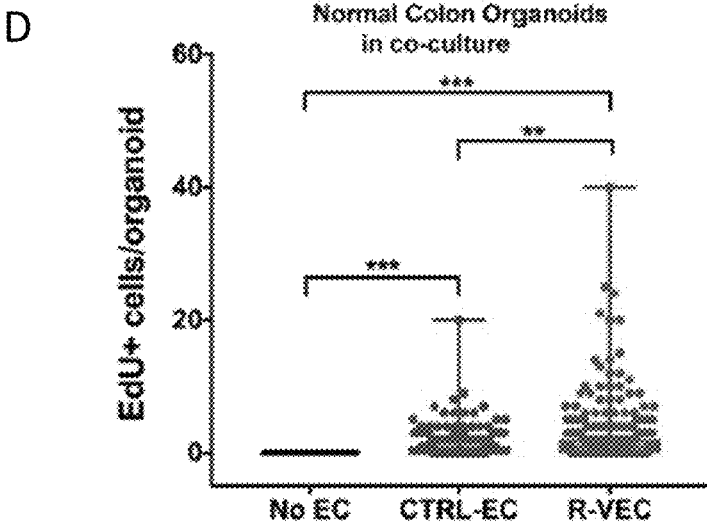
Figure 6E:
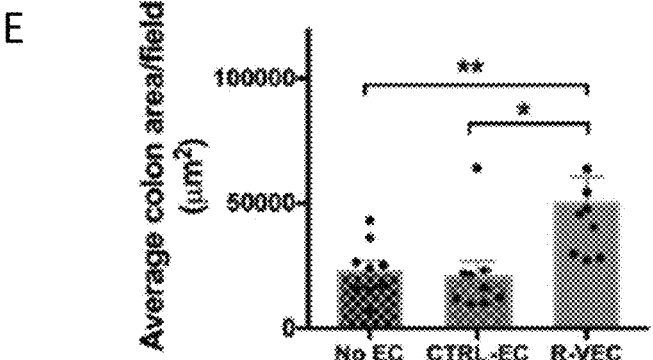

The inventors also interrogated the potential of R-VECs to arborize mouse and human normal or malignant epithelial organoid cultures with the goal of developing physiological organogenesis and disease models. This approach will also enable to uncover the potential tissue- and tumor-specific adaptive responses of R-VECs. Human normal colon organoids established from patient biopsies, were mixed with either CTRL-ECs or stage 1 induction phase R-VECs in 6 mm diameter static matrix domes, establishing a total volume of 50 microliters. R-VECs were able to remodel into highly organized interconnected vessels and associated with colon epithelial cells throughout the 50 microliter matrix dome, while CTRL-ECs were unable to form stable vessels in the presence of the organoids (FIGS. 6A-6C). At day 8, human colon organoids had a significantly higher frequency of EdU$^+$ proliferating cells and an increase in number and size when co-cultured with R-VECs than with CTRL-EC or without ECs (FIGS. 6D-6F).

Human colon organoids were also stained for goblet cells by MUC2 and there was a decrease in staining intensity of individual organoids co-cultured with R-VEC compared to organoids co-cultured with CTRL-EC or alone. There was no significant difference by qRT-PCR of various differentiation and stem and progenitor markers in the human colon organoids cultured across all three co-culture conditions (n=5 independent experiments). However, qRT-PCR revealed a trend towards Ngn3 upregulation and decrease of MUC2 levels upon co-culture with R-VECs indicating a tipping of the balance and trend towards an endocrine progenitor fate, rather than goblet cell differentiation of the human colon organoids. Thus, R-VECs, most likely through the release of paracrine factors, sustain the proliferation and integrity of the human normal colon organoids, while overall maintaining their differentiation state potential.

Figure 6F:
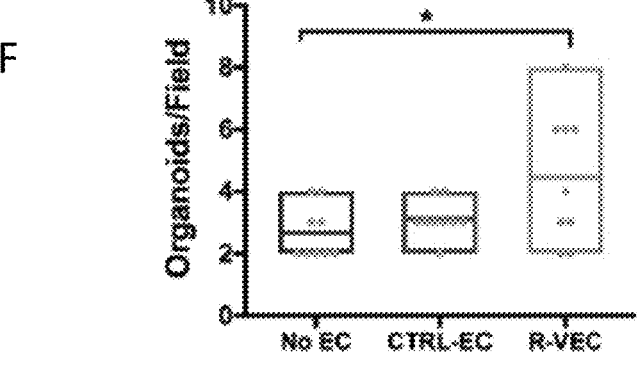
Figure 6G:
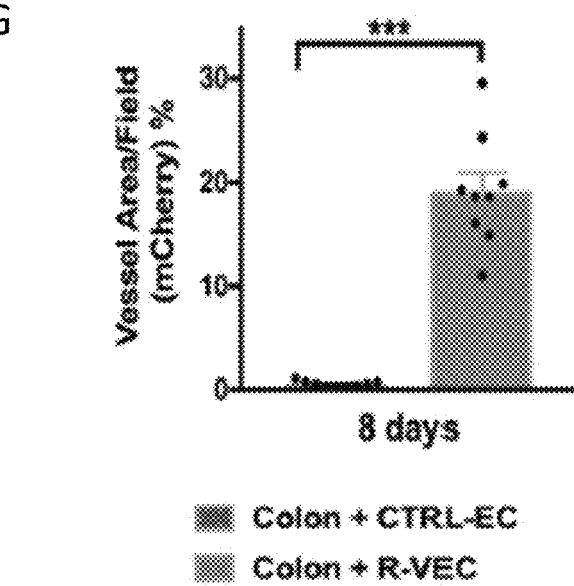
Figure 6H:
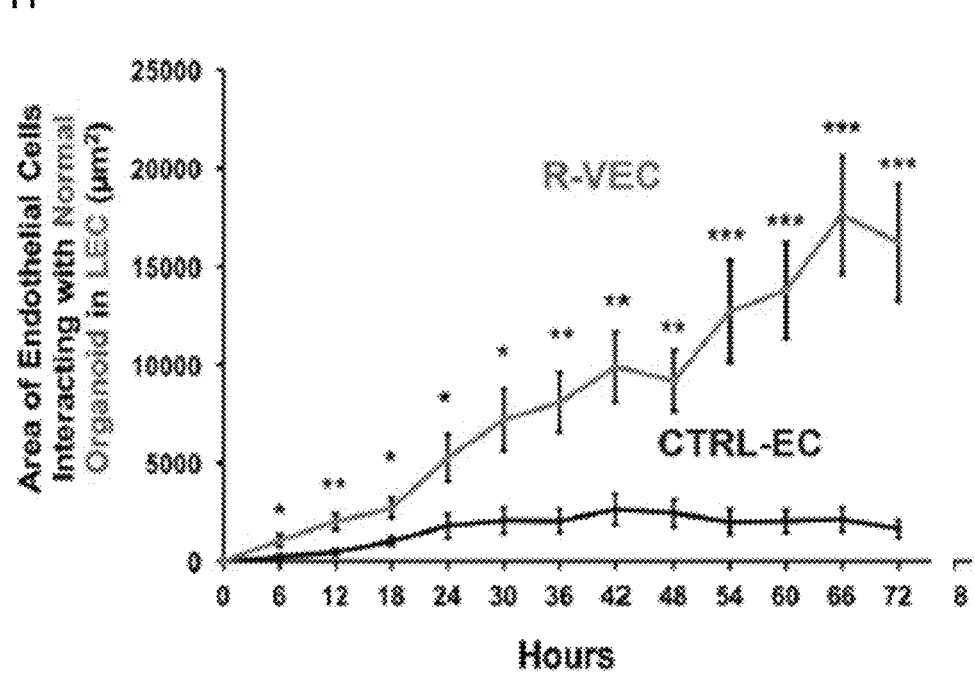
Figure 61:
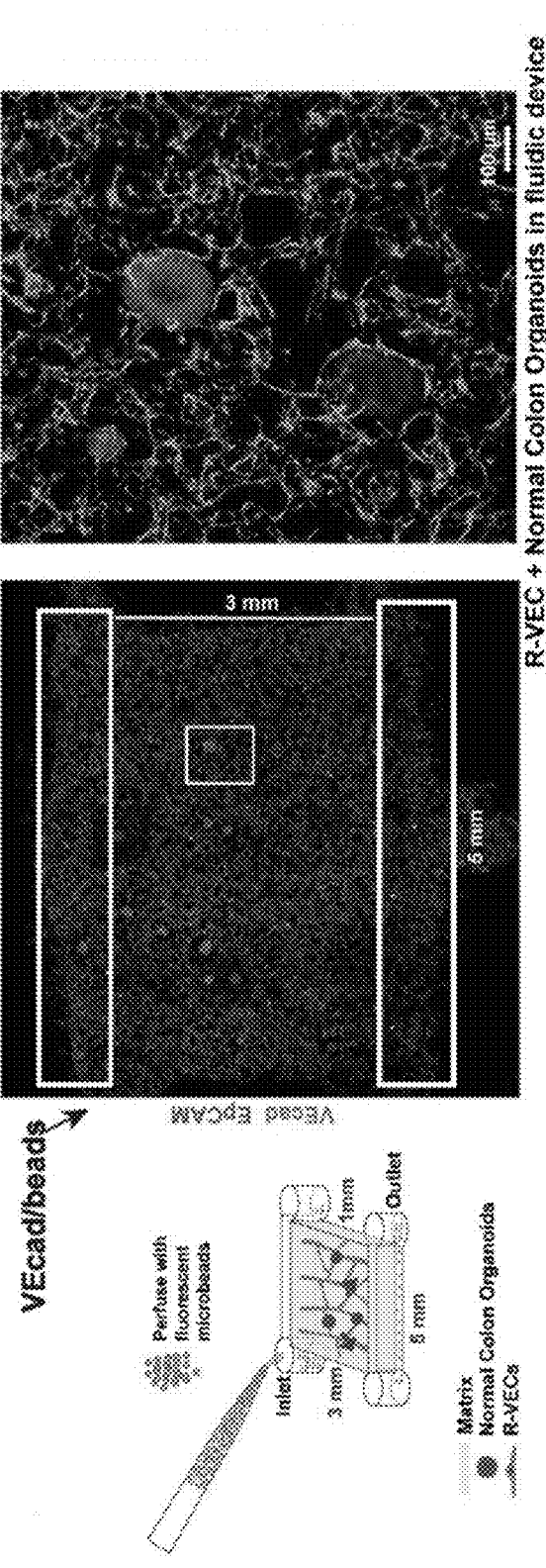

Vessel area was significantly higher in R-VEC wells compared to CTRL-EC and direct interaction of both R-VECs and CTRL-ECs with human normal colon organoids in L.E.C. was further assessed in a time-lapse movie through multi-zonal confocal microscopy (FIG. 6F). The intimate interaction between the R-VEC vessels with each organoid was followed over 72 hours in 3D 150 µm z-stacks. To compare CTRL-ECs to R-VECs co-cultures, the inventors performed a projection of z-stack confocal images and quantified the extent of interacting vessel networks with organoids, by a custom MATLAB code written to track the area of vessel networks that were recruited and interacted with the organoids over time (FIG. 6H). R-VECs were quantified to cover a significant larger surface area of epithelial cells, co-opting organoids in a web of interconnected vascular networks. The inventors also demonstrated that R-VECs avidly seek out and arborize mouse small intestinal organoids. Vessel area and number of endothelial sprouts interacting with the organoids were significantly higher when using R-VECs compared to CTRL-ECs.

Figure 6J:
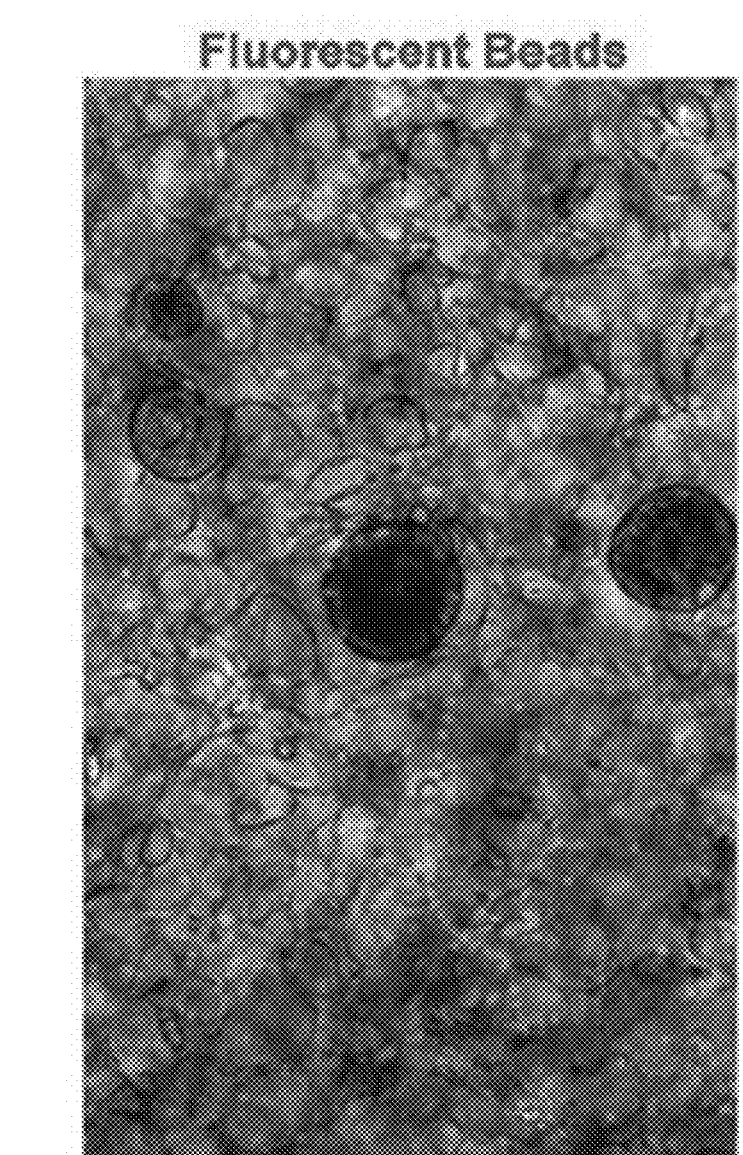

Next, the inventors explored the potential of R-VECs to physiologically vascularize human colon organoids in a large volume 15 microliter microfluidic device (FIGS. 6I-6J). The inventors found that R-VECs self-assembled into an interconnected multi-layered vessel network that spanned the entire 15 microliter volume of the microfluidic device, while intimately interacting with the colon organoids. The patency and perfusibility of the R-VEC vessels in co-culture with the colon organoids was demonstrated by injection of fluorescently-labeled VEcad antibody in the inlet of the device, which was able to stain the whole vessel network throughout the device. Lumen patency was further confirmed by flowing fluorescently labeled microbeads (FIGS. 6I-6J).

Example 12: R-VECs Avidly Co-Opt and Adapt to Tumor Organoids

Figures 7B, 7C, 7D:
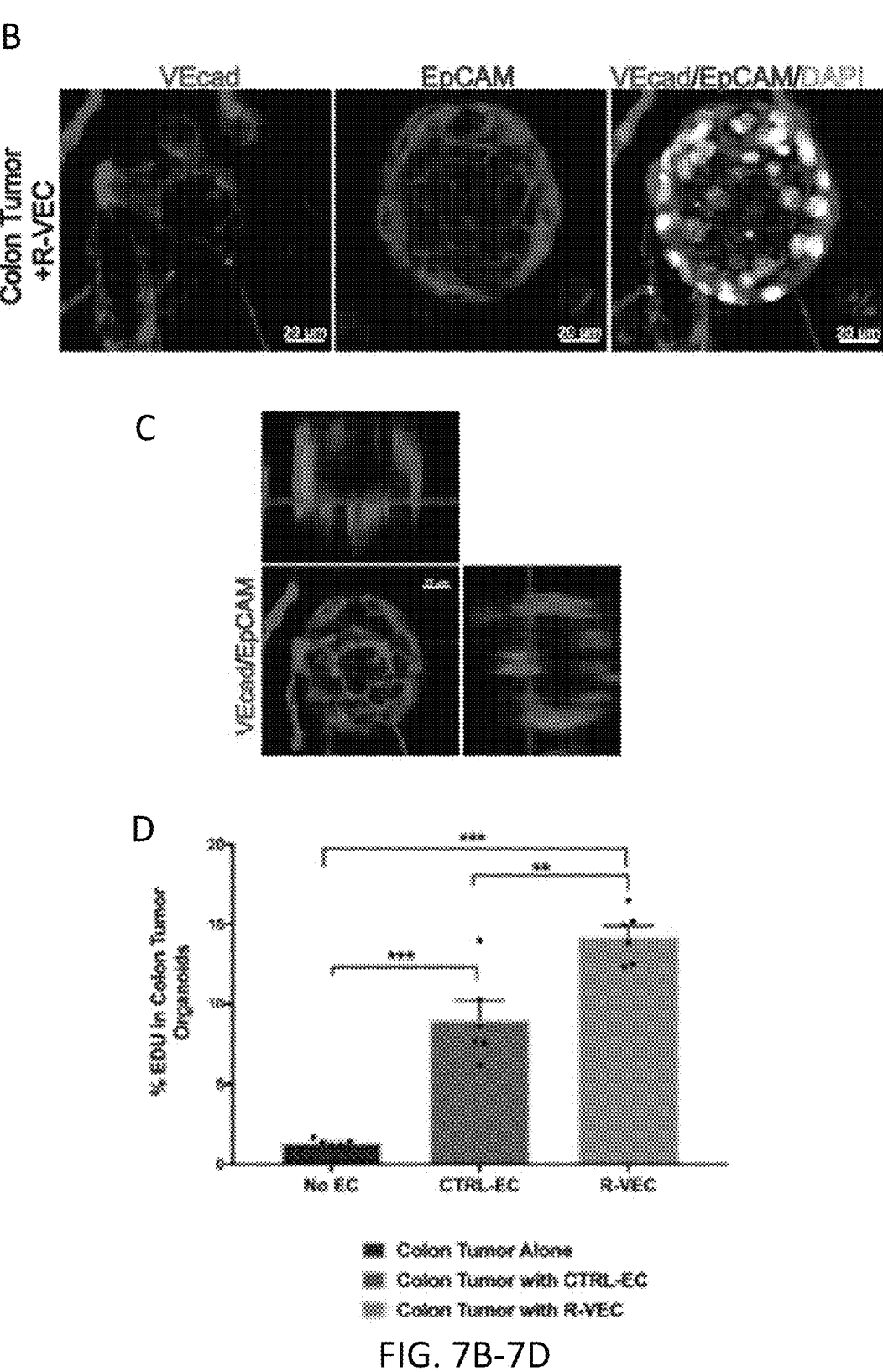

Endothelial cells recruited to tumor vascular beds often form structurally and functionally abnormal capillaries. In turn, corrupted tumor ECs supply aberrant factors that promote tumor growth. To determine whether R-VECs can acquire maladapted features of tumor vessels, the inventors co-cultured stage 1 induction R-VECs with patient-derived colorectal tumor organoids (FIG. 7A-7C). Within 24 hours, R-VECs migrated and arborized the tumor organoids. Over eight days, all organoids were arborized with dense populations of R-VEC vessels, while CTRL-ECs were unable to do so (FIG. 7A). Staining for the epithelial marker EpCAM, revealed the intimate cell-cell interactions between the tumor colon organoid cells and the R-VECs (FIGS. 7B-7C). Quantification of tumor cells showed a significantly higher percentage of EdU$^+$ proliferating tumor cells in the R-VEC co-cultures (FIG. 7D).

Figure 7E:
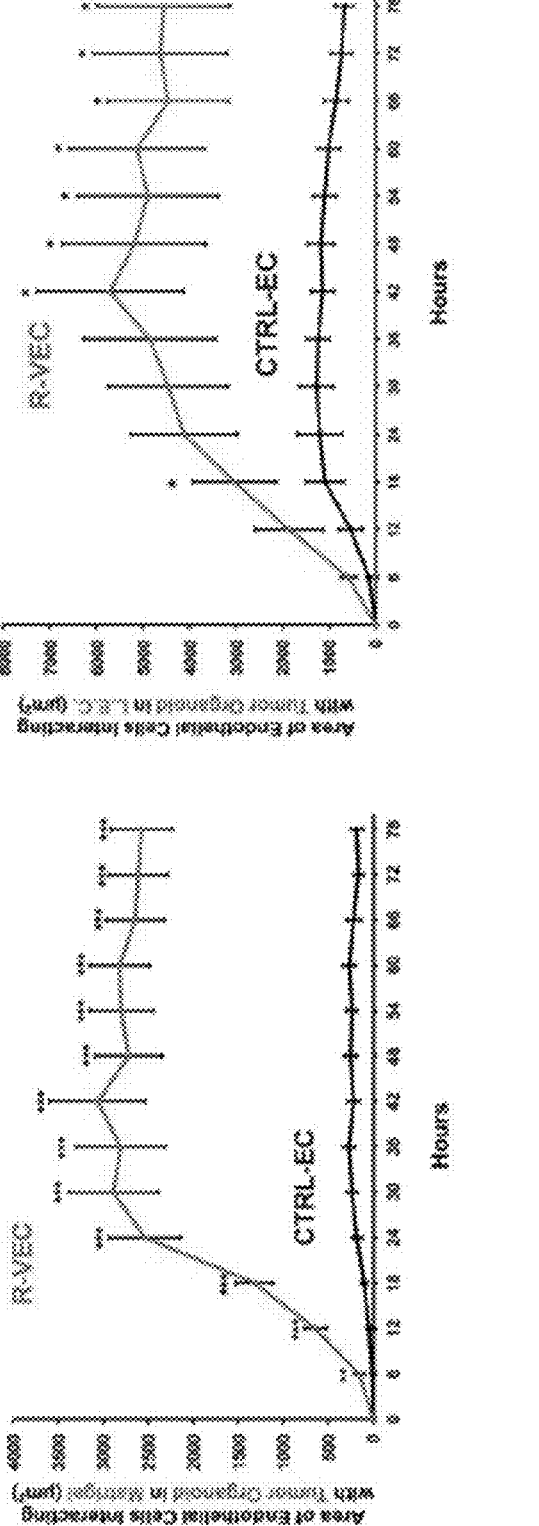
Figure 7F:
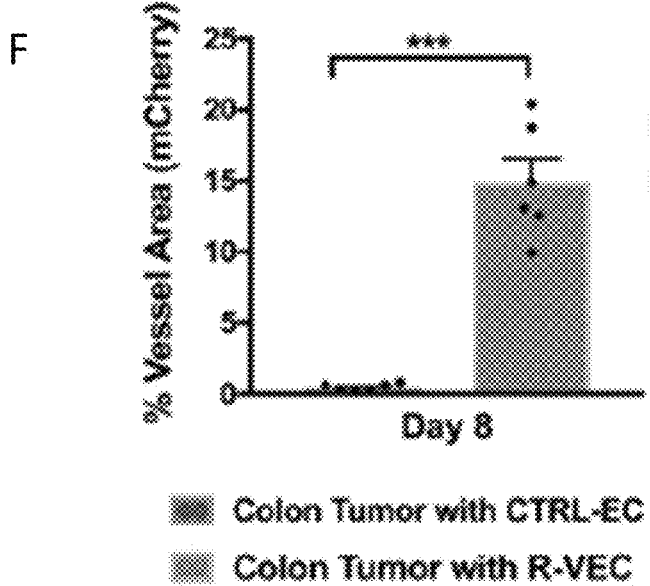

The dynamic interaction of CTRL-ECs and R-VECs with tumor organoids in 3D matrices, in both Matrigel and laminin-entactin-collagen IV (L.E.C) matrix, was assessed through multi-zonal confocal microscopy, performing live cell imaging of 150 µm z-stack movies over 78 hours. Using the z-projection images and a custom MATLAB code, the inventors quantified the area of interconnected vessel networks that co-opted the tumor organoids for both CTRL-ECs and R-VECs. Similar to normal colon organoids, the interaction of R-VECs with colon tumoroids was significantly higher than that of CTRL-EC in both Matrigel and the L.E.C matrix (FIG. 7E). The vessel area was also higher in the R-VEC co-cultures as compared to naïve non-ETV2 transduced co-culture wells (FIG. 7F). Other patient derived-tumor organoids, including triple negative breast tumors, yielded similar results.

Figure 7G:
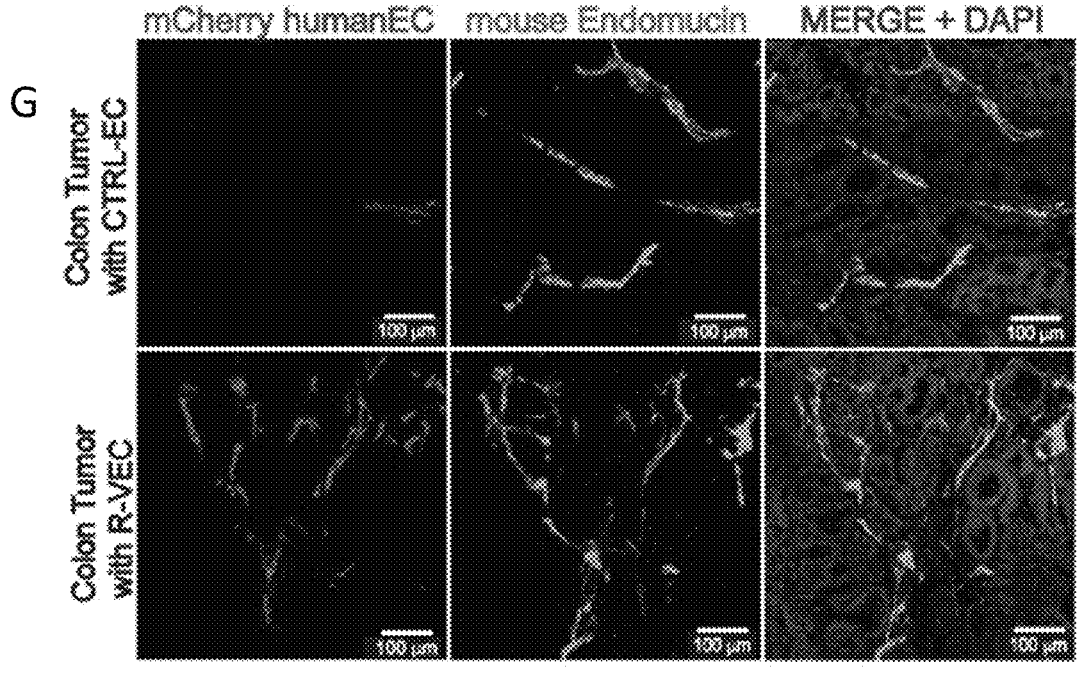
Figure 7H:
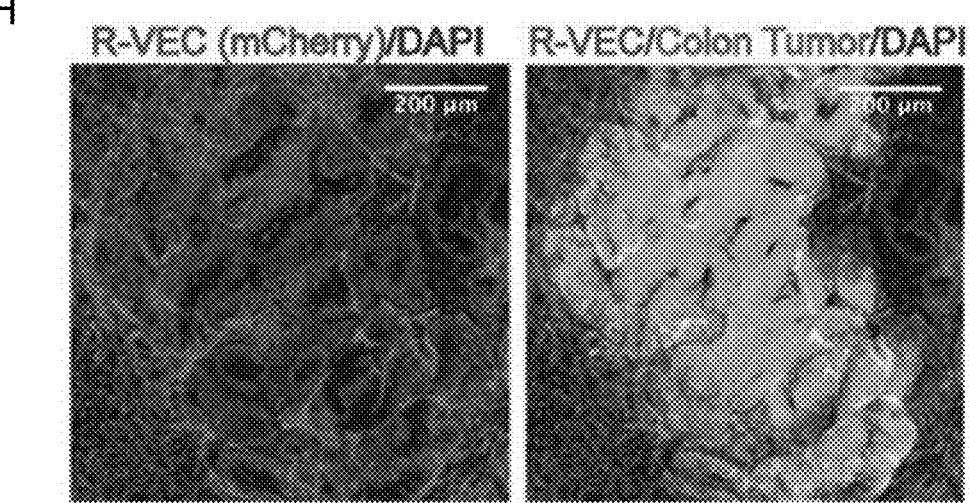
Figure 7I:
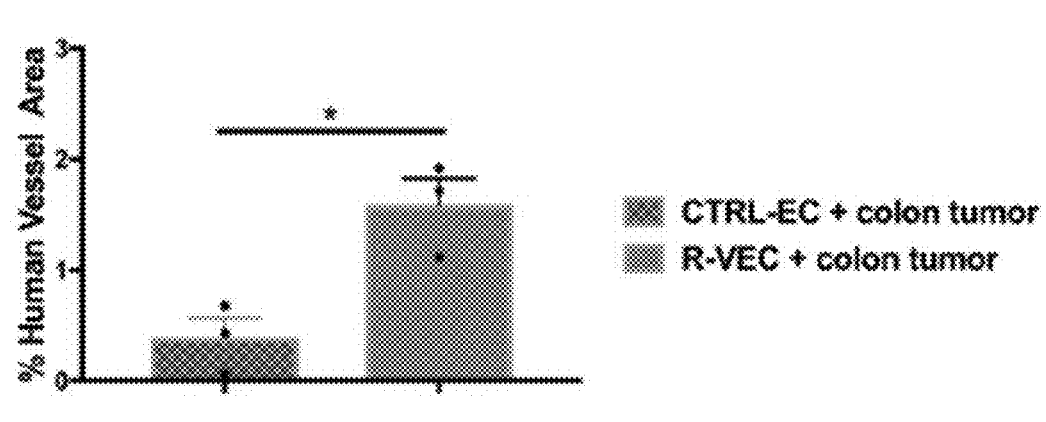

Next, the inventors assessed whether R-VECs could sustain humanized tumor vascularization in vivo, stage 1 induction mCherry-labeled R-VECs or CTRL-ECs were co-mingled with colon-tumor organoids (GFP-labeled) and implanted subcutaneously in SCID-Beige mice and sacrificed after 5 months. R-VECs, unlike CTRL-EC, persisted and sustained their vascular network patterning and vascularization within the growing tumor colon organoids (FIGS. 7G-7I). R-VECs anastomosed to the mouse circulation, establishing mosaic vessels with the Endomucin$^+$ painted mouse ECs (FIG. 7G). The vessel coverage of the tumor mass by human ECs, was augmented in the presence of R-VECs compared to those co-mingled with CTRL-EC (FIG. 7I). Therefore, R-VECs are empowered with adaptive capacity to respond to signals from tumoroids and instructively arborize tumor organoids both in vitro and in vivo. This approach could allow for deciphering the mechanism by which tumor ECs acquire their aberrant tumor vasculature features.

Example 13: Single Cell Transcriptomics Reveals Differential Adaptability of R-VEC to Cross-Talk with Normal or Tumor Organoids Study of the cross-talk between ECs and organoids has so far been cumbersome due to limited vascular integrity of CTRL-EC in 3D cultures. To this end, the inventors embarked upon harnessing the potential of large numbers of R-VECs to sustain their 3D vascular integrity over time, and assessed their capacity to respond to the microenvironmental signals, when in co-culture with various normal and malignant organoids. Indeed, the reciprocal responsive and adaptive remodeling of the R-VECs with organoids observed in FIG. 6 and FIG. 7, indicates intimate cross-communication among these cell types. To investigate the molecular profile of this interaction, the inventors performed transcriptomic analyses on the 3D co-cultures of R-VECs with normal or malignant colon and alterations in the RNA expression profile were compared to R-VECs cultured alone in 3D matrix.

After 7 days of co-culture, the whole population of R-VECs cultured alone and those co-cultured with accompanying normal or malignant colon cells were isolated and subjected to single cell RNA-sequencing (scRNA-seq) using 10× Chromium platform (FIG. 8A-8H). Endothelial and epithelial cell clusters were identified in the merged samples. The ECs were identified by focusing on single cells expressing vascular specific markers, VEcadherin (CDH5), CD31 (PECAM1) and VEGFR2 (KDR) and the epithelial cells were identified by the expression of the epithelial markers EpCAM, CDH1 and KRT19.

Figure 8A:
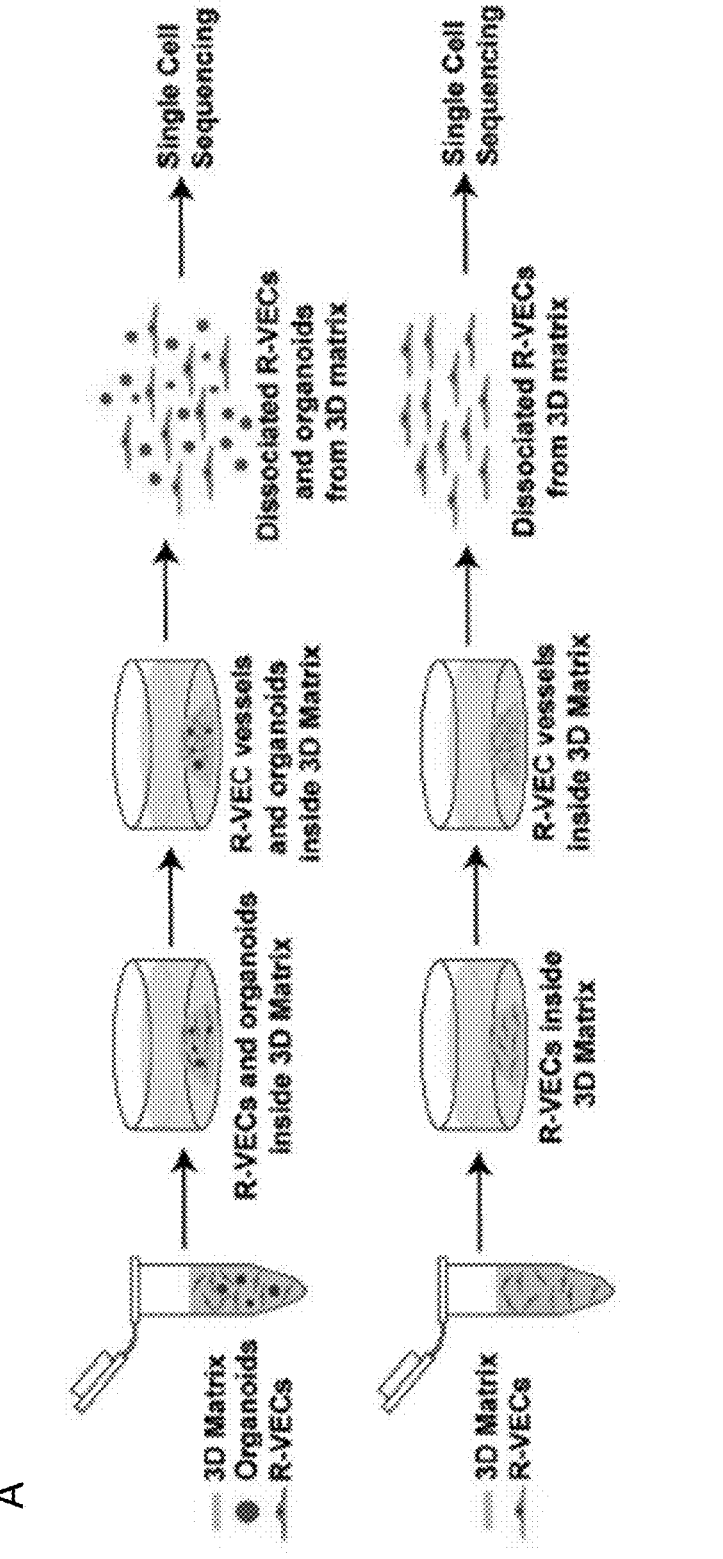
Figure 8C:
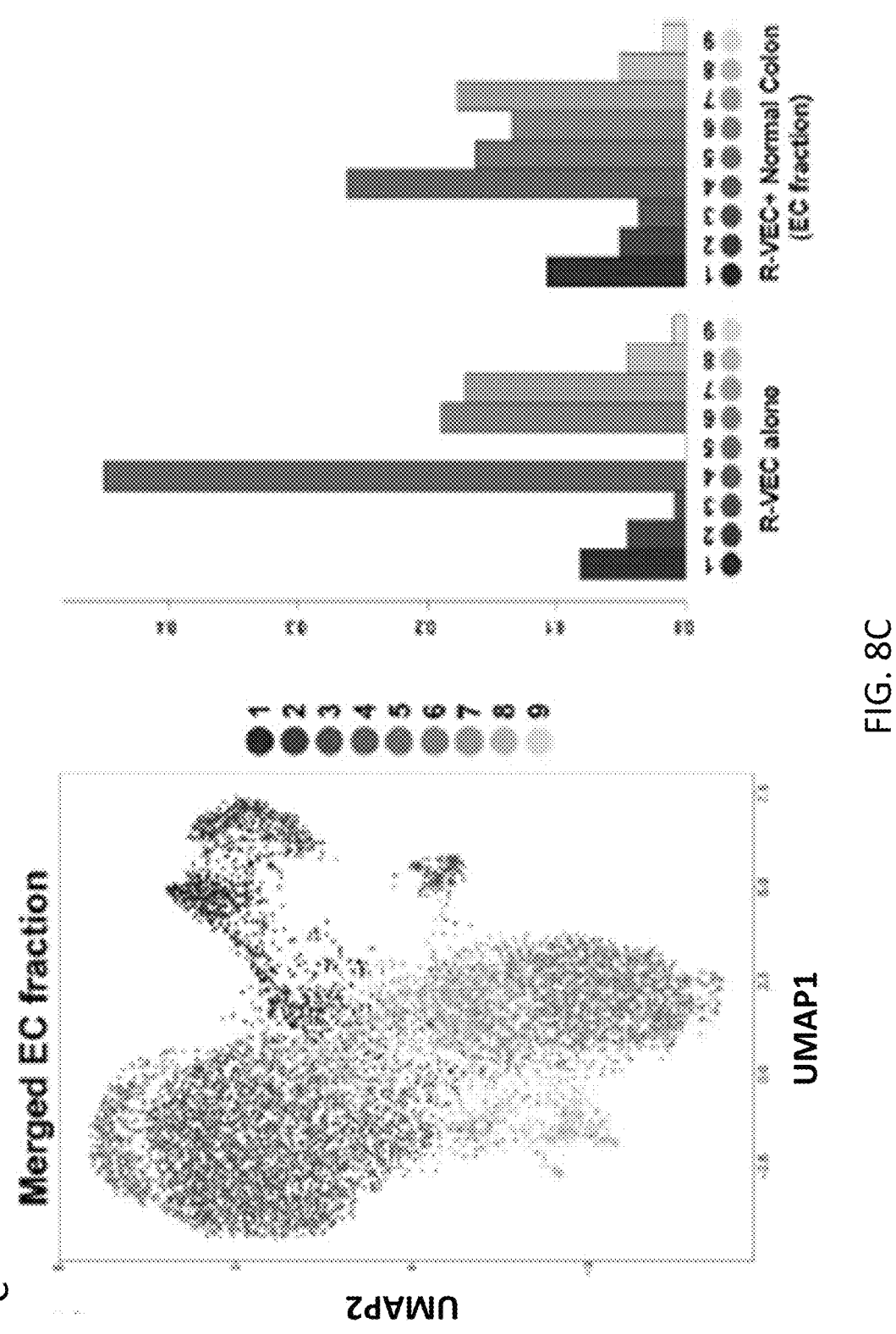
Figure 8D:
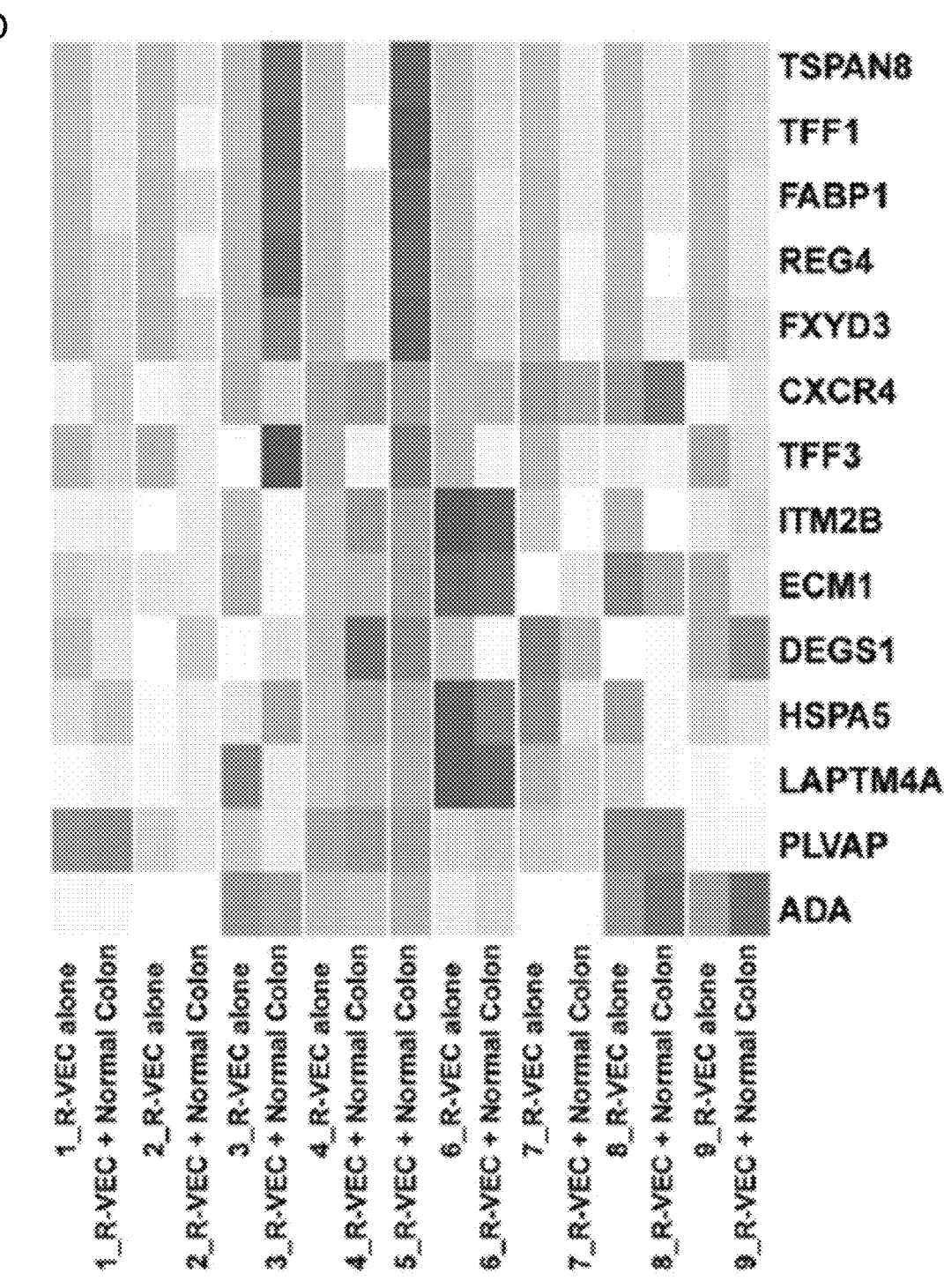
Figure 8E:
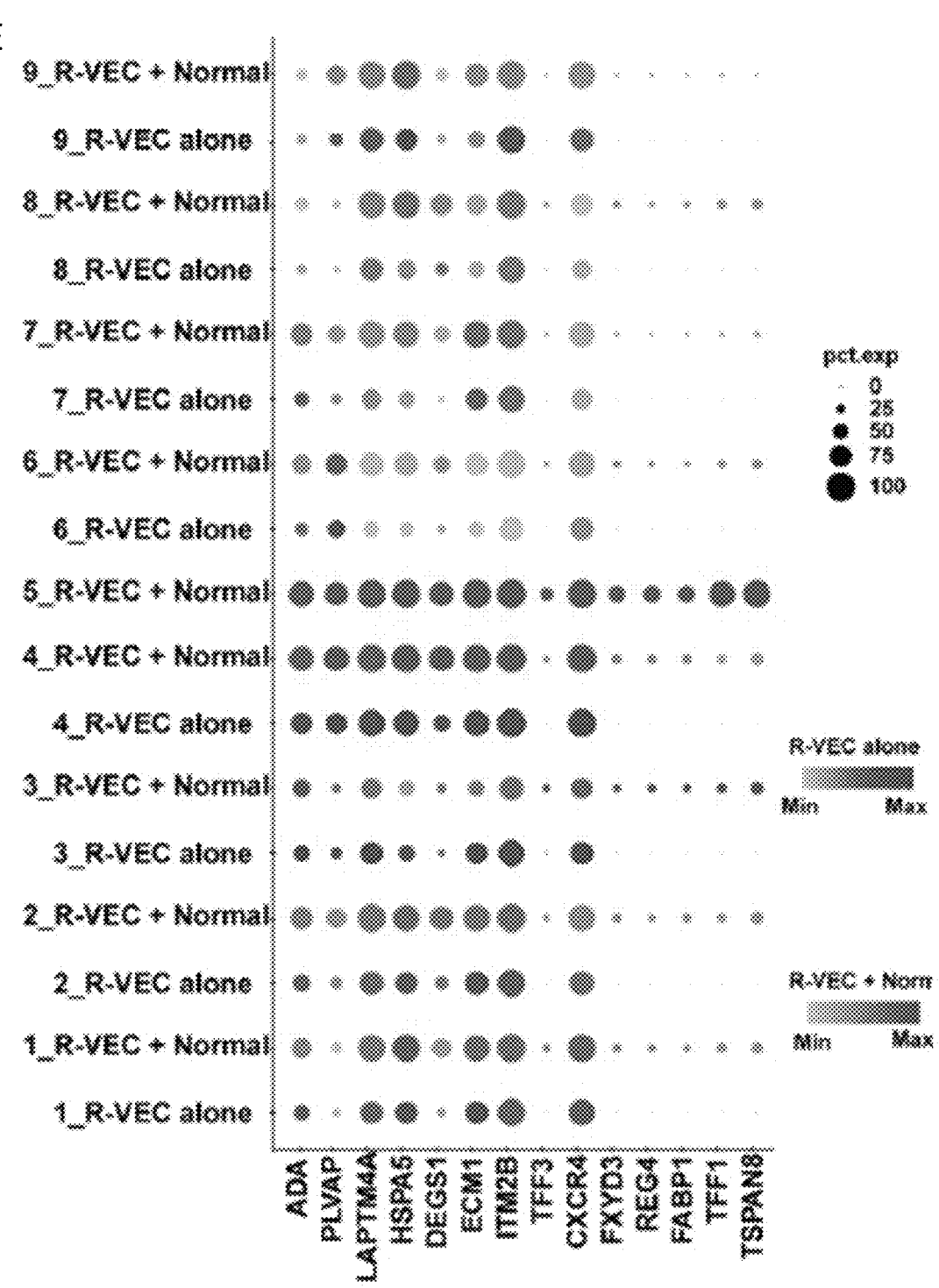
Figure 8H:
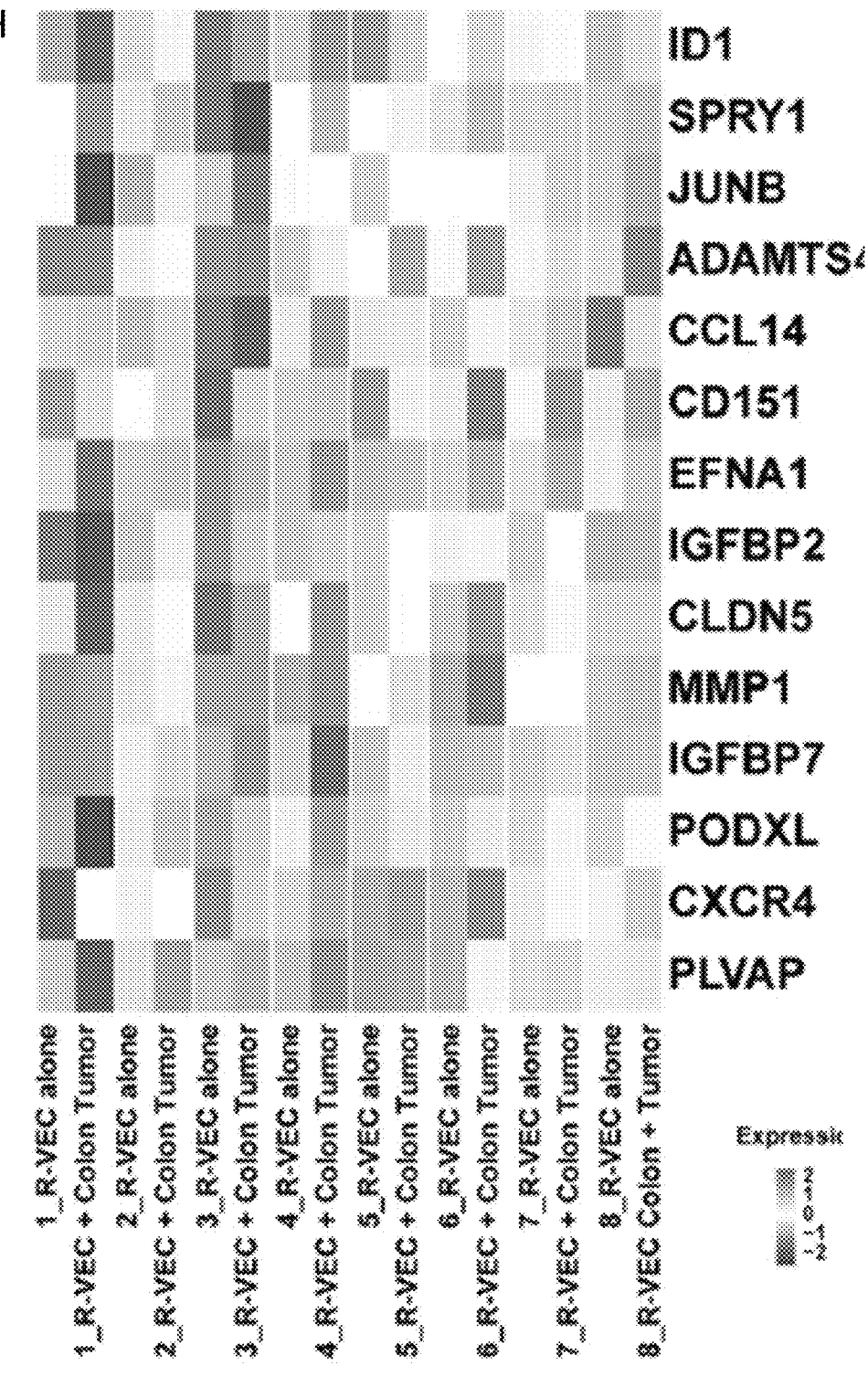
Figure 8I:
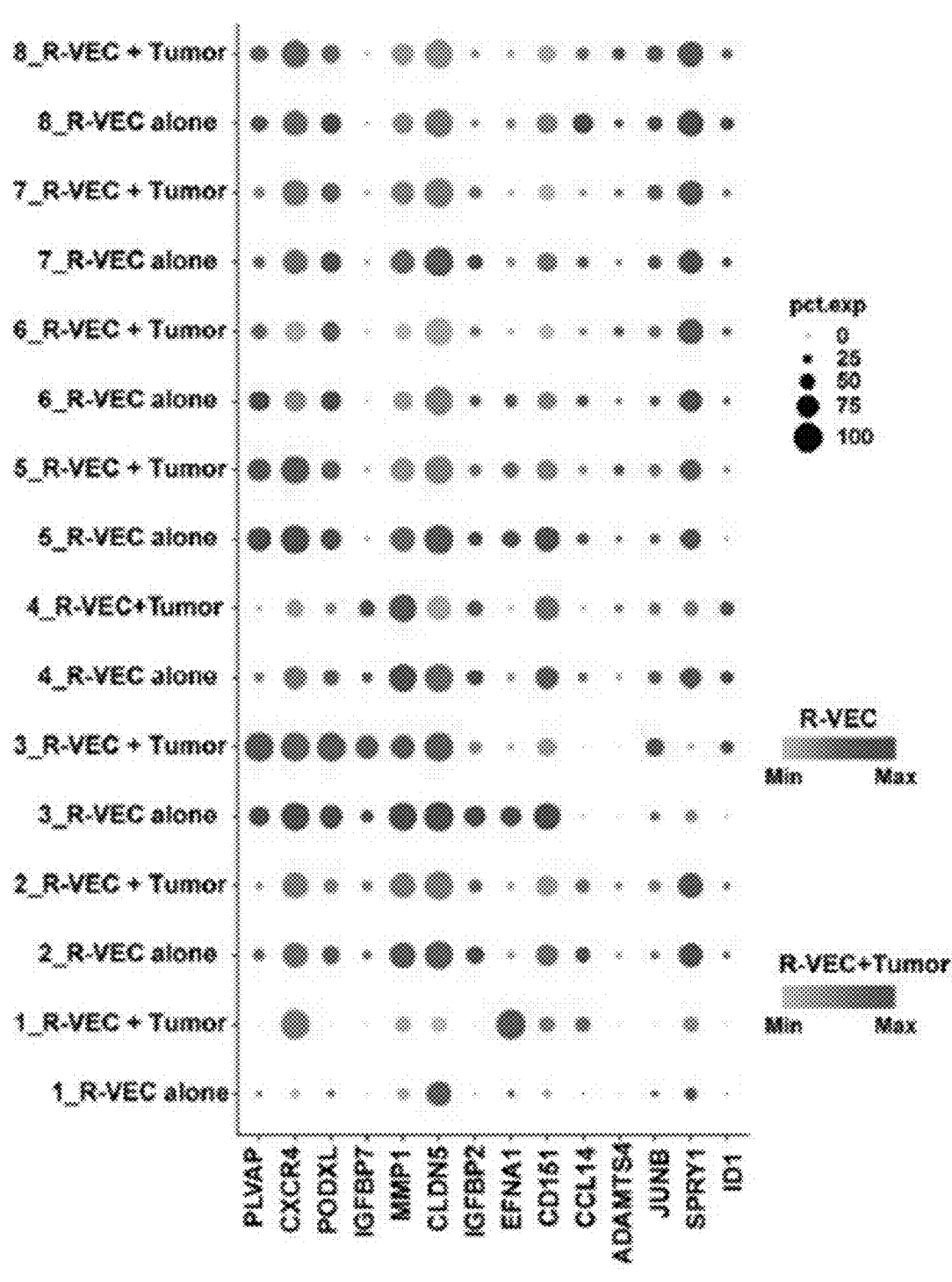

In the endothelial cell fraction, those R-VECs co-cultured with malignant or normal organoids, as compared to R-VECs alone, manifested significant changes in their clustering patterns and gene expression (FIGS. 8B-8E). R-VECs that interacted with normal colon epithelial cells were enriched in ECs expressing organotypic EC markers such as PLVAP and TFF3 (cluster 5) (Augustin, H. G. & Koh, G. Y., *Science* 357, doi:10.1126/science.aal2379, (2017); Blundell, C. et al., *Lab Chip* 16, 3065-3073, (2016)) (FIGS. 8D-8E). By contrast, R-VECs that arborized colon tumoroids were enriched in clusters of cells that upregulated factors that have been previously shown to be expressed by prototypical tumor ECs, such as ID1, JUNB and ADAMTS4 (cluster 8), while genes responsible for junctional integrity, such as Claudin-5 (cluster 5, cluster 7) were selected against (Lyden, D. et al., *Nature* 401, 670, (2019)) (FIGS. 8F-8I). Thus, R-VECs respond to extrinsic microenvironmental stimuli by turning on defined sets of genes. Of note, these experiments could not be performed with naïve human ECs as these cells do not sustain their arborization of the organoids beyond a few days, and as such their cross-talk with organoids could not be assessed.

By the same token, epithelial cells themselves displayed changes in their molecular profile reflecting their interactions with R-VECs. Notably, in response to association with R-VECs, cells with markers linked with poorer prognosis and higher metastasis, including higher levels of MSLN (Li, S. et al. in J Cancer Vol. 8, 1355-1361 (2017)), and lower levels of MT1G, MT1X and MT2A (Si, M. & Lang, J., *J Hematol Oncol Vol.* 11, (2018)) were selected for, in colon tumor cells co-cultured with R-VECs.

Figure 9A:
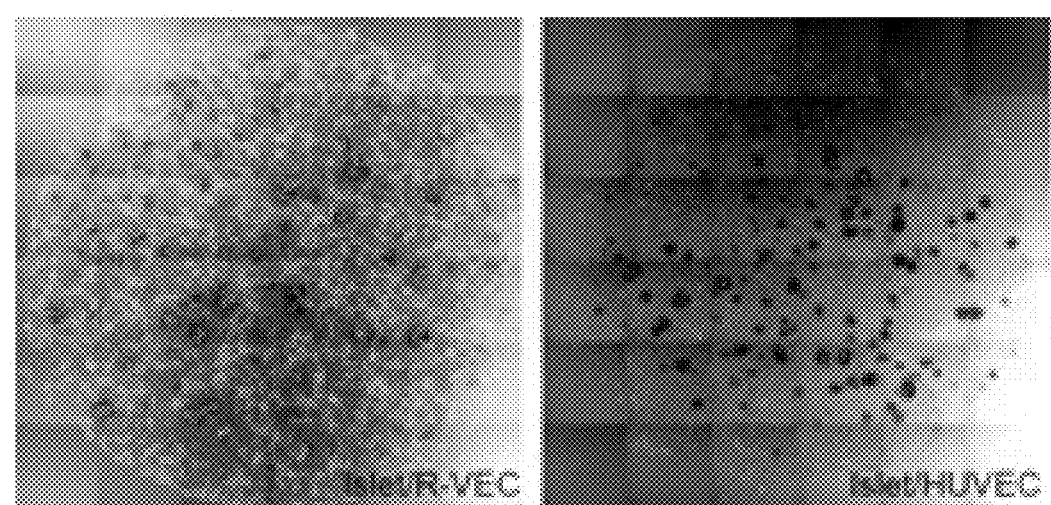
FIGS. 9A-9C. Engraftment of islet/R-VEC was found in the subcutaneous space 1 month after the transplantation. (A) Cell-carrying droplet for transplantation. (B) Islet/R-VEC plug were connected with adequate blood supply. (C) Insulin+ cells and R-VECs with EGFP were found in the plug.
Figure 9B:
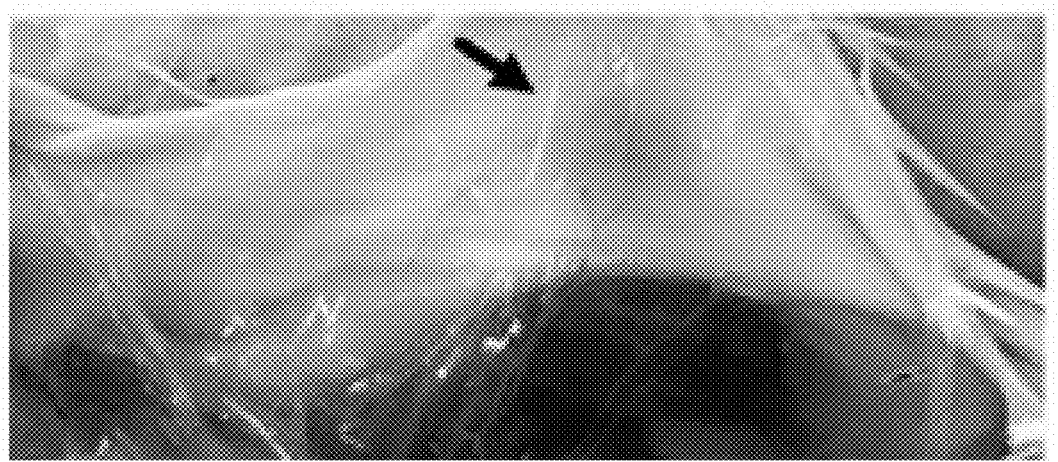
Figure 9C:
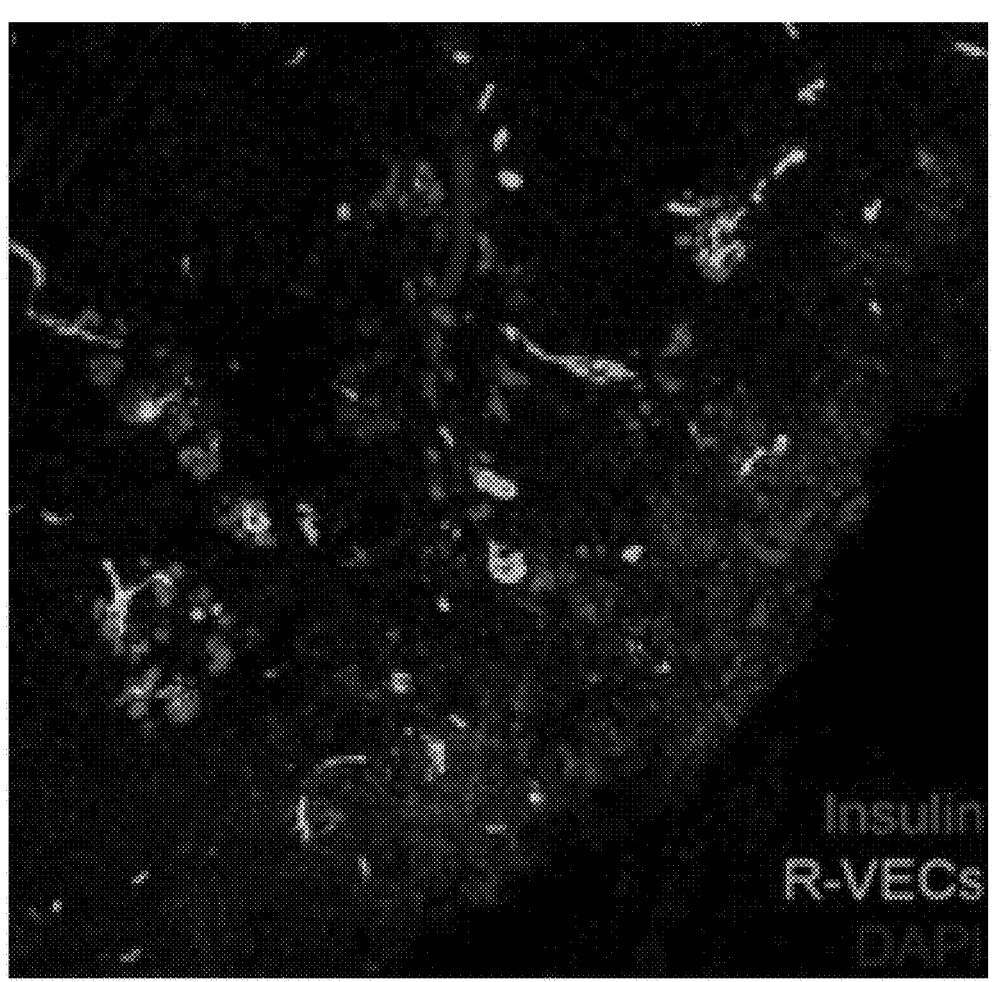

Example 14: Islet/R-VECs Established Adequate Blood Supply in the Subcutaneous Space The pre-vascularized islets were prepared by co-culturing islets with R-VECs in a 40 µL droplet of 3D matrix. As shown in FIG. 9A, only R-VECs, but not HUVECs, self-assembled into connected vascular net. Five droplets of such pre-vascularized islets were then inserted into the subcutaneous space on the back of a SCID-beige mouse. The graft was examined 1 month later. While nothing could be found in mice received islet/HUVECs, the engrafted islet/R-VECs resulted in a plug with adequate blood supply (FIG. 9B). Sectioning and staining the plug revealed subcutaneous islets with insulin+ cells that were vascularized with blood vessels formed by R-VECs (FIG. 9C).

Example 15: Subcutaneous Transplantation Reduced Body Weight Lost and Reverse Hyperglycemia The inventors next induced diabetes in SCID-beige mice by i.p. injection of streptozotocin (STZ). Development of diabetes was confirmed by non-fasting blood glucose higher than 300 mg/dl for 3 sequential days. Once diabetes is developed, the general symptoms are loss of body weight, increased blood glucose, and reduced plasma insulin. To treat the mice, the inventors transplanted the cell-carrying matrix to the subcutaneous space on the back. Each mouse received 5 droplets of the cell-carrying matrix. Each droplet was 40 µL and contains ~200 islets only, co-culture with HUVECs, or with R-VECs (FIG. 9A). Thus, each mouse received approximately 1000 human islets. As expected, subcutaneous transplantation of islet alone barely ameliorated the hyperglycemia.

Figures 10A, 10B, 10C:
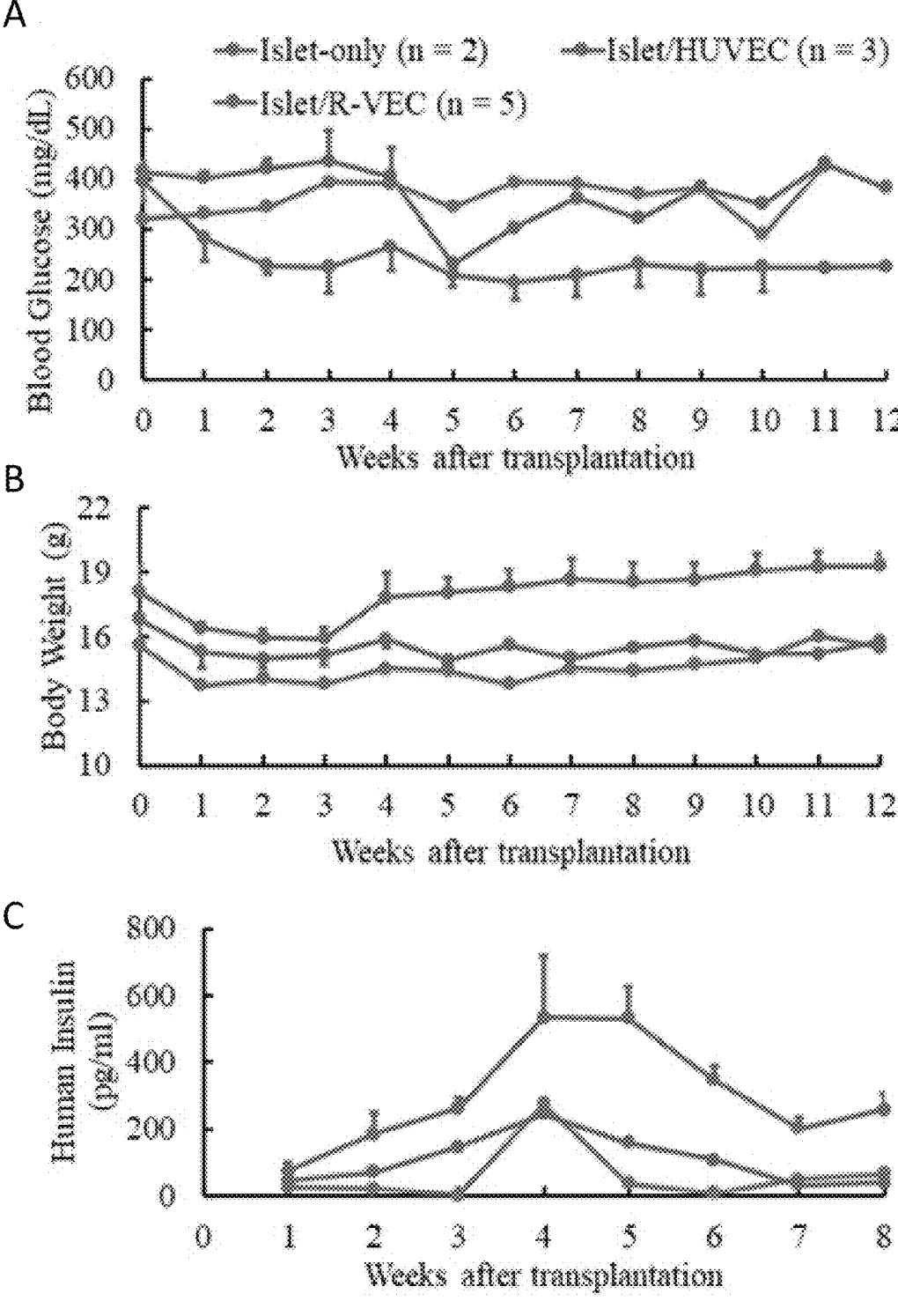
FIGS. 10A-10C. Subcutaneous transplantation of islet/R-VEC ameliorated STZ induced diabetes. (A) Blood glucose levels after 6 hours of fasting. (B) Body weights examined in the morning before fasting. (C) Serum human insulin levels at 20 minutes after glucose challenging as 2 g per kg body weight.

Meanwhile, islet/R-VEC quickly reduced the blood glucose starting from the 1st week after transplantation and stably controlled the blood glucose around 200 mg/dl for the rest of the observation period for at least 12 weeks (FIG. 10A). Such results suggest that R-VECs quickly adapted to the subcutaneous environment and maintained a long-lasting vascular niche to support the function and/or survival of the engrafted human islets. Notably, islet/HUVEC explants dramatically reduced blood glucose only at week 4, and the blood glucose levels rebound to >300 mg/dl in about 2 weeks later. Accordingly, the body weight of the mice received islet-only or islet/HUVEC remained abnormally low at all the time; and the body weight of islet/R-VEC mice went back to normal range at week 4 and gradually increased thereafter (FIG. 10B).

To further verify that the amelioration was indeed contributed by the engraftment of pre-vascularized islets, the inventors further examined the presence of human insulin in the serum. The mice were first fasted for 6 hours and then received i.p. injection of a high dose of glucose. After 20 minutes of glucose challenging, serum was obtained and examined for human insulin. As shown in FIG. 10C, substantial level of human insulin was detected in islet/R-VEC mice, much lower in islet/HUVEC samples, and almost none in islet-only samples. Interesting, in all groups, the inventors found peaks of human insulin level at week 4, which is consistent exactly with the observations that islet/R-VEC mice started to re-gain body weight at week 4 and the islet/HUVEC mouse has a temporary euglycemia at week 4. Here, the inventors set forth cogent evidence that human islets pre-vascularized by R-VECs survive and function in a physiological manner to reverse hyperglycemia in STZ induced diabetic mice. It is also intriguing to further interrogate the dynamic adaption processes of islet/R-VEC graft in the subcutaneous space.

Example 16

Mature adult human ECs lack the capacity to establish and sustain long-lasting lumenized vessels in a defined matrix in vitro or in vivo in mice beyond a few days or weeks. Adult derived ECs are also resistant to proper self-assembly into stable long-lasting vessels, unable to interact instructively with normal or tumor organoids or pancreatic islets, and sparsely colonize the inner surface of decellularized scaffolds. These suboptimal functions could be due to poor cellular adaptability and the impliable state of mature human endothelium. Here, the inventors show that re-introduction of the ETV2 transcription factor-silenced during fetal development-back into adult human ECs can induce a 'molecular reset', to endow these mature, tissue-specific ECs with primitive-like vasculogenic, tubulogenic and adaptability potential. R-VECs have unique durable large-volume tubulogenic potential capable of self-organizing into the 3D lumenized vascular networks that maintain their geometric patterning, lumen stability and frequency of the branching hubs, both in vitro and in vivo for 5 to 10 months. R-VECs self-organize into vessels that could transport whole human heparinized peripheral blood and support physiological vascularization of human pancreatic islets and colon organoids. Notably, the R-VECs that were implanted in the L.E.C matrices in the mice for over five months, sustained their capacity to anastomose to the mouse circulation, while maintaining their capillary network patterning. The inventors show that mice with R-VEC plugs did not form tumor or metastatic lesions even 10 months post implantation. These attributes of R-VECs to establish long-lasting stable vessels and to facilitate vascularization of organoids, pancreatic islets or decellularized tissues, will enable to capitalize on the potential of R-VECs for uncovering vascular heterogeneity and set the stage for organ repair.

The mechanism by which R-VECs acquire these vascular malleable features is mediated through balanced activation of numerous vasculogenic, morphogenic and angiogenic factors that are extinguished in mature tissue-specific adult human ECs. Most likely, reactivation of ETV2 turns on silenced vascular programs that augment tubulogenesis and self-assembly attributes of the mature ECs, without the constraint of a pre-fabricated scaffold, requirement of enforced perfusion and pericyte investment. This notion is supported by the molecular profiling of the R-VECs that reveals the induction of numerous signaling pathways that are primarily expressed in the primitive vascular plexus. Similar to aortic development and primary vessel formation in the yolk sac, which develop by vasculogenesis. R-VECs activate the Rap1 pathway through several Rap1-GEFs and the RASIP1 effector to allow lumen formation in flow- and pericyte-independent, cell-autonomous manner. By reviving vasculogenesis pathways, ETV2 resets the vascular epigenetic memory to an early plastic stage to render R-VECs more receptive to microenvironmental cues relayed from normal parenchyma or malignant tissue.

R-VECs accelerate arborization of organoids and pancreatic islet explants, in 50 microliter static matrix domes, and physiological vascularization of these organoids and islets in large-volume 15 microliter microfluidic devices. In both models, the robust potential of R-VECs to self-assemble into multi-layered interconnected vasculature, without dependency on forced patterning by pre-fabricated scaffolds, allows R-VECs the cellular freedom to instructively interact with various epithelial and tumor cells without the constraints of synthetic barriers. Within these static matrix domes, R-VEC capillary networks support maintenance and expansion of the various mature and immature epithelial cells within human organoids, and sustain insulin release in human pancreatic islet cells.

The inventors observed modest GSIS response when islets were cultured alone or with CTRL-ECs, while R-VEC co-culture significantly increased GSIS in static Matrigel domes and in perfusable microfluidic devices. The mechanisms underlying the beneficial effects of R-VECs in islet co-cultures may involve the depositing of extracellular matrix proteins, such as Laminins and likely islet-specific angiocrine factors that are yet to be elucidated. The inventors showed that the intimate association of the R-VEC vascular network with the organoids augments the proliferation and size of the epithelial and tumor organoids as shown by EdU staining. Thus, R-VECs serve as a prototypical vascular niche that support the growth and choreograph the proper morphogenesis of normal colon organoids. On the other hand, R-VECs co-opted by colon tumor organoids in vitro and in vivo establish patterned, but less organized vascular networks. Studying the two way cross-talk between R-VECs and epithelial cells could facilitate uncovering signals that specify normal and tumor vascular heterogeneity.

Current approaches to generating vascular conduits for delivery of oxygen and nutrients require culturing ECs in pre-fabricated scaffolds, restrictive biomaterials, enforced perfusion and inclusion of perivascular cells (Zhang, B. et al., *Nat Mater* 15, 669-678, (2016); Kim, S. et al., *Lab Chip* 13, 1489-1500, (2013); Wang, X. et al., *Lab Chip* 16, 282-290, (2016)). While these microenvironmental interventions bring the vascularized organoids closer to recreating the in vivo conditions, they also pose significant technical hurdles and limit the affordability and technical feasibility of constructing vascularized organoids for in vitro or for therapeutic in vivo use. Indeed, because of suboptimal vascular network self-assembly, naïve human ECs can only establish small perfusable chambers of up 2 microliters (Chen, M. B. et al., *Nat Protoc* 12, 865-880, (2017); Campisi, M. et al., *Biomaterials* 180, 117-129, (2018); Phan, D. T. T. et al., *Lab Chip* 17, 511-520, (2017)), often with vessels with small bore lumens preventing the flow of human hematopoietic cells. Furthermore, in most cases, these primitive vessels are separated from organoids or other cell types by synthetic porous barriers, thereby limiting cross-talk between the blood vessels and other cells (Huh, D. et al., *Science* 328, 1662-1668, (2010); Blundell, C. et al., *Lab Chip* 16, 3065-3073, (2016)). By contrast, R-VECs readily self-organize into a patterned perfusable continuous capillary network within large chambers with a 15 microliters capacity enabling physiological vascularization of colon organoids and pancreatic islets. Importantly, as shown in FIGS. 5-7 and Movies 2-4, R-VECs have the cellular liberty to readily inter-mingle and interact with organoids and pancreatic islet explants.

The present disclosure provides evidence that R-VECs self-organize into hemodynamically stable patterned vessels that can physiologically vascularize pancreatic islets and organoids. Most importantly, given the capacity of R-VECs to form unprecedented extensive interconnected vascular webs within large volume microfluidic chambers, allowed the inventors to accommodate larger-sized organoids and islets some of which measure 250 microns in diameter. Current devices in use by other groups have on average limited chamber height of up to 150 microns, which could undermine the study of large islets and organoids. For the first time, the inventors demonstrate that R-VEC are capable of forming stable vessels with lumenal and hemodynamic integrity allowing for perfusion of heparinized whole human peripheral blood that compose of full complement of platelets, RBC and WBC cells, as well as unperturbed plasma. Furthermore, the inventors showed that R-VECs can promote physiological vascularization as infusion of high glucose induces the production of insulin by the pancreatic islets, detectable in the outflow tract of the perfused chambers. Perfusable R-VECs can also vascularize colon organoids, sustaining the frequency of the number of cocultured organoids. Control non-ETV2 transduced human ECs, fail to sustain tubulogenic vessels and fail to promote physiological vascularization of the islets or organoid cultures. Thus, R-VECs represent structurally adaptable ECs that have the resilience to physiologically interact and cross-talk with tissue-specific cells.

It is plausible that as compared to implanting organoids alone, in vivo inoculation of R-VEC arborized organoid modules may augment engraftment and anastomosis to the pre-existing vessels. The two way cross-talk of R-VECs with the organoids also sets up the stage to determine how ECs might acquire tissue-specific and tumor-specific heterogeneity. In this vein, utilizing single cell transcriptomics analyses (scRNA-seq) and epigenetic profiling, the inventors were able to uncover the malleability of R-VECs in response to co-culturing with normal or tumor organoids. Tumor epithelial cells were also found to upregulate several markers associated with poorer outcome when arborized by R-VECs. This finding renders this co-culture platform suitable for more physiological and relevant drug screening for resistant tumor phenotypes. Tumor or normal organoids are traditionally generated and propagated using Matrigel matrix. The uncertainty of the various digested matrix components variably present in Matrigel obfuscates mechanistic studies to decipher the adhesion molecules and chemokines that enable the self-assembly of organoids. Here, the inventors show that defined L.E.C matrix, in part through interaction with integrins, such as β1 integrin, is sufficient to not only permit co-integration of vascular plexus with epithelial and tumor organoids, but also to perform targeted mechanistic studies.

The main impetus for employing ETV2 in our studies was the uniqueness of this ETS transcription factor that is only transiently expressed during embryonic development and only turned on in stressed adult ECs. The physiological significance of this ephemeral expression of ETV2 is under scrutiny, but it may point to its important function as a pioneer factor that needs to be expressed in a short interval to exert its potent pro-vasculogenic effects. The inventors' finding that even during lentiviral-ETV2 constitutive enforced expression, stage 3 stable 3D vessels composed of ECs that express low and decreased ETV2 levels, is attestation to the complex regulation of ETV2 expression in vascular cells. Indeed, the inventors show that ubiquitination might play a role in silencing of the ETV2.

In summary, the generation of R-VECs in a defined extracellular matrix, serves as an interrogable model system to uncover the complex 3D cellular interactions of hemodynamically stable and resilient tissue-specific ECs with non-vascular cells.

Example 17: Static Co-Culture with R-VECs Improved the Function of Stem Cell-Derived p Cells (SC-β Cells) as Evidenced by Augmentation of Glucose Stimulated Insulin Secretion (GSIS)

Figure 11A:
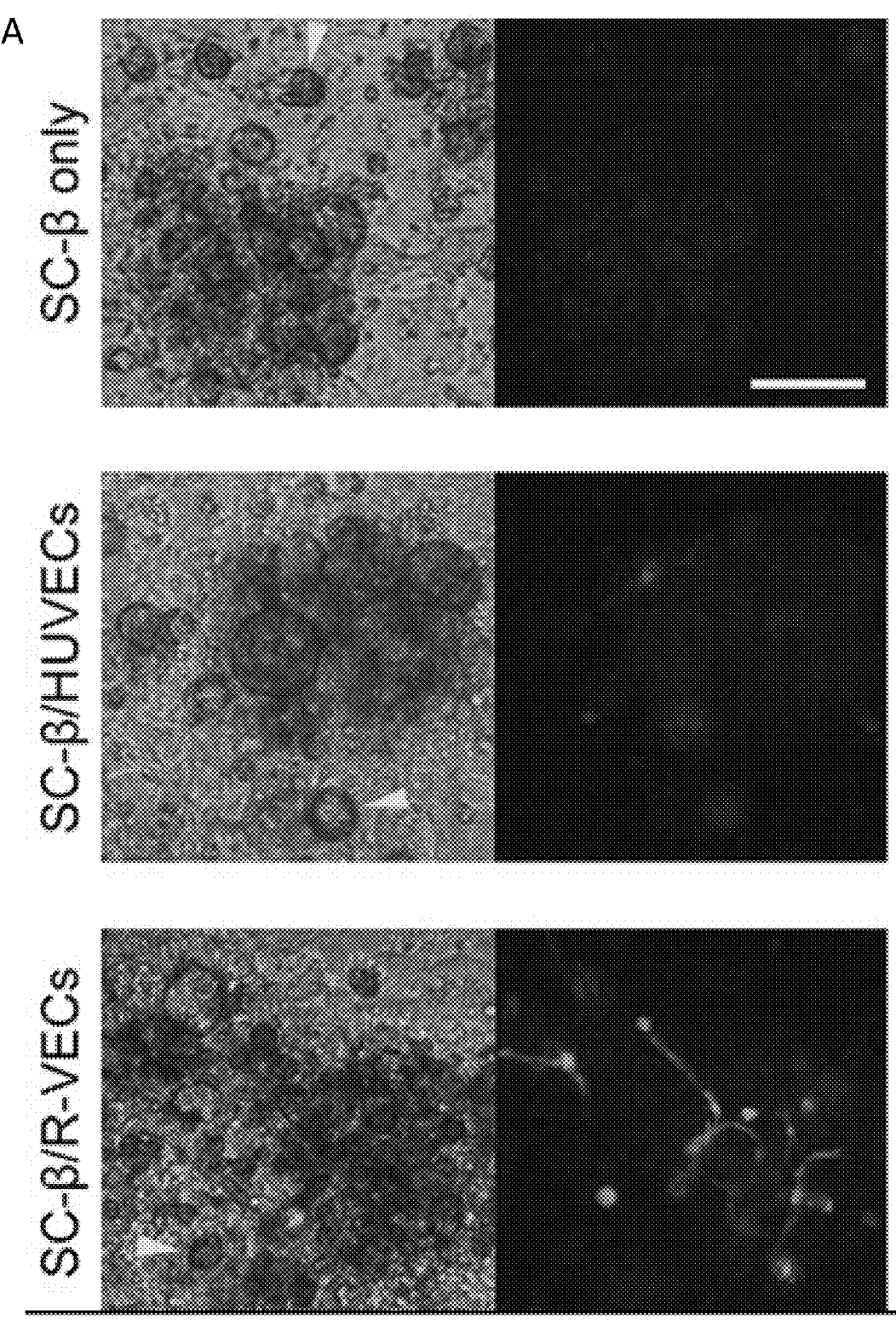
FIGS. 11A-11B. R-VECs co-culture promoted SC-β maturation. (A) Images of SC-β cells with or without EC co-culture. Scale bar: 100 μm. (B) Fold changes of GSIS of SC-β cells.
Figure 11B:
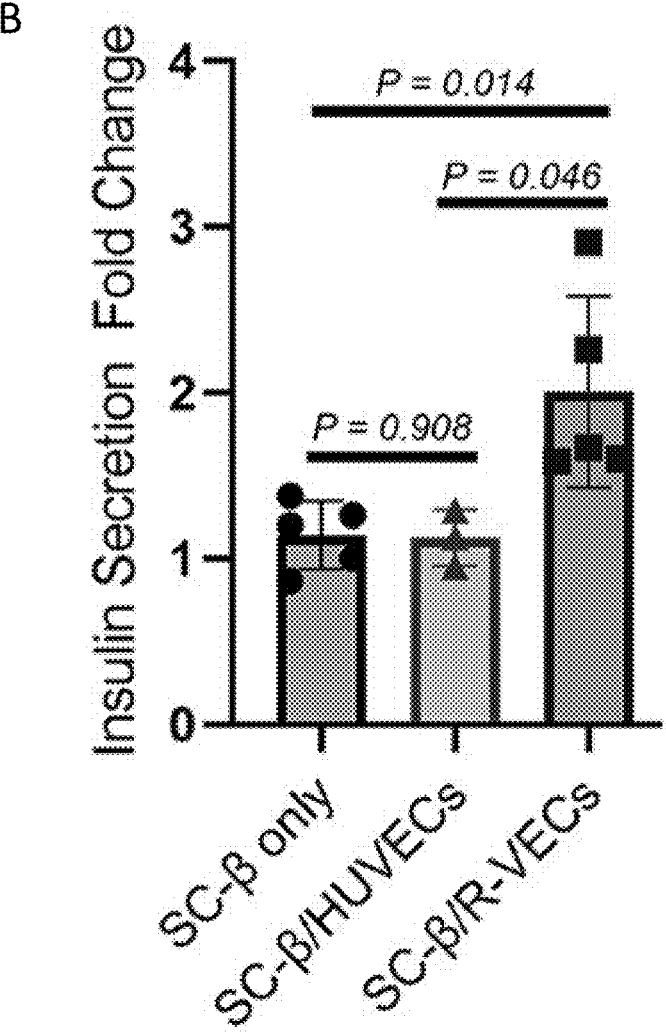

The inventors obtained pluripotent-derived SC-β cells and cultured them in 3D matrix by themselves, with generic human umbilical vein ECs (HUVECs), or with R-VECs (HUVECs transduced transiently with ETV2). In all 3 groups, SC-β continued to differentiate in the 3D matrix and formed small sized spheroids (indicated with yellow arrow heads in FIG. 11A left panels). Possibly resulting from fusion of small islet spheroids, cell clusters with sizes of regular islets (100-200 μm) were also observed in all 3 groups (FIG. 11A left panels). As expected, only when co-cultured with R-VECs, the islet-like cell clusters were vascularized by ECs (EGFP+ cells in FIG. 11A right panels). After 2 weeks of 3D culture, SC-β cells' function was examined with glucose-stimulated insulin secretion (GSIS) assay. Each sample was first incubated with low glucose (2 mM) to determine the basal insulin secretion, and then incubated with high glucose (16.7 mM) to determine the stimulated insulin secretion. The GSIS folds were calculated as dividing the stimulated insulin levels by the basal insulin level. Consistent with the inventors' hypothesis, SC-β/R-VECs samples showed significantly higher folds of insulin secretion than SC-β only or SC-β/HUVECs samples (FIG. 11B). Notably, neither basal nor stimulated insulin levels of SC-β/R-VECs were significantly different than the other 2 groups. Rather, the higher folds in SC-β/R-VECs were the results of modest decrease of basal insulin and modest increase of stimulated insulin levels, which, as discussed above, is the best scenario that could be expected as the functional maturation of SC-β cells.

Example 18: Materials and Methods

Cell Culture of Endothelial Cells (ECs)

The approval for procuring discarded left-over human umbilical vein endothelial cells (HUVEC) and human adipose tissue ECs were obtained through Weill Cornell Medicine investigational review board. The ECs were isolated in lab as previously described using collagenase-based digestion approach (Baudin, B. et al., *Nature Protocols* 2, 481, (2007)). The cells were then grown in tissue culture dishes coated with 0.2% gelatin in complete EC media. Media is composed of 400 ml of M199, 100 ml heat inactivated FBS, 7.5 ml Hepes, 5 ml antibiotics (Thermo Fisher, 15070063), 5 ml glutamax (Thermo Fisher, 35050061), 5 ml of lipid mixture (Thermo Fisher, 11905031), and ½ bottle of endothelial cell growth supplement (Alpha Aesar, J64516-MF). The cells were transduced with lenti PGK-ETV2 or an empty lenti vector at P1/P2. In some instances, the cells were also labeled by using PGK-mCherry or PGK-GFP lentivirus. The cells were split 1:2 using accutase and passaged on gelatinized plates. As needed, cells in 2D (induction stage) were frozen down to be used in future experiments. All comparisons for all assays and co-cultures were done using the same parental endothelial cell line with and without ETV2. Overall, HUVECs from more than 10 different isolations were used for the experiments. Cells used for tube formation assays were of passage 5-10.

Human adipose-derived ECs were isolated by mechanical fragmentation followed by collagenase digestion for 30 minutes. After plating the crude population of cells on the plastic dish and expansion for 5 to 7 days, the cells were then sorted to purify VEcadherin⁺CD31⁺ ECs and expanded as described above. Human adipose ECs were cultured in the same media described above for HUVECs. At least three different isolations of adipose ECs were used in our experiments. Microvascular cardiac (PromoCell, C12286), aortic (PromoCell, C12272), and microvascular dermal (Promo-Cell, C12265) ECs were acquired from Promocell and cultured in EC growth medium MV (PromoCell, C22020). Lentiviral Transduction of ECs Endothelial cells were transduced with ETV2 lenti-particles or empty vector lenti-particles. ETV2 cDNA [NM_014209.3] was introduced into the pCCL-PGK lentivirus vector [Genecopeia]. For purposes of ChIP analysis, a triple Flag-tag was subcloned in the ETV2 construct at the amino terminus (Ginsberg, M. et al., *Cell* 151, 559-575, (2012)). After 1 week of transduction, ECs were collected for mRNA isolation and qPCR analysis. The relative ETV2 RNA unit was determined by calculating the ratio between the mRNA level of expression of ETV2 over the level of expression of GAPDH (Primers found in the Table 1).

TABLE 1

Primers

| Genes | Application | Primers |
|---|---|---|
| RASGRP3 (Promoter 2 NM_0011 39488) | ChIp-qPCR | GTGATCCTCTCTCTTGCCGT (SEQ ID NO: 1) ATGTGTTTGCGTGTGTGTGT (SEQ ID NO: 2) |
| RASIP1 | ChIp-qPCR | GGAGATCTGGGTAGGGTTGG (SEQ ID NO: 3) GAGGGAGGAAGGGCAGAAAA (SEQ ID NO: 4) |
| DLL4 | ChIp-qPCR | CCCTCCCCAGATTTCCTTGT (SEQ ID NO: 5) GGAGACTGGTGAGAGCCTTT (SEQ ID NO: 6) |
| IGFBP2 | ChIp-qPCR | GAAGTCCTCGCGAACTGAAC (SEQ ID NO: 7) GCACTCTTCTGGCCTGACTA (SEQ ID NO: 8) |
| COL4a1 | ChIp-qPCR | GGTACAAAGGGCAAACGTGT (SEQ ID NO: 9) CTCCTCATCACTCACTGCCT (SEQ ID NO: 10) |
| CHR9 (non region) specific | ChIp-qPCR | GTAACCCACTTTCTCCACA TATCTC (SEQ ID NO: 11) TGCTCAGGCTAGTATCCAATTCC (SEQ ID NO: 12) |
| ETV2 | qPCR | GGGCTTGAAGGAGCCAAATTA (SEQ ID NO: 13) CAGGGATGAGCTTGTACCTTTC (SEQ ID NO: 14) |
| GAPDH | qPCR | GGAGCGAGATCCCTCCAAAAT (SEQ ID NO: 15) GGCTGTTGTCATACTTCTCA TGG (SEQ ID NO: 16) |
| EPHB2 | qPCR | CTTCGAGGCCGTTGAGAAT (SEQ ID NO: 17) TTGATGGGACAGTGGGTACA (SEQ ID NO: 18) |
| HOPX | qPCR | GCCTTTCCGAGGAGGAGAC (SEQ ID NO: 19) TCTGTGACGGATCTGCACTC (SEQ ID NO: 20) |
| TPH1 | qPCR | CCTTAAAGAATGAAGTTGGA GGA (SEQ ID NO: 21) TTTTTGATTTTCGGGACTCG (SEQ ID NO: 22) |
| KRT20 | qPCR | TTGAAGAGCTGCGAAGTCAG (SEQ ID NO: 23) GAAGTCCTCAGCAGCCAGTT (SEQ ID NO: 24) |
| MUC2 | qPCR | TGTAGGCATCGCTCTTCTCA (SEQ ID NO: 25) GAGTCCATCCTGCTGACCAT (SEQ ID NO: 26) |
| BMI1 | qPCR | GCTGGTCTCCAGGTAACGAA (SEQ ID NO: 27) AATCCCCACCTGATGTGTGT (SEQ ID NO: 28) |

TABLE 1-continued

Primers

| Genes | Application | Primers |
|---|---|---|
| Vil1 | qPCR | CCAAAGGCCTGAGTGAAATC (SEQ ID NO: 29) AACCTCAGTTCTGGGCCTCT (SEQ ID NO: 30) |
| NGN3 | qPCR | AGTTGGCACTGAGCAAGC (SEQ ID NO: 31) AGTGCCGAGTTGAGGTTG (SEQ ID NO: 32) |
| CHGA | qPCR | AAAGTGTGTCGGAGATGAC CTCAA (SEQ ID NO: 33) TCCCTGTGAACAGCCCTAT GAATAA (SEQ ID NO: 34) |
| LGR5 | qPCR | CTTCTAATAGGTTGTAAGACA (SEQ ID NO: 35) ATCTCATCTCTTCCTCAAA (SEQ ID NO: 36) |

Cells with relative ETV2 RNA unit within the range of 40-100 were used for all experiments unless otherwise indicated in the text. An MOI of 3 gave us relative expression levels of 60-80 as calculated by mRNA expression. MOI was calculated by converting particles of P24 to IFU and then to MOI based on cell number (kit: Katara, 632200). MOI of 3 was also found to be adequate for Cardiac and Aortic ECs. An MOI of 6 was instead required for adipose and dermal ECs. Polybrene at 2 μg/ml was utilized for all of the transductions. ETS1, myrAKT, mCherry, GFP, were also introduced into the pCCL-PGK lentivirus vector and an MOI of 3 was used for all transductions.

For inducible expression of ETV2, ECs were transduced with doxycycline inducible ETV2 lenti-viruses (pLV[Exp]-Puro-TRE>hETV2 [NM_014209.3], VectorBuilder VB170514-1062dfs and pLV[Exp]-Neo-CMV>tTS/rt-TA_M2, VectorBuilder VB160419-1020mes) where presence of doxycycline turns on ETV2 expression. Post 1 week doxycycline induction of ETV2, cells were collected to determine the relative ETV2 mRNA unit. Cells with relative ETV2 RNA unit within 40-100 were used for all experiments. An MOI of 50 was required for the inducible ETV2 lentiviral particles and tTA lentiviral particles.

Lentivirus Production

All lentiviral plasmids were prepared with a DNA Midiprep kit (Qiagen, 12145). Viruses were packaged in 293T cells by co-transduction with 2nd- or 3rd-generation of packaging plasmids. Culture media were collected 48 hrs post transduction and virus particles concentrated using a Lenti-X concentrator (Katara, 631232), resuspended in PBS without magnesium (Corning, 21040CV), and stored at −80° C. in small aliquots. Virus titers were determined with a Lenti-X p24 titer kit (Katara, 632200).

Tube Formation Assays 24 well plates were coated with 300 μl of Matrigel (Corning) for 30 min in the incubator. Meanwhile, cells with or without ETV2 were accutased and counted. Cells were then resuspended in StemSpan (Stem Cell Technologies) supplemented with 10% knock out serum (Thermo Fisher, 10828028) and cytokines: 10 ng/ml FGF (Peprotech, 1000-18B), 10 ng/ml IGF1 (Peprotech, 100-11), 20 ng/ml EGF (Peprotech, AF-100-15), 20 ng/ml SCF (Peprotech, 300-07), 10 ng/ml IL6 (Peprotech, 200-06). 100,000 cells either with or without ETV2 were then dispersed in each well in 1 ml of media. Cultures were placed in a 37° C. incubator with 5% oxygen for the remainder of the experiments. Media was changed every other day, by replacing 750 μl with fresh media. Care was taken to not disrupt the tubes during all media changes. For several occasions, a mixture of defined matrices comprised of Laminin, Entactin mixture (Corning, 354259) and Collagen IV (Corning, 354245) (L.E.C) was used in place of Matrigel as indicated in the text. The inventors combined these defined matrices at different ratios between Laminin, Entactin and Collagen IV and ultimately found the most effective combination of these gel mixtures for tube formation assays, which was comprised of 200 μl of (Concentrations slightly vary for each lot #, always diluted to 16.5 mg/ml in PBS first) Laminin, Entactin and 100 μl of Collagen IV (Concentrations slightly vary for each lot #, first diluted to 0.6 mg/ml in PBS) mixed together on ice and stored at 4° C. overnight before usage. Final concentration of Laminin, Entactin mixture (11 mg/ml) and Collagen IV (0.2 mg/ml). Volume of L.E.C was increased as needed, as long as the ratios/final concentrations were maintained. Vessel area was measured over a course of 24 hrs to 12 weeks for stage 2 Remodeling and stage 3 Stabilization phases. For the smooth muscle experiments, 2000 mCherry labeled human aortic smooth muscle cells were added to stage 3 GFP labeled R-VEC vessels on Matrigel, and then imaged 1 week after. Human aortic smooth muscle cells were purchased from Promocell (C-12533). EVOS inverted microscope was used to capture images in their different/randomized places in each well for each condition and time point with a 4× objective. All the images were then analyzed for lumenized vessel area using ImageJ to trace vessel area. The same procedure was used for cells transduced with ETS1 or myrAKT1 transduced ECs.

Tube Formation Assay in Different Media Formulations

Endothelial cells were accutased and plated on Matrigel at 100,000 cells/well of 24 well plate as described above. To assess the tube formation assays of ETV2 ECs vs Control ECs, the inventors compared their capabilities to form tubular network in 3 different medium formulations. Medium formulation 1 is the serum-free medium containing StemSpan supplemented with knockout serum and cytokines. Medium formulation 2 is a commercialized EC growth medium (PromoCell, C22111). Medium formulation 3 is a complete EC medium with serum that was used to maintain and propagate ECs. Media were changed every other day. Images were acquired at different time points. ImageJ was utilized to measure the vessel areas over time.

Immunofluorescent Staining of Tubes In Vitro

At 8 to 12 weeks all media was removed from the wells. The tubes were washed once with PBS and fixed for 30 min in 4% PFA at room temperature. Then they were washed again with PBS and put in blocking buffer (containing 0.1% Triton-X) for 1 hr at room temperature. The tubes were then stained with antibodies against Laminin (R&D), Collagen IV (Abcam) and/or podocalyxin (R&D) overnight at 4° C. The next day, the tubes were washed again in PBS, incubated for 3 hrs with secondary antibodies, and counterstained with DAPI (Sigma, 0.5 μg/ml). All images were obtained through confocal microscope Zeiss 710. For proliferation studies, a 16 hour pulse of EdU (Click-iT EdU kit, Thermofisher scientific C10337) was used for all three stages of vessel formation and then the cells stained as described above.

Electron Microscopy

Tissues were washed with serum-free media or PBS then fixed with a modified Karmovsky's fix of 2.5% glutaraldehyde, 4% parafomaldehyde and 0.02% picric acid in 0.1M sodium cacodylate buffer at pH 7.2. Following a secondary fixation in 1% osmium tetroxide, 1.5% potassium ferricyanide samples were dehydrated through a graded ethanol series, and embedded in an Epon analog resin. Ultrathin sections were cut using a Diatome diamond knife (Diatome, USA, Hatfield, PA) on a Leica Ultracut S ultramicrotome (Leica, Vienna, Austria). Sections were collected on copper grids and further contrasted with lead and viewed on a JEM 1400 electron microscope (JEOL, USA, Inc., Peabody, MA) operated at 100 kV. Images were Recorded with a Veleta 2K×2K digital camera (Olympus-SIS, Germany).

AFM Measurements

AFM was used to examine the stiffness of HUVECs, as well as for adult human adipose ECs. Brightfield images of cells, for determination of location of stiffness measurements, were acquired using an inverted microscope (Zeiss Axio Observer Z1) as the AFM base (20×0.8 NA objective). An MFP-3D-BIO Atomic Force Microscope (Asylum Research) was used to collect force maps. A 5 μm borosilicate glass beaded probe (Novascan) with a nominal spring constant of 0.12 N/m was used for all measurements. Each force map sampled a 60 μm×60 μm region, in a 20×20 grid of force curves (400 force curves total) under fluid conditions which covered an area of 360 μm². The trigged point was set to 2 nN with an approach velocity of 5 μm/sec. The force-indentation curves were fit to the Hertz model for spherical tips utilizing the Asylum Research Software to determine the Young's modulus, with an assumed Poisson's ratio value of 0.45 for the sample. Force maps of stiffness along with individual stiffness values for each measured point were then exported from the Asylum Research Software for further analysis. A custom-made MATLAB (MathWorks) script was written to correctly analyze the data for the stiffness of the cells and filter measurements such that only data 1 μm from the glass bottom dish was analyzed (to remove any substrate effect from the measurements).

Bead Flow Movie to Interrogate Perfusion of CTRL-EC Vs R-VEC Vessels in Microfluidic Devices Devices were fabricated as previously described (Nguyen, D. H. et al., *Proc Natl Acad Sci USA* 110, 6712-6717, (2013)). Briefly, each device was comprised of two layers of poly(dimethylsiloxane) (PDMS; Sylgard 184; Dow-Corning), which were cast from silicon wafer masters. The devices were plasma-treated with plasma etcher (Plasma Etch) and subsequently treated with (3-Glycidyloxypropyl) trimethoxysilane (Sigma, 440167) overnight. Prior to usage, the devices were washed with MiliQ H₂O overnight. A mixture of 3 million/ml ETV2 HUVECs or control HUVECs in 2.5 mg/ml bovine Fibrinogen (Sigma) and 3 U/ml bovine thrombin (Sigma) was injected into the devices with two 400 μm acupuncture needles (Hwato). After the cell and gel mixture polymerized, the acupuncture needles were pulled out leaving two hollow channels. HUVECs were seeded into the hollow channels to form two parent vessels on the next day. The devices were placed on a platform rocker for the entire experiment (Benchmark). Cells were cultured in endothelial cell growth medium 2 (PromoCell, C22111) and refreshed daily until day 6. On day 6, the devices were connected to a syringe pump (Harvard Apparatus) and 4 μm red fluorescent microspheres (Invitrogen) were injected into one of the parent vessels in each device at 50 μL/min. Timelapse of fluorescent beads flowing in the devices was captured at 50 ms interval with Nikon Eclipse TiE (Nikon) equipped with an Andor Zyla sCMOS 5.5MP camera (Andor). Time-lapse images of fluorescent beads were stacked together and overlaid with EC vessels using ImageJ.

Rap1 Pull Down and Western Blots

A 10 cm plate of either HUVECs or ETV2-transduced HUVECs (flat-2D induction stage) were used for the active Rap1 assay (Cell Signaling, 8818S) according to the manufacturer's guidelines for the kit. Briefly, the cells were washed once with PBS and then starved for three hours in M199 medium with 0.5% BSA. The cells were then scraped in the lysis buffer for the kit and resuspended at 1 mg/ml. A fraction was saved as input and the rest of the cells were used for Rap1-GTP. Positive and negative controls, as well as a beads only control, were performed according to the manufacturers guidelines. Proteins were solved on 5-15% gradient Tris-glycine SDS-PAGE and semi-dry transferred to nitrocellulose membranes. The membranes were then blocked in 5% milk in PBST and incubated in the provided Rap1 (1:1000) antibody, GAPDH and/or ETV2 antibody for 48 hours. After 48 hours, the membranes were washed 3× for 5 min and incubated in HRP conjugated secondary antibody. Finally, upon secondary washings, the membrane was blotted in ECL and chemiluminescent signals captured with a digital camera (Kindle Biosciences) and images of proteins bands were taken for densitometric quantification using ImageJ.

RNA and Protein Collection from Endothelial Tubes

At indicated time points, tubes of ECs from tube formation assays were collected for RNA sequencing and Western blotting. Before the cells were collected, media was completely removed from the well. 0.5 ml of 2 mg/ml Dispase (Sigma) was added into the well to dissociate the endothelial tubes for 45 mins at 37° C. Dissociated cells were washed once in PBS and subsequently collected for either mRNA or protein isolation. In several occasions, dissociated endothelial cells from tubes were pooled from multiple wells of the same endothelial cell line to allow sufficient isolation of mRNA and protein for downstream analysis.

Western Immunoblot

Cells were lysed into 1×SDS loading buffer (50 mM Tris-HCl pH 6.8, 5% beta-mercaptoethanol, 2% SDS, 0.01% bromophenol blue, 10% glycerol) followed by sonication (Bioruptor, 2×30 seconds at high setting). Proteins were solved on 5-15% gradient Tris-glycine SDS-PAGE and semi-dry transferred to nitrocellulose membranes. The following primary antibodies were used at indicated dilutions: Rap1 (CST, #2399, 1:1,000); RASGRP3 (CST, #3334, 1:1, 000), GAPDH (CST, #5174, 1:10,000); AKT (CST, 34685, 1:5,000); p-S473-Akt (CST, #4060, 1:2,000); ETS1 (CST, #14069, 1,000); and ETV2 (Abcam, ab181847, 1:1,000). HRP-conjugated secondary antibodies and the ECL Prime Western Blotting System (GE Healthcare, RPN2232) were then used. Chemiluminescent signals were captured with a digital camera (Kindle Biosciences) and images of protein bands taken for quantification using ImageJ.

Rap1 Inhibition Experiment

Tube formation assays for endothelial cells with or without ETV2 were set up in 24 wells as described above. The next day, Rap1 inhibitor (GGTI-298, Tocris) resuspended in DMSO was added to the wells at a 1:1000 dilution at the final concentration of 10 μM, while the same amount of DMSO was added to the control wells. The inhibitor and media were changed every other day for 4 weeks. Images were obtained and calculated as described above at 1 week and 4 week time points.

RASGRP3 Knockdown Experiments shERWOOD-UltramiR RASGRP3 shRNA lentiviral constructs (in pZIP-TRE3G) were purchased from TransOMIC Technologies. The clone # and targeted RASGRP3 sequences are as follow: ULTRA-3265848, AAGGGCAGAAGTCATCACAAA (SEQ ID NO: 39);UL-TRA-3265850, CCTTGGAGTACACTTGAAAGA (SEQ ID NO: 40). The control shRNA (ULTRA-NT, ATGCTTTG-CATACTTCTGCCT (SEQ ID NO: 41)) targets a fly luciferase RNA sequence. Lentivirus was prepared as described above, using $2^{nd}$ generation packaging plasmids. R-VECs (stage 1) were transduced with either shRNA virus or control shRNA virus (MOI=3). Doxycycline was added at day 1 of remodeling stage (stage 2) and media with doxycycline was replaced every other day for 4 weeks. Images were obtained as calculated and described above at 2 and 4 week time points. To confirm RASGRP3 knockdown, doxycycline was added in stage 1 R-VEC cells for 1 week and then the cells were collected for Western Blot analysis.

β1 Inhibition Experiment

A 300 uL of pre-mixed defined matrices containing Laminin, Entactin, CollagenIV (L.E.C) was pipetted into a well of 24 well plate and let cure in a 37° C. incubator for 30 mins. R-VECs were accutased and plated directly on L.E.C at a density of 100,000 cells/well in StemSpan medium (Stemcell Technologies) supplemented with knock out serum and cytokines (10 ng/ml FGF, 10 ng/ml IGF1, 20 ng/ml EGF, 20 ng/ml SCF 10 ng/ml IL6) (Peprotech). Immediately, an azide-free neutralization antibody for β1 integrin (EMD Millipore, MABT409) was added into the culture medium at 1 μg/ml concentration. Culture was maintained in a 37° C. incubator with 5% oxygen, and medium was refreshed every 2 days. Vessel area was quantified using ImageJ.

Proteasome Inhibition Experiment

R-VEC vessels were prepared on Matrigel as described above. At stabilization stage (4 weeks), R-VEC tubes were treated with either 20 μM of MG132 (Selleck Chemicals) or DMSO for 6 hrs. The media was removed and the wells were washed once with PBS. R-VEC tubes were then incubated in a solution of 2 mg/ml Dispase (Sigma) for 45 mins at 37° C. to dissociate the tubes. 20 μM of MG132 (Selleck Chemicals) or DMSO was continuously provided during the dissociation period. Dissociated cells were collected and further processed for Western blotting as described above.

In Vivo Experiments

HUVECs and adipose derived human endothelial cells that were transduced with an empty vector or ETV2, and labeled with GFP or mCherry (2 million cells/plug) were injected subcutaneously in male or female 8-12 week old SCID-beige mice (Taconic). The cells were first resuspended in PBS (50 μl) and then mixed with Matrigel (Corning, 356237) or L.E.C. mixture as described above to a final volume of 350 μl. The gels were also supplied with FGF2 (10 ng/ml)(Peprotech, 1000-18B), VEGF-A (20 ng/ml) (Peprotech, 100-20), and heparin (100 μg/ml) (Sigma H3149-100KU). Each mouse R-VECeived two plugs: one with control cells and the other with cells transduced with ETV2. Mice implanted with were injected retro-orbitally with anti-human VEcad (clone BV9—Biolegend) conjugated to Alexa-647 (25 μg in 100 μl of PBS) or 70 kDa fluorescently labeled lysine fixable dextran (ThermoFisher) and sacrificed 8 min post injection. Whole mount images were taken directly on the confocal microscope Zeiss 710 using a well containing a coverslip bottom. The plugs were fixed in 4% PFA overnight and then dehydrated in ethanol or put in sucrose for further immunostaining. The dehydrated plugs were sent to Histoserv Inc. for further processing, sectioning and H&E, Picrosirus, or Masson staining. The sections were processed for immunostaining as described below. For experiments with HUVECs transduced with ETS1, myrAKT1, k-RAS, cells were injected in mice with Matrigel. Plugs were harvested at 1 month and processed with the same procedure.

Immunostaining of Sections

OCT frozen sections (20 µm), previously fixed in 4% PFA and treated in sucrose, were washed once with PBS. Then the slides were incubated in blocking buffer (0.1% Triton-X, 5% normal donkey serum, 0.1% BSA), for 30 minutes at room temperature and overnight in primary antibodies at 4° C. in blocking buffer. For thicker sections (50 µm) tissues were blocked overnight in blocking buffer 4° C. (0.3% Triton-X, 5% normal donkey serum, 0.1% BSA) and then for two days in primary antibody in blocking buffer at 4° C. (0.3% Triton-X, 5% normal donkey serum, 0.1% BSA). The next day, the slides were washed 3× for 10 min at room temperature and then incubated for three hours in fluorescently conjugated secondary antibodies (1:1000). Finally, the slides were washed 3× for 10 min and counter stained with DAPI. The sections were mounted on coverslips. Zeiss 710 confocal or Zeiss Cell Observer confocal spinning disk microscope (Zeiss) were utilized to acquire images. For stroma staining, a mouse anti-PDGFRβ antibody (1:500, Biolegend) or a anti-mouse SMA (1:200, Abcam) were used. Pericyte coverage was quantified as signal of PDGFRβ antibody staining over the signal of the fluorescently labeled human endothelial cells (GFP) using the threshold function in ImageJ. Mouse endothelial cells were counterstained with mouse anti-endomucin antibody (1:100, Satna Cruz). (Several images were taken from sections from different layers of each plug. At least 12 pictures (4/mouse) from different slides were taken for each condition and time point. Images were processed using ImageJ and the percentage of vessel area over the area of each image field was quantified by using the threshold feature in ImageJ.

Intestinal Tissue Harvesting and Decellularization

Intestines were harvested from Sprague Dawley rats ranging 250-350 g in weight. Briefly, under aseptic conditions a midline laparotomy was performed and the intestine exposed. A 5 cm long intestine segment was isolated, preserving the mesenteric artery and the mesenteric vein that perfuse the isolated segment. Both vessels were cannulated with a 26G cannula, intestinal lumen was cannulated using ¼" barbed connectors. The isolated segments were decellularized providing perfusion through vasculature and lumen at 1 ml/min using a peristaltic pump (iPump). Decellularization process consisted of milliQ water for 24 h, sodium deoxycholate (Sigma) for 4 h and DNAse I (Sigma) for 3 h. Decellularized intestines were sterilized with gamma radiation before use.

Bioreactor Culture

Decellularized intestine were seeded either with 5 million GFP⁺ETV2⁺ human endothelial cells or with 5 million GFP⁺ Control-endothelial cells (CTRL-ECs). Cells were seeded through the mesenteric artery and mesenteric vein. Seeded intestines were mounted inside a custom made bioreactor under sterile conditions. After 24 h, perfusion was started through the mesenteric artery at 1 ml/min using a peristaltic pump (iPump). Cells were grown in M199/EBSS (HyClone, SH302503.01) supplemented with 20% Heat inactivated FBS, 1% Pen-Strep, 1.5% HEPES (Corning 25-060-Cl), 1% Glutamax (Gibco 35050-061), 1% Lipid mixture (Gibco 11905-031), 1% Heparin (Sigma H3149-100KU) and 15 ug/ml Endothelial Cell Growth Supplement (Merck 324845) for the first 5 days, then cells were grown for 2 days in Stem Span (Stemcell Technologies) supplemented with 10% knock out serum (Thermo 10828028), 1% Pen-Strep, 1% Glutatamax, 10 ng/ml FGF (Peprotech 1000 18B), 20 ng/ml EGF (Invitrogen PHG0311), 10 ng/ml IGF2 (Peprotech 100-12), 20 ng/ml SCF (Peprotech 300-07) and 10 ng/ml IL6 (Peprotech 200-06). After 7 days, re-endothelialized intestines were harvested under sterile conditions and segments 5×7 mm were excised for heterotopic implantation. Remaining intestinal tissue was then fixed in 4% paraformaldehyde, mounted and prepared for imaging by fluorescent microscopy. To assess patency of the vessels, some re-endothelialized intestines were perfused with fluorescently-labeled LDL.

Heterotopic Graft Implantation

Animals used for these studies were maintained, and the experiments performed, in accordance with the UK Animals (Scientific Procedures) Act 1986 and approved by the University College London Biological Services Ethical Review Process (PPL 70/7622). Animal husbandry at UCL Biological Services was in accordance with the UK Home Office Certificate of Designation. NOD-SCID-gamma (NSG) mice, aged between 8 and 12 weeks, were anaesthetized with a 2-5% isoflurane-oxygen gas mix for induction and maintenance. Buprenorphine 0.1 mg/Kg was administered at the induction for analgesia. Under aseptic conditions a midline laparotomy was performed. The stomach was externalized from the incision and the omentum stretched from the great curvature. A segment of the engineered intestine was then enveloped in the omentum, using 8/0 Prolene suture to secure the closure of the omental wrap. The stomach and the omentum were placed back in the abdomen and the laparotomy closed using 6/0 Vicryl suture. Animals were allowed to normally eat and drink immediately after surgery and no further medications were administered during the post-operative periods. After 1 week or 4 weeks mice were intravenously injected with fluorescently-labeled anti-VEcad (BV9 Biolegend) or fluorescently-labeled Isolectin, then euthanized. Grafts were retrieved together with the omental envelope and fixed in 4% paraformaldehyde, mounted and prepared for imaging by fluorescent microscopy.

Analysis of Vascular Parameters for Decellularized Intestine Experiments

Quantification of in-vitro endothelial revascularization was performed on an area of 5×5 10× fields of view. Images were processed using ImageJ by setting a threshold and quantifying the area covered by CD31 signal with respect to the intestine area. In-vivo quantification of cells positive for GFP and VEcadherin was performed on images acquired with a confocal microscope (Zeiss LSM710) evaluating an area of 3×3 20× fields of view. Evaluation of vascular parameter was performed using Angiotool software (National Cancer Institute).

Quantification of Proliferating Cells and Apoptotic Cells in Decellularized Scaffolds Explanted intestinal grafts were fixed in 4% PFA, embedded in OCT and sectioned. Sections were stained for Cleaved-Caspase3 (Cell Signaling, 9661S) and for Ki67 (Abcam, AB15580). Blocking solution consisting of PBS+/+ with 10% donkey serum was added on the scaffolds for 1 hours prior the staining. Primary antibodies were incubated overnight at 4° C. in blocking solution with the addition of 0.5% Tx. Cleaved-Caspase3 antibody was used at 1:100 concentration, Ki67 antibody at 1:200. Primary antibody buffer was washed 3 times with PBT+/+ before secondary antibody was added. Secondary antibody for donkey anti-mouse or rabbit (Alexa Fluor 547 or 647; Life Tech) was used at a dilution of 1:500 in blocking solution with 0.5% Triton X-100 and incubated at room temperature for 1 hours. Secondary antibody buffer was washed off with PBT+/+3 times and mounting containing DAPI was added before applying a cover slip. Images acquired with a confocal microscope (Zeiss LSM710) evaluating 3 fields of view per animal, 425.10 μm×425.10 μm in size and counting the ratio between human VEcadherin (injected intra-vitally before sacrifice) and Cleaved-Caspase3 or Ki67 positive cells.

Isolation of ECs from ETV2 Reporter Mice

ETV2-Venus reporter mice were a kind gift of Dr. Valerie Kouskoff (Wareing, S. et al., *Dev Dyn* 241, 1454-1464, (2012)). Briefly, embryos were isolated at E9.5 from pooled litters of ETV2-Venus reporter mice. For each independent biological replicate, five litters of mice at E9.5 were pooled together. All embryos were accutased for 20 min at 37° C. and then triturated several times with a pipette. The cells were post-stained for anti mouse CD31 and anti mouse CD45 antibodies, and then sorted as either ETV2Venus⁺, CD31⁺, CD45⁻ or as CD31⁺, CD45⁻ (ARIAII, BD). Cells were sorted straight into Trizol-LS and RNA further purified using Qiagen RNA-easy isolation kit.

Movie Set Up for HUVECs Cultured in 3D Matrices in Different Medium Formulations Control HUVECs and R-VECs were embedded inside L.E.C at 5 million cells/ml. Gels were polymerized on glass-bottom culture dishes at 37° C. incubator for 15 mins. Subsequently, either a commercialized endothelial cell medium (PromoCell, C-22111) or serum-free medium containing StemSpan supplemented with knockout serum and cytokines was added into the cell culture. Medium was also supplemented with Trolox, Vitamin E analog (6-hydroxy-2, 5,7,8-tetramethylchroman-2-Carboxylic Acid) (Sigma) at 100 μM to enable long-term imaging. Culture was mounted on temperature- and gas-controlled chamber for live cell imaging. Time lapse movies were acquired with a Zeiss Cell Observer confocal spinning disk microscope (Zeiss) equipped with a Photometrics Evolve 512 EMCCD camera at an interval of 40 mins over 3 days. Media was refreshed every 2 days.

Isolation and Culture of Mouse Small Intestine Organoids

Mouse small intestine organoids were isolated as previously described (O'Rourke, K. P. et al., *Bio Protoc* 6 (2016)). 15 cm of the proximal small intestine was removed and flushed with cold PBS. After opening longitudinally, it was washed in cold PBS until the supernatant was clear. The intestine was then cut into 5 mm pieces and placed into 10 ml cold 5 mM EDTA-PBS and vigorously resuspended using a 10 ml pipette. The supernatant was aspirated and replaced with 10 ml EDTA and placed at 4° C. on a benchtop roller for 10 minutes. This was then repeated for a second time for 30 minutes. The supernatant was aspirated and then 10 ml of cold PBS was added to the intestine and resuspended with a 10 ml pipette. After collecting this 10 ml fraction of PBS containing crypts, this was repeated and each successive fraction was collected and examined underneath the microscope for the presence of intact intestinal crypts and lack of villi. The 10 ml fraction was then mixed with 10 ml DMEM Basal Media (Advanced DMEM F/12 containing Pen/Strep, Glutamine, HEPES (10 mM), 1 mM N-Acetylcysteine (Sigma Aldrich A9165-SG)) containing 10 U/ml DNAse I (Roche, 04716728001), and filtered through a 100 μm filter into a BSA (1%) coated tube. It was then filtered through a 70 μm filter into a BSA (1%) coated tube and spun at 1200 RPM for 3 minutes. The supernatant was aspirated and the cell pellet mixed with 5 ml Basal Media containing 5% FBS and centrifuged at 200 g for 5 minutes. The purified crypts were then resuspended in basal media and mixed 1:10 with Growth Factor Reduced Matrigel (Corning, 354230). 40 μl of the resuspension was plated in a 48 well plate and allowed to polymerize. Organoid growth media (Basal Media containing 40 ng/mL EGF (Invitrogen PMG8043), 100 ng/ml Noggin (Peprotech 250-38), and 500 ng/mL R-spondin (R&D Systems, 3474-RS-050) was then laid on top of the Matrigel. In some experiments, small intestinal organoid growth media was made R-spondin1 from conditioned media, collected from HEK293 cell lines expressing recombinant R-spondin1 (kindly provided by Calvin Kuo).

Maintenance of Mouse Small Intestine Organoids

Media was changed on organoids every two days and they were passaged 1:4 every 5-7 days. To passage, the growth media was removed and the Matrigel was resuspended in cold PBS and transferred to a 15 ml falcon tube. The organoids were mechanically disassociated using a p1000 or a p200 pipette and pipetting 50-100 times. 7 ml of cold PBS was added to the tube and pipetted 20 times to fully wash the cells. The cells were then centrifuged at 1000 RPM for 5 minutes and the supernatant was aspirated. They were then resuspended in GFR Matrigel and replated as above. For freezing, after spinning the cells were resuspended in Basal Media containing 10% FBS and 10% DMSO and stored in liquid nitrogen indefinitely.

Mouse Small Intestine Organoid Co-Culture and Staining

Mouse small intestine organoids were co-cultured for 4-7 days either alone, or with CTRL-EC, or R-VEC and 5 million cell/ml of Matrigel final concentration. Organoids were mechanically dissociated as described above and mixed with the endothelial cells, spun down and resuspended in GFR Matrigel. The mixture was then dispersed in 30 μl droplets in 8-well chamber slides (Lab-Tek II, 154534) or in 50 μl droplets in Nunc IVF 4-well dish (Thermo Scientific, cat #144444). Media compromised of mouse small intestinal media as described above (EGF 40 ng/ml, Noggin 50 ng/ml, R-Spondin1 conditioned media (10%)+ FGF-2 (10 ng/ml) (Peprotech, 1000-18B) and heparin (100 μg/ml) (Sigma H3149-100KU). Vessel area was quantified by the threshold function in ImageJ and individual sprouts in contact with the mouse small intestine organoids were counted and reported as vessel sprouts/organoids. Organoids were stained as previously described (O'Rourke, K. P. et al., *Bio Protoc* 6 (2016)). Where indicated, 10 μM EdU was added to the growth media for 6 hours before fixing. The growth media was removed and the cells were fixed in 4% PFA for 20 minutes. They were then permeabilized in 0.5% Triton for 20 minutes and blocked in IF Buffer (PBS, 0.2% Triton, 0.05% Tween, 1% BSA) for 1 hour or immediately processed for EdU staining performed according to directions provided with the Click-iT Edu Imaging Kit (Invitrogen C10340). For immunofluorescent staining, cells were incubated in primary antibodies overnight in IF buffer: anti-KRT20 (1:200, Cell Signaling Technologies, #13063). They were then washed 3 times with PBS 0.1% Tween. Secondary antibodies (1:1000, same reagents as above) were incubated for 3 hours. The solution was removed and DAPI in PBS was added for 5 minutes and washed twice with PBS 0.1% Tween. The chambers were then removed and cover slips were mounted using Prolong Gold antifade medium (Invitrogen P36930).

Human Normal Colon and Tumor Organoid Isolation and Culture

Isolation of human colonic crypts and adenomas; culture and maintenance of organoid cultures were performed as previously described (Sugimoto, S. & Sato, T., *Methods Mol*

*Biol* 1612, 97-105, (2017)). Normal and adenoma tissues were collected from colonic resections according to protocols approved by Weill Cornell Medicine Institutional Review Board. Briefly, human colonic mucosa samples were obtained by trimming surgically resected specimens. The underlying muscle layer was removed using fine scissors under a stereomicroscope leaving the mucosa, which was cut into 5-mm pieces on a Petri dish, placed into a 15-ml centrifuge tube containing 10 ml of cold DPBS and washed 3 times. 10-ml of cold DPBS supplemented with 2.5 mM EDTA was added to the tube and incubated for 1 hr room temp with gentle shaking. Isolated crypts were mixed with Matrigel (Corning, 354230), dispensed in the center of each well of a 6 well plate using a 200-1 pipette and placed at 37° C. for 10 min to solidify the Matrigel.

Normal colon organoids were also procured from Jason Spence's laboratory at University of Michigan and were previously described in Tsai et al, 2018 (Tsai, Y. H. et al., *Cell Mol Gastroenterol Hepatol* 6, 218-222, (2018)) (specifically lines 87 and 89). Normal colon organoids were passaged 1:3 every 7 days by mechanical dissociation (pipetting) and grown in 12 well low attachment plates in 30 µl Matrigel droplets. Normal colon organoids were cultured in media comprised of Advanced DMEM/F12, Pen/Strep, 4 mM glutamax, 1% HEPES, primocin (100 µg/ml), 50% L-WRN (Wnt3a, R-spondin, Noggin) conditioned media, N2, B27 without vitamin A, N-acetylcysteine (1 mM), human recombinant EGF (50 ng/ml), Y-27632 (10 µM), A-83-01 (500 nM), SB202190 (10 µM). The L-WRN conditioned medium was generated by using L-WRN cells (ATCC CRL-3276). Following the protocol from Jason Spence's laboratory at University of Michigan, the inventors collected the L-WRN conditioned media for 4 days. Conditioned media was pooled, sterile-filtered and frozen into aliquots until usage.

Human tumor organoids were procured through the Institute for Precision Medicine at Weill Cornell Medicine. Tumor colon organoids were split 1:3 every 7 days by digesting in TrypLE Select (Thermofisher) supplemented with 10 µM Y27632 (Tocris Bioscience). Colon tumor organoids were maintained in media comprised of Advanced DMEM/F12, 1% Pen/Strep, 1% glutamax, 1% HEPES, R-spondin1 conditioned media (5%) N-acetylcysteine (1.25 mM), human Recombinant EGF (50 ng/ml), human Recombinant FGF-10 (20 ng/ml), FGF-2 (1 ng/ml), Y-27632 (10 µM), A-83-01 (500 nM), SB202190 (10 µM), Nicotinamide (10 mM), PGE2 (1 µM), NRG (10 ng/ml), Human Gastrin1 (10 nM) and propagated in GFR Matrigel.

Normal and Tumor Human Organoid Co-Cultures with Endothelial Cells

R-VEC or control CTRL-EC (at a final concentration of 5 million cells/ml) were mixed with normal colon or patient-derived tumor organoids, spun down and resuspended in Matrigel (Corning, 354230) or L.E.C mixture as described above. The cells were then dispersed in 30-70 µl Matrigel (or L.E.C) droplets in 8-well chamber slides (Lab-Tek II, 154534) or Nunc IVF 4-well dish (Thermo Scientific, cat #144444) cultured in the respective organoid media with the addition of FGF-2 (10 ng/ml) (Peprotech, 1000-18B) and heparin (100 µg/ml) (Sigma H3149-100KU). Media was changed every other day. A 16 hour EdU pulse was used for normal colon organoids and a 4.5 hour pulse of EdU was used for all tumor organoid co-culture experiments (Click-iT EdU kit, Invitrogen C10340). The co-cultures were maintained in 37° C. incubator with 20% oxygen. Triple negative breast cancer organoids were also procured from the Institute of Precision Medicine at Weill Cornell Medicine; media for maintenance and co-culture was the same as for colon tumor organoids described above (minus the presence of Gastrin). Normal and tumor colon organoids were stained similarly to mouse small intestinal organoid co-cultures. Antibodies against human EpCAM (Biolegend) and VEcad (R&D) were incubated overnight, followed by secondary antibody staining. The staining with MUC2 antibody (Santa Cruz) was modified to allow for 48 hours of primary antibody incubation and each wash was extended to 3×—20 min each to eliminate potential background.

For single cell sequencing, co-cultures were maintained for 7 days. To collect cells in co-culture for single cell sequencing, medium was removed from the culture and the organoid-endothelial cell droplets were incubated in 2 mg/ml of Dispase (Sigma) for 1 hr at 37° C. with shaking. The cells were then spun down and incubated for an additional 15 min at 37° C. in accutase. At this point the endothelial cells were mostly released from the co-cultures and collected by filtering through a 40 µm mesh. The rest of the undigested cells (mainly organoid clusters) were further dissociated into single cells by incubating with TryplE for an additional 30 mins at 37° C. until the cells were completely separated as single cells. This two-step digestion allowed for increased viability and efficient dissociation of both endothelial cells and organoids. Both the first and the second fraction were further processed for single cell analysis. Single cells were collected and filtered through a 35 µm nylon mesh and processed for single cell sequencing.

For qPCR experiments, co-cultures were maintained for 7 days in Matrigel. To collect cells and dissociate organoids in co-cultures, the inventors incubated the Matrigel droplets with TrypLE-Express enzyme (Thermo Fisher Scientific, 3 ml/50 µl Matrigel droplet) for 45 mins at 37° C. with vigorous shaking. The dissociated cells were then washed twice, once with organoid culture medium and once with MACs buffer. Dissociated cells were resuspended in 100 µL of MACS buffer and anti-human CD31 (Biolegend, 10 µg/ml) was used to stain for endothelial cells for 30 mins on ice. Cell suspension was washed with MACS buffer and resuspended in MACS buffer with DAPI (1 µg/ml). Subsequently, cells were sorted to collect for the DAPI-CD31-population. Accurus PicoPure RNA isolation kit (ThermoFisher) was used to isolate RNA from the collected cells.

For in vivo experiments, 500,000 GFP labeled tumor colon organoids, dissociated to single cells for 10 min with TryplE, were mixed with 2 million mCherry labeled CTRL-EC or R-VECs and implanted subcutaneously in NSG mice. The tumors were retrieved 5 months post implantation.

Quantifying Interacting Vessels with Patient Derived Normal and Tumor Colon Organoids Documented in Serial Confocal Movies Tumor and normal colon organoids were stained with CellTracker (Invitrogen, C34565) per instruction manual by the manufacturer. Tumor and normal colon organoids were embedded inside Matrigel or L.E.C with either CTRL-ECs or R-VECs at 5 million cells/ml. A mixture of gel and cells was pipetted onto glass-bottom dish and polymerized inside 37° C. incubator for 15 mins. The culture was then fed with organoid medium supplemented with 10 ng/ml bFGF (Peprotech), and 100 µg/ml Heparin (Sigma H3149-100KU). To enable long-term imaging, 6-hydroxy-2,5,7,8-tetramethylchroman-2-Carboxylic Acid (Sigma), as an antioxidant, was also added into the medium at 100 µM. Immediately, the culture was mounted onto a temperature- and gas-controlled chamber. Time lapse movies were acquired with a Zeiss Cell Observer confocal spinning disk microscope (Zeiss) equipped with a Photometrics Evolve 512 EMCCD camera at an interval of 40 mins over 3-4 days. Media was refreshed every two days.

To quantify the vessels interacting with normal and tumor colon organoids, Z-projection images of time lapse movies from several time points were obtained using ImageJ. Custom MATLAB codes were written to quantify the interacting vessel areas with all individual organoids. Briefly, the code was used to manually trace the perimeter of all vessels where endothelial cells were wrapping and tapping the organoids. The area of the manually traced interacting vessels was quantified and reported.

Quantifying Signal Intensity for Mucin 2 (MUC2)

Human normal colon organoids were set up in co-culture with endothelial cells as described above. At day 8, cultures were fixed and processed for staining with Mucin 2 and EpCAM. After the staining procedure was complete, the inventors utilized 710 Zeiss confocal microscope to image the whole well of all cultures under a 10× air objective. To ensure accurate comparison between different culture conditions, the inventors used the same microscopic settings to image all the samples: same objective, same laser intensity, and same number of slices for each z-stack. Maximum projection of z-stack images was performed with ImageJ for all conditions. From maximum projection images, several organoids were blindly picked for each condition for quantification. Utilizing a custom MATLAB code, all organoids across all conditions were subjected to the same level of thresholding for Mucin 2 to remove the background. Using the merged image of EpCAM and Mucin2, the area of individual organoid was then traced and generated a binary image. The binary image of organoid area was overlaid with signal in Mucin 2 to isolate the signal of Mucin 2 within each organoid. The inventors then calculated the total signal intensity of Mucin 2 per area of each individual organoid. To enable comparison across different conditions, the signal intensity of Mucin 2 was normalized to the average value of signal intensity of Mucin 2/organoid area quantified from the culture with intestinal organoids alone.

Primary Human Pancreatic Islets in Static Co-Culture with Endothelial Cells:

Primary human islets were purchased from Prodo Laboratories Inc, California. 25 human islets were either cultured alone, co-cultured with CTRL-ECs, or co-cultured with R-VECs. CTRL-ECs and R-VECs were used at 5 million cells/ml. The human islets with and without endothelial cells were mixed in 40 μL of Matrigel and plated into wells of Nunc IVF 4-well dish (Thermo Scientific, cat #144444). The medium was comprised of glucose-free RPMI 1640 and supplemented with 0.1% human serum albumin, 10 μg/ml human transferrin, 50 μM Ethanolamine, 50 μM Phosphoethanolamine, 6.7 μg/ml sodium selenite, 10 ng/ml bFGF, 100 μg/ml heparin, and 5.5 mM Glucose. After two weeks of co-culture, samples were prepared for glucose stimulated insulin secretion (GSIS). Samples were starved in Krebs-Ringer bicarbonate HEPES (KRBH) buffer containing 2 mM glucose for 2 hrs, followed by 45 min in 2 mM glucose as the basal insulin secretion and 45 min in 16.7 mM glucose as the stimulated insulin secretion. Insulin concentrations at the end of basal and stimulated phases were determined using STELLUX Chemi human Insulin ELISA (ALPCO). For each group, there were 11 replicates, with islets derived from 4 different donors. In other experiments, 200 human islets were cultured alone, or mixed with 250,000 CTRL-ECs or 250,000 R-VECs in 50 μl Matrigel droplets (domes). Human islet explants in co-culture were stained and imaged at 1 and 2 weeks. EpCAM and VEcad antibodies were used to post-stain the co-cultures as described above for the mouse/human intestine and colon organoids.

To quantify the interacting vessels with human pancreatic islets, co-cultures were imaged using a 10× objective to capture both GFP-labeled vessels and human pancreatic islets in bright field. Using the custom MATLAB code, the area of GFP-labeled vessels that surrounded and wrapped the human pancreatic islets were traced for both cocultures with CTRL-ECs and with R-VECs.

Organoids and Human Pancreatic Islet Co-Culture in Microfluidic Devices.

To incorporate several human normal colon organoids and human pancreatic islets into the culture in a microfluidic device, the inventors manufactured a larger scale device using photo-lithography. The dimensions of the devices were extended and lengthened. The distance between the two fluidic channels or the width of the device is 3 mm (increased from 1 mm). The length of the device or the length of the fluidic channels is 5 mm long. The height of the device is 1 mm high. The device was cast off from the silicon wafer using PDMS (Dow-Corning) and adhered to a glass coverslip. Overall, the cell culture chamber is enclosed in a PDMS gasket of 5 mm×3 mm×1 mm with the large volume capacity of 15 microliters. Before usage, the devices were plasma-etched and immediately treated with (3-Glycidyloxypropyl)trimethoxysilane (Sigma) overnight. The next day, they were submerged in water to wash overnight before usage. All experiments with human normal colon organoids, and human pancreatic islets were performed in the devices with 5 mm×3 mm×1 mm dimension. All devices were kept in 37° C. incubator with 20% oxygen.

For organoid co-culture in microfluidic device, human normal colon organoids (~40) were mixed with R-VECs in 5 mg/ml bovine fibrinogen and 3 U/ml bovine thrombin to a total of 30 μL. R-VECs were used at 3 million cells/ml. Two acupuncture needles 400 μm diameter were also inserted inside the cell culture chamber. The gel and cell mixture was then injected into the cell culture chamber. After polymerization of fibrin gel, the needles were removed leaving two hollow fluidic channels in the devices. 200 μL of human normal colon organoid medium supplemented with 10 ng/ml FGF-2, 100 μg/ml Heparin, and 5000 U/ml Aprotinin (Sigma) was added into each of the two fluidic channels and refreshed daily. The devices were placed on a platform rocker (Benchmark 2000) during the entire experiment.

For human pancreatic islet culture experiments, devices were also set up similar to how human normal colon organoid experiments were set up. Approximately 75 human pancreatic islets were mixed either alone or with CTRL-EC or R-VECs (4 million cells/ml) cells in 5 mg/ml bovine fibrinogen and 3 U/ml bovine thrombin to a total volume of 30 μL and injected into the devices with two acupuncture needles of 400 μm diameter. The needles were removed after fibrin gel polymerization, and 200 μL of medium for human pancreatic islet co-culture medium (described above) was added into each of the fluidic channels. The devices were placed on a platform rocker (Benchmark 2000) during the entire experiment.

Glucose Stimulation Insulin Secretion (GSIS) Assay for Human Pancreatic Islets in the Devices.

Human pancreatic islets were placed in the devices as described above either alone, or in co-culture with CTRL-ECs or R-VECs. Cadaveric islets (from Prodo Labs, California) were procured from three separate donors, with a total of n=4 devices for No-EC, n=4 devices for CTRL-EC, n=8 devices for R-VEC. After 4 days in culture, a semi-dynamic GSIS assay was performed for islet co-culture in the devices. First, the media was removed in all the devices. The devices were then starved with 2 mM glucose for 2 hours in the incubator. At the end of starvation, 300 μL of 2 mM glucose KRBH buffer was added at the inlet of the device, and devices were incubated at 37° C. for 3 minutes. Driven by gravity, KRBH buffer flew through to the other side (outlet) of the device during the incubation. After the 3-minute incubation, fluid from the outlets was collected for insulin measurement through ELISA. The inlets were also emptied of any remaining fluid. Then, another 300 μL KRBH buffer was added to inlets, leaving the outlets empty. In R-VECs co-culture devices, 30-150 μL fluid was collected in the outlets due to high perfusion rates. In islets alone and CTRL-EC co-culture devices, only a small amount of fluid (<10 μL) was found in the outlets. To enable sample collection, the inventors rinsed the outlets of islets alone and CTRL-ECs co-culture devices with 150 μL KRBH buffer and collected all outlet liquid for insulin measurement through ELISA. Such sample collection was repeated for a total of 8 times using 2 mM glucose KRBH buffer, and another 8 times using 16.7 mM glucose KRBH buffer. At the end, a series of semi-dynamic GSIS samples was acquired. The inventors examined the insulin concentration at the outlet of the device at the $3^{rd}$ (at t=9 min) and $8^{th}$ (t=24 min) collections at both 2 mM and 16.7 mM glucose phases. The insulin level per device was calculated as: insulin per device=insulin concentration x collected volume. Basal insulin levels were determined as the average of the 3rd and 8th collections at 2 mM glucose. Insulin concentration was determined using STELLUX Chemi human Insulin ELISA (ALPCO).

Staining Protocol for Experiments in Devices.

To stain for endothelial cells in the devices, right before the experiment was terminated, the inventors aspirated all medium in both fluidic channels in the devices. 200 μL VEcadherin antibody conjugated with Alexa 647 at 10 μg/ml (Biolegend) was placed on one of the fluidic channels and allowed to slowly perfuse through the lumenized R-VEC vessels for 15-20 mins in the incubator from one fluidic channel to the other fluidic channel. The device was then washed 3× with basal medium and fixed with PFA for 30-45 mins.

When co-culture experiments were set up with human normal colon organoids and human pancreatic islets, the same protocol was utilized to stain for R-VEC lumenized vessels with VE-cadherin conjugated antibody. Post-fixation, the device was permeabalized with 0.1% Triton-X for 45 mins and further stained with either EpCAM for human colon organoids or human pancreatic islets. To stain for EpCAM (Biolegend) the conjugated antibodies were added to both fluidic channels at 10 μg/ml for 48 hrs on a rocker at 4° C. The devices were washed 3× with 1×PBS and subsequently washed submerged into 1×PBS for 24 hrs on a rocker at 4° C. A similar staining procedure was used for insulin and post-VEcad staining, except permeabilization was done over night, followed by primary antibody staining as described above and secondary staining for 24 hrs on a rocker at 4° C. The devices went through a washing for another 24 hrs with 1×PBS on a rocker at 4° C. and then imaged were imaged using a Zeiss 710 confocal.

Perfusion Movies for Beads and Whole Blood Perfusion in Larger Scale Devices (Dimensions: 5 mm×3 mm×1 mm).

For bead movie with human normal colon organoids in devices: the device (dimensions of 5 mm×3 mm×1 mm) with human normal organoids was set up as described above. After 4 days, the device was placed on a Zeiss microscope.

Using vacuum grease, the inventors sealed one end of both fluidic channels such that the two fluidic reservoirs diagonally to one another were left open for perfusion experiment. 4 μm fluorescent microbeads (Invitrogen, F8858) were perfused into the open entrance of one of the fluidic channels at 20 μL/min with a syringe pump (Harvard apparatus). The 4 μm fluorescent microbeads entered the fluidic channel, traversed through the lumenized R-VEC vessels and exited to the other reservoir diagonally to reservoir where the beads entered.

For blood perfusion movie, the device (dimensions of 5 mm×3 mm×1 mm) was prepared with 3 million/ml R-VEC cells. 400 μL medium was refreshed daily (PromoCell). At day 7, blood was collected from a donor following IRB protocol in a heparinized tube. Similar to how the device was prepared for bead movies with human normal colon organoids, the inventors sealed one end of both of the fluidic channels leaving two reservoirs diagonal to one another open for perfusion experiment. Whole heparinized human peripheral blood was obtained from consented healthy subjects with phlebotomy. Immediately, 200 microliters of whole blood was pipetted into one of the fluidic channels at the open reservoir, the blood cells along with intact plasma entered the fluidic channel, traversed through the lumenized R-VEC vessels and exited to the reservoir diagonal to the reservoir where blood entered. In experiments to perfuse blood in devices with R-VECs in co-culture with human pancreatic islets, the inventors stained blood cells with Pkh26 Red fluorescent dye (Sigma, MMIDI26-1KT) according to the manufacturer protocol for 5 mins on ice. Fluorescently labeled blood cells were pipetted into the reservoir, traversed through the lumenized R-VEC vessels, and exited to the diagonal reservoir. In other devices (CTRL-ECs+ human pancreatic islets, and human pancreatic islets alone), fluorescently labeled blood cells were not able to traverse from one fluidic channel to the other fluidic channel. Images were taken with Axio Observer Z1 equipped with Hamamatsu Flash 4.0 v2, sCMOS camera and 10×/0.45 objective.

RNA Library Preparation and Sequence Data Processing

RNA was isolated and purified using Qiagen's Rneasy Mini Kit or Accurus PicoPure RNA isolation kit (ThermoFisher). RNA quality was verified using an Agilent Technologies 2100 Bioanalyzer. RNA library preps were prepared and multiplexed using Illumina TruSeq RNA Library Preparation Kit v2 (non-stranded and poly-A selection) and 10 nM of cDNA was used as input for high-throughput sequencing via Illumina's HiSeq 2500 or HiSeq 4000 producing 51 bp paired-end reads. Sequencing reads were de-multiplexed (bcl2fastq) and mapped with STAR v2.6.0c (Dobin, A. et al., *Bioinformatics* 29, 15-21, (2013)) with default parameters to the appropriate NCBI reference genome (GRCh38.p12 for human samples and GRCm38.p6 for mouse samples). Fragments per gene were counted with feature Counts v1.6.2 (Liao, Y. et al., *Bioinformatics* 30, 923-930, (2014)) with respect to Gencode comprehensive gene annotations (release 28 for human samples and M17 for mouse samples).

Transcriptome Data Analysis

Differential gene expression analysis was performed using DESeq2 v1.18.1 (Love, M. I. et al., *Genome Biol* 15, 550, (2014)), and only FDR adjusted P-values <0.05 were considered statistically significant. Prior to differential gene expression analysis, lowly expressed genes were filtered out by only keeping genes that have more than 1 counts-per-million (CPM) in the condition with the least number of replicates. Base-2 log-transformed CPM values were used for heatmap plots, which were centered and scaled by row. Prior to visualization, tissue specific effects were removed using the removeBatchEffect function from limma v3.34.9 (Ritchie, M. E. et al., *Nucleic Acids Res* 43, e47, (2015)). Gene ontology analysis was performed using DAVID Bioinformatics Resource Tools v 6.8 (Huang da, W. et al., *Nat Protoc* 4, 44-57, (2009)).

ChIP and Antibodies

To identify genome-wide localization of ETV2, K4me3, and K27ac modification in R-VEC or CTRL-EC, ChIP assays were performed with approximately $1 \times 10^7$ cells per experiment. Cells introduced with triple flagged ETV2 lentivirus (as described above) were used for the ETV2 ChIP. Briefly, cells were crosslinked in 1% paraformaldehyde (PFA) for 10 min at 37° C., then quenched by 0.125M glycine. Chromatin was sheared using a Bioruptor (Diagenode) to create fragments of 200-400 bp, immunoprecipitated by 2-5 μg of antibody or mouse IgG bound to 75 μl Dynabeads M-280 (Invitrogen) and incubated overnight at 4° C. Magnetic beads were washed and chromatin was eluted. The ChIP DNA was reverse-crosslinked and column-purified. All ChIP antibodies are identified at attached in table below.

ChIP-qPCR

Primers are listed in Table 1. DNA samples collected before (input) or after ChIP experiment were diluted 1:100 in $H_2O$ and applied to qPCR analysis with SYBR Green PCR master mix in an Applied Biosystems StepOnePlus system. The signal was calculated as fold enrichment relative to an intergenetic region.

ChIP-Seq Library Construction and Sequencing

ChIP-seq libraries were prepared with the Illumina TruSeq ChIP Library Preparation Kit for DNA from ETV2, K4me3, and K27ac modification ChIP; and with the KAPA Hyper Prep Kit for DNA from K4me3, K27ac and K27me3 modification collected from small-scale ChIP assays. ChIP-seq libraries were sequenced with Illumina HiSeq 4000 system.

ChIP-Seq Data Processing and Analysis

ChIP-seq reads were aligned to the reference human genome (hg19, Genome Reference Consortium GRCh37) using the BWA alignment software (version 0.5.9) (Li, H. & Durbin, R., *Bioinformatics* 25, 1754-1760, (2009)). Unique reads that mapped to a single best-matching location with no more than 4% of the read length of mismatches were kept for peak identification and profile generation. Sequence data were visualized with IGV by normalizing to 1 million reads. The software MACS2 (Zhang, Y. et al., *Genome Biol* 9, R137, (2008)) was applied to the ChIP-seq data with sequencing data from input DNA as control to identify genomic enrichment (peak) of ETV2. SICER (version 1.1) (Zang, C. et al., *Bioinformatics* 25, 1952-1958, (2009)) algorithm was applied to the ChIP-seq data with sequencing data from input DNA as control to identify genomic regions with significant enrichment differences in different cell types. The resulting peaks were filtered by p-value<0.05 for ETV2 and FDR<0.01 for histone modifications. The inventors computed the read counts in individual promoters by HOMER (Heinz, S. et al., *Mol Cell* 38, 576-589, (2010)). Each identified peak was annotated to promoters (±2 kb from transcription start site), gene body, or intergenic region by HOMER.

10× Chromium Single Cell Transcriptomics and Analysis

Once the inventors established a stable 3D model of arborized organoids (both normal and tumor organoids) with R-VECs, the inventors set forth to study the molecular crosstalk between endothelial cells and the organoids. Tissue-specific endothelial cells manifest remarkable vascular heterogeneity in vivo, therefore the inventors proposed that R-VECs could model this adaptation to surrounding tissue when co-cultured with either normal colon organoids or tumor colon organoids in vitro. Single cell analysis could help elucidate this interaction by molecularly defining the adaptation or maladaptation of R-VECs at the single cell level, therefore informing the inventors not only of inter-sample heterogeneity, but also of intrasample heterogeneity of endothelial cells upon 3D co-culture. The following two experiments were performed for single cell library preparation to establish adaptation of R-VECs upon co-culture with organoids:

Experiment 1: R-VECs were co-cultured alone or together with Normal Colon Organoids for 7 days in complete organoid growth media with FGF and Heparin. Normal Colon Organoids were also cultured alone in complete organoid growth media with FGF and Heparin for 7 days. After 7 days, all three conditions (R-VEC alone, R-VEC+ Normal Colon Organoids, or Normal Colon Organoids alone) were dissociated with collagenase, dispase and TryplE and submitted for 10× Chromium single cell analysis. All three samples were processed and run at the same time.

Experiment 2: R-VECs were co-cultured alone or together with Colon Tumor Organoids for 7 days in complete organoid growth media with FGF and Heparin. Tumor Colon Organoids were also cultured alone in complete organoid growth media with FGF and Heparin for 7 days. After 7 days, all three conditions (R-VEC alone, R-VEC+Colon Tumor Organoids, or Tumor Colon Organoids alone) were dissociated with collagenase, dispase and TryplE and submitted for 10× Chromium single cell analysis. All three samples were processed and run at the same time.

The single cell suspension was loaded onto a well on a 10× Chromium Single Cell instrument (10× Genomics). Barcoding and cDNA synthesis were performed according to the manufacturer's instructions. Briefly, the 10×™ GemCode™ Technology partitions thousands of cells into nanoliter-scale Gel Bead-In-EMulsions (GEMs), where all the cDNA generated from an individual cell share a common 10× Barcode. In order to identify the PCR duplicates, Unique Molecular Identifier (UMI) was also added. The GEMs were incubated with enzymes to produce full length cDNA, which was then amplified by PCR to generate enough quantity for library construction. Qualitative analysis was performed using the Agilent Bioanalyzer High Sensitivity assay. The cDNA libraries were constructed using the 10× Chromium™ Single cell 3' Library Kit according to the manufacturer's original protocol. Briefly, after the cDNA amplification, enzymatic fragmentation and size selection were performed using SPRI select reagent (Beckman Coulter, Cat # B23317) to optimize the cDNA size. P5, P7, a sample index and read 2 (R2) primer sequence were added by end repair, A-tailing, adaptor ligation and sample-index PCR. The final single cell 3' library contains a standard Illumina paired-end constructs (P5 and P7), Read 1 (R1) primer sequence, 16 bp 10× barcode, 10 bp randomer, 98 bp cDNA fragments, R2 primer sequence and 8 bp sample index. For post library construction QC, 1 ul of sample was diluted 1:10 and ran on the Agilent Bioanalyzer High Sensitivity chip for qualitative analysis. For quantification, Illumina Library Quantification Kit (KAPA Biosystems, Cat # KK4824) was used.

Libraries were sequenced on Illumina NextSeq500 with 150 cycle kit using the following read length: 26 bp Read1 for cell barcode and UMI, 8 bp 17 index for sample index and 132 bp Read2 for transcript. Cell Ranger 2.2.0 was used to process Chromium single cell 3' RNA-seq output. First, "cellranger mkfastq" demultiplexed the sequencing samples based on the 8 bp sample index read to generate fastq files for the Read1 and Read2, followed by extraction of 16 bp cell barcode and 10 bp UMI. Second, "cellranger count" aligned the Read2 to the huma Dobin, A. et al., *Bioinformatics* 29, 15-21, (2013)). Then, aligned reads were used to generate data matrix only when they have valid barcodes and UMI, map to exons (Ensembl GRCh38) without PCR duplicates. Valid cell barcodes were defined based on UMI distribution.

All single cell analyses were performed using the Seurat package in R (version 2.3.4) (Butler, A. et al., *Nat Biotechnol* 36, 411-420, (2018)). Once the gene-cell data matrix was generated, poor quality cells were excluded, including cells with more than 6,000 unique expressed genes (as they are potentially cell doublets). Only genes expressed in 3 or more cells in a sample were used for further analysis. Cells were also discarded if their mitochondrial gene percentages were over 10% or if they expressed less than 600 unique genes, resulting in 20,778 genes across 24,478 cells and median UMI count for each cell across the entire dataset being 7,845 and the median number of unique genes per cell being 2,397. Following best practices in the package suggestions UMI counts were log-normalized and after the most highly variable genes selected the data matrices were scaled using a linear model with variation arising from UMI counts and mitochondrial gene expression mitigated for. Principal component analysis was subsequently performed on this matrix and after reviewing principal component heatmaps and jackstraw plots Uniform Manifold Approximation and Projection (UMAP) visualization were performed on the top 29 components and clustering resolution was set at 1.0 for visualizations. Differential gene expression for gene marker discovery across the clusters were performed using the Wilcoxon rank sum test as used in the Seurat package.

Epithelial cells were identified by epithelial cell markers EpCAM, CDH1, KRT19 and endothelial cells were identified by endothelial cell markers VEcadherin (CDH5), PECAM1 (CD31) and VEGFR2 (KDR). Subsequent to this, epithelial cells were filtered out from the next analysis to identify heterogeneity amongst the endothelial cell populations of the cocultured normal and tumor cell populations. The epithelial cell fraction was also analyzed on its own in the tumor and cocultured samples. In both these analyses best practices were again followed for cluster discovery using the top 20 components and cluster resolution 0.6 in the matched tumor and normal sample sets and differential gene expression for gene marker discovery across the clusters were performed using the Wilcoxon rank sum test as used in the Seurat package.

Statistical Analysis:

Data were assessed and analyzed using appropriate statistical methods. Normality of data was assessed using Kolmogorov-Smirnov test. Sample sizes and statistics for each experiment are provided in figure legends. GraphPad Prism 7 was used for all statistical analysis, unless otherwise indicated.

What is claimed is:

1. A method for vascularizing a pancreatic islet comprising:

coculturing a pancreatic islet comprising β cells with an endothelial cell which comprises an exogenous nucleic acid encoding an ETV2 transcription factor, wherein the ETV2 transcription factor is expressed in the endothelial cell, thereby generating a vascularized pancreatic islet.

2. The method of claim 1, wherein the endothelial cell further comprises an exogenous nucleic acid encoding a Sox17 transcription factor, and wherein the Sox 17 transcription factor is expressed in the endothelial cell.

3. The method of claim 1, wherein the coculturing is performed for at least 3-4 weeks.

4. The method of claim 3, further comprising coculturing the pancreatic islet and the endothelial cell for an additional period of time, wherein the further coculturing occurs under conditions wherein the endothelial cell does not express the ETV2 transcription factor.

5. The method of claim 4, wherein the further coculturing is performed for at least one week.

6. The method of claim 1, wherein the endothelial cell comprises a human umbilical vein endothelial cell (HU-VEC), an adipose-derived endothelial cell, or an organ-specific endothelial cell.

7. The method of claim 6, wherein the organ-specific endothelial cell is selected from the group consisting of a heart-specific endothelial cell, a muscle-specific endothelial cell, a kidney-specific endothelial cell, a testis-specific endothelial cell, an ovary-specific endothelial cell, a lymphoid-specific endothelial cell, a liver-specific endothelial cell, a pancreas-specific endothelial cell, a brain-specific endothelial cell, a lung-specific endothelial cell, a bone marrow-specific endothelial cell, a spleen-specific endothelial cell, a large intestine-specific endothelial cell, and a small intestine-specific endothelial cell.

8. The method of claim 1, wherein the coculturing comprises culturing in media comprising basic FGF (FGF-2) and heparin.

9. The method of claim 1, wherein the coculturing is performed in a bioreactor or a microfluidic device.

10. The method of claim 1, wherein the coculturing is performed on an extracellular matrix comprising a laminin and entactin mixture of between 10 and 12 mg/ml final combined concentration and collagen IV of between 0.2 and 0.5 mg/ml.

11. The method of claim 1, wherein the vascularization comprises the formation of an artery, a vein, a capillary, an arteriole, a venule, lymphatic vessels, or a combination thereof.

12. A method for making a vascularized β-cell organoid, comprising coculturing β-cells with an adult endothelial cell comprising an exogenous nucleic acid encoding an ETV2 transcription factor under conditions wherein the endothelial cell expresses the ETV2 transcription factor.

13. The method of claim 12, wherein the endothelial cell further comprises an exogenous nucleic acid encoding Sox17 transcription factor and wherein the Sox17 transcription factor is expressed in the endothelial cell.

14. The method of claim 12, wherein the coculturing comprises culturing in media comprising basic FGF (FGF-2) and heparin.

15. The method of claim 12, wherein the coculturing is performed for at least 3-4 weeks.

16. The method of claim 15, further comprising coculturing the β-cells and the endothelial cell for an additional period of time, wherein the further coculturing is performed under conditions wherein the endothelial cell does not express the ETV2 transcription factor.

17. The method of claim 16, wherein said further coculturing is performed for at least one week.

18. The method of claim 12, wherein the endothelial cell comprises a human umbilical vein endothelial cell (HU-VEC), an adipose-derived endothelial cell or an organ-specific endothelial cell.

19. The method of claim 18, wherein the organ-specific endothelial cell is selected from the group consisting of a heart-specific endothelial cell, a muscle-specific endothelial cell, a kidney-specific endothelial cell, a testis-specific endothelial cell, an ovary-specific endothelial cell, a lymphoid-specific endothelial cell, a liver-specific endothelial cell, a pancreas-specific endothelial cell, a brain-specific endothelial cell, a lung-specific endothelial cell, a bone marrow-specific endothelial cell, a spleen-specific endothelial cell, a large intestine-specific endothelial cell, and a small intestine-specific endothelial cell.

20. The method of claim 12, wherein the coculturing is carried out on an extracellular matrix comprising a laminin and entactin mixture of between 10 and 12 mg/ml final combined concentration and collagen IV of between 0.2 and 0.5 mg/ml.

21. The method of claim 12, wherein the coculturing is performed in a bioreactor or a microfluidic device.

22. The method of claim 12, wherein the vascularization comprises the formation of an artery, a vein, a capillary, an arteriole, a venule or lymphatic vessels or a combination thereof.

* * * * *

SEQUENCE LISTING

```
<160> NUMBER OF SEQ ID NOS: 41

<210> SEQ ID NO 1
<211> LENGTH: 20
<212> TYPE: DNA
<213> ORGANISM: Artificial Sequence
<220> FEATURE:
<223> OTHER INFORMATION: polynucleotide

<400> SEQUENCE: 1
gtgatcctct ctcttgccgt                                         20

<210> SEQ ID NO 2
<211> LENGTH: 20
<212> TYPE: DNA
<213> ORGANISM: Artificial Sequence
<220> FEATURE:
<223> OTHER INFORMATION: polynucleotide

<400> SEQUENCE: 2
atgtgtttgc gtgtgtgtgt                                         20

<210> SEQ ID NO 3
<211> LENGTH: 20
<212> TYPE: DNA
<213> ORGANISM: Artificial Sequence
<220> FEATURE:
<223> OTHER INFORMATION: polynucleotide

<400> SEQUENCE: 3
ggagatctgg gtagggttgg                                         20

<210> SEQ ID NO 4
<211> LENGTH: 20
```

```
<212> TYPE: DNA
<213> ORGANISM: Artificial Sequence
<220> FEATURE:
<223> OTHER INFORMATION: polynucleotide

<400> SEQUENCE: 4
gagggaggaa gggcagaaaa                                                  20

<210> SEQ ID NO 5
<211> LENGTH: 20
<212> TYPE: DNA
<213> ORGANISM: Artificial Sequence
<220> FEATURE:
<223> OTHER INFORMATION: polynucleotide

<400> SEQUENCE: 5
ccctccccag atttccttgt                                                  20

<210> SEQ ID NO 6
<211> LENGTH: 20
<212> TYPE: DNA
<213> ORGANISM: Artificial Sequence
<220> FEATURE:
<223> OTHER INFORMATION: polynucleotide

<400> SEQUENCE: 6
ggagactggt gagagccttt                                                  20

<210> SEQ ID NO 7
<211> LENGTH: 20
<212> TYPE: DNA
<213> ORGANISM: Artificial Sequence
<220> FEATURE:
<223> OTHER INFORMATION: polynucleotide

<400> SEQUENCE: 7
gaagtcctcg cgaactgaac                                                  20

<210> SEQ ID NO 8
<211> LENGTH: 20
<212> TYPE: DNA
<213> ORGANISM: Artificial Sequence
<220> FEATURE:
<223> OTHER INFORMATION: polynucleotide

<400> SEQUENCE: 8
gcactcttct ggcctgacta                                                  20

<210> SEQ ID NO 9
<211> LENGTH: 20
<212> TYPE: DNA
<213> ORGANISM: Artificial Sequence
<220> FEATURE:
<223> OTHER INFORMATION: polynucleotide

<400> SEQUENCE: 9
ggtacaaagg gcaaacgtgt                                                  20

<210> SEQ ID NO 10
<211> LENGTH: 20
<212> TYPE: DNA
<213> ORGANISM: Artificial Sequence
<220> FEATURE:
<223> OTHER INFORMATION: polynucleotide
```

-continued

<400> SEQUENCE: 10
ctcctcatca ctcactgcct                                          20

<210> SEQ ID NO 11
<211> LENGTH: 25
<212> TYPE: DNA
<213> ORGANISM: Artificial Sequence
<220> FEATURE:
<223> OTHER INFORMATION: polynucleotide

<400> SEQUENCE: 11
gtaacccact ttctccacat atctc                                    25

<210> SEQ ID NO 12
<211> LENGTH: 23
<212> TYPE: DNA
<213> ORGANISM: Artificial Sequence
<220> FEATURE:
<223> OTHER INFORMATION: polynucleotide

<400> SEQUENCE: 12
tgctcaggct agtatccaat tcc                                      23

<210> SEQ ID NO 13
<211> LENGTH: 21
<212> TYPE: DNA
<213> ORGANISM: Artificial Sequence
<220> FEATURE:
<223> OTHER INFORMATION: polynucleotide

<400> SEQUENCE: 13
gggcttgaag gagccaaatt a                                        21

<210> SEQ ID NO 14
<211> LENGTH: 22
<212> TYPE: DNA
<213> ORGANISM: Artificial Sequence
<220> FEATURE:
<223> OTHER INFORMATION: polynucleotide

<400> SEQUENCE: 14
cagggatgag cttgtacctt tc                                       22

<210> SEQ ID NO 15
<211> LENGTH: 21
<212> TYPE: DNA
<213> ORGANISM: Artificial Sequence
<220> FEATURE:
<223> OTHER INFORMATION: polynucleotide

<400> SEQUENCE: 15
ggagcgagat ccctccaaaa t                                        21

<210> SEQ ID NO 16
<211> LENGTH: 23
<212> TYPE: DNA
<213> ORGANISM: Artificial Sequence
<220> FEATURE:
<223> OTHER INFORMATION: polynucleotide

<400> SEQUENCE: 16
ggctgttgtc atacttctca tgg                                      23

<210> SEQ ID NO 17

```
<211> LENGTH: 19
<212> TYPE: DNA
<213> ORGANISM: Artificial Sequence
<220> FEATURE:
<223> OTHER INFORMATION: polynucleotide

<400> SEQUENCE: 17
cttcgaggcc gttgagaat                                                                      19

<210> SEQ ID NO 18
<211> LENGTH: 20
<212> TYPE: DNA
<213> ORGANISM: Artificial Sequence
<220> FEATURE:
<223> OTHER INFORMATION: polynucleotide

<400> SEQUENCE: 18
ttgatgggac agtgggtaca                                                                     20

<210> SEQ ID NO 19
<211> LENGTH: 19
<212> TYPE: DNA
<213> ORGANISM: Artificial Sequence
<220> FEATURE:
<223> OTHER INFORMATION: polynucleotide

<400> SEQUENCE: 19
gcctttccga ggaggagac                                                                      19

<210> SEQ ID NO 20
<211> LENGTH: 20
<212> TYPE: DNA
<213> ORGANISM: Artificial Sequence
<220> FEATURE:
<223> OTHER INFORMATION: polynucleotide

<400> SEQUENCE: 20
tctgtgacgg atctgcactc                                                                     20

<210> SEQ ID NO 21
<211> LENGTH: 23
<212> TYPE: DNA
<213> ORGANISM: Artificial Sequence
<220> FEATURE:
<223> OTHER INFORMATION: polynucleotide

<400> SEQUENCE: 21
ccttaaagaa tgaagttgga gga                                                                 23

<210> SEQ ID NO 22
<211> LENGTH: 20
<212> TYPE: DNA
<213> ORGANISM: Artificial Sequence
<220> FEATURE:
<223> OTHER INFORMATION: polynucleotide

<400> SEQUENCE: 22
tttttgattt tcgggactcg                                                                     20

<210> SEQ ID NO 23
<211> LENGTH: 20
<212> TYPE: DNA
<213> ORGANISM: Artificial Sequence
<220> FEATURE:
<223> OTHER INFORMATION: polynucleotide
```

-continued

```
<400> SEQUENCE: 23
ttgaagagct gcgaagtcag                                            20

<210> SEQ ID NO 24
<211> LENGTH: 20
<212> TYPE: DNA
<213> ORGANISM: Artificial Sequence
<220> FEATURE:
<223> OTHER INFORMATION: polynucleotide

<400> SEQUENCE: 24
gaagtcctca gcagccagtt                                            20

<210> SEQ ID NO 25
<211> LENGTH: 20
<212> TYPE: DNA
<213> ORGANISM: Artificial Sequence
<220> FEATURE:
<223> OTHER INFORMATION: polynucleotide

<400> SEQUENCE: 25
tgtaggcatc gctcttctca                                            20

<210> SEQ ID NO 26
<211> LENGTH: 20
<212> TYPE: DNA
<213> ORGANISM: Artificial Sequence
<220> FEATURE:
<223> OTHER INFORMATION: polynucleotide

<400> SEQUENCE: 26
gagtccatcc tgctgaccat                                            20

<210> SEQ ID NO 27
<211> LENGTH: 20
<212> TYPE: DNA
<213> ORGANISM: Artificial Sequence
<220> FEATURE:
<223> OTHER INFORMATION: polynucleotide

<400> SEQUENCE: 27
gctggtctcc aggtaacgaa                                            20

<210> SEQ ID NO 28
<211> LENGTH: 20
<212> TYPE: DNA
<213> ORGANISM: Artificial Sequence
<220> FEATURE:
<223> OTHER INFORMATION: polynucleotide

<400> SEQUENCE: 28
aatccccacc tgatgtgtgt                                            20

<210> SEQ ID NO 29
<211> LENGTH: 20
<212> TYPE: DNA
<213> ORGANISM: Artificial Sequence
<220> FEATURE:
<223> OTHER INFORMATION: polynucleotide

<400> SEQUENCE: 29
ccaaaggcct gagtgaaatc                                            20

<210> SEQ ID NO 30
```

-continued

```
<211> LENGTH: 20
<212> TYPE: DNA
<213> ORGANISM: Artificial Sequence
<220> FEATURE:
<223> OTHER INFORMATION: polynucleotide

<400> SEQUENCE: 30
aacctcagtt ctgggcctct                                               20

<210> SEQ ID NO 31
<211> LENGTH: 18
<212> TYPE: DNA
<213> ORGANISM: Artificial Sequence
<220> FEATURE:
<223> OTHER INFORMATION: polynucleotide

<400> SEQUENCE: 31
agttggcact gagcaagc                                                 18

<210> SEQ ID NO 32
<211> LENGTH: 18
<212> TYPE: DNA
<213> ORGANISM: Artificial Sequence
<220> FEATURE:
<223> OTHER INFORMATION: polynucleotide

<400> SEQUENCE: 32
agtgccgagt tgaggttg                                                 18

<210> SEQ ID NO 33
<211> LENGTH: 24
<212> TYPE: DNA
<213> ORGANISM: Artificial Sequence
<220> FEATURE:
<223> OTHER INFORMATION: polynucleotide

<400> SEQUENCE: 33
aaagtgtgtc ggagatgacc tcaa                                          24

<210> SEQ ID NO 34
<211> LENGTH: 25
<212> TYPE: DNA
<213> ORGANISM: Artificial Sequence
<220> FEATURE:
<223> OTHER INFORMATION: polynucleotide

<400> SEQUENCE: 34
tccctgtgaa cagccctatg aataa                                         25

<210> SEQ ID NO 35
<211> LENGTH: 21
<212> TYPE: DNA
<213> ORGANISM: Artificial Sequence
<220> FEATURE:
<223> OTHER INFORMATION: polynucleotide

<400> SEQUENCE: 35
cttctaatag gttgtaagac a                                             21

<210> SEQ ID NO 36
<211> LENGTH: 19
<212> TYPE: DNA
<213> ORGANISM: Artificial Sequence
<220> FEATURE:
<223> OTHER INFORMATION: polynucleotide
```

-continued

<400> SEQUENCE: 36
atctcatctc ttcctcaaa                                              19

<210> SEQ ID NO 37
<211> LENGTH: 3697
<212> TYPE: DNA
<213> ORGANISM: Homo sapiens

<400> SEQUENCE: 37
attacaggcg tgaatcaccg cgcccaacca caagttacag acattataac atttcatctc      60
tgagttcatt ttctaaatga tatctttcct cctgaatacc attatcaaat ctaagaaaag     120
aattctatga tatttcatat tcagttcata ctccagtttc cccaattgtc ctaaactatt     180
acagcgcgga agggcatggg gtctggagaa ggagagcagt gggaggatgc ctgccttacc     240
ttccccctct atcaaatgag agtatgtatt gtacttgcct catagaagga ttcaatgaag     300
gggtatggca cagttggttt cacacaatga gccctcattt aatgttggcc gttattgcta     360
ctattgttat tgttgaaatt gttgatgtca atattgctat gattggcact cctgggaagc     420
agccccagga cgccctccct actgggcctg gtggaggatt gggtgggcct tcactcctgc     480
tccacgcccc cgcagttact ctgccgattg tgacgtcagc tgacgctggg ggcgggtggg     540
ggaatctggc cggaaatccc tcttcctgtt gcagataagc ccagcttagc ccagctgacc     600
ccagaccctc tcccctcact cccccccatgt cgcaggatcg agaccctgag gcagacagcc     660
cgttcaccaa gccccccgcc ccgcccccat caccccgtaa acttctccca gcctccgccc     720
tgccctcacc cagcccgctg ttccccaagc ctcgctccaa gcccacgcca ccctgcagc     780 agggcagccc cagaggccag cacctatccc cgaggctggg gtcgaggctc ggccccgccc     840
ctgcctctgc aacttgagcc tggctgcgac ccctgctctg acgtctcgga aaattccccc     900
ttgcccaggc ccttgggggaa ggggggtgcat ggtatgaaat ggggctgaga cccccggctg     960
ggggcagagg aacccgccag aggtgagcga tgaactgagg actagatgcc tgggtgtctg    1020
ggttaggaag gacctggggg actagactcc caagaagccg ggggcctgga ctcctgggtc    1080
taacagagga agagagctgg ggtccctcac tcccaggacc aagattttag gctcctgggg    1140
aaggagggag cggaggcctg gactcctggc tctgagggaa gctagggctg gggcccagac    1200
tccagggcct ccaagtgtca ccagctcacc cattgccatc tggactttttc ccgacccaga    1260 acattcagaa ggccttcatc gcatccatgg acctgtggaa ctgggatgag gcatccccac    1320
aggaagtgcc tccagggaac aagctggcag ggcttggtag gctgccgagg ctgccacaac    1380
gtgtgtgggg agggtgtcca ggtggggcct ctgctgaccc taacccctta tcgcctgcag    1440
aaggagccaa attaggcttc tgtttccctg atctggcact ccaaggggac acgccgacag    1500
cgacagcaga gacatgctgg aaaggtggct gcgggctggg acccctaagt gctggagaag    1560
aagcggggag gctgggatcc tagggcaaag ggaggagggg ggcgtgccta ggttcctggg    1620
actgggtggg gaggggccgc gtgcttgacc cctgagggtg aaggaaaagg gggcgcgggg    1680
tgctgaaata cgggctgggg ggccataact cccagtccct gacaagtaga gactagagag    1740
tgggtagttg aggggtctct ttcattgctc acagtcctcc ctaaactcag gtacaagctc    1800
atccctggca agcttcccac agctggactg gggctccgcg ttactgcacc cagaagttcc    1860
atggggggcg ggtgagtgtg gggagaggcg gtggaggtg gggactgggg tcccgaggca    1920
ccggggctag aggtgtagac tccctgatct ttgaggactg agaacacctg cgccctcaag    1980

-continued

```
gtggcatgac ctggatccgg gtcagccggg ccccaagtgc cagggttgag agcttagacc      2040
ctagagtttt tgagggggca cctgggctcc cctcactcgg gatccgttac tcctcacaga      2100
gcccgactct caggctcttc cgtggtccgg ggactggaca gacatggcgt gcacagcctg      2160
ggactcttgg agcggcgcct cgcagaccct gggccccgcc cctctcggcc cgggcccat       2220 ccccgccgcc ggctccgaag gcgccgcggg ccagaactgc gtcccgtgg  cgggagaggc      2280 cacctcgtgg tcgcgcgccc aggccgccgg gagcaacacc agctgggact gttctgtggg      2340
gcccgacggc gatacctact ggggcagtgg cctgggcggg gagccgcgca cggactgtac      2400
catttcgtgg ggcgggcccg cgggcccgga ctgtaccacc tcctggaacc cggggctgca      2460
tgcgggtggc accacctctt tgaagcggta ccagagctca gctctcaccg tttgctccga      2520
accgagcccg cagtcggacc gtgccagttt ggctcgatgc cccaaaacta accaccgagg      2580
tgagagggcc gcaaagactg cggggagggc gaagctggag tcctgagccg ggacccaggc      2640
acctaagggg gcggggcccg ggagactgac agtgaggggg cggggcctta gggaccaggg      2700
gctcgaagga ggggccggtg gcccgcactc caggtccttg gggaggagag ggctaagaaa      2760
ctggtagtct tatagggacc aaggggatga ggacccaggc tcctggatta tataaaacga      2820
aagcgataaa ggcccagatt cctgggtctc cgagatgggg aggccaaact cctaaatctc      2880
tgagactggg gccctggacg cttgagtctc caaggctgac tgttggatct cagagaaggg      2940
ggggcggatc cccttctcgg gtcctgggtc ccgagttggg aggacccgga cctctagatc      3000
attgaagtgg tgtgatctag ggccgggaag actgagtgtg cccctccctt catcccgcag      3060
gtcccattca gctgtggcag ttcctcctgg agctgctcca cgacggggcg cgtagcagct      3120
gcatccgttg gactggcaac agccgcgagt tccagctgtg cgaccccaaa gaggtggggc      3180
agctcccctg cccagccaaa tccgccccgt ctcttctagt tcaatttagc tccgcccaag      3240
ggctaggttc aaccgcgtag ccctcggccc cgccgctccc cggcccactc gaggccccgc      3300
ccaacccttc tcaaacccaa tctcccgcct gtactcctgc ctcaaccaac ccagtctcca      3360
ccgggctctg cgaggcctcg cccaggtctg cactgcacac cgcccccagg cccggccctc      3420
cccactatcg ccaagccccg ccccttccca ctccgaccga gcgggcctct gtcctaggtg      3480
gctcggctgt ggggcgagcg caagagaaag ccgggcatga attacgagaa gctgagccgg      3540
ggccttcgct actactatcg ccgcgacatc gtgcgcaaga gcggggggcg aaagtacacg      3600
taccgcttcg ggggccgcgt gcccagccta gcctatccgg actgtgcggg aggcggacgg      3660
ggagcagaga cacaataaaa attcccggtc aaacctc                               3697
```

<210> SEQ ID NO 38
<211> LENGTH: 342
<212> TYPE: PRT
<213> ORGANISM: Homo sapiens

<400> SEQUENCE: 38

```
Met Asp Leu Trp Asn Trp Asp Glu Ala Ser Pro Gln Glu Val Pro Pro
1               5                   10                  15

Gly Asn Lys Leu Ala Gly Leu Glu Gly Ala Lys Leu Gly Phe Cys Phe
            20                  25                  30

Pro Asp Leu Ala Leu Gln Gly Asp Thr Pro Thr Ala Thr Ala Glu Thr
        35                  40                  45

Cys Trp Lys Gly Thr Ser Ser Ser Leu Ala Ser Phe Pro Gln Leu Asp
    50                  55                  60
```

```
Trp Gly Ser Ala Leu Leu His Pro Glu Val Pro Trp Gly Ala Glu Pro
65                  70                  75                  80

Asp Ser Gln Ala Leu Pro Trp Ser Gly Asp Trp Thr Asp Met Ala Cys
                85                  90                  95

Thr Ala Trp Asp Ser Trp Ser Gly Ala Ser Gln Thr Leu Gly Pro Ala
            100                 105                 110

Pro Leu Gly Pro Gly Pro Ile Pro Ala Ala Gly Ser Glu Gly Ala Ala
        115                 120                 125

Gly Gln Asn Cys Val Pro Val Ala Gly Glu Ala Thr Ser Trp Ser Arg
    130                 135                 140

Ala Gln Ala Ala Gly Ser Asn Thr Ser Trp Asp Cys Ser Val Gly Pro
145                 150                 155                 160

Asp Gly Asp Thr Tyr Trp Gly Ser Gly Leu Gly Gly Glu Pro Arg Thr
                165                 170                 175

Asp Cys Thr Ile Ser Trp Gly Gly Pro Ala Gly Pro Asp Cys Thr Thr
            180                 185                 190

Ser Trp Asn Pro Gly Leu His Ala Gly Gly Thr Thr Ser Leu Lys Arg
            195                 200                 205

Tyr Gln Ser Ser Ala Leu Thr Val Cys Ser Glu Pro Ser Pro Gln Ser
    210                 215                 220

Asp Arg Ala Ser Leu Ala Arg Cys Pro Lys Thr Asn His Arg Gly Pro
225                 230                 235                 240

Ile Gln Leu Trp Gln Phe Leu Leu Glu Leu Leu His Asp Gly Ala Arg
                245                 250                 255

Ser Ser Cys Ile Arg Trp Thr Gly Asn Ser Arg Glu Phe Gln Leu Cys
            260                 265                 270

Asp Pro Lys Glu Val Ala Arg Leu Trp Gly Glu Arg Lys Arg Lys Pro
            275                 280                 285

Gly Met Asn Tyr Glu Lys Leu Ser Arg Gly Leu Arg Tyr Tyr Tyr Arg
    290                 295                 300

Arg Asp Ile Val Arg Lys Ser Gly Gly Arg Lys Tyr Thr Tyr Arg Phe
305                 310                 315                 320

Gly Gly Arg Val Pro Ser Leu Ala Tyr Pro Asp Cys Ala Gly Gly Gly
                325                 330                 335

Arg Gly Ala Glu Thr Gln
            340
```

```
<210> SEQ ID NO 39
<211> LENGTH: 21
<212> TYPE: DNA
<213> ORGANISM: Artificial Sequence
<220> FEATURE:
<223> OTHER INFORMATION: polynucleotide

<400> SEQUENCE: 39
aagggcagaa gtcatcacaa a                                                21

<210> SEQ ID NO 40
<211> LENGTH: 21
<212> TYPE: DNA
<213> ORGANISM: Artificial Sequence
<220> FEATURE:
<223> OTHER INFORMATION: polynucleotide

<400> SEQUENCE: 40
ccttggagta cacttgaaag a                                                21
```

-continued

```
<210> SEQ ID NO 41
<211> LENGTH: 21
<212> TYPE: DNA
<213> ORGANISM: Artificial Sequence
<220> FEATURE:
<223> OTHER INFORMATION: polynucleotide

<400> SEQUENCE: 41
atgctttgca tacttctgcc t                                                    21
```